US010234934B2

(12) United States Patent
Connor

(10) Patent No.: US 10,234,934 B2
(45) Date of Patent: Mar. 19, 2019

(54) SENSOR ARRAY SPANNING MULTIPLE RADIAL QUADRANTS TO MEASURE BODY JOINT MOVEMENT

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 389 days.

(21) Appl. No.: 15/079,447

(22) Filed: Mar. 24, 2016

(65) Prior Publication Data
US 2016/0202755 A1 Jul. 14, 2016

Related U.S. Application Data

(63) Continuation of application No. 14/463,741, filed on Aug. 20, 2014, now Pat. No. 9,588,582, and a
(Continued)

(51) Int. Cl.
A41D 13/12 (2006.01)
G06F 3/01 (2006.01)
(Continued)

(52) U.S. Cl.
CPC ........ *G06F 3/011* (2013.01); *A41D 13/1281* (2013.01); *A61B 5/1126* (2013.01); *G06F 3/017* (2013.01); *A61B 5/002* (2013.01); *A61B 5/0024* (2013.01); *A61B 5/1071* (2013.01); *A61B 5/1121* (2013.01); *A61B 5/4528* (2013.01); *A61B 5/4585* (2013.01);
(Continued)

(58) Field of Classification Search
CPC ..... G06F 3/011; G06F 3/017; A41D 13/1281; A41D 12/1281
See application file for complete search history.

(56) References Cited

U.S. PATENT DOCUMENTS 3,974,491 A 8/1976 Sipe
4,542,291 A 9/1985 Zimmerman
(Continued)

FOREIGN PATENT DOCUMENTS

WO WO 2005001678 1/2005
WO WO 2014001843 1/2014

OTHER PUBLICATIONS

Gibbs et al., Wearable Conductive Fiber Sensors for Multi-Axis Human Joint Angle Measurements, Mar. 2005, Journal of NeuroEngineering and Rehabilitation, 2005.*
(Continued)

*Primary Examiner* — Erika J Villaluna

(57) ABSTRACT

This invention is a sensor array which longitudinally spans a body joint in order to measure movement of that body joint. In an example, this sensor array can comprise four longitudinal sensors which span the body joint in four different radial quadrants, respectively. In an example, this sensor array can comprise six longitudinal sensors which span the body joint in six different radial hextants, respectively. In an example, this sensor array can further comprise a first accelerometer which is proximal to the body joint and a second accelerometer which is distal to the body joint.

2 Claims, 37 Drawing Sheets

Related U.S. Application Data continuation-in-part of application No. 14/664,832, filed on Mar. 21, 2015, now Pat. No. 9,582,072, which is a continuation-in-part of application No. 14/463,741, filed on Aug. 20, 2014, now Pat. No. 9,588,582.

(60) Provisional application No. 61/976,650, filed on Apr. 8, 2014, provisional application No. 62/150,886, filed on Apr. 22, 2015, provisional application No. 61/878,893, filed on Sep. 17, 2013.

(51) Int. Cl.
  *A61B 5/11* (2006.01)
  *A61B 5/00* (2006.01)
  *A61B 5/107* (2006.01)

(52) U.S. Cl.
  CPC ........... *A61B 5/6804* (2013.01); *A61B 5/6831* (2013.01); *A61B 2505/09* (2013.01); *A61B 2562/0247* (2013.01); *A61B 2562/046* (2013.01); *Y10T 29/49826* (2015.01)

(56) References Cited

U.S. PATENT DOCUMENTS

| | | | |
|---|---|---|---|
| 5,012,819 A | 5/1991 | Marras et al. | |
| 5,086,785 A | 2/1992 | Gentile et al. | |
| 5,184,009 A | 2/1993 | Wright et al. | |
| 5,184,319 A | 2/1993 | Kramer | |
| 5,280,265 A | 1/1994 | Kramer et al. | |
| 5,316,017 A | 5/1994 | Edwards et al. | |
| 5,337,758 A | 8/1994 | Moore et al. | |
| 5,375,610 A | 12/1994 | LaCourse et al. | |
| 5,442,729 A | 8/1995 | Kramer et al. | |
| 5,469,861 A | 11/1995 | Piscopo et al. | |
| 5,474,088 A | 12/1995 | Zaharkin et al. | |
| 5,516,249 A | 5/1996 | Brimhall | |
| 5,533,531 A | 7/1996 | Edwards et al. | |
| 5,592,401 A | 1/1997 | Kramer | |
| 5,615,132 A | 3/1997 | Horton et al. | |
| 5,640,971 A | 6/1997 | Martin | |
| 5,656,904 A | 8/1997 | Lander | |
| 5,676,157 A | 10/1997 | Kramer | |
| 5,694,497 A | 12/1997 | Sansone | |
| 5,813,406 A | 9/1998 | Kramer et al. | |
| 5,819,206 A | 10/1998 | Horton et al. | |
| 5,915,673 A | 6/1999 | Kazerooni | |
| 5,930,741 A | 7/1999 | Kramer | |
| 5,961,541 A | 10/1999 | Ferrati | |
| 5,980,472 A | 11/1999 | Seyl | |
| 5,989,700 A | 11/1999 | Krivopal | |
| 6,003,340 A | 12/1999 | Borak et al. | |
| 6,005,548 A | 12/1999 | Latypov et al. | |
| 6,018,705 A | 1/2000 | Gaudet et al. | |
| 6,032,530 A | 3/2000 | Hock | |
| 6,035,274 A | 3/2000 | Kramer et al. | |
| 6,042,555 A | 3/2000 | Kramer et al. | |
| 6,050,962 A | 4/2000 | Kramer et al. | |
| 6,059,576 A | 5/2000 | Brann | |
| 6,095,991 A | 8/2000 | Krausman et al. | |
| 6,104,379 A | 8/2000 | Petrich et al. | |
| 6,110,130 A | 8/2000 | Kramer | |
| 6,119,516 A | 9/2000 | Hock | |
| 6,127,672 A * | 10/2000 | Danisch ................ | G01B 11/18 250/227.14 |
| 6,148,280 A | 11/2000 | Kramer | |
| 6,162,190 A | 12/2000 | Kramer | |
| 6,162,191 A | 12/2000 | Foxlin | |
| 6,210,301 B1 | 4/2001 | Abraham-Fuchs et al. | |
| 6,210,771 B1 | 4/2001 | Post et al. | |
| 6,239,784 B1 | 5/2001 | Holmes | |
| 6,246,390 B1 | 6/2001 | Rosenberg | |
| 6,304,840 B1 | 10/2001 | Vance et al. | |
| 6,334,852 B1 | 1/2002 | Seyl | |
| 6,341,504 B1 | 1/2002 | Istook | |
| 6,360,615 B1 | 3/2002 | Smela | |
| 6,361,507 B1 | 3/2002 | Foxlin | |
| 6,381,482 B1 | 4/2002 | Jayaraman et al. | |
| 6,389,187 B1 | 5/2002 | Greenaway et al. | |
| 6,409,687 B1 | 6/2002 | Foxlin | |
| 6,413,229 B1 | 7/2002 | Kramer et al. | |
| 6,428,490 B1 | 8/2002 | Kramer et al. | |
| 6,429,421 B1 | 8/2002 | Meller et al. | |
| 6,466,200 B1 | 10/2002 | Anton et al. | |
| 6,487,906 B1 | 12/2002 | Hock | |
| 6,497,672 B2 | 12/2002 | Kramer | |
| 6,513,532 B2 | 2/2003 | Mault et al. | |
| 6,543,299 B2 | 4/2003 | Taylor | |
| 6,563,107 B2 | 5/2003 | Danisch et al. | |
| 6,579,248 B1 | 6/2003 | Cascone et al. | |
| 6,611,141 B1 | 8/2003 | Schulz et al. | |
| 6,611,789 B1 | 8/2003 | Darley | |
| 6,621,948 B1 | 9/2003 | Devenyi | |
| 6,640,202 B1 | 10/2003 | Dietz et al. | |
| 6,666,831 B1 | 12/2003 | Edgerton et al. | |
| 6,673,027 B2 | 1/2004 | Fischer | |
| 6,691,074 B1 | 2/2004 | Moriya et al. | |
| 6,700,499 B2 | 3/2004 | Kubo et al. | |
| 6,701,296 B1 | 3/2004 | Kramer et al. | |
| 6,703,939 B2 | 3/2004 | Lehrman et al. | |
| 6,728,431 B2 | 4/2004 | Ames et al. | |
| 6,731,268 B2 | 5/2004 | Anton et al. | |
| 6,786,877 B2 | 9/2004 | Foxlin | |
| 6,809,462 B2 | 10/2004 | Pelrine et al. | |
| 6,826,968 B2 | 12/2004 | Manaresi et al. | |
| 6,834,436 B2 | 12/2004 | Townsend et al. | |
| 6,836,744 B1 | 12/2004 | Asphahani et al. | |
| 6,856,715 B1 | 2/2005 | Ebbesen et al. | |
| 6,864,796 B2 | 3/2005 | Lehrman et al. | |
| 6,866,643 B2 | 3/2005 | Kramer | |
| 6,871,413 B1 | 3/2005 | Arms et al. | |
| 6,890,312 B1 | 5/2005 | Priester et al. | |
| 6,912,475 B2 | 6/2005 | Moriya et al. | |
| 6,940,062 B2 | 9/2005 | Kwon et al. | |
| 6,942,496 B2 | 9/2005 | Sweetland et al. | |
| 6,957,164 B2 | 10/2005 | Dietz et al. | |
| 6,964,205 B2 | 11/2005 | Papakostas et al. | |
| 6,979,164 B2 | 12/2005 | Kramer | |
| 6,985,134 B2 | 1/2006 | Suprun et al. | |
| 7,020,508 B2 | 3/2006 | Stivoric et al. | |
| 7,028,547 B2 | 4/2006 | Shiratori et al. | |
| 7,070,571 B2 | 7/2006 | Kramer et al. | |
| 7,082,570 B1 | 7/2006 | von Wiegand et al. | |
| 7,095,331 B2 | 8/2006 | Lehrman et al. | |
| 7,135,227 B2 | 11/2006 | Karayianni et al. | |
| 7,141,026 B2 | 11/2006 | Aminian et al. | |
| 7,144,830 B2 | 12/2006 | Hill et al. | |
| 7,145,461 B2 | 12/2006 | Lehrman et al. | |
| 7,149,584 B1 | 12/2006 | Koh et al. | |
| 7,153,242 B2 | 12/2006 | Goffer | |
| 7,167,743 B2 | 1/2007 | Heruth et al. | |
| 7,191,652 B2 | 3/2007 | Pristup et al. | |
| 7,191,803 B2 | 3/2007 | Orr et al. | |
| 7,209,028 B2 | 4/2007 | Boronkay et al. | |
| 7,210,240 B2 | 5/2007 | Townsend et al. | |
| 7,212,943 B2 | 5/2007 | Aoshima et al. | |
| 7,219,033 B2 | 5/2007 | Kolen | |
| 7,230,610 B2 | 6/2007 | Jung et al. | |
| 7,245,292 B1 | 7/2007 | Custy | |
| 7,258,026 B2 | 8/2007 | Papakostas et al. | |
| 7,261,690 B2 | 8/2007 | Teller et al. | |
| 7,264,554 B2 | 9/2007 | Bentley | |
| 7,285,090 B2 | 10/2007 | Stivoric et al. | |
| 7,292,151 B2 | 11/2007 | Ferguson et al. | |
| 7,292,223 B2 | 11/2007 | Suprun et al. | |
| 7,295,184 B2 | 11/2007 | Suprun et al. | |
| 7,296,469 B2 | 11/2007 | Simonenko et al. | |
| 7,313,440 B2 | 12/2007 | Miesel | |
| 7,324,714 B1 | 1/2008 | Cranch et al. | |
| 7,330,760 B2 | 2/2008 | Heruth et al. | |
| 7,365,031 B2 | 4/2008 | Swallow et al. | |
| 7,383,728 B2 | 6/2008 | Noble et al. | |

(56) References Cited

U.S. PATENT DOCUMENTS

| | | |
|---|---|---|
| 7,390,157 B2 | 6/2008 | Kramer |
| 7,394,385 B2 | 7/2008 | Franco et al. |
| 7,395,113 B2 | 7/2008 | Heruth et al. |
| 7,395,181 B2 | 7/2008 | Foxlin |
| 7,410,338 B2 | 8/2008 | Schiele et al. |
| 7,413,802 B2 | 8/2008 | Karayianni et al. |
| 7,421,369 B2 | 9/2008 | Clarkson |
| 7,447,545 B2 | 11/2008 | Heruth et al. |
| 7,450,002 B2 | 11/2008 | Choi et al. |
| 7,451,056 B2 | 11/2008 | Flentov et al. |
| 7,468,332 B2 | 12/2008 | Avloni |
| 7,471,290 B2 | 12/2008 | Wang et al. |
| 7,479,890 B2 | 1/2009 | Lehrman et al. |
| 7,487,043 B2 | 2/2009 | Adams |
| 7,492,268 B2 | 2/2009 | Ferguson et al. |
| 7,500,853 B2 | 3/2009 | Bevirt et al. |
| 7,509,870 B2 | 3/2009 | Aebersold et al. |
| 7,512,515 B2 | 3/2009 | Vock et al. |
| 7,559,768 B2 | 7/2009 | Marmaropoulos et al. |
| 7,565,295 B1 | 7/2009 | Hernandez-Rebollar |
| 7,592,276 B2 | 9/2009 | Hill et al. |
| 7,602,301 B1 | 10/2009 | Stirling et al. |
| 7,602,310 B2 | 10/2009 | Mann et al. |
| 7,627,451 B2 | 12/2009 | Vock et al. |
| 7,628,074 B2 | 12/2009 | Vannucci et al. |
| 7,630,591 B2 | 12/2009 | Allen et al. |
| 7,634,379 B2 | 12/2009 | Noble |
| 7,647,196 B2 | 1/2010 | Kahn et al. |
| 7,653,214 B2 | 1/2010 | Schroeder et al. |
| 7,653,508 B1 | 1/2010 | Kahn et al. |
| 7,661,200 B2 | 2/2010 | Bonnet et al. |
| 7,665,288 B2 | 2/2010 | Karayianni et al. |
| 7,668,588 B2 | 2/2010 | Kovacs |
| 7,672,781 B2 | 3/2010 | Churchill et al. |
| 7,689,378 B2 | 3/2010 | Kolen |
| 7,698,101 B2 | 4/2010 | Alten et al. |
| 7,698,830 B2 | 4/2010 | Townsend et al. |
| 7,703,333 B2 | 4/2010 | Hayakawa et al. |
| 7,725,279 B2 | 5/2010 | Luinge et al. |
| 7,742,894 B2 | 6/2010 | Chen et al. |
| 7,753,861 B1 | 7/2010 | Kahn et al. |
| 7,770,473 B2 | 8/2010 | Von Lilienfeld-Toal et al. |
| 7,771,318 B2 | 8/2010 | Narayanaswami |
| 7,772,541 B2 | 8/2010 | Froggatt et al. |
| 7,781,051 B2 | 8/2010 | Burr et al. |
| 7,781,724 B2 | 8/2010 | Childers et al. |
| 7,792,583 B2 | 9/2010 | Miesel et al. |
| 7,805,196 B2 | 9/2010 | Miesel et al. |
| 7,811,333 B2 | 10/2010 | Jonsson et al. |
| 7,815,376 B2 | 10/2010 | Rogers et al. |
| 7,821,407 B2 | 10/2010 | Shears et al. |
| 7,825,815 B2 | 11/2010 | Shears et al. |
| 7,827,000 B2 | 11/2010 | Stirling et al. |
| 7,845,228 B2 | 12/2010 | Bremer et al. |
| 7,849,888 B2 | 12/2010 | Karayianni et al. |
| 7,850,574 B2 | 12/2010 | Narayanaswami |
| 7,854,174 B2 | 12/2010 | Aebersold et al. |
| 7,881,902 B1 | 2/2011 | Kahn et al. |
| 7,899,556 B2 | 3/2011 | Nathan et al. |
| 7,901,756 B2 | 3/2011 | Burr et al. |
| 7,902,095 B2 | 3/2011 | Hassonjee et al. |
| 7,911,620 B2 | 3/2011 | Digonnet et al. |
| 7,926,254 B2 | 4/2011 | Karayianni et al. |
| 7,930,065 B2 | 4/2011 | Larkin et al. |
| 7,952,483 B2 | 5/2011 | Ferguson et al. |
| 7,978,081 B2 | 7/2011 | Shears et al. |
| 7,980,141 B2 * | 7/2011 | Connor ............... A61B 5/1126 73/849 |
| 7,981,057 B2 | 7/2011 | Stewart |
| 7,981,058 B2 | 7/2011 | Akay |
| 7,998,092 B2 | 8/2011 | Avni et al. |
| 7,999,946 B2 | 8/2011 | Andersen et al. |
| 8,010,308 B1 | 8/2011 | Churchill |
| 8,011,229 B2 | 9/2011 | Lieberman et al. |
| 8,025,632 B2 | 9/2011 | Einarsson |
| 8,033,916 B2 | 10/2011 | Caldwell et al. |
| 8,036,850 B2 | 10/2011 | Kulach et al. |
| 8,036,851 B2 | 10/2011 | Vock et al. |
| 8,055,021 B2 | 11/2011 | Caritu et al. |
| 8,060,337 B2 | 11/2011 | Kulach et al. |
| 8,068,231 B2 | 11/2011 | Digonnet |
| 8,073,707 B2 | 12/2011 | Teller et al. |
| 8,075,499 B2 | 12/2011 | Nathan et al. |
| 8,083,693 B1 | 12/2011 | McKeon et al. |
| 8,099,258 B2 | 1/2012 | Alten et al. |
| 8,109,149 B2 | 2/2012 | Kotovsky |
| 8,111,165 B2 | 2/2012 | Ortega et al. |
| 8,116,601 B2 | 2/2012 | Prisco |
| 8,125,448 B2 | 2/2012 | Ranta et al. |
| 8,135,473 B2 | 3/2012 | Miesel et al. |
| 8,140,339 B2 | 3/2012 | Hernandez-Rebollar |
| 8,146,171 B2 | 4/2012 | Chung et al. |
| 8,150,531 B2 | 4/2012 | Skelton |
| 8,151,648 B2 | 4/2012 | Yu et al. |
| 8,152,694 B2 | 4/2012 | Srinivasan et al. |
| 8,157,730 B2 | 4/2012 | Leboeuf et al. |
| 8,157,731 B2 | 4/2012 | Teller et al. |
| 8,157,752 B2 | 4/2012 | Fischer |
| 8,159,354 B2 | 4/2012 | Ferguson et al. |
| 8,161,826 B1 | 4/2012 | Taylor |
| 8,162,857 B2 | 4/2012 | Lanfermann et al. |
| 8,165,840 B2 | 4/2012 | Hatlestad et al. |
| 8,165,844 B2 | 4/2012 | Luinge et al. |
| 8,171,570 B2 | 5/2012 | Adarraga |
| 8,175,720 B2 | 5/2012 | Skelton et al. |
| 8,180,591 B2 | 5/2012 | Yuen et al. |
| 8,180,592 B2 | 5/2012 | Yuen et al. |
| 8,182,158 B2 | 5/2012 | Rogers et al. |
| 8,187,182 B2 | 5/2012 | Kahn et al. |
| 8,200,340 B2 | 6/2012 | Skelton et al. |
| 8,203,455 B2 | 6/2012 | Lee et al. |
| 8,203,487 B2 | 6/2012 | Hol et al. |
| 8,206,325 B1 | 6/2012 | Najafi et al. |
| 8,209,028 B2 | 6/2012 | Skelton et al. |
| 8,209,147 B2 | 6/2012 | Solinsky |
| 8,219,206 B2 | 7/2012 | Skelton et al. |
| 8,231,555 B2 | 7/2012 | Skelton et al. |
| 8,233,151 B2 | 7/2012 | Digonnet |
| 8,240,207 B2 | 8/2012 | Andersen et al. |
| 8,249,718 B2 | 8/2012 | Skelton et al. |
| 8,263,215 B2 | 9/2012 | Burr et al. |
| 8,275,635 B2 | 9/2012 | Stivoric et al. |
| 8,280,517 B2 | 10/2012 | Skelton et al. |
| 8,280,681 B2 | 10/2012 | Vock et al. |
| 8,282,580 B2 | 10/2012 | Skelton et al. |
| 8,284,847 B2 | 10/2012 | Adermann |
| 8,298,968 B2 | 10/2012 | Swallow et al. |
| 8,301,575 B2 | 10/2012 | Bonnet et al. |
| 8,308,489 B2 | 11/2012 | Lee et al. |
| 8,311,769 B2 | 11/2012 | Yuen et al. |
| 8,311,770 B2 | 11/2012 | Yuen et al. |
| 8,315,710 B2 | 11/2012 | Skelton et al. |
| 8,316,719 B2 | 11/2012 | Majidi et al. |
| 8,323,218 B2 | 12/2012 | Davis et al. |
| 8,328,718 B2 | 12/2012 | Tran |
| 8,331,097 B2 | 12/2012 | Yang et al. |
| 8,332,041 B2 | 12/2012 | Skelton et al. |
| 8,334,226 B2 | 12/2012 | Nhan et al. |
| 8,342,045 B2 | 1/2013 | Maxwell et al. |
| 8,348,865 B2 | 1/2013 | Jeong et al. |
| 8,352,211 B2 | 1/2013 | Vock et al. |
| 8,358,883 B2 | 1/2013 | Prisco |
| 8,362,882 B2 | 1/2013 | Heubel et al. |
| 8,366,641 B2 | 2/2013 | Wang et al. |
| 8,373,079 B2 | 2/2013 | Walkington |
| 8,382,590 B2 | 2/2013 | Stivoric et al. |
| 8,384,551 B2 | 2/2013 | Ross et al. |
| 8,386,008 B2 | 2/2013 | Yuen et al. |
| 8,388,555 B2 | 3/2013 | Panken et al. |
| 8,393,229 B2 | 3/2013 | Tao et al. |
| 8,393,282 B2 | 3/2013 | Fujita et al. |
| 8,395,109 B2 | 3/2013 | Muravsky |
| 8,396,554 B2 | 3/2013 | Miesel et al. |
| 8,396,565 B2 | 3/2013 | Singhal et al. |

(56) References Cited

U.S. PATENT DOCUMENTS

| | | |
|---|---|---|
| 8,397,568 B2 | 3/2013 | Cardarelli |
| 8,401,666 B2 | 3/2013 | Skelton et al. |
| 8,414,507 B2 | 4/2013 | Asada |
| 8,416,088 B2 | 4/2013 | Ortega et al. |
| 8,416,102 B2 | 4/2013 | Yin |
| 8,421,448 B1 | 4/2013 | Tran et al. |
| 8,421,854 B2 | 4/2013 | Zerkin |
| 8,427,325 B2 | 4/2013 | Ferguson et al. |
| 8,427,651 B2 | 4/2013 | Digonnet |
| 8,435,177 B2 | 5/2013 | Lanfermann et al. |
| 8,436,737 B1 | 5/2013 | Trout |
| 8,437,824 B2 | 5/2013 | Moon et al. |
| 8,437,861 B2 | 5/2013 | Skelton et al. |
| 8,437,980 B2 | 5/2013 | Yuen et al. |
| 8,446,275 B2 | 5/2013 | Utter |
| 8,447,401 B2 | 5/2013 | Miesel et al. |
| 8,447,411 B2 | 5/2013 | Skelton et al. |
| 8,459,128 B2 | 6/2013 | Bhat et al. |
| 8,460,197 B1 | 6/2013 | Brady et al. |
| 8,463,573 B2 | 6/2013 | Flentov et al. |
| 8,463,576 B2 | 6/2013 | Yuen et al. |
| 8,463,577 B2 | 6/2013 | Yuen et al. |
| 8,504,150 B2 | 8/2013 | Skelton |
| 8,515,549 B2 | 8/2013 | Panken et al. |
| 8,515,550 B2 | 8/2013 | Skelton et al. |
| 8,520,472 B2 | 8/2013 | Murray et al. |
| 8,527,217 B2 | 9/2013 | Moodie |
| 8,536,075 B2 | 9/2013 | Leonard |
| 8,543,185 B2 | 9/2013 | Yuen et al. |
| 8,543,351 B2 | 9/2013 | Yuen et al. |
| 8,548,740 B2 | 10/2013 | Hesch et al. |
| 8,548,770 B2 | 10/2013 | Yuen et al. |
| 8,554,297 B2 | 10/2013 | Moon et al. |
| 8,579,834 B2 | 11/2013 | Davis et al. |
| 8,583,252 B2 | 11/2013 | Skelton et al. |
| 8,583,402 B2 | 11/2013 | Yuen et al. |
| 8,616,782 B2 | 12/2013 | Rogers et al. |
| 8,616,989 B2 | 12/2013 | Bentley |
| 8,626,472 B2 | 1/2014 | Solinsky |
| 8,643,494 B1 | 2/2014 | Trout |
| 8,651,964 B2 | 2/2014 | Brick |
| 8,655,117 B2 | 2/2014 | Donlagic et al. |
| 8,655,618 B2 | 2/2014 | Flaction et al. |
| 8,657,772 B2 | 2/2014 | Einarsson |
| 8,661,915 B2 | 3/2014 | Taylor |
| 8,665,241 B2 | 3/2014 | Heubel et al. |
| 8,669,195 B2 | 3/2014 | Swallow et al. |
| 8,670,953 B2 | 3/2014 | Yuen et al. |
| 8,678,979 B2 | 3/2014 | Stark et al. |
| 8,704,758 B1 | 4/2014 | Figley et al. |
| 8,708,825 B2 | 4/2014 | Crisco |
| 8,708,904 B2 | 4/2014 | Stivoric et al. |
| 8,712,723 B1 | 4/2014 | Kahn et al. |
| 8,760,392 B2 | 6/2014 | Lloyd et al. |
| 8,764,651 B2 | 7/2014 | Tran |
| 8,777,878 B2 | 7/2014 | Deitz |
| 8,780,339 B2 | 7/2014 | Udd |
| 8,784,303 B2 | 7/2014 | Laby et al. |
| 8,784,342 B2 | 7/2014 | Hyde et al. |
| 8,788,055 B2 | 7/2014 | Gerber et al. |
| 8,795,137 B2 | 8/2014 | Ellis et al. |
| 8,818,748 B2 | 8/2014 | Hatlestad et al. |
| 8,821,417 B2 | 9/2014 | McGregor et al. |
| 8,823,490 B2 | 9/2014 | Libbus et al. |
| 8,823,639 B2 | 9/2014 | Jackson et al. |
| 8,849,610 B2 | 9/2014 | Molettiere et al. |
| 8,876,738 B1 | 11/2014 | Kahn et al. |
| 8,904,876 B2 | 12/2014 | Taylor et al. |
| 8,905,948 B2 | 12/2014 | Davis et al. |
| 8,909,543 B2 | 12/2014 | Tropper et al. |
| 8,928,484 B2 | 1/2015 | Chang et al. |
| 8,929,085 B2 | 1/2015 | Franklin et al. |
| 8,929,966 B2 | 1/2015 | LeBoeuf et al. |
| 8,932,236 B1 | 1/2015 | McKeon et al. |
| 8,944,939 B2 | 2/2015 | Clark et al. |
| 8,947,441 B2 | 2/2015 | Hodgins et al. |
| 8,948,839 B1 | 2/2015 | Longinotti-Buitoni et al. |
| 8,949,070 B1 | 2/2015 | Kahn et al. |
| 8,958,885 B2 | 2/2015 | Panken et al. |
| 9,001,082 B1 | 4/2015 | Rosenberg et al. |
| 9,009,955 B2 | 4/2015 | Slade et al. |
| 9,043,004 B2 | 5/2015 | Casillas et al. |
| 2001/0003712 A1 | 6/2001 | Roelofs |
| 2001/0020140 A1 | 9/2001 | Kramer |
| 2001/0049470 A1 | 12/2001 | Mault et al. |
| 2002/0024656 A1 | 2/2002 | Kwon et al. |
| 2002/0088931 A1 | 7/2002 | Danisch et al. |
| 2002/0151824 A1 | 10/2002 | Fischer |
| 2002/0198472 A1 | 12/2002 | Kramer |
| 2003/0023192 A1 | 1/2003 | Foxlin |
| 2003/0036858 A1 | 2/2003 | Friedrichs et al. |
| 2003/0045816 A1 | 3/2003 | Foxlin |
| 2003/0047002 A1 | 3/2003 | Arms et al. |
| 2003/0054923 A1 | 3/2003 | Brassil et al. |
| 2003/0083596 A1 | 5/2003 | Kramer et al. |
| 2003/0091966 A1 | 5/2003 | Collodi |
| 2003/0120448 A1 | 6/2003 | Moriya et al. |
| 2003/0211797 A1 | 11/2003 | Hill et al. |
| 2004/0009729 A1 | 1/2004 | Hill et al. |
| 2005/0069695 A1 | 3/2005 | Jung et al. |
| 2005/0126026 A1 | 6/2005 | Townsend et al. |
| 2005/0140651 A1 | 6/2005 | Suprun et al. |
| 2006/0022833 A1 | 2/2006 | Ferguson et al. |
| 2006/0059976 A1 | 3/2006 | Simonenko et al. |
| 2006/0059988 A1 | 3/2006 | Pristup |
| 2006/0059990 A1 | 3/2006 | Simonenko et al. |
| 2006/0059991 A1 | 3/2006 | Pristup et al. |
| 2006/0070443 A1 | 4/2006 | Pristup |
| 2006/0130347 A1 | 6/2006 | Bergamasco et al. |
| 2006/0135883 A1 | 6/2006 | Jonsson et al. |
| 2006/0157334 A1 | 7/2006 | Marmaropoulos et al. |
| 2006/0166737 A1 | 7/2006 | Bentley |
| 2006/0167564 A1 | 7/2006 | Flaherty et al. |
| 2006/0184336 A1 | 8/2006 | Kolen |
| 2006/0189899 A1 | 8/2006 | Flaherty et al. |
| 2006/0212097 A1 | 9/2006 | Varadan et al. |
| 2006/0217233 A1 | 9/2006 | Lee |
| 2006/0240953 A1 | 10/2006 | Shahinpoor |
| 2006/0241521 A1 | 10/2006 | Cohen |
| 2006/0281382 A1 | 12/2006 | Karayianni et al. |
| 2006/0282017 A1 | 12/2006 | Avni et al. |
| 2006/0284979 A1 | 12/2006 | Clarkson |
| 2007/0000324 A9 | 1/2007 | Pristup et al. |
| 2007/0038038 A1 | 2/2007 | Stivoric et al. |
| 2007/0049147 A1 | 3/2007 | Hill et al. |
| 2007/0073482 A1 | 3/2007 | Churchill et al. |
| 2007/0100666 A1 | 5/2007 | Stivoric et al. |
| 2007/0123997 A1 | 5/2007 | Herr et al. |
| 2007/0132722 A1 | 6/2007 | Kim et al. |
| 2007/0169364 A1 | 7/2007 | Townsend et al. |
| 2007/0173705 A1 | 7/2007 | Teller et al. |
| 2007/0178716 A1 | 8/2007 | Glaser et al. |
| 2007/0202765 A1 | 8/2007 | Krans et al. |
| 2007/0214889 A1 | 9/2007 | Pristup |
| 2007/0219744 A1 | 9/2007 | Kolen |
| 2007/0248799 A1 | 10/2007 | DeAngelis et al. |
| 2007/0256502 A1 | 11/2007 | Aebersold et al. |
| 2007/0270214 A1 | 11/2007 | Bentley |
| 2008/0036737 A1 | 2/2008 | Hernandez-Rebollar |
| 2008/0050550 A1 | 2/2008 | Orth |
| 2008/0061949 A1 | 3/2008 | Ferguson et al. |
| 2008/0084385 A1 | 4/2008 | Ranta et al. |
| 2008/0105527 A1 | 5/2008 | Leftly |
| 2008/0167535 A1 | 7/2008 | Andre et al. |
| 2008/0223131 A1 | 9/2008 | Vannucci et al. |
| 2008/0285805 A1 | 11/2008 | Luinge et al. |
| 2009/0025483 A1 | 1/2009 | Connor et al. |
| 2009/0025819 A1 | 1/2009 | Douglas |
| 2009/0030345 A1 | 1/2009 | Bonnet et al. |
| 2009/0076419 A1 | 3/2009 | Namineni et al. |
| 2009/0149257 A1 | 6/2009 | Ferguson et al. |
| 2009/0159149 A1 | 6/2009 | Karayianni et al. |
| 2009/0171180 A1 | 7/2009 | Pering et al. |
| 2009/0188325 A1 | 7/2009 | Aebersold et al. |

(56) References Cited

U.S. PATENT DOCUMENTS

| | | |
|---|---|---|
| 2009/0204031 A1 | 8/2009 | McNames et al. |
| 2009/0253325 A1 | 10/2009 | Brookstein et al. |
| 2009/0278791 A1 | 11/2009 | Slycke et al. |
| 2009/0321238 A1 | 12/2009 | Nhan et al. |
| 2010/0026809 A1 | 2/2010 | Curry |
| 2010/0036288 A1 | 2/2010 | Lanfermann et al. |
| 2010/0076348 A1 | 3/2010 | McNames et al. |
| 2010/0176952 A1 | 7/2010 | Bajcsy et al. |
| 2010/0183297 A1 | 7/2010 | Barboutis et al. |
| 2010/0198113 A1 | 8/2010 | Coulston |
| 2010/0211349 A1 | 8/2010 | Flaction et al. |
| 2010/0219943 A1 | 9/2010 | Ilmari et al. |
| 2010/0225473 A1 | 9/2010 | Leuthardt et al. |
| 2010/0225474 A1 | 9/2010 | Leuthardt et al. |
| 2010/0225490 A1 | 9/2010 | Leuthardt et al. |
| 2010/0225491 A1 | 9/2010 | Leuthardt et al. |
| 2010/0225498 A1 | 9/2010 | Leuthardt et al. |
| 2010/0228153 A1 | 9/2010 | Leuthardt et al. |
| 2010/0228154 A1 | 9/2010 | Leuthardt et al. |
| 2010/0228158 A1 | 9/2010 | Leuthardt et al. |
| 2010/0228159 A1 | 9/2010 | Leuthardt et al. |
| 2010/0228487 A1 | 9/2010 | Leuthardt et al. |
| 2010/0228488 A1 | 9/2010 | Leuthardt et al. |
| 2010/0228489 A1 | 9/2010 | Leuthardt et al. |
| 2010/0228490 A1 | 9/2010 | Leuthardt et al. |
| 2010/0228492 A1 | 9/2010 | Leuthardt et al. |
| 2010/0228493 A1 | 9/2010 | Leuthardt et al. |
| 2010/0228494 A1 | 9/2010 | Leuthardt et al. |
| 2010/0228495 A1 | 9/2010 | Leuthardt et al. |
| 2010/0271200 A1 | 10/2010 | Leuthardt et al. |
| 2010/0309209 A1 | 12/2010 | Hodgins et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0324456 A1 | 12/2010 | Jonsson et al. |
| 2011/0025562 A1 | 2/2011 | Hol et al. |
| 2011/0028865 A1 | 2/2011 | Luinge et al. |
| 2011/0040216 A1 | 2/2011 | Herr et al. |
| 2011/0046518 A1 | 2/2011 | Fischer |
| 2011/0046915 A1 | 2/2011 | Hol et al. |
| 2011/0052005 A1 | 3/2011 | Selner |
| 2011/0181422 A1 | 7/2011 | Tran |
| 2011/0201428 A1 | 8/2011 | Ferguson et al. |
| 2011/0208444 A1 | 8/2011 | Solinsky |
| 2011/0248773 A1 | 10/2011 | Poupyrev et al. |
| 2011/0313705 A1 | 12/2011 | Esser et al. |
| 2012/0030935 A1 | 2/2012 | Slade et al. |
| 2012/0046901 A1 | 2/2012 | Green et al. |
| 2012/0089348 A1 | 4/2012 | Perlin et al. |
| 2012/0092156 A1 | 4/2012 | Tran |
| 2012/0108917 A1 | 5/2012 | Libbus et al. |
| 2012/0116257 A1 | 5/2012 | Leuthardt et al. |
| 2012/0118066 A1 | 5/2012 | Majidi et al. |
| 2012/0118427 A1 | 5/2012 | Brookstein et al. |
| 2012/0157263 A1* | 6/2012 | Sivak ............ G06F 3/014 482/4 |
| 2012/0172126 A1 | 7/2012 | Padovani et al. |
| 2012/0178534 A1 | 7/2012 | Ferguson et al. |
| 2012/0223880 A1 | 9/2012 | Birnbaum et al. |
| 2012/0234105 A1 | 9/2012 | Taylor |
| 2012/0274554 A1 | 11/2012 | Kinoshita et al. |
| 2012/0313854 A1 | 12/2012 | Senanayake et al. |
| 2012/0316455 A1 | 12/2012 | Rahman et al. |
| 2012/0319940 A1 | 12/2012 | Bress et al. |
| 2012/0323501 A1 | 12/2012 | Sarrafzadeh et al. |
| 2013/0015976 A1 | 1/2013 | Chang et al. |
| 2013/0068017 A1 | 3/2013 | Perkins et al. |
| 2013/0072765 A1 | 3/2013 | Kahn et al. |
| 2013/0073248 A1 | 3/2013 | Perkins et al. |
| 2013/0110011 A1 | 5/2013 | McGregor et al. |
| 2013/0113506 A1 | 5/2013 | Poupyrev et al. |
| 2013/0123665 A1 | 5/2013 | Mariani et al. |
| 2013/0158444 A1 | 6/2013 | Herr et al. |
| 2013/0158686 A1 | 6/2013 | Zhang et al. |
| 2013/0173171 A1 | 7/2013 | Drysdale et al. |
| 2013/0176737 A1 | 7/2013 | Zhou et al. |
| 2013/0204411 A1 | 8/2013 | Clark et al. |
| 2013/0204435 A1 | 8/2013 | Moon et al. |
| 2013/0207889 A1 | 8/2013 | Chang et al. |
| 2013/0211259 A1* | 8/2013 | Komistek ............ A61B 8/5223 600/440 |
| 2013/0211291 A1 | 8/2013 | Tran |
| 2013/0215230 A1 | 8/2013 | Miesnieks et al. |
| 2013/0222565 A1 | 8/2013 | Guerin et al. |
| 2013/0229338 A1 | 9/2013 | Sohn et al. |
| 2013/0253875 A1 | 9/2013 | Flentov et al. |
| 2013/0275057 A1 | 10/2013 | Perlin et al. |
| 2013/0289932 A1 | 10/2013 | Baechler |
| 2013/0303286 A1 | 11/2013 | Ferguson et al. |
| 2013/0324888 A1 | 12/2013 | Solinsky |
| 2013/0328783 A1 | 12/2013 | Martin et al. |
| 2014/0031698 A1 | 1/2014 | Moon et al. |
| 2014/0070957 A1 | 3/2014 | Longinotti-Buitoni et al. |
| 2014/0088764 A1 | 3/2014 | Naidu et al. |
| 2014/0142733 A1 | 5/2014 | Tropper et al. |
| 2014/0143031 A1 | 5/2014 | Tropper et al. |
| 2014/0143038 A1 | 5/2014 | Tropper et al. |
| 2014/0159894 A1 | 6/2014 | Tropper et al. |
| 2014/0170919 A1 | 6/2014 | Manipatruni et al. |
| 2014/0171834 A1 | 6/2014 | Degoede et al. |
| 2014/0172134 A1 | 6/2014 | Meschter |
| 2014/0188499 A1 | 7/2014 | Bell et al. |
| 2014/0194781 A1 | 7/2014 | Einarsson |
| 2014/0197946 A1 | 7/2014 | Park |
| 2014/0197963 A1 | 7/2014 | Park et al. |
| 2014/0197965 A1 | 7/2014 | Park et al. |
| 2014/0206327 A1 | 7/2014 | Ziemianska et al. |
| 2014/0213856 A1 | 7/2014 | Teller et al. |
| 2014/0213857 A1 | 7/2014 | Teller et al. |
| 2014/0221769 A1 | 8/2014 | Teller et al. |
| 2014/0223407 A1 | 8/2014 | Teller et al. |
| 2014/0240103 A1 | 8/2014 | Lake et al. |
| 2014/0240122 A1 | 8/2014 | Roberts et al. |
| 2014/0249381 A1 | 9/2014 | LeBoeuf et al. |
| 2014/0275812 A1 | 9/2014 | Stivoric et al. |
| 2014/0275813 A1 | 9/2014 | Stivoric et al. |
| 2014/0288875 A1 | 9/2014 | Donaldson |
| 2014/0288877 A1 | 9/2014 | Donaldson |
| 2014/0288878 A1 | 9/2014 | Donaldson |
| 2014/0318699 A1 | 10/2014 | Longinotti-Buitoni et al. |
| 2014/0342844 A1 | 11/2014 | Mooney |
| 2014/0366675 A1 | 12/2014 | Gosselin et al. |
| 2015/0005608 A1 | 1/2015 | Evans et al. |
| 2015/0015417 A1 | 1/2015 | Libbus et al. |
| 2015/0019135 A1 | 1/2015 | Kacyvenski et al. |
| 2015/0040282 A1 | 2/2015 | Longinotti-Buitoni et al. |
| 2015/0045699 A1 | 2/2015 | Mokaya et al. |
| 2015/0091820 A1 | 4/2015 | Rosenberg et al. |
| 2015/0091857 A1 | 4/2015 | Rosenberg et al. |
| 2015/0091859 A1 | 4/2015 | Rosenberg et al. |
| 2015/0116920 A1 | 4/2015 | Franklin et al. |
| 2015/0143601 A1 | 5/2015 | Longinotti-Buitoni et al. |

OTHER PUBLICATIONS

Advanced Motion Measurement, 2014 ~ Advanced Motion Measurement, 2014, Phoenix, Arizona. http://www.amm3d.com/.

Animazoo, 2004 ~ Animazoo 3D Motion Capture Equipment: Gypsy Products from Animazoo, [online]. © 2004 Animazoo [retrieved Jul. 16, 2007]. Retrieved from the Internet: <URL: http://www.animazoo.com/oroducts/index.htm>, 1 PQ.

Ascension, 2007 ~ Ascension Products. Flock of Birds®, [online]. [retrieved Jul. 16, 2007]. Retrieved from the Internet: <URL: http://www.ascension-tech.com/products/flockofbirds.php>, 2 pgs.

Biometrics, 2007 Biometrics Ltd Research. Goniometers and Torsiometers, [online]. [retrieved Jul. 16, 2007]. Retrieved: htto://www.biometricsltd.com/v%20oonio.htm>, 2 pgs.

Biopac, 2007 ~ Biopac—TSD130AI Twin Axis Goniometer, 110mm, [online]. [retrieved Jul. 16, 2007]. Retrieved from the Internet:

(56) References Cited

OTHER PUBLICATIONS

<URL: http://www.biopac.com/ Research.asp?Pid=3695&Main=Transducers>, 1 pg.

Charndyn, 2007 ~ Codamotion Products—Hardware and Software, [online]. [retrieved Jul. 16, 2007]. Retrieved from the Internet: <URL: http://www.charndyn.com/Products/ Products Intro.html>, 1 pg.

Deyo, R. A., et al., 2006, "Back Pain Prevalence and Visit Rates: Estimates From U.S. National Surveys, 2002", Spine, Nov. 2006, 31923), 2724-2727. [Mar. 28, 2008]. <URL: http://ovidsp.tx.ovid.com.floyd.lib.umn.edu/spa/>, 5 pgs.

Gibbs, P. T., and Asada, "Wearable Conductive Fiber Sensors for Multi-Axis Human Joint Angle Measurements", Journal of NeuroEngineering and Rehabilitation, Mar. 2, 2005, 2(7), 7-25. [Jul. 16, 2007]. <URL: http://www.pubmedcentral.nih.gov/ articlerender.fcgi?artid=555561>, 15 pgs.

Greenleaf, 2007 ~ Greenleaf Products, [online]. [retrieved Jul. 16, 2007]. Retrieved from the Internet: <URL: http://www.oreanleafmed.com/products.htm>, 1 pg.

Huddleston et al., "Ambulatory Measurement of Knee Motion and Physical Activity: Preliminary Evaluation of a Smart Activity Monitor", Journal of NeuroEngineering and Rehab, 2006; 1(3), 21. [Mar. 28, 2008]. <URL: http://www.jneuroengrehab.com/content/3/1/21>, 6 pgs.

Immersion, 2007 ~ Immersion Corporation. 3D Interaction, [online]. © 2007 Immersion Corporation. [retrieved Jul. 16, 2007]. Retrieved from the Internet: <URL: http://www.immersion.com/3d/>, 1 oo.

Lim et al., 2010 ~ Lim et al., 2010, "A Low Cost Wearable Wireless Sensing System for Upper Limb Home Rehabilitation," Robotics Automation and Mechatronics (RAM), 2010 IEEE Conf, Jun. 28-30, 2010, 1-8, ISBN:978-1-4244-6503-3.

Measurand, 2007 ~ Measurand. Motion Capture for the Classroom, [online]. [retrieved Jul. 16, 2007]. Retrieved from the Internet: <URL: http://www.measurand.com>, 1 pg.

Metamotion, 2007 ~ Meta Motion. Motion Capture Hardware. Face Trackers, 2006 Meta Motion. [ret. Jul. 16, 2007]. <URL: http://www.metamotion.com/hardware/motion-capture-hardware.htm>, 1 pg.—http://www.metamotion.com/motion-capture/magnetic-motion- capture-1.htm.

Microstrain, 2007 ~ MicroStrain® Inclinometers: Orientation Sensors, [online]. [retrieved Jul. 16, 2007]. Retrieved from the Internet: <URL: http://www.microstrain.com/ inclinometers.as_px 1 _pg.

Mikomak, 2007 ~ Mikromak Service Brinkmann Human Motion, [online]. © Mikromak Service Brinkmann [retrieved Jul. 16, 2007]. Retrieved from the Internet: http://www.mikromak.com/en/en mensch! beweg htm>, 1 pg.

Minisun, 2007 ~ MiniSun. IDEEA Information, [online]. © MiniSun 2000-2007. [retrieved Jul. 16, 2007]. Retrieved from Internet: <URL: http://www.minisun.com/ ideea.asp>, 1 pg.

Motek, 2007 ~ Motek Medical, [online]. [archived Jul. 8, 2007]. Retrieved from the Internet: <URL: http://web.archive.org/web/20070708132130/http:l/www.e-motek.com/medical/index.htm> 2 pgs.

Motion Analysis, 2007 ~ MotionAnalysis—Movement Analysis Products, [online]. © 2007 Motion Analysis Corporation [retrieved Jul. 16, 2007]. Retrieved from the Internet: <URL: http://www.motionanalysis.com/applications/movementl movementproducts.html >, 1 pg.

Motion Lab, 2007 ~ Motion Lab Systems, Inc., [online]. © 1995-2007 Motion Lab Systems, Inc. [retrieved Jul. 16, 2007]. Retrieved via the Internet: <URL: http://www.emgsrus.com>, 2 pgs.

Motionwerx, 2010 ~ http://www.motionwerx.com, Motionwerx. Motionwerx produces the Gypsy 7.

NoDNA, 2007 ~ noDNA. Sensoric Systems, [online]. [retrieved Jul. 16, 2007]. Retrieved from the Internet: <URL: http://www.nodna.com/index.Q_hp?id=7&L=1>, 1 pg.

Noraxon, 2007 ~ Noraxon. Manufacturers of Professional Surface Electromyography Products, [online]. [retrieved Jul. 16, 2007]. Retrieved from Internet: <URL: http://www.noraxon.com/index.php3>, 1 pg.

Northern Digital, 2007 ~ NDI: The Aurora Electromagnetic Measurement System, [online]. © 2007 Northern Digital Inc. [retrieved Jul. 16, 2007]. Retrieved from the Internet: <URL: http://www.ndigital.com/medical/aurora.php>, 1 pg.

Phase Space, 2007 ~ PhaseSpace Inc. / Optical Motion Capture, [online]. [retrieved Jul. 16, 2007]. Retrieved from the Internet: <URL: http://www.phasespace.com/ hardware.html>, 2 pgs.

Phoenix Technologies, 2007 ~ High Performance Real-Time 3D Motion Capture Systems for Professionals, [online]. © 1997-2007 Phoenix Technologies Inc. [retrieved Jul. 16, 2007]. Retrieved from the Internet: <URL: http://www.ptiphoenix.com/Products.php>, 1 pg.

Polhemus, 2007 ~ Liberty™ Latus™ Wireless Motion Tracking System from Polhemus, [online]. [retrieved Jul. 16, 2007]. Retrieved from the Internet: <URL:. http://www.polhemus.com/?page=Motion Liberty Latus>, 2 pgs.

Qualisys, 2008 ~ Qualisys Motion Capture, [online]. [retrieved Mar. 31, 2008]. Retrieved from the Internet: <URL: http://www.qualisys.com/tem_Qiates/Q01.asQ_?sida=34>, 1 pg.

Vicon, 2007 ~ Vicon I Products—Cameras, [online]. [retrieved Jul. 16, 2007]. Retrieved via the Internet: <URL: http://www.vicon.com/products/cameras.html>, 1 pg.

Vista Medical, 2007 ~ Vista Medical—Store, [online]. [retrieved Jul. 16, 2007]. Retrieved from the Internet: <URL: http://www.pressuremapping.com/ index.cfm?pageiD=13&section=9>, 1 pg.

Vivometrics, 2007 ~VivoMetrics® Sports & Fitness Product Line, [online]. © 2007 VivoMetrics. [retrieved Jul. 16, 2007]. Retrieved from the Internet: <URL: http://www.vivometrics.com/s_Q_ort/view our products/product line.php>, 2 pgs.

Xsens, 2007 ~ Xsens Motion Technologies—Maven-Inertial Motion Capturing, [online}. © 2007 Xsens Motion Technologies. [archived Jul. 17, 2007]. Retrieved from Internet: <URL: http:l/web.archive.org/web/20070717123324/www.xsens.com/index.php?mainmenu=products&submenu=human_motion&sub submenu=Moven>, 2 pgs.

\* cited by examiner

SENSOR ARRAY SPANNING MULTIPLE RADIAL QUADRANTS TO MEASURE BODY JOINT MOVEMENT

CROSS-REFERENCE TO RELATED APPLICATIONS

This patent application: (a) is a continuation in part of U.S. patent application Ser. No. 14/463,741 by Robert A. Connor et al. entitled "Motion Recognition Clothing™ with Two Different Sets of Tubes Spanning a Body Joint" filed on Aug. 20, 2014 which claims the priority benefit of U.S. Provisional Patent Application No. 61/878,893 by Robert A. Connor et al. entitled "Motion Recognition Clothing™ with Two Different Sets of Tubes Spanning a Body Joint" filed on Sep. 17, 2013; (b) is a continuation in part of U.S. patent application Ser. No. 14/664,832 by Robert A. Connor entitled "Motion Recognition Clothing™ with Flexible Electromagnetic, Light, or Sonic Energy Pathways" filed on Mar. 21, 2015, which is a continuation in part of U.S. patent application Ser. No. 14/463,741 by Robert A. Connor et al. entitled "Motion Recognition Clothing™ with Two Different Sets of Tubes Spanning a Body Joint" filed on Aug. 20, 2014, and which claims the priority benefit of U.S. Provisional Patent Application No. 61/976,650 entitled "Motion Recognition Clothing™ with Electromagnetic, Light, or Sonic Energy Pathways" by Robert A. Connor filed on Apr. 8, 2014; and (c) claims the priority benefit of U.S. Provisional Patent Application No. 62/150,886 entitled "Nerd of the Rings: Devices for Measuring Finger Motion and Recognizing Hand Gestures" by Robert A. Connor filed on Apr. 22, 2015. The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to articles of clothing for measuring body motion, posture, and/or configuration.

INTRODUCTION

This invention is a sensor array which can be part of Motion Recognition Clothing™ for mobile non-intrusive measurement of body motion, posture, and/or configuration. Such clothing has many potential applications including: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

Review and Categorization of the Prior Art

There are motion capture technologies in the prior art, but they have limitations compared to this invention. As an example of prior art technology, there are camera-based motion capture systems. Some of these camera-based motion capture systems are very complex, comprising a circle of multiple cameras which each track a moving individual from a different perspective. These multi-camera systems can be accurate, but they also constrain a person to a space comprising the intersection of the fields of vision of these cameras. In addition to being relatively immobile, these multi-camera systems can also be relatively expensive.

There are also single-camera motion capture systems which are designed for home use. Some relatively-simple and reasonably-priced single-camera systems are used for home computer gaming, exercise routines, and other applications. However, these single-camera motion capture systems also restrict a person to remain in the field of vision of the camera. They are not mobile for outdoor activities such as golf or running or swimming. Further, relying on one camera (or even two cameras which are close together) means that the system cannot track the locations of body members when the camera's direct line of sight to them is obscured by other body members or objects.

As another example of prior art technology, there are complex full-body portable motion capture suits comprising a relatively-large number of accelerometers and gyroscopes. However, the more-accurate versions of such full-body motion capture suits tend to be relatively cumbersome and expensive. They can be great for motion capture for specialized purposes such as creating a video game or performance art, but are not well suited for contact sports or sports that involve extensive locational movement.

As another example of prior art technology, there is growing use of inertial sensors in wearable devices. These devices tend to be much less expensive and less intrusive than either the complex camera-based motion capture systems or the sophisticated full-body motion capture suits. They can perform adequately for measuring generalized "activity level", but they are not well-suited for capturing complex full-body motion such as that which occurs in sports like golf or gymnastics. Due to the limitations of camera-based systems, cumbersome full-body motion capture suits, and single-location accelerometer devices in the prior art, there remains a need for a wearable, mobile, reasonably-priced, and relatively-unobtrusive full-body motion-capture system which can be used in diverse environments.

It can be challenging trying to classify prior art in this field into discrete categories. However, classification of the prior art into categories, even if imperfect, can be an invaluable part of reviewing the prior art. Towards this end, I herein identify and briefly discuss 11 categories of prior art related to measurement and modeling of body motion, posture, and/or configuration. For the most relevant categories of prior art, I also provide specific examples of prior art (including patent or patent application number, inventor, publication date, and title). Some examples of prior art disclose multiple concepts and thus appear in more than one category. I hope that the reader finds this review and categorization of the prior art to be useful. The 11 categories of art used for this review and categorization are as follows: (1) wearable GPS for tracking geographic position; (2) fixed-location camera-based motion capture; (3) hand-held game controller, ball, bat, or other held object; (4) wearable RFID or other electromagnetic energy emitters; (5) wearable electromyographic (EMG) sensors; (6) rigid or partially-rigid exoskeleton; (7) wearable inertial sensors; (8) wearable pressure sensors; (9) wearable electromagnetic energy bend sensors and/or electrogoniometers; (10) wearable light energy bend sensors; and (11) wearable sonic energy bend sensors.

1. Wearable GPS for Tracking Geographic Position

Prior art in this category uses a wearable GPS unit to track a person's geographic position and macroscale body movement. Such art can be very useful for tracking movement distance and speed, but is not useful for mobile three-dimensional recognition of body motion, posture, and/or configuration and is less relevant to the technology of this present invention. Accordingly, although the category is mentioned here, specific examples of this large category of art are not listed.

2. Fixed-Location Camera-Based Motion Capture

Prior art in this widely-used category, traditionally known as "motion capture" or "mocap," uses one or more fixed-location cameras to take and analyze images of a person in order to estimate and/or model the person's movement. Such motion capture systems are widely used for animation in motion pictures and video games, using full-body motion for controlling a video game or other computer application, fixed-location sport-related motion analysis, medical body motion diagnostic assessment, and other applications. Such art can be very useful for all of these purposes, but is generally constrains a person to a fixed location and is subject to occlusion when a direct line of sight from the camera to a portion of a person's body is blocked. Accordingly, such art is less useful for mobile, ambulatory, and/or long-duration applications and is less relevant to the technology of this present invention. Thus, although the category is mentioned here, specific examples of art in this large category of prior art are not listed.

3. Hand-Held Game Controller, Ball, Bat, or Other Held Object

Prior art in this widely-used category tracks the location, orientation, and/or configuration of a hand-held game controller, sports ball, bat, club, or other held object in order to analyze the motion dynamics of a particular activity (such as a sport activity), control a computer game, interact with a virtual reality environment, or other motion-related application. Such art can be very useful for these purposes, but since the tracked object is not worn and be only in limited contact with the user's body, it is limited for tracking three-dimensional body motion, posture, and/or configuration. Accordingly, such art is less relevant to this present invention. This category is mentioned here, but specific examples of art in this category are not listed.

4. Wearable RFID or Other Electromagnetic Energy Emitters

Prior art in this category uses an array of wearable RFID or other electromagnetic energy emitters to track body motion and/or configuration in a three-dimensional space. Since this art generally constrains the user to motion within a defined space with fixed-location energy sensors, it is generally subject to similar location constraints as traditional camera-based motion capture. The technology is quite different than that used in the present invention and thus, although the category is mentioned here, specific examples of art in this category are not listed.

5. Wearable ElectroMyoGraphic (EMG) Sensors

Prior art in this category uses wearable sensors to measure electromagnetic energy which is naturally emitted from body muscles and nerves in order to estimate and model body motion. This category of prior art is relatively new and there are few examples in it as compared to the previous categories, but it is growing. Art in this category has the potential to eventually be very useful for mobile three-dimensional recognition of body motion, posture, and configuration. However, the technology is different than the technology used in this present invention. Unlike this present invention, EMG sensors measure naturally emitted electromagnetic energy and thus are less relevant to this present invention. Accordingly, this category is mentioned here, but specific examples of art in this category are not listed.

6. Rigid or Partially-Rigid Exoskeleton

Prior art in this category uses a rigid or partially-rigid exoskeleton which is attached to a person in order to measure and/or affect the person's body motion. Some exoskeletons are used primarily for measuring and modeling body motion. Other exoskeletons are used primarily for affecting body motion, such as with actuators which provide haptic feedback or help the person to move. This present invention focuses on flexible wearable pathways (which can be incorporated into an article of clothing) rather than a rigid or semi-rigid exoskeleton which is attached to a person. This rigid or semi-rigid nature of an exoskeleton can limit the range of body motion and limit its use for long-duration applications. Nonetheless, this category of art is more relevant than the previous categories and thus specific examples of art in this category are now listed.

Examples of prior art which appear to be within this category include the following U.S. patents: U.S. Pat. No. 5,012,819 (Marras et al., May 7, 1991, "Apparatus for Monitoring the Motion Components of the Spine"); U.S. Pat. No. 5,280,265 (Kramer et al., Jan. 18, 1994, "Strain-Sensing Goniometers, Systems and Recognition Algorithms"); U.S. Pat. No. 5,442,729 (Kramer et al., Aug. 15, 1995, "Strain-Sensing Goniometers, Systems and Recognition Algorithms"); U.S. Pat. No. 5,474,088 (Zaharkin et al., Dec. 12, 1995, "Device for Measuring Motion Characteristics of a Human Joint"); U.S. Pat. No. 5,516,249 (Brimhall, May 14, 1996, "Exoskeleton with Kinesthetic Feedback and Robotic Control"); U.S. Pat. No. 5,656,904 (Lander, Aug. 12, 1997, "Movement Monitoring and Control Apparatus for Body Members"); U.S. Pat. No. 5,676,157 (Kramer, Oct. 14, 1997, "Determination of Kinematically Constrained Multi-Articulated Structures"); U.S. Pat. No. 5,813,406 (Kramer et al., Sep. 29, 1998, "Strain-Sensing Goniometers, Systems and Recognition Algorithms"); U.S. Pat. No. 5,915,673 (Kazerooni, Jun. 29, 1999, "Pneumatic Human Power Amplifer Module"); U.S. Pat. No. 5,930,741 (Kramer, Jul. 27, 1999, "Accurate, Rapid, Reliable Position Sensing using Multiple Sensing Technologies"); and U.S. Pat. No. 5,961,541 (Ferrati, Oct. 5, 1999, "Orthopedic Apparatus for Walking and Rehabilitating Disabled Persons Including Tetraplegic Persons and for Facilitating and Stimulating the Revival of Comatose Patients Through the Use of Electronic and Virtual Reality Units").

Examples of prior art in this category also include U.S. patents: U.S. Pat. No. 6,005,548 (Latypov et al., Dec. 21, 1999, "Method for Tracking and Displaying User's Spatial Position and Orientation, a Method for Representing Virtual Reality for a User, and Systems of Embodiment of Such Methods"); U.S. Pat. No. 6,035,274 (Kramer et al., Mar. 7, 2000, "Strain-Sensing Goniometers, Systems and Recognition Algorithms"); U.S. Pat. No. 6,042,555 (Kramer et al., Mar. 28, 2000, "Force-Feedback Interface Device for the Hand"); U.S. Pat. No. 6,050,962 (Kramer et al., Apr. 18, 2000, "Goniometer-Based Body-Tracking Device and Method"); U.S. Pat. No. 6,104,379 (Petrich et al., Aug. 15, 2000, "Forearm-Supported Exoskeleton Hand-Tracking Device"); U.S. Pat. No. 6,110,130 (Kramer, Aug. 29, 2000, "Exoskeleton Device for Directly Measuring Fingertip Position and Inferring Finger Joint Angle"); U.S. Pat. No. 6,162,190 (Kramer, Dec. 19, 2000, "Determination of Kinematically Constrained Multi-Articulated Structures"); U.S. Pat. No. 6,239,784 (Holmes, May 29, 2001, "Exo-Skeletal Haptic Computer Human/Computer Interface Device"); U.S. Pat. No. 6,246,390 (Rosenberg, Jun. 12, 2001, "Multiple Degree-of-Freedom Mechanical Interface to a Computer System"); U.S. Pat. No. 6,413,229 (Kramer et al., Jul. 2, 2002, "Force-Feedback Interface Device for the Hand"); and U.S. Pat. No. 6,428,490 (Kramer et al., Aug. 6, 2002, "Goniometer-Based Body-Tracking Device and Method").

Examples of prior art in this category also include U.S. patents: U.S. Pat. No. 6,497,672 (Kramer, Dec. 24, 2002, "Device and Method for Measuring the Position of Animate Links"); U.S. Pat. No. 6,666,831 (Edgerton et al., Dec. 23, 2003, "Method, Apparatus and System for Automation of Body Weight Support Training (BWST) of Biped Locomotion Over a Treadmill Using a Programmable Stepper Device (PSD) Operating Like an Exoskeleton Drive System from a Fixed Base"); U.S. Pat. No. 6,701,296 (Kramer et al., Mar. 2, 2004, "Strain-Sensing Goniometers, Systems, and Recognition Algorithms"); U.S. Pat. No. 6,866,643 (Kramer, Mar. 15, 2005, "Determination of Finger Position"); U.S. Pat. No. 6,890,312 (Priester et al., May 10, 2005, "Joint Angle Indication System"); U.S. Pat. No. 7,070,571 (Kramer et al., Jul. 4, 2006, "Goniometer-Based Body-Tracking Device"); U.S. Pat. No. 7,153,242 (Goffer, Dec. 26, 2006, "Gait-Locomotor Apparatus"); U.S. Pat. No. 7,410,338 (Schiele et al., Aug. 12, 2008, "Exoskeleton for the Human Arm, in Particular for Space Applications"); U.S. Pat. No. 7,500,853 (Bevirt et al., Mar. 10, 2009, "Mechanical Interface for a Computer System"); U.S. Pat. No. 7,899,556 (Nathan et al., Mar. 1, 2011, "Orthosis for a Gait Modulation System"); U.S. Pat. No. 8,055,021 (Caritu et al., Nov. 8, 2011, "Motion Capture Device and Associated Method"); U.S. Pat. No. 8,171,570 (Adarraga, May 8, 2012, "Exoskeleton"); U.S. Pat. No. 8,678,979 (Stark et al., Mar. 25, 2014, "Remote Monitoring of a Patient"); U.S. Pat. No. 8,708,825 (Crisco, Apr. 29, 2014, "Device Controller with Conformable Fitting System"); and U.S. Pat. No. 8,777,878 (Deitz, Jul. 15, 2014, "Devices, Systems, and Methods for Measuring and Evaluating the Motion and Function of Joints and Associated Muscles").

Examples of prior art which appear to be within this category include the following U.S. patent applications: 20010003712 (Roelofs, Jun. 14, 2001, "Exoskeletal Platform for Controlling Multi-Directional Avatar Kinetics in a Virtual Environment"); 20010020140 (Kramer, Sep. 6, 2001, "Device and Method for Measuring the Position of Animate Links"); 20020198472 (Kramer, Dec. 26, 2002, "Determination of Finger Position"); 20030083596 (Kramer et al., May 1, 2003, "Goniometer-Based Body-Tracking Device and Method"); 20030091966 (Collodi, May 15, 2003, "Excercise/Simulation Device"); 20060130347 (Bergamasco et al., Jun. 22, 2006, "Device for Gioniometric Measurements"); 20060167564 (Flaherty et al., Jul. 27, 2006, "Limb and Digit Movement System"); 20060189899 (Flaherty et al., Aug. 24, 2006, "Joint Movement Apparatus"); 20060217233 (Lee, Sep. 28, 2006, "Apparatus and Method for Lower-Limb Rehabilitation Training Using Weight Load and Joint Angle as Variables"); 20060240953 (Shahinpoor, Oct. 26, 2006, "Human Lower Limb Performance Enhancement Outfit"); 20070123997 (Herr et al., May 31, 2007, "Exoskeletons for Running and Walking"); 20070132722 (Kim et al., Jun. 14, 2007, "Hand Interface Glove Using Miniaturized Absolute Position Sensors and Hand Interface System Using the Same"); 20110040216 (Herr et al., Feb. 17, 2011, "Exoskeletons for Running and Walking"); 20130158444 (Herr et al., Jun. 20, 2013, "Robotic System for Simulating a Wearable Device and Method of Use"); 20130204435 (Moon et al., Aug. 8, 2013, "Wearable Robot and Teaching Method of Motion using the Same"); and 20140366675 (Gosselin et al., Dec. 18, 2014, "Articulated Limb for a Robot or Haptic Interface and Robot and Haptic Interface Comprising at Least One Such Articulated Limb").

7. Wearable Inertial Sensors

Prior art in this category uses one or more wearable inertial sensors (such as accelerometers or gyroscopes) to estimate and/or model body motion, posture, and/or configuration. With reductions in the cost and size of inertial sensors, they are now being incorporated into a wide array of wearable devices. Currently, devices in this category most commonly include one or more inertial sensors at a single location on a person's body, wherein movement of the body at that location is used to estimate overall level of activity or infer overall patterns of body motion, posture, and/or configuration. However, there is a growing body of art which uses an array of inertial sensors worn at different locations on a person's body to measure and/or model three-dimensional body motion, posture, and/or configuration. The data processing demands of estimating three-dimensional body motion using a large array of wearable inertial sensors can be challenging, but there is a lot of progress being made in this area. The motion capture technology of this present invention is different than that used in this category, but this category of art is relevant and thus specific examples of art in this category are now listed.

Examples of prior art which appear to be within this category include the following U.S. patents: U.S. Pat. No. 5,337,758 (Moore et al., Aug. 16, 1994, "Spine Motion Analyzer and Method"); U.S. Pat. No. 5,375,610 (LaCourse et al., Dec. 27, 1994, "Apparatus for the Functional Assessment of Human Activity"); U.S. Pat. No. 5,592,401 (Kramer, Jan. 7, 1997, "Accurate, Rapid, Reliable Position Sensing using Multiple Sensing Technologies"); U.S. Pat. No. 5,615,132 (Horton et al., Mar. 25, 1997, "Method and Apparatus for Determining Position and Orientation of a Moveable Object Using Accelerometers"); U.S. Pat. No. 5,819,206 (Horton et al., Oct. 6, 1998, "Method and Apparatus for Determining Position and Orientation of a Moveable Object Using Accelerometers"); U.S. Pat. No. 6,018,705 (Gaudet et al., Jan. 25, 2000, "Measuring Foot Contact Time and Foot Loft Time of a Person in Locomotion"); U.S. Pat. No. 6,032,530 (Hock, Mar. 7, 2000, "Biofeedback System for Sensing Body Motion and Flexure"); U.S. Pat. No. 6,059,576 (Brann, May 9, 2000, "Training and Safety Device, System and Method to Aid in Proper Movement During Physical Activity"); U.S. Pat. No. 6,095,991 (Krausman et al., Aug. 1, 2000, "Ambulatory Body Position Monitor"); U.S. Pat. No. 6,148,280 (Kramer, Nov. 14, 2000, "Accurate, Rapid, Reliable Position Sensing using Multiple Sensing Technologies"); U.S. Pat. No. 6,162,191 (Foxlin, Dec. 19, 2000, "Inertial Orientation Tracker Having Automatic Drift Compensation for Tracking Human Head and Other Similarly Sized Body"); U.S. Pat. No. 6,210,301 (Abraham-Fuchs et al., Apr. 3, 2001, "Patient Monitoring System"); and U.S. Pat. No. 6,304,840 (Vance et al., Oct. 16, 2001, "Fingerless Glove for Interacting with Data Processing System").

Examples of prior art in this category also include U.S. patents: U.S. Pat. No. 6,361,507 (Foxlin, Mar. 26, 2002, "Inertial Orientation Tracker Having Gradual Automatic Drift Compensation for Tracking Human Head and Other Similarly Sized Body"); U.S. Pat. No. 6,409,687 (Foxlin, Jun. 25, 2002, "Motion Tracking System"); U.S. Pat. No. 6,466,200 (Anton et al., Oct. 15, 2002, "Computer Input Device"); U.S. Pat. No. 6,513,532 (Mault et al., Feb. 4, 2003, "Diet and Activity Monitoring Device"); U.S. Pat. No. 6,611,141 (Schulz et al., Aug. 26, 2003, "Hybrid 3-D Probe Tracked by Multiple Sensor"); U.S. Pat. No. 6,691,074 (Moriya et al., Feb. 10, 2004, "System for Three Dimensional Positioning and Tracking"); U.S. Pat. No. 6,700,499 (Kubo et al., Mar. 2, 2004, "Body Motion Detector"); U.S. Pat. No. 6,703,939 (Lehrman et al., Mar. 9, 2004, "System and Method for Detecting Motion of a Body"); U.S. Pat. No. 6,731,268 (Anton et al., May 4, 2004, "Computer Input Device"); U.S. Pat. No. 6,786,877 (Foxlin, Sep. 7, 2004, "Inertial Orientation Tracker Having Automatic Drift Compensation using an at Rest Sensor for Tracking Parts of a Human Body"); U.S. Pat. No. 6,834,436 (Townsend et al., Dec. 28, 2004, "Posture and Body Movement Measuring System"); U.S. Pat. No. 6,836,744 (Asphahani et al., Dec. 28, 2004, "Portable System for Analyzing Human Gait"); U.S. Pat. No. 6,864,796 (Lehrman et al., Mar. 8, 2005, "Systems Within a Communication Device for Evaluating Movement of a Body and Methods of Operating the Same"); U.S. Pat. No. 6,871,413 (Arms et al., Mar. 29, 2005, "Miniaturized Inclinometer for Angle Measurement with Accurate Measurement Indicator"); U.S. Pat. No. 6,912,475 (Moriya et al., Jun. 28, 2005, "System for Three Dimensional Positioning and Tracking"); U.S. Pat. No. 6,985,134 (Suprun et al., Jan. 10, 2006, "Computer Input Device"); and U.S. Pat. No. 7,020,508 (Stivoric et al., Mar. 28, 2006, "Apparatus for Detecting Human Physiological and Contextual Information").

Examples of prior art in this category also include U.S. patents: U.S. Pat. No. 7,028,547 (Shiratori et al., Apr. 18, 2006, "Body Motion Detector"); U.S. Pat. No. 7,095,331 (Lehrman et al, Aug. 22, 2006, "System and Method for Detecting Motion of a Body"); U.S. Pat. No. 7,141,026 (Aminian et al., Nov. 28, 2006, "Body Movement Monitoring System and Method"); U.S. Pat. No. 7,145,461 (Lehrman et al., Dec. 5, 2006, "System and Method for Analyzing Activity of a Body"); U.S. Pat. No. 7,149,584 (Koh et al., Dec. 12, 2006, "System and Method for Determining Patient Posture Based on 3-D Trajectory using an Implantable Medical Device"); U.S. Pat. No. 7,167,743 (Heruth et al., Jan. 23, 2007, "Collecting Activity Information to Evaluate Therapy"); U.S. Pat. No. 7,191,652 (Pristup et al., Mar. 20, 2007, "Magnetofluidic Accelerometer with Partial Filling of Cavity with Magnetic Fluid"); U.S. Pat. No. 7,210,240 (Townsend et al., May 1, 2007, "Posture and Body Movement Measuring System"); U.S. Pat. No. 7,212,943 (Aoshima et al., May 1, 2007, "Body Motion Detection Device, Pitch Meter, Wristwatch-Type Information Processing Device, Method for Controlling Thereof, Control Program, and Storage Medium"); and U.S. Pat. No. 7,219,033 (Kolen, May 15, 2007, "Single/Multiple Axes Six Degrees of Freedom (6 DOF) Inertial motion capture System with Initial Orientation Determination Capability").

Examples of prior art in this category also include U.S. patents: U.S. Pat. No. 7,261,690 (Teller et al., Aug. 28, 2007, "Apparatus for Monitoring Health, Wellness and Fitness"); U.S. Pat. No. 7,264,554 (Bentley, Sep. 4, 2007, "Method and System for Athletic Motion Analysis and Instruction"); U.S. Pat. No. 7,285,090 (Stivoric et al., Oct. 23, 2007, "Apparatus for Detecting, Receiving, Deriving and Displaying Human Physiological and Contextual Information"); U.S. Pat. No. 7,292,151 (Ferguson et al., Nov. 6, 2007, "Human Movement Measurement System"); U.S. Pat. No. 7,292,223 (Suprun et al., Nov. 6, 2007, "Location Tracking Device"); U.S. Pat. No. 7,295,184 (Suprun et al., Nov. 13, 2007, "Computer Input Device"); U.S. Pat. No. 7,296,469 (Simonenko et al., Nov. 20, 2007, "Magnetofluidic Accelerometer with Active Suspension"); U.S. Pat. No. 7,313,440 (Miesel, Dec. 25, 2007, "Collecting Posture and Activity Information to Evaluate Therapy"); U.S. Pat. No. 7,330,760 (Heruth et al., Feb. 12, 2008, "Collecting Posture Information to Evaluate Therapy"); U.S. Pat. No. 7,383,728 (Noble et al., Jun. 10, 2008, "Orientation and Motion Sensing in Athletic Training Systems, Physical Rehabilitation and Evaluation Systems, and Hand-Held Devices"); U.S. Pat. No. 7,394,385 (Franco et al., Jul. 1, 2008, "Comprehensive Monitoring System"); U.S. Pat. No. 7,395,113 (Heruth et al., Jul. 1, 2008, "Collecting Activity Information to Evaluate Therapy"); U.S. Pat. No. 7,395,181 (Foxlin, Jul. 1, 2008, "Motion Tracking System"); U.S. Pat. No. 7,421,369 (Clarkson, Sep. 2, 2008, "Activity Recognition Apparatus, Method and Program"); U.S. Pat. No. 7,447,545 (Heruth et al., Nov. 4, 2008, "Collecting Posture Information to Evaluate Therapy"); U.S. Pat. No. 7,450,002 (Choi et al., Nov. 11, 2008, "Method and Apparatus for Monitoring Human Activity Pattern"); and U.S. Pat. No. 7,451,056 (Flentov et al., Nov. 11, 2008, "Activity Monitoring Systems and Methods").

Examples of prior art in this category also include U.S. patents: U.S. Pat. No. 7,471,290 (Wang et al., Dec. 30, 2008, "Posture Detection System"); U.S. Pat. No. 7,479,890 (Lehrman et al., Jan. 20, 2009, "System and Method for Analyzing Activity of a Body"); U.S. Pat. No. 7,487,043 (Adams, Feb. 3, 2009, "Relative Positioning System"); U.S. Pat. No. 7,492,268 (Ferguson et al., Feb. 17, 2009, "Human Movement Measurement System"); U.S. Pat. No. 7,512,515 (Vock et al., Mar. 31, 2009, "Activity Monitoring Systems and Methods"); U.S. Pat. No. 7,565,295 (Hernandez-Rebollar, Jul. 21, 2009, "Method and Apparatus for Translating Hand Gestures"); U.S. Pat. No. 7,602,301 (Stirling et al., Oct. 13, 2009, "Apparatus, Systems, and Methods for Gathering and Processing Biometric and Biomechanical Data"); U.S. Pat. No. 7,602,310 (Mann et al., Oct. 13, 2009, "Telemetered Characteristic Monitor System and Method of using the Same"); U.S. Pat. No. 7,627,451 (Vock et al., Dec. 1, 2009, "Movement and Event Systems and Associated Methods"); U.S. Pat. No. 7,634,379 (Noble, Dec. 15, 2009, "Newtonian Physical Activity Monitor"); U.S. Pat. No. 7,647,196 (Kahn et al., Jan. 12, 2010, "Human Activity Monitoring Device with Distance Calculation"); U.S. Pat. No. 7,653,214 (Schroeder et al., Jan. 26, 2010, "Accelerometer Utilizing Image-Based Movement Tracking"); U.S. Pat. No. 7,653,508 (Kahn et al., Jan. 26, 2010, "Human Activity Monitoring Device"); and U.S. Pat. No. 7,661,200 (Bonnet et al., Feb. 16, 2010, "Method and Device for Determining a Person's Motions").

Examples of prior art in this category also include U.S. patents: U.S. Pat. No. 7,668,588 (Kovacs, Feb. 23, 2010, "Dual-Mode Physiologic Monitoring Systems and Methods"); U.S. Pat. No. 7,672,781 (Churchill et al., Mar. 2, 2010, "Miniaturized Wireless Inertial Sensing System"); U.S. Pat. No. 7,689,378 (Kolen, Mar. 30, 2010, "Motion Sensing Apparatus, Systems and Techniques"); U.S. Pat. No. 7,698,101 (Alten et al., Apr. 13, 2010, "Smart Garment"); U.S. Pat. No. 7,698,830 (Townsend et al., Apr. 20, 2010, "Posture and Body Movement Measuring System"); U.S. Pat. No. 7,725,279 (Luinge et al., May 25, 2010, "System and a Method for Motion Tracking using a Calibration Unit"); U.S. Pat. No. 7,742,894 (Chen et al., Jun. 22, 2010, "Multi-Person Pose Recognition System Using a Zigbee Wireless Sensor Network"); U.S. Pat. No. 7,753,861 (Kahn et al., Jul. 13, 2010, "Chest Strap Having Human Activity Monitoring Device"); U.S. Pat. No. 7,792,583 (Miesel et al., Sep. 7, 2010, "Collecting Posture Information to Evaluate Therapy"); U.S. Pat. No. 7,805,196 (Miesel et al., Sep. 28, 2010, "Collecting Activity Information to Evaluate Therapy"); U.S. Pat. No. 7,811,333 (Jonsson et al., Oct. 12, 2010, "Systems and Methods for Processing Limb Motion"); U.S. Pat. No. 7,821,407 (Shears et al., Oct. 26, 2010, "Apparatus, Systems, and Methods for Gathering and Processing Biometric and Biomechanical Data"); U.S. Pat. No. 7,825,815 (Shears et al., Nov. 2, 2010, "Apparatus, Systems, and Methods for Gathering and Processing Biometric and Biomechanical Data"); U.S. Pat. No. 7,827,000 (Stirling et al., Nov. 2, 2010, "Method and Apparatus for Estimating a Motion Parameter"); U.S. Pat. No. 7,845,228 (Bremer et al., Dec. 7, 2010, "Activity Monitoring"); U.S. Pat. No. 7,881,902 (Kahn et al., Feb. 1, 2011, "Human Activity Monitoring Device"); U.S. Pat. No. 7,952,483 (Ferguson et al., May 31, 2011, "Human Movement Measurement System"); and U.S. Pat. No. 7,978,081 (Shears et al., Jul. 12, 2011, "Apparatus, Systems, and Methods for Communicating Biometric and Biomechanical Information").

Examples of prior art in this category also include U.S. patents: U.S. Pat. No. 7,981,058 (Akay, Jul. 19, 2011, "Intelligent Wearable Monitor Systems and Methods"); U.S. Pat. No. 8,010,308 (Churchill, Aug. 30, 2011, "Inertial Measurement System with Self Correction"); U.S. Pat. No. 8,025,632 (Einarsson, Sep. 27, 2011, "Wearable Device Having Feedback Characteristics"); U.S. Pat. No. 8,036,850 (Kulach et al., Oct. 11, 2011, "Method and Apparatus for Estimating a Motion Parameter"); U.S. Pat. No. 8,036,851 (Vock et al., Oct. 11, 2011, "Activity Monitoring Systems and Methods"); U.S. Pat. No. 8,060,337 (Kulach et al., Nov. 15, 2011, "Method and Apparatus for Estimating a Motion Parameter"); U.S. Pat. No. 8,073,707 (Teller et al., Dec. 6, 2011, "System for Detecting Monitoring and Reporting an Individual's Physiological or Contextual Status"); U.S. Pat. No. 8,075,499 (Nathan et al., Dec. 13, 2011, "Abnormal Motion Detector and Monitor"); U.S. Pat. No. 8,099,258 (Alten et al., Jan. 17, 2012, "Smart Garment"); U.S. Pat. No. 8,125,448 (Ranta et al., Feb. 28, 2012, "Wearable Computer Pointing Device"); U.S. Pat. No. 8,135,473 (Miesel et al., Mar. 13, 2012, "Collecting Posture and Activity Information to Evaluate Therapy"); U.S. Pat. No. 8,140,339 (Hernandez-Rebollar, Mar. 20, 2012, "Method and Apparatus for Translating Hand Gestures"); and U.S. Pat. No. 8,150,531 (Skelton, Apr. 3, 2012, "Associating Therapy Adjustments with Patient Posture States").

Examples of prior art in this category also include U.S. patents: U.S. Pat. No. 8,152,694 (Srinivasan et al., Apr. 10, 2012, "Activity Monitoring Device and Method"); U.S. Pat. No. 8,157,730 (Leboeuf et al., Apr. 17, 2012, "Physiological and Environmental Monitoring Systems and Methods"); U.S. Pat. No. 8,157,731 (Teller et al., Apr. 17, 2012, "Method and Apparatus for Auto Journaling of Continuous or Discrete Body States Utilizing Physiological and/or Contextual Parameters"); U.S. Pat. No. 8,159,354 (Ferguson et al., Apr. 17, 2012, "Human Movement Measurement System"); U.S. Pat. No. 8,162,857 (Lanfermann et al., Apr. 24, 2012, "Limb Movement Monitoring System"); U.S. Pat. No. 8,165,840 (Hatlestad et al., Apr. 24, 2012, "Posture Sensor Automatic Calibration"); U.S. Pat. No. 8,165,844 (Luinge et al., Apr. 24, 2012, "Motion Tracking System"); U.S. Pat. No. 8,175,720 (Skelton et al., May 8, 2012, "Posture-Responsive Therapy Control Based on Patient Input"); U.S. Pat. No. 8,180,591 (Yuen et al., May 15, 2012, "Portable Monitoring Devices and Methods of Operating Same"); U.S. Pat. No. 8,180,592 (Yuen et al., May 15, 2012, "Portable Monitoring Devices and Methods of Operating Same"); U.S. Pat. No. 8,187,182 (Kahn et al., May 29, 2012, "Sensor Fusion for Activity Identification"); U.S. Pat. No. 8,200,340 (Skelton et al., Jun. 12, 2012, "Guided Programming for Posture-State Responsive Therapy"); and U.S. Pat. No. 8,203,487 (Hol et al., Jun. 19, 2012, "Tightly Coupled UWB/IMU Pose Estimation System and Method").

Examples of prior art in this category also include U.S. patents: U.S. Pat. No. 8,206,325 (Najafi et al., Jun. 26, 2012, "Ambulatory System for Measuring and Monitoring Physical Activity and Risk of Falling and for Automatic Fall Detection"); U.S. Pat. No. 8,209,028 (Skelton et al., Jun. 26, 2012, "Objectification of Posture State-Responsive Therapy Based on Patient Therapy Adjustments"); U.S. Pat. No. 8,209,147 (Solinsky, Jun. 26, 2012, "Geolocation System and Method for Determining Mammal Locomotion Movement"); U.S. Pat. No. 8,219,206 (Skelton et al., Jul. 10, 2012, "Dwell Time Adjustments for Posture State-Responsive Therapy"); U.S. Pat. No. 8,231,555 (Skelton et al., Jul. 31, 2012, "Therapy System Including Multiple Posture Sensor"); U.S. Pat. No. 8,249,718 (Skelton et al., Aug. 21, 2012, "Programming Posture State-Responsive Therapy with Nominal Therapy Parameters"); U.S. Pat. No. 8,275,635 (Stivoric et al., Sep. 25, 2012, "Integration of Lifeotypes with Devices and Systems"); U.S. Pat. No. 8,280,517 (Skelton et al., Oct. 2, 2012, "Automatic Validation Techniques for Validating Operation of Medical Devices"); U.S. Pat. No. 8,282,580 (Skelton et al., Oct. 9, 2012, "Data Rejection for Posture State Analysis"); U.S. Pat. No. 8,284,847 (Adermann, Oct. 9, 2012, "Detecting Motion for a Multifunction Sensor Device"); U.S. Pat. No. 8,301,575 (Bonnet et al., Oct. 30, 2012, "Method and Device for the Recognition of the Position or Movement of a Device or a Person"); U.S. Pat. No. 8,311,769 (Yuen et al., Nov. 13, 2012, "Portable Monitoring Devices and Methods of Operating Same"); and U.S. Pat. No. 8,311,770 (Yuen et al., Nov. 13, 2012, "Portable Monitoring Devices and Methods of Operating Same").

Examples of prior art in this category also include U.S. patents: U.S. Pat. No. 8,315,710 (Skelton et al., Nov. 20, 2012, "Associating Therapy Adjustments with Patient Posture States"); U.S. Pat. No. 8,323,218 (Davis et al., Dec. 4, 2012, "Generation of Proportional Posture Information Over Multiple Time Intervals"); U.S. Pat. No. 8,328,718 (Tran, Dec. 11, 2012, "Health Monitoring Appliance"); U.S. Pat. No. 8,332,041 (Skelton et al., Dec. 11, 2012, "Patient Interaction with Posture-Responsive Therapy"); U.S. Pat. No. 8,342,045 (Maxwell et al., Jan. 1, 2013, "Activity Monitor"); U.S. Pat. No. 8,352,211 (Vock et al., Jan. 8, 2013, "Activity Monitoring Systems and Methods"); U.S. Pat. No. 8,366,641 (Wang et al., Feb. 5, 2013, "Posture Detector Calibration and Use"); U.S. Pat. No. 8,382,590 (Stivoric et al., Feb. 26, 2013, "Entertainment, Gaming and Interactive Spaces Based on Lifeotypes"); U.S. Pat. No. 8,384,551 (Ross et al., Feb. 26, 2013, "Sensor Device and Method for Monitoring Physical Stresses Placed on a User"); U.S. Pat. No. 8,386,008 (Yuen et al., Feb. 26, 2013, "Activity Monitoring Systems and Methods of Operating Same"); U.S. Pat. No. 8,388,555 (Panken et al., Mar. 5, 2013, "Posture State Classification for a Medical Device"); U.S. Pat. No. 8,396,554 (Miesel et al., Mar. 12, 2013, "Collecting Posture Information to Evaluate Therapy"); U.S. Pat. No. 8,396,565 (Singhal et al., Mar. 12, 2013, "Automatic Therapy Adjustments"); U.S. Pat. No. 8,397,568 (Cardarelli, Mar. 19, 2013, "Bias Measurement for MEMS Gyroscopes and Accelerometers"); and U.S. Pat. No. 8,401,666 (Skelton et al., Mar. 19, 2013, "Modification Profiles for Posture-Responsive Therapy").

Examples of prior art in this category also include U.S. patents: U.S. Pat. No. 8,414,507 (Asada, Apr. 9, 2013, "Body Motion Balance Detection Device, Body Motion Balance Detection Program, Body Motion Balance Detection Method, and Body Motion Balance Diagnosis Method"); U.S. Pat. No. 8,416,102 (Yin, Apr. 9, 2013, "Activity Monitoring System Insensitive to Accelerations Induced by External Motion Factors"); U.S. Pat. No. 8,421,854 (Zerkin, Apr. 16, 2013, "System and Method for Motion Capture"); U.S. Pat. No. 8,427,325 (Ferguson et al., Apr. 23, 2013, "Human Movement Measurement System"); U.S. Pat. No. 8,435,177 (Lanfermann et al., May 7, 2013, "Process and System for Monitoring Exercise Motions of a Person"); U.S. Pat. No. 8,436,737 (Trout, May 7, 2013, "Postural State Attitude Monitoring, Caution, and Warning Systems and Methods"); U.S. Pat. No. 8,437,824 (Moon et al., May 7, 2013, "Body-Worn Pulse Oximeter"); U.S. Pat. No. 8,437,861 (Skelton et al., May 7, 2013, "Posture State Redefinition Based on Posture Data and Therapy Adjustments"); U.S. Pat. No. 8,437,980 (Yuen et al., May 7, 2013, "Portable Monitoring Devices and Methods of Operating Same"); U.S. Pat. No. 8,446,275 (Utter, May 21, 2013, "General Health and Wellness Management Method and Apparatus for a Wellness Application Using Data from a Data-Capable Band"); and U.S. Pat. No. 8,447,401 (Miesel et al., May 21, 2013, "Collecting Posture Information to Evaluate Therapy").

Examples of prior art in this category also include U.S. patents: U.S. Pat. No. 8,447,411 (Skelton et al., May 21, 2013, "Patient Interaction with Posture-Responsive Therapy"); U.S. Pat. No. 8,460,197 (Brady et al., Jun. 11, 2013, "Monitoring Device with a Pedometer"); U.S. Pat. No. 8,463,573 (Flentov et al., Jun. 11, 2013, "Movement Monitoring Systems and Associated Methods"); U.S. Pat. No. 8,463,576 (Yuen et al., Jun. 11, 2013, "Portable Monitoring Devices and Methods of Operating Same"); U.S. Pat. No. 8,463,577 (Yuen et al., Jun. 11, 2013, "Portable Monitoring Devices and Methods of Operating Same"); U.S. Pat. No. 8,504,150 (Skelton, Aug. 6, 2013, "Associating Therapy Adjustments with Posture States using a Stability Timer"); U.S. Pat. No. 8,515,549 (Panken et al., Aug. 20, 2013, "Associating Therapy Adjustments with Intended Patient Posture States"); U.S. Pat. No. 8,515,550 (Skelton et al., Aug. 20, 2013, "Assignment of Therapy Parameter to Multiple Posture States"); U.S. Pat. No. 8,527,217 (Moodie, Sep. 3, 2013, "Apparatus and Method for Physical Evaluation"); U.S. Pat. No. 8,543,185 (Yuen et al., Sep. 24, 2013, "Activity Monitoring Systems and Methods of Operating Same"); U.S. Pat. No. 8,543,351 (Yuen et al., Sep. 24, 2013, "Portable Monitoring Devices and Methods of Operating Same"); U.S. Pat. No. 8,548,740 (Hesch et al., Oct. 1, 2013, "System and Method for Wavelet-Based Gait Classification"); U.S. Pat. No. 8,548,770 (Yuen et al., Oct. 1, 2013, "Portable Monitoring Devices and Methods of Operating Same"); U.S. Pat. No. 8,554,297 (Moon et al., Oct. 8, 2013, "Body-Worn Pulse Oximeter"); U.S. Pat. No. 8,579,834 (Davis et al., Nov. 12, 2013, "Display of Detected Patient Posture State"); U.S. Pat. No. 8,583,252 (Skelton et al., Nov. 12, 2013, "Patient Interaction with Posture-Responsive Therapy"); U.S. Pat. No. 8,583,402 (Yuen et al., Nov. 12, 2013, "Portable Monitoring Devices and Methods of Operating Same"); and U.S. Pat. No. 8,616,989 (Bentley, Dec. 31, 2013, "Method and System for Athletic Motion Analysis and Instruction").

Examples of prior art in this category also include U.S. patents: U.S. Pat. No. 8,643,494 (Trout, Feb. 4, 2014, "Postural State Attitude Monitoring, Caution, and Warning Systems and Methods"); U.S. Pat. No. 8,651,964 (Brick, Feb. 18, 2014, "Advanced Video Controller System"); U.S. Pat. No. 8,655,618 (Flaction et al., Feb. 18, 2014, "Accelerometer and Method for Controlling an Accelerometer"); U.S. Pat. No. 8,657,772 (Einarsson, Feb. 25, 2014, "Wearable Device Having Feedback Characteristics"); U.S. Pat. No. 8,670,953 (Yuen et al., Mar. 11, 2014, "Portable Monitoring Devices and Methods of Operating Same"); U.S. Pat. No. 8,708,904 (Stivoric et al., Apr. 29, 2014, "Device Utilizing Data of a User's Context or Activity to Determine the User's Caloric Consumption or Expenditure"); U.S. Pat. No. 8,712,723 (Kahn et al., Apr. 29, 2014, "Human Activity Monitoring Device"); U.S. Pat. No. 8,760,392 (Lloyd et al., Jun. 24, 2014, "Wireless Motion Processing Sensor Systems Suitable for Mobile and Battery Operation"); U.S. Pat. No. 8,764,651 (Tran, Jul. 1, 2014, "Fitness Monitoring"); U.S. Pat. No. 8,784,342 (Hyde et al., Jul. 22, 2014, "Shape Sensing Clothes to Inform the Wearer of a Condition"); U.S. Pat. No. 8,788,055 (Gerber et al., Jul. 22, 2014, "Multi-Location Posture Sensing"); U.S. Pat. No. 8,795,137 (Ellis et al., Aug. 5, 2014, "Position Tracking and Guidance Methods"); U.S. Pat. No. 8,818,748 (Hatlestad et al., Aug. 26, 2014, "Posture Sensor Automatic Calibration"); U.S. Pat. No. 8,821,417 (McGregor et al., Sep. 2, 2014, "Method of Monitoring Human Body Movement"); and U.S. Pat. No. 8,823,490 (Libbus et al., Sep. 2, 2014, "Patient Monitoring Systems and Methods").

Examples of prior art in this category also include U.S. patents: U.S. Pat. No. 8,849,610 (Molettiere et al., Sep. 30, 2014, "Tracking User Physical Activity With Multiple Devices"); U.S. Pat. No. 8,876,738 (Kahn et al., Nov. 4, 2014, "Human Activity Monitoring Device"); U.S. Pat. No. 8,905,948 (Davis et al., Dec. 9, 2014, "Generation of Proportional Posture Information over Multiple Time Intervals"); U.S. Pat. No. 8,909,543 (Tropper et al., Dec. 9, 2014, "Methods for Detecting and Recording Physical Activity of Person"); U.S. Pat. No. 8,928,484 (Chang et al., Jan. 6, 2015, "System and Method of Biomechanical Posture Detection and Feedback"); U.S. Pat. No. 8,929,966 (LeBoeuf et al., Jan. 6, 2015, "Physiological Monitoring Methods"); U.S. Pat. No. 8,944,939 (Clark et al., Feb. 3, 2015, "Inertial Measurement of Sports Motion"); U.S. Pat. No. 8,947,441 (Hodgins et al., Feb. 3, 2015, "System and Method for Database Driven Action Capture"); U.S. Pat. No. 8,949,070 (Kahn et al., Feb. 3, 2015, "Human Activity Monitoring Device with Activity Identification"); and U.S. Pat. No. 8,958,885 (Panken et al., Feb. 17, 2015, "Posture State Classification for a Medical Device").

Examples of prior art which appear to be within this category include the following U.S. patent applications: 20010049470 (Mault et al., Dec. 6, 2001, "Diet and Activity Monitoring Device"); 20030023192 (Foxlin, Jan. 30, 2003, "Inertial Orientation Tracker Having Automatic Drift Compensation using an at Rest Sensor for Tracking Parts of a Human Body"); 20030045816 (Foxlin, Mar. 6, 2003, "Motion Tracking System"); 20030047002 (Arms et al., Mar. 13, 2003, "MEMS Based Angular Accelerometer"); 20030120448 (Moriya et al., Jun. 26, 2003, "System for Three Dimensional Positioning and Tracking"); 20050126026 (Townsend et al., Jun. 16, 2005, "Posture and Body Movement Measuring System"); 20050140651 (Suprun et al., Jun. 30, 2005, "Computer Input Device"); 20060022833 (Ferguson et al., Feb. 2, 2006, "Human Movement Measurement System"); 20060059976 (Simonenko et al., Mar. 23, 2006, "Accelerometer with Real-Time Calibration"); 20060059988 (Pristup, Mar. 23, 2006, "Magnetofluidic Accelerometer with Non-Magnetic Film on Drive Magnets"); and 20060059990 (Simonenko et al., Mar. 23, 2006, "Magnetofluidic Accelerometer with Active Suspension").

Examples of prior art in this category also include U.S. patent applications: 20060059991 (Pristup et al., Mar. 23, 2006, "Magnetofluidic Accelerometer with Partial Filling of Cavity with Magnetic Fluid"); 20060070443 (Pristup, Apr. 6, 2006, "Magnetofluidic Accelerometer with Capacitive Sensing of Inertial Body Position"); 20060135883 (Jonsson et al., Jun. 22, 2006, "Systems and Methods for Processing Limb Motion"); 20060166737 (Bentley, Jul. 27, 2006, "Method and System for Athletic Motion Analysis and Instruction"); 20060184336 (Kolen, Aug. 17, 2006, "Single/Multiple Axes Six Degrees of Freedom (6 DOF) Inertial motion capture System with Initial Orientation Determination Capability"); 20060212097 (Varadan et al., Sep. 21, 2006, "Method and Device for Treatment of Medical Conditions and Monitoring Physical Movements"); 20060241521 (Cohen, Oct. 26, 2006, "System for Automatic Structured Analysis of Body Activities"); 20060284979 (Clarkson, Dec. 21, 2006, "Activity Recognition Apparatus, Method and Program"); 20070000324 (Pristup et al., Jan. 4, 2007, "Magnetofluidic Accelerometer with Partial Filling of Cavity with Magnetic Fluid"); 20070038038 (Stivoric et al., Feb. 15, 2007, "Wearable Human Physiological and Environmental Data Sensors and Reporting System Therefor"); and 20070073482 (Churchill et al., Mar. 29, 2007, "Miniaturized Wireless Inertial Sensing System").

Examples of prior art in this category also include U.S. patent applications: 20070100666 (Stivoric et al., May 3, 2007, "Devices and Systems for Contextual and Physiological-Based Detection, Monitoring, Reporting, Entertainment, and Control of Other Devices"); 20070169364 (Townsend et al., Jul. 26, 2007, "Posture and Body Movement Measuring System"); 20070173705 (Teller et al., Jul. 26, 2007, "Apparatus for Monitoring Health, Wellness and Fitness"); 20070214889 (Pristup, Sep. 20, 2007, "Magnetofluidic Unidirectional Accelerometer"); 20070219744 (Kolen, Sep. 20, 2007, "Motion Sensing Apparatus, Systems and Techniques"); 20070270214 (Bentley, Nov. 22, 2007, "Method and System for Athletic Motion Analysis and Instruction"); 20080036737 (Hernandez-Rebollar, Feb. 14, 2008, "Arm Skeleton for Capturing Arm Position and Movement"); 20080061949 (Ferguson et al., Mar. 13, 2008, "Human Movement Measurement System"); 20080084385 (Ranta et al., Apr. 10, 2008, "Wearable Computer Pointing Device"); and 20080167535 (Andre et. al, Jul. 10, 2008, "Devices and Systems for Contextual and Physiological-Based Reporting, Entertainment, Control of Other Devices, Health Assessment and Therapy").

Examples of prior art in this category also include U.S. patent applications: 20080285805 (Luinge et al., Nov. 20, 2008, "Motion Tracking System"); 20090030345 (Bonnet et al., Jan. 29, 2009, "Method and Device for the Recognition of the Position or Movement of a Device or a Person"); 20090149257 (Ferguson et al., Jun. 11, 2009, "Human Movement Measurement System"); 20090171180 (Pering et al., Jul. 2, 2009, "Method and Apparatus for Configuring Wearable Sensor"); 20090204031 (McNames et al., Aug. 13, 2009, "Joint Angle Tracking with Inertial Sensor"); 20090278791 (Slycke et al., Nov. 12, 2009, "Motion Tracking System"); 20100026809 (Curry, Feb. 4, 2010, "Camera-Based Tracking and Position Determination for Sporting Events"); 20100036288 (Lanfermann et al., Feb. 11, 2010, "Limb Movement Monitoring System"); 20100076348 (McNames et al., Mar. 25, 2010, "Complete Integrated System for Continuous Monitoring and Analysis of Movement Disorders"); 20100176952 (Bajcsy et al., Jul. 15, 2010, "System for Detection of Body Motion"); 20100211349 (Flaction et al., Aug. 19, 2010, "Accelerometer and Method for Controlling an Accelerometer"); and 20100225473 (Leuthardt et al., Sep. 9, 2010, "Postural Information System and Method").

Examples of prior art in this category also include U.S. patent applications: 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); 20100228487 (Leuthardt et al., Sep. 9, 2010, "Postural Information System and Method"); and 20100228488 (Leuthardt et al., Sep. 9, 2010, "Postural Information System and Method"); 20100228489 (Leuthardt et al., Sep. 9, 2010, "Postural Information System and Method").

Examples of prior art in this category also include U.S. patent applications: 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); 20100309209 (Hodgins et al., Dec. 9, 2010, "System and Method for Database Driven Action Capture"); 20100324384 (Moon et al., Dec. 23, 2010, "Body-Worn Pulse Oximeter"); 20100324385 (Moon et al., Dec. 23, 2010, "Body-Worn Pulse Oximeter"); and 20100324386 (Moon et al., Dec. 23, 2010, "Body-Worn Pulse Oximeter").

Examples of prior art in this category also include U.S. patent applications: 20100324387 (Moon et al., Dec. 23, 2010, "Body-Worn Pulse Oximeter"); 20100324388 (Moon et al., Dec. 23, 2010, "Body-Worn Pulse Oximeter"); 20100324389 (Moon et al., Dec. 23, 2010, "Body-Worn Pulse Oximeter"); 20100324456 (Jonsson et al., Dec. 23, 2010, "Systems and Methods for Processing Limb Motion"); 20110025562 (Hol et al., Feb. 3, 2011, "Tightly Coupled UWB/IMU Pose Estimation System and Method"); 20110028865 (Luinge et al., Feb. 3, 2011, "Inertial Sensor Kinematic Coupling"); 20110046915 (Hol et al., Feb. 24, 2011, "Use of Positioning Aiding System for Inertial Motion Capture"); 20110181422 (Tran, Jul. 28, 2011, "Personal Emergency Response (PER) System"); 20110201428 (Ferguson et al., Aug. 18, 2011, "Human Movement Measurement System"); 20110313705 (Esser et al., Dec. 22, 2011, "Gait Monitor"); 20120046901 (Green et al., Feb. 23, 2012, "Motion Capture Apparatus"); 20120092156 (Tran, Apr. 19, 2012, "Personal Emergency Response (PER) System"); 20120108917 (Libbus et al., May 3, 2012, "Patient Monitoring Systems and Methods"); and 20120116257 (Leuthardt et al., May 10, 2012, "Postural Information System and Method Including Determining Response to Subject Advisory Information").

Examples of prior art in this category also include U.S. patent applications: 20120172126 (Padovani et al., Jul. 5, 2012, "Method and Apparatus for Tracking Orientation of a User"); 20120178534 (Ferguson et al., Jul. 12, 2012, "Human Movement Measurement System"); 20120223880 (Birnbaum et al., Sep. 6, 2012, "Method and Apparatus for Producing a Dynamic Haptic Effect"); 20120274554 (Kinoshita et al., Nov. 1, 2012, "Body Movement Detection Device and Display Control Method of body movement Detection Device"); 20120316455 (Rahman et al., Dec. 13, 2012, "Wearable Device and Platform for Sensory Input"); 20120319940 (Bress et al., Dec. 20, 2012, "Wearable Digital Input Device for Multipoint Free Space Data Collection and Analysis"); 20130015976 (Chang et al., Jan. 17, 2013, "System and Method of Biomechanical posture Detection and Feedback"); 20130068017 (Perkins et al., Mar. 21, 2013, "Apparatus and Method for Analyzing the Motion of a Body"); 20130072765 (Kahn et al., Mar. 21, 2013, "Body-Worn Monitor"); 20130073248 (Perkins et al., Mar. 21, 2013, "Apparatus and Method for Employing Miniature Inertial Measurement Units for Deducing Forces and Moments on Bodies"); 20130110011 (McGregor et al., May 2, 2013, "Method of Monitoring Human Body Movement"); and 20130123665 (Mariani et al., May 16, 2013, "System and Method for 3D Gait Assessment").

Examples of prior art in this category also include U.S. patent applications: 20130158686 (Zhang et al., Jun. 20, 2013, "Intelligent Activity Monitor"); 20130173171 (Drysdale et al., Jul. 4, 2013, "Data-Capable Strapband"); 20130204411 (Clark et al., Aug. 8, 2013, "Inertial Measurement of Sports Motion"); 20130207889 (Chang et al., Aug. 15, 2013, "System and Method of Biomechanical Posture Detection and Feedback Including Sensor Normalization"); 20130211291 (Tran, Aug. 15, 2013, "Personal Emergency Response (PER) System"); 20130215230 (Miesnieks et al., Aug. 22, 2013, "Augmented Reality System using a Portable Device"); 20130222565 (Guerin et al., Aug. 29, 2013, "System and Method for Sensor Fusion of Single Range Camera Data and Inertial Measurement for motion capture"); 20130253875 (Flentov et al., Sep. 26, 2013, "Movement Monitoring Systems and Associated Methods"); 20130289932 (Baechler, Oct. 31, 2013, "Method for Configuring a Motion Sensor as Well as a Configurable Motion Sensor and a System for Configuring Such a Motion Sensor"); 20130303286 (Ferguson et al., Nov. 14, 2013, "Human Movement Measurement System"); and 20140070957 (Longinotti-Buitoni et al., Mar. 13, 2014, "Wearable Communication Platform").

Examples of prior art in this category also include U.S. patent applications: 20140142733 (Tropper et al., May 22, 2014, "Methods for Detecting and Recording Activity and Devices for Performing the Same"); 20140143031 (Tropper et al., May 22, 2014, "Methods for Detecting and Recording Physical Activity of Person"); 20140143038 (Tropper et al., May 22, 2014, "Personal Activity Tracking System"); 20140159894 (Tropper et al., Jun. 12, 2014, "Personal Activity Tracking Device"); 20140171834 (Degoede et al., Jun. 19, 2014, "Electronic-Movement Analysis Tool for Motor Control Rehabilitation and Method of Using the Same"); 20140172134 (Meschter, Jun. 19, 2014, "Apparel Having Sensor System"); 20140188499 (Bell et al., Jul. 3, 2014, "Human Action Monitor"); 20140194781 (Einarsson, Jul. 10, 2014, "Wearable Device Having Feedback Characteristics"); 20140197946 (Park, Jul. 17, 2014, "Portable Monitoring Devices and Methods of Operating the Same"); 20140197963 (Park et al., Jul. 17, 2014, "Portable Monitoring Devices and Methods of Operating the Same"); and 20140197965 (Park et al., Jul. 17, 2014, "Portable Monitoring Devices and Methods of Operating the Same").

Examples of prior art in this category also include U.S. patent applications: 20140206327 (Ziemianska et al., Jul. 24, 2014, "Method and Apparatus for Automatically Adjusting the Operation of Notifications Based on Changes in Physical Activity Level"); 20140213856 (Teller et al., Jul. 31, 2014, "System for Automatic Journaling of a User's Context"); 20140213857 (Teller et al., Jul. 31, 2014, "System for Automatic Journaling of a User's Context"); 20140221769 (Teller et al., Aug. 7, 2014, "Systems and Methods for Measuring Energy Expenditure of an Individual"); 20140223407 (Teller et al., Aug. 7, 2014, "Systems and Methods for Measuring Energy Expenditure"); 20140240103 (Lake et al., Aug. 28, 2014, "Methods and Devices for Combining Muscle Activity Sensor Signals and Inertial Sensor Signals for Gesture-Based Control"); 20140240122 (Roberts et al., Aug. 28, 2014, "Notifications on a User Device Based on Activity Detected by an Activity Monitoring Device"); 20140249381 (LeBoeuf et al., Sep. 4, 2014, "Light-Guiding Devices and Monitoring Devices Incorporating Same"); and 20140275812 (Stivoric et al., Sep. 18, 2014, "Flexible Wearable Body Monitor Device with Sensor").

Examples of prior art in this category also include U.S. patent applications: 20140275813 (Stivoric et al., Sep. 18, 2014, "Wearable Body Monitor Device with a Flexible Section and Sensor Therein"); 20140288875 (Donaldson, Sep. 25, 2014, "Methods and Architecture for Determining Activity and Activity Types From Sensed Motion Signals"); 20140288877 (Donaldson, Sep. 25, 2014, "Intermediate Motion Signal Extraction to Determine Activity"); 20140288878 (Donaldson, Sep. 25, 2014, "Identification of Motion Characteristics to Determine Activity"); 20150015417 (Libbus et al., Jan. 15, 2015, "Patient Monitoring Systems and Methods"); 20150019135 (Kacyvenski et al., Jan. 15, 2015, "Motion Sensor and Analysis"); and 20150045699 (Mokaya et al., Feb. 12, 2015, "Musculoskeletal Activity Recognition System and Method").

8. Wearable Pressure Sensors

Prior art in this category uses one or more wearable pressure sensors to estimate and/or model body motion, posture, and/or configuration. This category is relatively small and is most commonly focused on some type of pressure sensor in a person's shoes, but there are examples of pressure sensors worn on other body locations. Although this present invention does not focus on pressure sensors, the parent application of this present invention uses pressure-sensing tubes to estimate and/or model body motion, posture, and/or configuration so this category of art is relevant and specific examples are now listed.

Examples of prior art which appear to be within this category include the following U.S. patents: U.S. Pat. No. 3,974,491 (Sipe, Aug. 10, 1976, "Load Signaling Device for a Patient's Foot"); U.S. Pat. No. 5,592,401 (Kramer, Jan. 7, 1997, "Accurate, Rapid, Reliable Position Sensing using Multiple Sensing Technologies"); U.S. Pat. No. 5,989,700 (Krivopal, Nov. 23, 1999, "Pressure Sensitive Ink Means, and Methods of Use"); U.S. Pat. No. 6,148,280 (Kramer, Nov. 14, 2000, "Accurate, Rapid, Reliable Position Sensing using Multiple Sensing Technologies"); U.S. Pat. No. 6,210,301 (Abraham-Fuchs et al., Apr. 3, 2001, "Patient Monitoring System"); U.S. Pat. No. 6,611,789 (Darley, Aug. 26, 2003, "Monitoring Activity of a User in Locomotion on Foot"); U.S. Pat. No. 6,836,744 (Asphahani et al., Dec. 28, 2004, "Portable System for Analyzing Human Gait"); U.S. Pat. No. 6,964,205 (Papakostas et al., Nov. 15, 2005, "Sensor with Plurality of Sensor Elements Arranged with Respect to a Substrate"); and U.S. Pat. No. 7,245,292 (Custy, Jul. 17, 2007, "Apparatus and Method for Incorporating Tactile Control and Tactile Feedback Into a Human-Machine Interface").

Examples of prior art in this category also include U.S. patents: U.S. Pat. No. 7,258,026 (Papakostas et al., Aug. 21, 2007, "Sensor with a Plurality of Sensor Elements Arranged with Respect to a Substrate"); U.S. Pat. No. 7,980,141 (Connor et al., Jul. 19, 2011, "Wearable Position or Motion Sensing Systems or Methods"); U.S. Pat. No. 7,998,092 (Avni et al., Aug. 16, 2011, "Force Sensor System for Use in Monitoring Weight Bearing"); U.S. Pat. No. 8,011,229 (Lieberman et al., Sep. 6, 2011, "Determining Postural Stability"); U.S. Pat. No. 8,033,916 (Caldwell et al., Oct. 11, 2011, "Grip Pressure Sensor"); U.S. Pat. No. 8,109,149 (Kotovsky, Feb. 7, 2012, "Contact Stress Sensor"); U.S. Pat. No. 8,111,165 (Ortega et al., Feb. 7, 2012, "Active On-Patient Sensor, Method and System"); U.S. Pat. No. 8,151,648 (Yu et al., Apr. 10, 2012, "Ultra-Miniature Fiber-Optic Pressure Sensor System and Method of Fabrication"); U.S. Pat. No. 8,161,826 (Taylor, Apr. 24, 2012, "Elastically Stretchable Fabric Force Sensor Arrays and Methods of Making"); U.S. Pat. No. 8,162,857 (Lanfermann et al., Apr. 24, 2012, "Limb Movement Monitoring System"); U.S. Pat. No. 8,280,681 (Vock et al., Oct. 2, 2012, "Pressure-Based Weight Monitoring System for Determining Improper Walking or Running"); and U.S. Pat. No. 8,316,719 (Majidi et al., Nov. 27, 2012, "Stretchable Two-Dimensional Pressure Sensor").

Examples of prior art in this category also include U.S. patents: U.S. Pat. No. 8,384,551 (Ross et al., Feb. 26, 2013, "Sensor Device and Method for Monitoring Physical Stresses Placed on a User"); U.S. Pat. No. 8,416,088 (Ortega et al., Apr. 9, 2013, "Active On-Patient Sensor, Method and System"); U.S. Pat. No. 8,459,128 (Bhat et al., Jun. 11, 2013, "Sub-Threshold Elastic Deflection FET Sensor for Sensing Pressure/Force, a Method and System Thereof"); U.S. Pat. No. 8,463,573 (Flentov et al., Jun. 11, 2013, "Movement Monitoring Systems and Associated Methods"); U.S. Pat. No. 8,626,472 (Solinsky, Jan. 7, 2014, "System and Method for Measuring Balance and Track Motion in Mammals"); U.S. Pat. No. 8,661,915 (Taylor, Mar. 4, 2014, "Elastically Stretchable Fabric Force Sensor Arrays and Methods of Making"); U.S. Pat. No. 8,784,342 (Hyde et al., Jul. 22, 2014, "Shape Sensing Clothes to Inform the Wearer of a Condition"); and U.S. Pat. No. 8,904,876 (Taylor et al., Dec. 9, 2014, "Flexible Piezocapacitive and Piezoresistive Force and Pressure Sensor").

Examples of prior art which appear to be within this category include the following U.S. patent applications: 20030054923 (Brassil et al., Mar. 20, 2003, "Hand Rehabilitation Glove"); 20060212097 (Varadan et al., Sep. 21, 2006, "Method and Device for Treatment of Medical Conditions and Monitoring Physical Movements"); 20060282017 (Avni et al., Dec. 14, 2006, "Force Sensor System for Use in Monitoring Weight Bearing"); 20090025483 (Connor et al., Jan. 29, 2009, "Wearable Position or Motion Sensing Systems or Methods"); 20090076419 (Namineni et al., Mar. 19, 2009, "Loss-of-Balance and Fall Detection System"); 20100036288 (Lanfermann et al., Feb. 11, 2010, "Limb Movement Monitoring System"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); and 20100225491 (Leuthardt et al., Sep. 9, 2010, "Postural Information System and Method").

Examples of prior art in this category also include U.S. patent applications: 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); 20100228487 (Leuthardt et al., Sep. 9, 2010, "Postural Information System and Method"); 20100228488 (Leuthardt et al., Sep. 9, 2010, "Postural Information System and Method"); 20100228489 (Leuthardt et al., Sep. 9, 2010, "Postural Information System and Method"); and 20100228490 (Leuthardt et al., Sep. 9, 2010, "Postural Information System and Method").

Examples of prior art in this category also include U.S. patent applications: 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); and 20100271200 (Leuthardt et al., Oct. 28, 2010, "Postural Information System and Method Including Determining Response to Subject Advisory Information").

Examples of prior art in this category also include U.S. patent applications: 20110208444 (Solinsky, Aug. 25, 2011, "System and Method for Measuring Balance and Track Motion in Mammals"); 20120089348 (Perlin et al., Apr. 12, 2012, "Sensor Having a Set of Plates, and Method"); 20120116257 (Leuthardt et al., May 10, 2012, "Postural Information System and Method Including Determining Response to Subject Advisory Information"); 20120118066 (Majidi et al., May 17, 2012, "Stretchable Two-Dimensional Pressure Sensor"); 20120323501 (Sarrafzadeh et al., Dec. 20, 2012, "Fabric-Based Pressure Sensor Arrays and Methods for Data Analysis"); 20120323501 (Sarrafzadeh et al., Dec. 20, 2012, "Fabric-Based Pressure Sensor Arrays and Methods for Data Analysis"); 20130253875 (Flentov et al., Sep. 26, 2013, "Movement Monitoring Systems and Associated Methods"); 20130275057 (Perlin et al., Oct. 17, 2013, "Sensor Having a Mesh Layer with Protrusions, and Method"); 20130324888 (Solinsky, Dec. 5, 2013, "System and Method for Measuring Balance and Track Motion in Mammals"); and 20140172134 (Meschter, Jun. 19, 2014, "Apparel Having Sensor System").

9. Wearable Electromagnetic Energy Bend Sensors and/or Electrogoniometers

Prior art in this category uses one or more electromagnetic energy bend sensors and/or electrogoniometers which are worn on the body in order to estimate and/or model body motion, posture, and/or configuration. This category is relatively large, especially with respect to devices to estimate the angle of a single body joint. Incorporation of multiple electromagnetic energy bend sensors into clothing is less common, but growing. Although the present invention discloses novel configurations and methods for incorporating bend sensors into an article of clothing which are not disclosed by the prior art, this category of prior art is relevant to the present invention and thus specific examples are now listed.

Examples of prior art which appear to be within this category include the following U.S. patents: U.S. Pat. No. 5,012,819 (Marras et al., May 7, 1991, "Apparatus for Monitoring the Motion Components of the Spine"); U.S. Pat. No. 5,086,785 (Gentile et al., Feb. 11, 1992, "Angular Displacement Sensor"); U.S. Pat. No. 5,184,319 (Kramer, Feb. 2, 1993, "Force Feedback and Textures Simulating Interface Device"); U.S. Pat. No. 5,280,265 (Kramer et al., Jan. 18, 1994, "Strain-Sensing Goniometers, Systems and Recognition Algorithms"); U.S. Pat. No. 5,316,017 (Edwards et al., May 31, 1994, "Man-Machine Interface for a Joint Measurement System"); U.S. Pat. No. 5,442,729 (Kramer et al., Aug. 15, 1995, "Strain-Sensing Goniometers, Systems and Recognition Algorithms"); U.S. Pat. No. 5,474,088 (Zaharkin et al., Dec. 12, 1995, "Device for Measuring Motion Characteristics of a Human Joint"); U.S. Pat. No. 5,533,531 (Edwards et al., Jul. 9, 1996, "Electronically Aligned Man-Machine Interface"); U.S. Pat. No. 5,592,401 (Kramer, Jan. 7, 1997, "Accurate, Rapid, Reliable Position Sensing using Multiple Sensing Technologies"); U.S. Pat. No. 5,640,971 (Martin, Jr., Jun. 24, 1997, "Back Movement Monitor and Warning Device"); U.S. Pat. No. 5,676,157 (Kramer, Oct. 14, 1997, "Determination of Kinematically Constrained Multi-Articulated Structures"); U.S. Pat. No. 5,813,406 (Kramer et al., Sep. 29, 1998, "Strain-Sensing Goniometers, Systems and Recognition Algorithms"); and U.S. Pat. No. 5,930,741 (Kramer, Jul. 27, 1999, "Accurate, Rapid, Reliable Position Sensing using Multiple Sensing Technologies").

Examples of prior art in this category also include U.S. patents: U.S. Pat. No. 5,980,472 (Seyl, Nov. 9, 1999, "Joint Movement Monitoring System"); U.S. Pat. No. 6,005,548 (Latypov et al., Dec. 21, 1999, "Method for Tracking and Displaying User's Spatial Position and Orientation, a Method for Representing Virtual Reality for a User, and Systems of Embodiment of Such Methods"); U.S. Pat. No. 6,035,274 (Kramer et al., Mar. 7, 2000, "Strain-Sensing Goniometers, Systems and Recognition Algorithms"); U.S. Pat. No. 6,042,555 (Kramer et al., Mar. 28, 2000, "Force-Feedback Interface Device for the Hand"); U.S. Pat. No. 6,050,962 (Kramer et al., Apr. 18, 2000, "Goniometer-Based Body-Tracking Device and Method"); U.S. Pat. No. 6,104,379 (Petrich et al., Aug. 15, 2000, "Forearm-Supported Exoskeleton Hand-Tracking Device"); U.S. Pat. No. 6,110,130 (Kramer, Aug. 29, 2000, "Exoskeleton Device for Directly Measuring Fingertip Position and Inferring Finger Joint Angle"); U.S. Pat. No. 6,119,516 (Hock, Sep. 19, 2000, "Biofeedback System for Monitoring the Motion of Body Joint"); U.S. Pat. No. 6,127,672 (Danisch, Oct. 3, 2000, "Topological and Motion Measuring Tool"); U.S. Pat. No. 6,148,280 (Kramer, Nov. 14, 2000, "Accurate, Rapid, Reliable Position Sensing using Multiple Sensing Technologies"); U.S. Pat. No. 6,162,190 (Kramer, Dec. 19, 2000, "Determination of Kinematically Constrained Multi-Articulated Structures"); U.S. Pat. No. 6,246,390 (Rosenberg, Jun. 12, 2001, "Multiple Degree-of-Freedom Mechanical Interface to a Computer System"); U.S. Pat. No. 6,304,840 (Vance et al., Oct. 16, 2001, "Fingerless Glove for Interacting with Data Processing System"); U.S. Pat. No. 6,334,852 (Seyl, Jan. 1, 2002, "Joint Movement Monitoring System"); U.S. Pat. No. 6,341,504 (Istook, Jan. 29, 2002, "Composite Elastic and Wire Fabric for Physiological Monitoring Apparel"); and U.S. Pat. No. 6,360,615 (Smela, Mar. 26, 2002, "Wearable Effect-Emitting Strain Gauge Device").

Examples of prior art in this category also include U.S. patents: U.S. Pat. No. 6,413,229 (Kramer et al., Jul. 2, 2002, "Force-Feedback Interface Device for the Hand"); U.S. Pat. No. 6,428,490 (Kramer et al., Aug. 6, 2002, "Goniometer-Based Body-Tracking Device and Method"); U.S. Pat. No. 6,487,906 (Hock, Dec. 3, 2002, "Flexible Film Sensor System for Monitoring Body Motion"); U.S. Pat. No. 6,497,672 (Kramer, Dec. 24, 2002, "Device and Method for Measuring the Position of Animate Links"); U.S. Pat. No. 6,563,107 (Danisch et al., May 13, 2003, "Topological and Motion Measuring Tool"); U.S. Pat. No. 6,579,248 (Cascone et al., Jun. 17, 2003, "Biofeedback Device"); U.S. Pat. No. 6,640,202 (Dietz et al., Oct. 28, 2003, "Elastic Sensor Mesh System for 3-Dimensional Measurement, Mapping and Kinematics Applications"); U.S. Pat. No. 6,673,027 (Fischer, Jan. 6, 2004, "Posture Measurement and Feedback Instrument for Seated Occupations"); U.S. Pat. No. 6,701,296 (Kramer et al., Mar. 2, 2004, "Strain-Sensing Goniometers, Systems, and Recognition Algorithms"); U.S. Pat. No. 6,834,436 (Townsend et al., Dec. 28, 2004, "Posture and Body Movement Measuring System"); U.S. Pat. No. 6,866,643 (Kramer, Mar. 15, 2005, "Determination of Finger Position"); U.S. Pat. No. 6,871,413 (Arms et al., Mar. 29, 2005, "Miniaturized Inclinometer for Angle Measurement with Accurate Measurement Indicator"); U.S. Pat. No. 6,957,164 (Dietz et al., Oct. 18, 2005, "Elastic Sensor Mesh System for 3-Dimensional Measurement, Mapping and Kinematics Applications"); U.S. Pat. No. 6,964,205 (Papakostas et al., Nov. 15, 2005, "Sensor with Plurality of Sensor Elements Arranged with Respect to a Substrate"); U.S. Pat. No. 6,979,164 (Kramer, Dec. 27, 2005, "Force Feedback and Texture Simulating Interface Device"); U.S. Pat. No. 7,070,571 (Kramer et al., Jul. 4, 2006, "Goniometer-Based Body-Tracking Device"); and U.S. Pat. No. 7,082,570 (von Wiegand et al., Jul. 25, 2006, "Distributed Haptic Interface System and Method").

Examples of prior art in this category also include U.S. patents: U.S. Pat. No. 7,135,227 (Karayianni et al., Nov. 14, 2006, "Electrically Conductive Elastic Composite Yarn, Methods for Making the Same, and Articles Incorporating the Same"); U.S. Pat. No. 7,191,803 (Orr et al., Mar. 20, 2007, "Elastic Fabric with Sinusoidally Disposed Wires"); U.S. Pat. No. 7,209,028 (Boronkay et al., Apr. 24, 2007, "Position Sensor with Resistive Element"); U.S. Pat. No. 7,210,240 (Townsend et al., May 1, 2007, "Posture and Body Movement Measuring System"); U.S. Pat. No. 7,258,026 (Papakostas et al., Aug. 21, 2007, "Sensor with a Plurality of Sensor Elements Arranged with Respect to a Substrate"); U.S. Pat. No. 7,390,157 (Kramer, Jun. 24, 2008, "Force Feedback and Texture Simulating Interface Device"); U.S. Pat. No. 7,413,802 (Karayianni et al., Aug. 19, 2008, "Energy Active Composite Yarn, Methods for Making the Same, and Articles Incorporating the Same"); U.S. Pat. No. 7,500,853 (Bevirt et al., Mar. 10, 2009, "Mechanical Interface for a Computer System"); and U.S. Pat. No. 7,509,870 (Aebersold et al., Mar. 31, 2009, "MEMS Capacitive Bending and Axial Strain Sensor").

Examples of prior art in this category also include U.S. patents: U.S. Pat. No. 7,665,288 (Karayianni et al., Feb. 23, 2010, "Energy Active Composite Yarn, Methods for Making the Same and Articles Incorporating the Same"); U.S. Pat. No. 7,698,830 (Townsend et al., Apr. 20, 2010, "Posture and Body Movement Measuring System"); U.S. Pat. No. 7,703,333 (Hayakawa et al., Apr. 27, 2010, "Deformation Sensor"); U.S. Pat. No. 7,771,318 (Narayanaswami, Aug. 10, 2010, "Device for Monitoring a User's Posture"); U.S. Pat. No. 7,850,574 (Narayanaswami, Dec. 14, 2010, "Device for Monitoring a User's Posture"); U.S. Pat. No. 7,854,174 (Aebersold et al., Dec. 21, 2010, "MEMS Capacitive Bending and Axial Strain Sensor"); U.S. Pat. No. 7,901,756 (Burr et al., Mar. 8, 2011, "Functional Elastic Textile Structures"); U.S. Pat. No. 7,902,095 (Hassonjee et al., Mar. 8, 2011, "Functional Textile Structures"); U.S. Pat. No. 7,926,254 (Karayianni et al., Apr. 19, 2011, "Electrically Conductive Elastic Composite Yarn, Methods for Making the Same, and Articles Incorporating the Same"); U.S. Pat. No. 7,981,057 (Stewart, Jul. 19, 2011, "Joint Motion Sensing to Make a Determination of a Positional Change of an Individual"); U.S. Pat. No. 8,083,693 (McKeon et al., Dec. 27, 2011, "Monitoring Posture"); U.S. Pat. No. 8,157,752 (Fischer, Apr. 17, 2012, "Posture Assessment and Feedback Instrument"); U.S. Pat. No. 8,161,826 (Taylor, Apr. 24, 2012, "Elastically Stretchable Fabric Force Sensor Arrays and Methods of Making"); and U.S. Pat. No. 8,203,455 (Lee et al., Jun. 19, 2012, "Posture Sensing Alert Apparatus").

Examples of prior art in this category also include U.S. patents: U.S. Pat. No. 8,362,882 (Heubel et al., Jan. 29, 2013, "Method and Apparatus for Providing Haptic Feedback from Haptic Textile"); U.S. Pat. No. 8,421,448 (Tran et al., Apr. 16, 2013, "Hall-Effect Sensor System for Gesture Recognition, Information Coding, and Processing"); U.S. Pat. No. 8,459,128 (Bhat et al., Jun. 11, 2013, "Sub-Threshold Elastic Deflection FET Sensor for Sensing Pressure/Force, a Method and System Thereof"); U.S. Pat. No. 8,626,472 (Solinsky, Jan. 7, 2014, "System and Method for Measuring Balance and Track Motion in Mammals"); U.S. Pat. No. 8,661,915 (Taylor, Mar. 4, 2014, "Elastically Stretchable Fabric Force Sensor Arrays and Methods of Making"); U.S. Pat. No. 8,665,241 (Heubel et al., Mar. 4, 2014, "System and Method for Providing Haptic Feedback from Haptic Textile"); U.S. Pat. No. 8,678,979 (Stark et al., Mar. 25, 2014, "Remote Monitoring of a Patient"); U.S. Pat. No. 8,784,342 (Hyde et al., Jul. 22, 2014, "Shape Sensing Clothes to Inform the Wearer of a Condition"); U.S. Pat. No. 8,904,876 (Taylor et al., Dec. 9, 2014, "Flexible Piezocapacitive and Piezoresistive Force and Pressure Sensor"); and U.S. Pat. No. 8,932,236 (McKeon et al., Jan. 13, 2015, "Monitoring Posture").

Examples of prior art which appear to be within this category include the following U.S. patent applications: 20010020140 (Kramer, Sep. 6, 2001, "Device and Method for Measuring the Position of Animate Links"); 20020088931 (Danisch et al., Jul. 11, 2002, "Topological and Motion Measuring Tool"); 20020151824 (Fischer, Oct. 17, 2002, "Posture Measurement and Feedback Instrument for Seated Occupations"); 20020198472 (Kramer, Dec. 26, 2002, "Determination of Finger Position"); 20030083596 (Kramer et al., May 1, 2003, "Goniometer-Based Body-Tracking Device and Method"); 20050126026 (Townsend et al., Jun. 16, 2005, "Posture and Body Movement Measuring System"); 20060130347 (Bergamasco et al., Jun. 22, 2006, "Device for Gioniometric Measurements"); 20060217233 (Lee, Sep. 28, 2006, "Apparatus and Method for Lower-Limb Rehabilitation Training Using Weight Load and Joint Angle as Variables"); 20070169364 (Townsend et al., Jul. 26, 2007, "Posture and Body Movement Measuring System"); 20070256502 (Aebersold et al., Nov. 8, 2007, "MEMS Capacitive Bending and Axial Strain Sensor"); and 20090188325 (Aebersold et al., Jul. 30, 2009, "MEMS Capacitive Bending and Axial Strain Sensor").

Examples of prior art in this category also include U.S. patent applications: 20090278791 (Slycke et al., Nov. 12, 2009, "Motion Tracking System"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); and 20100228487 (Leuthardt et al., Sep. 9, 2010, "Postural Information System and Method").

Examples of prior art in this category also include U.S. patent applications: 20100228488 (Leuthardt et al., Sep. 9, 2010, "Postural Information System and Method"); 20100228489 (Leuthardt et al., Sep. 9, 2010, "Postural Information System and Method"); 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); and 20110046518 (Fischer, Feb. 24, 2011, "Posture Assessment and Feedback Instrument").

Examples of prior art in this category also include U.S. patent applications: 20110046915 (Hol et al., Feb. 24, 2011, "Use of Positioning Aiding System for Inertial Motion Capture"); 20110052005 (Selner, Mar. 3, 2011, "Designation of a Characteristic of a Physical Capability by Motion Analysis, Systems and Methods"); 20110208444 (Solinsky, Aug. 25, 2011, "System and Method for Measuring Balance and Track Motion in Mammals"); 20110248773 (Poupyrev et al., Oct. 13, 2011, "System and Method for Sensing Human Activity by Monitoring Impedance"); 20120089348 (Perlin et al., Apr. 12, 2012, "Sensor Having a Set of Plates, and Method"); 20120116257 (Leuthardt et al., May 10, 2012, "Postural Information System and Method Including Determining Response to Subject Advisory Information"); 20120323501 (Sarrafzadeh et al., Dec. 20, 2012, "Fabric-Based Pressure Sensor Arrays and Methods for Data Analysis"); and 20120323501 (Sarrafzadeh et al., Dec. 20, 2012, "Fabric-Based Pressure Sensor Arrays and Methods for Data Analysis").

Examples of prior art in this category also include U.S. patent applications: 20130113506 (Poupyrev et al., May 9, 2013, "System and Method for Sensing Human Activity by Monitoring Impedance"); 20130275057 (Perlin et al., Oct. 17, 2013, "Sensor Having a Mesh Layer with Protrusions, and Method"); 20130324888 (Solinsky, Dec. 5, 2013, "System and Method for Measuring Balance and Track Motion in Mammals"); 20140172134 (Meschter, Jun. 19, 2014, "Apparel Having Sensor System"); 20140342844 (Mooney, Nov. 20, 2014, "Apparatus and Method for Analysing a Golf Swing"); and 20150005608 (Evans et al., Jan. 1, 2015, "Electrode Units for Sensing Physiological Electrical Activity").

10. Wearable Light Energy Bend Sensors

Prior art in this category uses one or more light energy bend sensors which are worn on the body in order to estimate and/or model body motion, posture, and/or configuration. Many of the examples in this category are fiber optic channels which detect bending by changes in light transmitted through these channels. Although the present invention discloses novel configurations and methods for incorporating bend sensors into an article of clothing which are not disclosed by the prior art, this category of prior art is relevant to the present invention and thus specific examples are now listed.

Examples of prior art which appear to be within this category include the following U.S. patents: U.S. Pat. No. 4,542,291 (Zimmerman, Sep. 17, 1985, "Optical Flex Sensor"); U.S. Pat. No. 5,184,009 (Wright et al., Feb. 2, 1993, "Optical Attenuator Movement Detection System"); U.S. Pat. No. 5,280,265 (Kramer et al., Jan. 18, 1994, "Strain-Sensing Goniometers, Systems and Recognition Algorithms"); U.S. Pat. No. 5,442,729 (Kramer et al., Aug. 15, 1995, "Strain-Sensing Goniometers, Systems and Recognition Algorithms"); U.S. Pat. No. 5,592,401 (Kramer, Jan. 7, 1997, "Accurate, Rapid, Reliable Position Sensing using Multiple Sensing Technologies"); U.S. Pat. No. 5,676,157 (Kramer, Oct. 14, 1997, "Determination of Kinematically Constrained Multi-Articulated Structures"); U.S. Pat. No. 5,694,497 (Sansone, Dec. 2, 1997, "Intrinsically Self Deforming Fiber Optic Microbend Pressure and Strain Sensor"); U.S. Pat. No. 5,813,406 (Kramer et al., Sep. 29, 1998, "Strain-Sensing Goniometers, Systems and Recognition Algorithms"); U.S. Pat. No. 5,930,741 (Kramer, Jul. 27, 1999, "Accurate, Rapid, Reliable Position Sensing using Multiple Sensing Technologies"); U.S. Pat. No. 6,003,340 (Borak et al., Dec. 21, 1999, "Method of Putting a Bend Into a Fiber to Make a Strain Sensor"); and U.S. Pat. No. 6,035,274 (Kramer et al., Mar. 7, 2000, "Strain-Sensing Goniometers, Systems and Recognition Algorithms").

Examples of prior art in this category also include U.S. patents: U.S. Pat. No. 6,042,555 (Kramer et al., Mar. 28, 2000, "Force-Feedback Interface Device for the Hand"); U.S. Pat. No. 6,050,962 (Kramer et al., Apr. 18, 2000, "Goniometer-Based Body-Tracking Device and Method"); U.S. Pat. No. 6,104,379 (Petrich et al., Aug. 15, 2000, "Forearm-Supported Exoskeleton Hand-Tracking Device"); U.S. Pat. No. 6,110,130 (Kramer, Aug. 29, 2000, "Exoskeleton Device for Directly Measuring Fingertip Position and Inferring Finger Joint Angle"); U.S. Pat. No. 6,127,672 (Danisch, Oct. 3, 2000, "Topological and Motion Measuring Tool"); U.S. Pat. No. 6,148,280 (Kramer, Nov. 14, 2000, "Accurate, Rapid, Reliable Position Sensing using Multiple Sensing Technologies"); U.S. Pat. No. 6,162,190 (Kramer, Dec. 19, 2000, "Determination of Kinematically Constrained Multi-Articulated Structures"); U.S. Pat. No. 6,304,840 (Vance et al., Oct. 16, 2001, "Fingerless Glove for Interacting with Data Processing System"); U.S. Pat. No. 6,389,187 (Greenaway et al., May 14, 2002, "Optical Fiber Bend Sensor"); U.S. Pat. No. 6,413,229 (Kramer et al., Jul. 2, 2002, "Force-Feedback Interface Device for the Hand"); U.S. Pat. No. 6,428,490 (Kramer et al., Aug. 6, 2002, "Goniometer-Based Body-Tracking Device and Method"); U.S. Pat. No. 6,429,421 (Meller et al., Aug. 6, 2002, "Flexible Fiber Optic Microbend Device, with Interlocking Flexible Fibers, Sensors, and Method Use"); U.S. Pat. No. 6,497,672 (Kramer, Dec. 24, 2002, "Device and Method for Measuring the Position of Animate Links"); U.S. Pat. No. 6,563,107 (Danisch et al., May 13, 2003, "Topological and Motion Measuring Tool"); and U.S. Pat. No. 6,621,948 (Devenyi, Sep. 16, 2003, "Apparatus and Method for Differential Output Optical Fiber Displacement Sensing").

Examples of prior art in this category also include U.S. patents: U.S. Pat. No. 6,701,296 (Kramer et al., Mar. 2, 2004, "Strain-Sensing Goniometers, Systems, and Recognition Algorithms"); U.S. Pat. No. 6,728,431 (Ames et al., Apr. 27, 2004, "Fiber Optic Curvature Sensor for Towed Hydrophone Arrays"); U.S. Pat. No. 6,866,643 (Kramer, Mar. 15, 2005, "Determination of Finger Position"); U.S. Pat. No. 6,940,062 (Kwon et al., Sep. 6, 2005, "Optical Fiber Curvature Sensor for Measuring Body Motion and Its Adhesive Method"); U.S. Pat. No. 7,070,571 (Kramer et al., Jul. 4, 2006, "Goniometer-Based Body-Tracking Device"); U.S. Pat. No. 7,324,714 (Cranch et al., Jan. 29, 2008, "Multicore Fiber Curvature Sensor"); U.S. Pat. No. 7,413,802 (Karayianni et al., Aug. 19, 2008, "Energy Active Composite Yarn, Methods for Making the Same, and Articles Incorporating the Same"); U.S. Pat. No. 7,630,591 (Allen et al., Dec. 8, 2009, "Optical Fiber Substrate Useful as a Sensor or Illumination Device Component"); U.S. Pat. No. 7,665,288 (Karayianni et al., Feb. 23, 2010, "Energy Active Composite Yarn, Methods for Making the Same and Articles Incorporating the Same"); and U.S. Pat. No. 7,771,318 (Narayanaswami, Aug. 10, 2010, "Device for Monitoring a User's Posture").

Examples of prior art in this category also include U.S. patents: U.S. Pat. No. 7,772,541 (Froggatt et al., Aug. 10, 2010, "Fiber Optic Position and/or Shape Sensing Based on Rayleigh Scatter"); U.S. Pat. No. 7,781,724 (Childers et al., Aug. 24, 2010, "Fiber Optic Position and Shape Sensing Device and Method Relating Thereto"); U.S. Pat. No. 7,815,376 (Rogers et al., Oct. 19, 2010, "Fixture for Shape-Sensing Optical Fiber in a Kinematic Chain"); U.S. Pat. No. 7,850,574 (Narayanaswami, Dec. 14, 2010, "Device for Monitoring a User's Posture"); U.S. Pat. No. 7,901,756 (Burr et al., Mar. 8, 2011, "Functional Elastic Textile Structures"); U.S. Pat. No. 7,902,095 (Hassonjee et al., Mar. 8, 2011, "Functional Textile Structures"); U.S. Pat. No. 7,911,620 (Digonnet et al., Mar. 22, 2011, "Optical Utilizing Hollow-Core Photonic Bandgap Fiber with Low Phase Thermal Constant"); U.S. Pat. No. 7,930,065 (Larkin et al., Apr. 19, 2011, "Robotic Surgery System Including Position Sensors using Fiber Bragg Gratings"); U.S. Pat. No. 7,999,946 (Andersen et al., Aug. 16, 2011, "Fiber Optic Particle Motion Sensor System"); U.S. Pat. No. 8,068,231 (Digonnet, Nov. 29, 2011, "Fiber Optic Sensor using a Bragg Fiber"); U.S. Pat. No. 8,116,601 (Prisco, Feb. 14, 2012, "Fiber Optic Shape Sensing"); U.S. Pat. No. 8,151,648 (Yu et al., Apr. 10, 2012, "Ultra-Miniature Fiber-Optic Pressure Sensor System and Method of Fabrication"); U.S. Pat. No. 8,162,857 (Lanfermann et al., Apr. 24, 2012, "Limb Movement Monitoring System"); and U.S. Pat. No. 8,182,158 (Rogers et al., May 22, 2012, "Fixture for Shape-Sensing Optical Fiber in a Kinematic Chain").

Examples of prior art in this category also include U.S. patents: U.S. Pat. No. 8,206,325 (Najafi et al., Jun. 26, 2012, "Ambulatory System for Measuring and Monitoring Physical Activity and Risk of Falling and for Automatic Fall Detection"); U.S. Pat. No. 8,233,151 (Digonnet, Jul. 31, 2012, "Fiber Optic Sensor using a Hollow Core Fiber"); U.S. Pat. No. 8,240,207 (Andersen et al., Aug. 14, 2012, "Fiber Optic Particle Motion Sensor and Measuring Method using the Sensor"); U.S. Pat. No. 8,358,883 (Prisco, Jan. 22, 2013, "Fiber Optic Shape Sensor"); U.S. Pat. No. 8,395,109 (Muraysky, Mar. 12, 2013, "Motion Sensor for Detecting Bending or Pivoting"); U.S. Pat. No. 8,427,651 (Digonnet, Apr. 23, 2013, "Optical using a Hollow Core Waveguide"); U.S. Pat. No. 8,520,472 (Murray et al., Aug. 27, 2013, "Compact Laser Sensors and Monitoring Systems Including Such Sensor"); U.S. Pat. No. 8,616,782 (Rogers et al., Dec. 31, 2013, "Fixture for Shape-Sensing Optical Fiber in a Kinematic Chain"); U.S. Pat. No. 8,655,117 (Donlagic et al., Feb. 18, 2014, "Optical Fiber Sensors Having Long Active Lengths, Systems, and Methods"); U.S. Pat. No. 8,780,339 (Udd, Jul. 15, 2014, "Fiber Shape Sensing Systems and Methods"); and U.S. Pat. No. 8,784,303 (Laby et al., Jul. 22, 2014, "System for Controlling an Instrument Using Shape Sensor").

Examples of prior art which appear to be within this category include the following U.S. patent applications: 20010020140 (Kramer, Sep. 6, 2001, "Device and Method for Measuring the Position of Animate Links"); 20020024656 (Kwon et al., Feb. 28, 2002, "Optical Fiber Curvature Sensor for Measuring Body Motion and Its Adhesive Method"); 20020088931 (Danisch et al., Jul. 11, 2002, "Topological and Motion Measuring Tool"); 20020198472 (Kramer, Dec. 26, 2002, "Determination of Finger Position"); 20030083596 (Kramer et al., May 1, 2003, "Goniometer-Based Body-Tracking Device and Method"); 20100036288 (Lanfermann et al., Feb. 11, 2010, "Limb Movement Monitoring System"); 20100183297 (Barboutis et al., Jul. 22, 2010, "Optical Fiber Sensor Having Electrical Connectors"); 20100198113 (Coulston, Aug. 5, 2010, "Extended Optical Range Reflective System for Monitoring Motion of a Member"); and 20100225473 (Leuthardt et al., Sep. 9, 2010, "Postural Information System and Method").

Examples of prior art in this category also include U.S. patent applications: 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); 20100225491 (Leuthardt et al., Sep. 9, 2010, "Postural Information System and Method"); 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); and 20100228158 (Leuthardt et al., Sep. 9, 2010, "Postural Information System and Method Including Device Level Determining of Subject Advisory Information Based on Subject Status Information and Postural Influencer Status Information").

Examples of prior art in this category also include U.S. patent applications: 20100228159 (Leuthardt et al., Sep. 9, 2010, "Postural Information System and Method"); 20100228487 (Leuthardt et al., Sep. 9, 2010, "Postural Information System and Method"); 20100228488 (Leuthardt et al., Sep. 9, 2010, "Postural Information System and Method"); 20100228489 (Leuthardt et al., Sep. 9, 2010, "Postural Information System and Method"); 20100228490 (Leuthardt et al., Sep. 9, 2010, "Postural Information System and Method"); 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); and 20100228494 (Leuthardt et al., Sep. 9, 2010, "Postural Information System and Method Including Determining Subject Advisory Information Based on Prior Determined Subject Advisory Information").

Examples of prior art in this category also include U.S. patent applications: 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); 20120116257 (Leuthardt et al., May 10, 2012, "Postural Information System and Method Including Determining Response to Subject Advisory Information"); and 20140031698 (Moon et al., Jan. 30, 2014, "Apparatus and Method for Sensing Bone Position and Motion").

11. Wearable Sonic Energy Bend Sensors

Prior art in this category uses one or more sound energy bend sensors which are worn on the body in order to estimate and/or model body motion, posture, and/or configuration. There appear to be fewer examples of bend sensors using sound energy than those using electromagnetic energy or light energy, but there are some examples. Generally these examples use ultrasonic energy. Although the present invention discloses novel configurations and methods for incorporating bend sensors into an article of clothing which are not disclosed by the prior art, this category of prior art is relevant to the present invention and thus specific examples are now listed.

Examples of prior art which appear to be within this category include the following U.S. patents: U.S. Pat. No. 5,469,861 (Piscopo et al., Nov. 28, 1995, "Posture Monitor"); U.S. Pat. No. 5,592,401 (Kramer, Jan. 7, 1997, "Accurate, Rapid, Reliable Position Sensing using Multiple Sensing Technologies"); U.S. Pat. No. 6,148,280 (Kramer, Nov. 14, 2000, "Accurate, Rapid, Reliable Position Sensing using Multiple Sensing Technologies"); U.S. Pat. No. 6,409,687 (Foxlin, Jun. 25, 2002, "Motion Tracking System"); U.S. Pat. No. 7,395,181 (Foxlin, Jul. 1, 2008, "Motion Tracking System"); U.S. Pat. No. 7,628,074 (Vannucci et al., Dec. 8, 2009, "System and Method for Motion Capture in Natural Environments"); and U.S. Pat. No. 8,784,342 (Hyde et al., Jul. 22, 2014, "Shape Sensing Clothes to Inform the Wearer of a Condition").

Examples of prior art which appear to be within this category include the following U.S. patent applications: 20030036858 (Friedrichs et al., Feb. 20, 2003, "Apparatus for Deformation and/or Movement Detection"); 20030045816 (Foxlin, Mar. 6, 2003, "Motion Tracking System"); 20080223131 (Vannucci et al., Sep. 18, 2008, "System and Method for Motion Capture in Natural Environments"); 20100225473 (Leuthardt et al., Sep. 9, 2010, "Postural Information System and Method"); 20100225474 (Leuthardt et al., Sep. 9, 2010, "Postural Information System and Method"); 20100225490 (Leuthardt et al., Sep. 9, 2010, "Postural Information System and Method Including Central Determining of Subject Advisory Information Based on Subject Status Information and Postural Influencer Status Information"); and 20100225491 (Leuthardt et al., Sep. 9, 2010, "Postural Information System and Method").

Examples of prior art in this category also include U.S. patent applications: 20100225498 (Leuthardt et al., Sep. 9, 2010, "Postural Information System and Method"); 20100228153 (Leuthardt et al., Sep. 9, 2010, "Postural Information System and Method"); 20100228154 (Leuthardt et al., Sep. 9, 2010, "Postural Information System and Method Including Determining Response to Subject Advisory Information"); 20100228158 (Leuthardt et al., Sep. 9, 2010, "Postural Information System and Method Including Device Level Determining of Subject Advisory Information Based on Subject Status Information and Postural Influencer Status Information"); 20100228159 (Leuthardt et al., Sep. 9, 2010, "Postural Information System and Method"); 20100228487 (Leuthardt et al., Sep. 9, 2010, "Postural Information System and Method"); 20100228488 (Leuthardt et al., Sep. 9, 2010, "Postural Information System and Method"); 20100228489 (Leuthardt et al., Sep. 9, 2010, "Postural Information System and Method"); and 20100228490 (Leuthardt et al., Sep. 9, 2010, "Postural Information System and Method").

Examples of prior art in this category also include U.S. patent applications: 20100228492 (Leuthardt et al., Sep. 9, 2010, "Postural Information System and Method Including Direction Generation Based on Collection of Subject Advisory Information"); 20100228493 (Leuthardt et al., Sep. 9, 2010, "Postural Information System and Method Including Direction Generation Based on Collection of Subject Advisory Information"); 20100228494 (Leuthardt et al., Sep. 9, 2010, "Postural Information System and Method Including Determining Subject Advisory Information Based on Prior Determined Subject Advisory Information"); 20100228495 (Leuthardt et al., Sep. 9, 2010, "Postural Information System and Method Including Determining Subject Advisory Information Based on Prior Determined Subject Advisory Information"); 20100271200 (Leuthardt et al., Oct. 28, 2010, "Postural Information System and Method Including Determining Response to Subject Advisory Information"); and 20120116257 (Leuthardt et al., May 10, 2012, "Postural Information System and Method Including Determining Response to Subject Advisory Information").

SUMMARY OF THIS INVENTION

The sensor array disclosed herein, which can be part of Motion Recognition Clothing™, longitudinally spans a body joint in order to measure movement of that body joint. In an example, this sensor array can comprise four longitudinal sensors which span the body joint in four different radial quadrants, respectively. In an example, this sensor array can comprise six longitudinal sensors which span the body joint in six different radial hextants, respectively. In an example, this sensor array can further comprise a first accelerometer which is proximal to the body joint and a second accelerometer which is distal to the body joint.

BRIEF INTRODUCTION TO THE FIGURES

Figure 32:
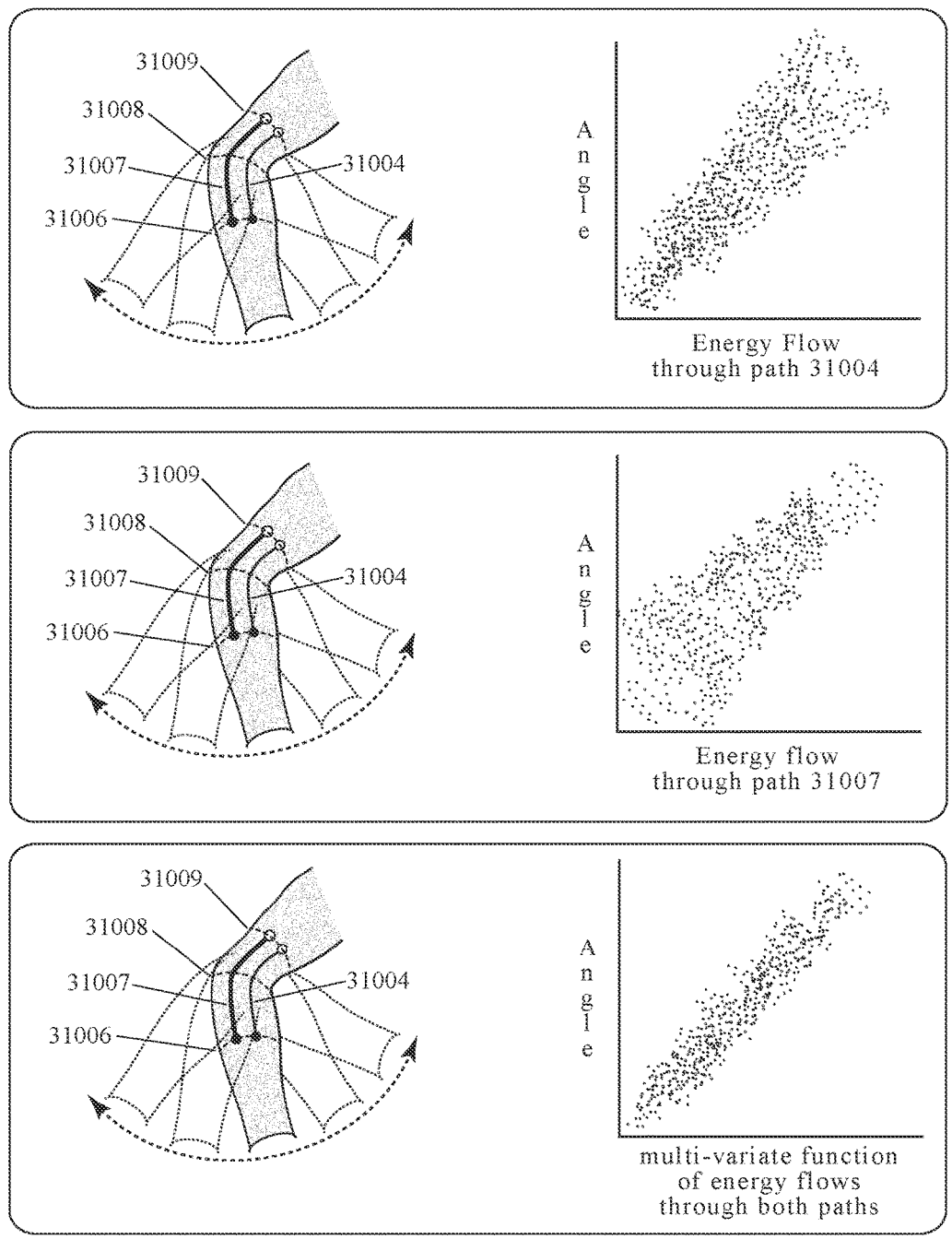

FIG. 32 graphically demonstrates how multivariate analysis of energy flows through two pathways can estimate body joint movement more accurately than analysis of energy flow through either pathway alone.

Figure 33:
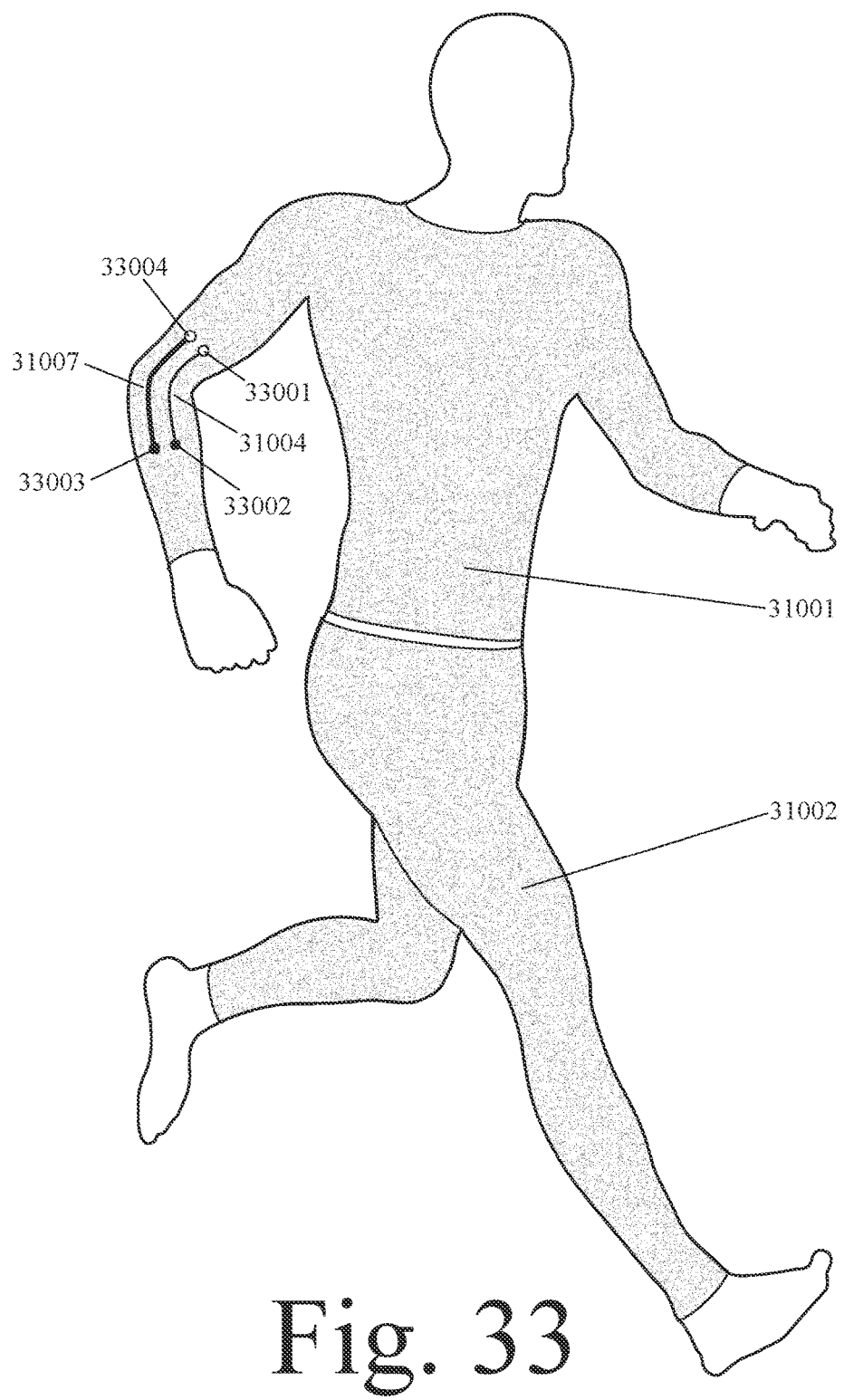

FIG. 33 shows a detailed view of flexible energy pathways including energy emitters and sensors.

Figure 34:
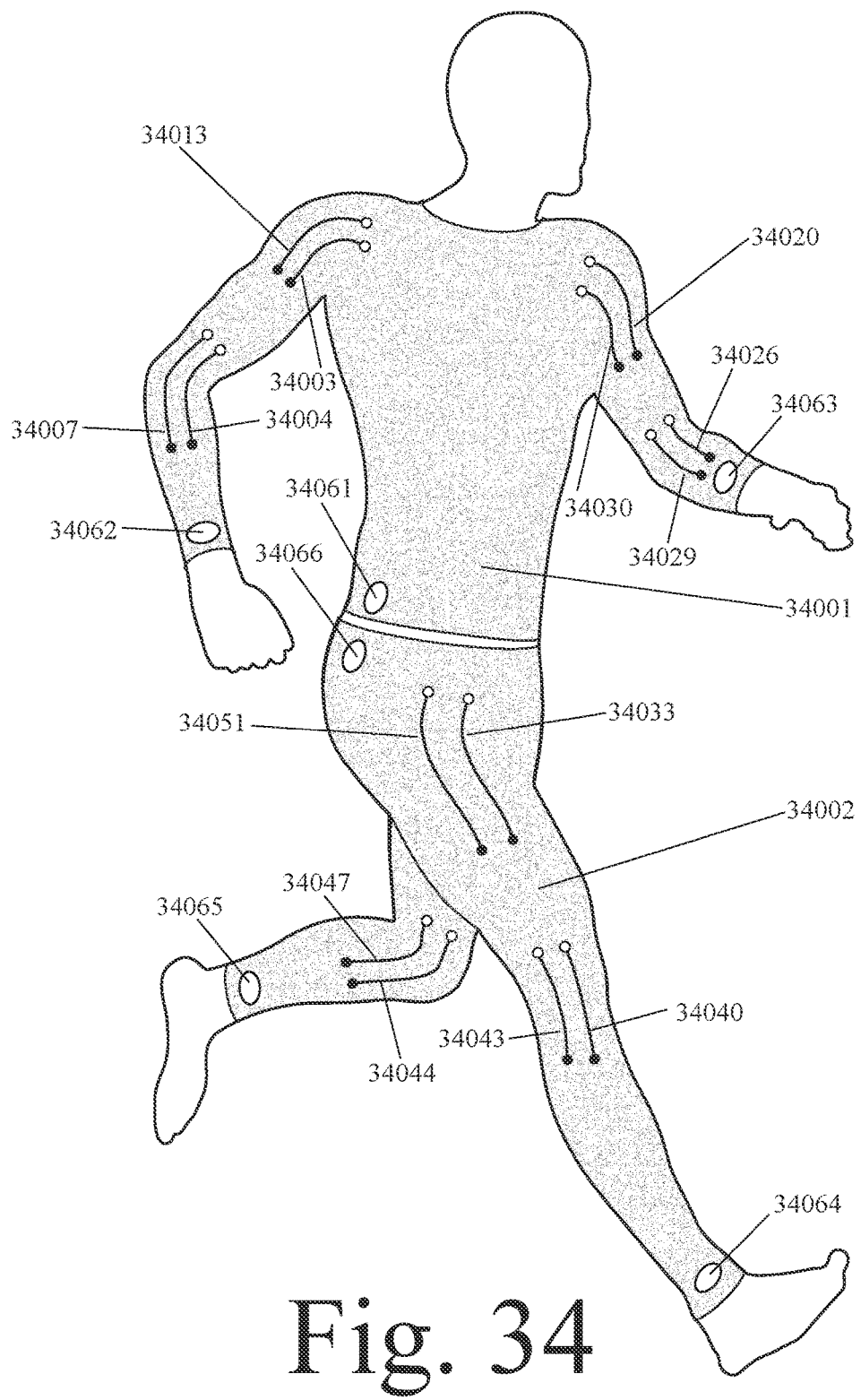

FIG. 34 shows an example which includes inertial sensors as well as flexible energy pathways.

Figure 35:
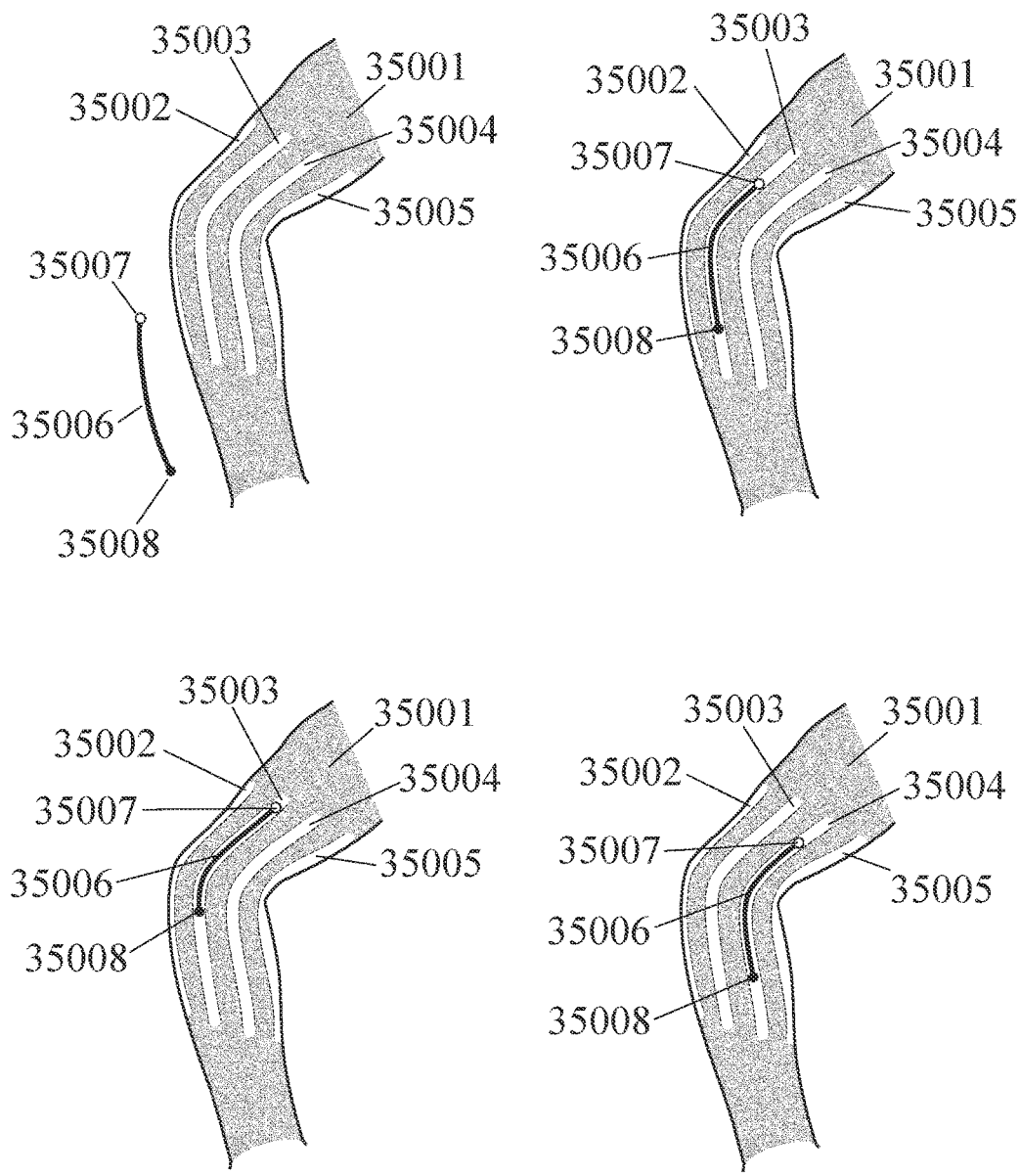

FIG. 35 shows an example with at least one modular flexible energy pathway.

Figure 36:
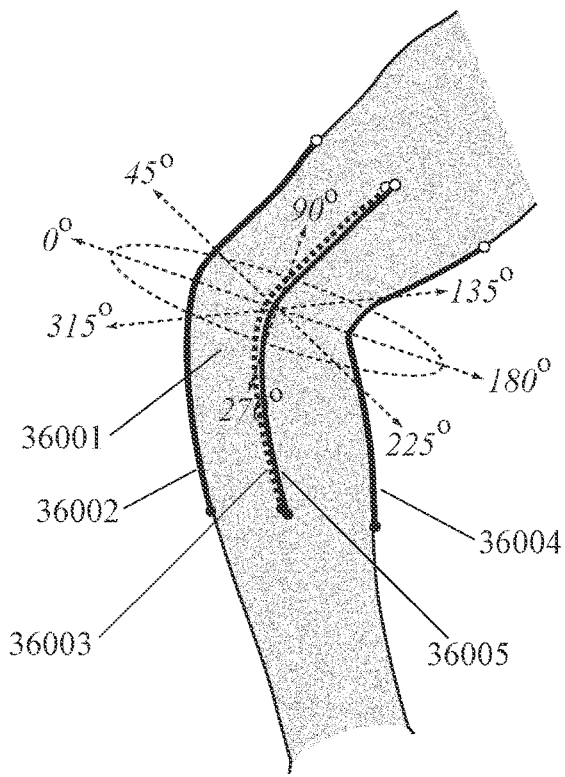
Figure 37:
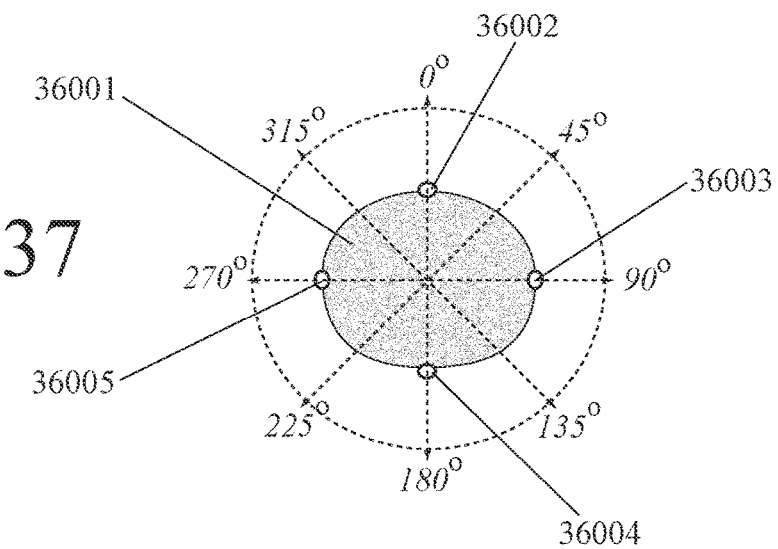

FIGS. 36 and 37 show an example of how this invention can be embodied in an array of four longitudinal sensors to measure movement of a body joint.

Figure 38:
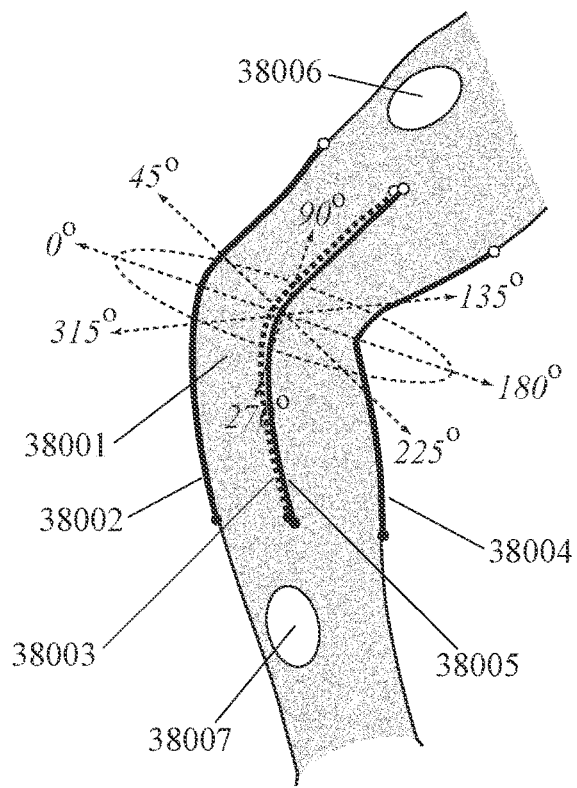
Figure 39:
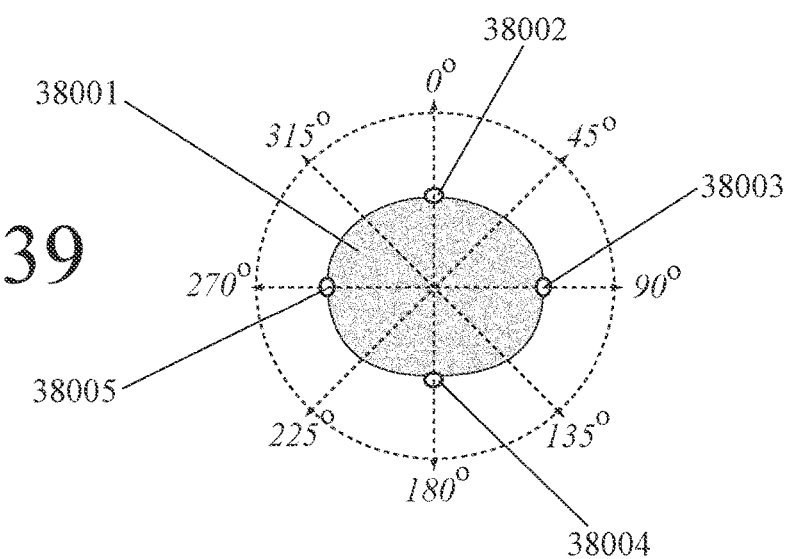

FIGS. 38 and 39 show an example like that in FIGS. 36 and 37, except that it also includes two accelerometers.

Figure 40:
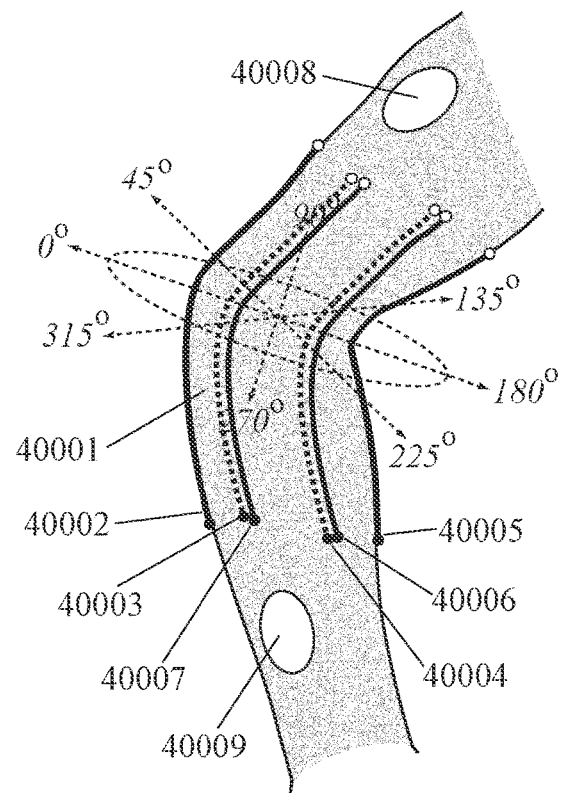
Figure 41:
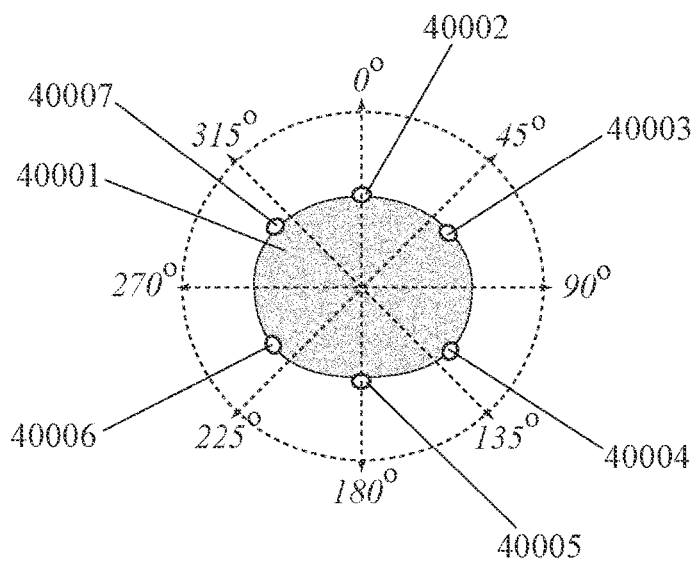

FIGS. 40 and 41 show an example like that in FIGS. 38 and 39, except that it has six longitudinal sensors instead of four.

DETAILED DESCRIPTION OF THE FIGURES

This invention comprises a sensor array, which can be part of Motion Recognition Clothing™, with redundant electromagnetic, light, or sonic energy pathways which measure body joint motion and/or configuration. In an example, this motion recognition clothing can comprise multiple sets of redundant energy pathways, wherein each set spans a body joint. As body joints move—they bend, stretch, elongate, and/or twist the energy pathways which span these joints. This bending, stretching, elongation, and/or twisting of the energy pathways changes the flows of energy through these energy pathways. These changes in energy flows are, in turn, measured by energy sensors and analyzed together to estimate the motions and/or configurations of body joints.

Multivariate analysis of data from redundant energy pathways spanning the same body joint can provide more accurate measurement of the motion and/or configuration of this body joint than data from a single energy pathway. When combined into full-body motion recognition clothing, multiple sets of redundant energy pathways can enable minimally-intrusive, ambulatory, full-body motion capture that does not confine a person to a narrow location in front of a camera. Such motion recognition clothing opens up opportunities for full-body motion capture of outdoor and large-scale activities such as playing golf, running, swimming, playing soccer and playing basketball.

In an example, this invention can be embodied in a wearable device for measuring body joint motion and/or configuration comprising: (a) a first energy pathway, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor which measures energy flow through or from the first energy pathway; (c) a second energy pathway, wherein this second energy pathway is configured to span the surface of the portion of a person's body which contains the at least one body joint, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor which measures energy flow through or from the second energy pathway, wherein data from the first energy sensor and data from the second energy sensor are analyzed together in order to measure the motion and/or configuration of the at least one body joint.

In an example, a first energy pathway and a second energy pathway can each have a longitudinal axis. In an example, a longitudinal axis of an energy pathway can span the surface of a body member containing a body joint in a proximal-to-distal manner. In this disclosure, the term "proximal" refers to locations in (or on) the person's body which are closer to the person's mass centroid or the person's heart. The term "distal" refers to locations in (or on) the person's body which are further from the person's mass centroid or the person's heart. In an example, a longitudinal axis of an energy pathway can span the surface of a body member containing a body joint in a circumferential or cross-sectional manner.

In an example, the geometric relationship between the longitudinal axis of a first energy pathway and the longitudinal axis of a second energy pathway can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially-parallel as they span a distal portion of a joint and diverging as they span a proximal portion of a joint; substantially-parallel as they span a proximal portion of a joint and diverging as they span a distal portion of a joint; substantially perpendicular; intersecting at an acute angle; forming vectors which intersect in 3D space at an acute angle; substantially diagonal to each other; plaited together; woven together; braided together; combining to form a 3D lattice, mesh, or grid; differing in length; nested; forming a rainbow arc configuration; radial vectors with a common point of convergence; straight vectors with a common convergence point; and arcuate elements with a common convergence point.

In an example, the motion and/or configuration of a body joint can be measured using multiple energy pathways which span a portion of the body member which contains the body joint, wherein these energy pathways span longitudinally-sequential cross-sectional perimeters of the body member along selected radial angles or polar coordinates. In an example, the motion and/or configuration of a body joint can be measured using multiple energy pathways which span a portion of the body member which contains the body joint, wherein these energy pathways span longitudinally-sequential cross-sectional perimeters of the body member along radial angles or polar coordinates which are evenly distributed around the 0 to 360 degree range. In an example, the motion and/or configuration of a body joint can be measured using two energy pathways which span a portion of the body member which contains the body joint, wherein these two energy pathways span longitudinally-sequential cross-sectional perimeters of the body member along radial angles or polar coordinates of approximately 0 degrees and 180 degrees. In an example, the 0-degree pathway can span the dorsal surface of the body member and the 180-degree member can span the ventral surface of the body member.

In an example, the motion and/or configuration of a body joint can be measured using four energy pathways which span a portion of the body member which contains the body joint, wherein these four energy pathways span longitudinally-sequential cross-sectional perimeters of the body member along radial angles or polar coordinates of approximately 0, 90, 180, and 270 degrees. In an example, the 0-degree pathway can span the dorsal surface of the body member, the 180-degree member can span the ventral surface of the body member, and the 90 and 270 degree pathways can span the lateral surfaces of the body member. In an example, a first energy pathway can span the dorsal surface of a body member containing a body joint, a second energy pathway can span the ventral surface of that body member, a third energy pathway can span a first lateral surface of that body member, and a fourth energy pathway can span a second lateral surface of that body member.

In an example, the motion and/or configuration of a body joint can be measured using six energy pathways which span a portion of the body member which contains the body joint, wherein these six energy pathways span longitudinally-sequential cross-sectional perimeters of the body member along radial angles or polar coordinates of approximately 0, 60, 120, 180, 240, and 300 degrees. In an example, the motion and/or configuration of a body joint can be measured using eight energy pathways which span a portion of the body member which contains the body joint, wherein these eight energy pathways span longitudinally-sequential cross-sectional perimeters of the body member along radial angles or polar coordinates of approximately 0, 45, 90, 135, 180, 225, 270, and 315 degrees.

In an example, the motion and/or configuration of a body joint can be measured using multiple energy pathways which span a portion of the body member which contains the body joint, wherein these energy pathways span the body member in a substantially parallel manner when the body joint is fully extended. In an example, the motion and/or configuration of a body joint can be measured using multiple energy pathways which span a portion of the body member which contains the body joint, wherein these energy pathways span the body member in a substantially parallel manner. In an example, the motion and/or configuration of a body joint can be measured using multiple energy pathways which span a portion of the body member which contains the body joint, wherein these energy pathways each have central longitudinal axes and wherein these central longitudinal axes are substantially parallel. In an example, the motion and/or configuration of a body joint can be measured using multiple energy pathways which span a portion of the body member which contains the body joint, wherein these energy pathways span the body member along substantially-parallel straight vectors.

In an example, the motion and/or configuration of a body joint can be measured using multiple energy pathways which span a portion of the body member which contains the body joint, wherein the distances between pairs of energy pathways are substantially constant as they span the body member. In an example, the motion and/or configuration of a body joint can be measured using multiple energy pathways which span a portion of the body member which contains the body joint, wherein these energy pathways span the body member along substantially-parallel actuate vectors. In an example, the motion and/or configuration of a body joint can be measured using multiple energy pathways which span a portion of the body member which contains the body joint, wherein these energy pathways span the body member in a nested or concentric manner with substantially constant distances between pairs of nested or concentric energy pathways.

In an example, two energy pathways spanning the same body joint can differ in the angles at which they span the longitudinal axis of the body member which contains the body joint. In an example, having different energy pathways span a body joint at different angles can be especially useful for measuring the motion and/or configuration of ball-and-socket or other complex motion joints. In an example, two energy pathways can have longitudinal axes which are substantially perpendicular as they span the body member which contains a body joint. In an example, multiple energy pathways spanning the same body joint can form inter-pathway areas which, when projected from 3D space onto a 2D plane, are squares or rectangles. In an example, two energy pathways can be woven together in a substantially-parallel manner to form a textile wherein this textile is then used to make a garment which spans a portion of a body member in a curvaceous 3D manner. In an example, two energy pathways can be woven together in a substantially-perpendicular manner to form a textile wherein this textile is then used to make a garment which spans a portion of a body member in a curvaceous 3D manner. In an example, two energy pathways can have longitudinal axes which intersect at acute angles as they span the body member which contains a body joint.

In an example, multiple energy pathways spanning the same body joint can form inter-pathway areas which, when projected from 3D space onto a 2D plane, are rhombuses, diamonds, trapezoids, parallelograms, triangles, or hexagons. In an example, energy pathways can be part of a mesh which is an array of one or more shapes selected from the group consisting of: square elements; rectangular elements; diamond elements; rhomboid elements; parallelogram elements; trapezoidal elements; triangular elements; hexagonal elements; circular elements; and elliptical elements.

In an example, a first energy pathway and a second energy pathway can each have a circular, semi-circular, or other conic section shape axis. In an example, a circular, semi-circular, or other conic section shape axis can span all or part of the cross-sectional perimeter of a body member containing a body joint. In an example, one or more aspects of the geometric relationship between these two axes can be selected from the group consisting of: substantially parallel; separated by a substantially-constant distance; intersecting at an acute angle; forming vectors which intersect in 3D space at an acute angle; combining to form a 3D mesh or grid; differing in length; substantially concentric; nested; differing in diameter; knitted together in loops; and tangential.

In an example, a first energy pathway can have an axis which spans a body member in a longitudinal manner and a second energy pathway can have an axis which spans the same body member in a circular, semi-circular, or other conic sectional manner. In an example, the first energy pathway can span the surface of a body member containing a body joint in a proximal-to-distal manner. In an example, the second energy pathway can span the surface of the body member in a circular, semi-circular, or other conic sectional manner. In an example, one or more aspects of the geometric relationship between the first energy pathway and the second energy pathway can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh or grid; overlapping; and tangential.

In an example, an energy pathway can have a substantially straight configuration when a joint is fully extended. In an example, an energy pathway can have an arcuate shape, even when a joint is fully extended. In an example, an energy pathway can have a shape comprising a repeating waveform selected from the group consisting of: simple sinusoidal wave; composite sinusoidal wave; saw-tooth wave or zig-zag; and square wave. In an example, an energy pathway can have a shape which is a conic section. In an example, an energy pathway can have a shape which is a spiral or helix. In an example, an energy pathway can have a shape which is a chain of loops.

In an example, the flows of energy through first and second energy pathways can be independent or be separate as these flows span a body member containing a body joint. In an example, the flows of energy through first and second energy pathways can interact or combine with each other as these flows span a body member containing a body joint. In an example, first and second energy pathways can be in electromagnetic communication with each other as they span a body joint. In an example, first and second energy pathways can be in mechanical communication with each other as they span a body joint. In an example, first and second energy pathways can be in optical communication with each other as they span a body joint. In an example, first and second energy pathways can be in sonic communication with each other as they span a body joint.

In an example, first and second energy pathways which span a body member which contains a body joint can differ in the angle at which they span the body member. In an example, combined multivariate analysis of data from both the first and second energy pathways can provide more accurate measurement of body joint motion and/or configuration than data from either the first energy pathway or the second energy pathway alone. In an example, data from the first energy pathway can provide more accurate measurement of body joint motion over a first range of motion and data from the second energy pathway can provide more accurate measurement of body joint motion over a second range of motion. When analyzed together, data from the first and second energy pathways reduce error in measuring the full range of joint motion.

In an example, first and second energy pathways which span a body member which contains a body joint can differ in length. In an example, combined multivariate analysis of data from both the first and second energy pathways can provide more accurate measurement of body joint motion than data from either the first energy pathway or the second energy pathway alone. In an example, data from a longer energy pathway can provide more accurate measurement of body joint motion over a first range of motion and data from a shorter energy pathway can provide more accurate measurement of body joint motion over a second range of motion. When analyzed together, data from the longer and shorter energy pathways reduce error in measuring the full range of joint motion.

In an example, first and second energy pathways which span a body member which contains a body joint can differ in longitudinal curvature or convolution. In an example, combined multivariate analysis of data from both the first and second energy pathways can provide more accurate measurement of body joint motion than data from either the first energy pathway or the second energy pathway alone. In an example, an energy pathway with a sinusoidal, zigzag, or other repeated wave shape can have a higher curvature or convolution if it has a waveform with a larger amplitude or higher wave frequency. In an example, data from a highly curved or convoluted energy pathway can provide more accurate measurement of body joint motion over a first range of motion and data from a less curved or convoluted energy pathway can provide more accurate measurement of body joint motion over a second range of motion. When analyzed together, data from the highly curved or convoluted and the less curved or convoluted energy pathways reduce error in measuring the full range of joint motion.

In an example, first and second energy pathways which span a body member which contains a body joint can differ in flexibility. In an example, combined multivariate analysis of data from both the first and second energy pathways can provide more accurate measurement of body joint motion than data from either the first energy pathway or the second energy pathway alone. In an example, data from a more-flexible energy pathway can provide more accurate measurement of body joint motion over a first range of motion and data from a less-flexible energy pathway can provide more accurate measurement of body joint motion over a second range of motion. When analyzed together, data from the more-flexible and less-flexible energy pathways reduce error in measuring the full range of joint motion.

In an example, first and second energy pathways which span a body member which contains a body joint can differ in elasticity. In an example, combined multivariate analysis of data from both the first and second energy pathways can provide more accurate measurement of body joint motion than data from either the first energy pathway or the second energy pathway alone. In an example, data from a more-elastic energy pathway can provide more accurate measurement of body joint motion over a first range of motion and data from a less-elastic energy pathway can provide more accurate measurement of body joint motion over a second range of motion. When analyzed together, data from the more-elastic and less-elastic energy pathways reduce error in measuring the full range of joint motion.

In an example, first and second energy pathways which span a body member which contains a body joint can differ in electrical resistance or impedance. In an example, combined multivariate analysis of data from both the first and second energy pathways can provide more accurate measurement of body joint motion than data from either the first energy pathway or the second energy pathway alone. In an example, data from a higher resistance or impedance energy pathway can provide more accurate measurement of body joint motion over a first range of motion and data from a lower resistance or impedance energy pathway can provide more accurate measurement of body joint motion over a second range of motion. When analyzed together, data from the higher resistance or impedance and the lower resistance or impedance pathways reduce error in measuring the full range of joint motion.

In an example, first and second energy pathways which span a body member which contains a body joint can differ in transparency. In an example, combined multivariate analysis of data from both the first and second energy pathways can provide more accurate measurement of body joint motion than data from either the first energy pathway or the second energy pathway alone. In an example, data from a higher transparency can provide more accurate measurement of body joint motion over a first range of motion and data from a lower transparency can provide more accurate measurement of body joint motion over a second range of motion. When analyzed together, data from the higher resistance or impedance and the lower resistance or impedance pathways reduce error in measuring the full range of joint motion.

In an example, first and second energy pathways which span a body member which contains a body joint can differ in cross-sectional shape. In an example, combined multivariate analysis of data from both the first and second energy pathways can provide more accurate measurement of body joint motion than data from either the first energy pathway or the second energy pathway alone. In an example, data from a first energy pathway with a first cross-sectional shape can provide more accurate measurement of body joint motion over a first range of motion and data from a second energy pathway with a second cross-sectional shape can provide more accurate measurement of body joint motion over a second range of motion. When analyzed together, data from the first and second energy pathways reduce error in measuring the full range of joint motion.

In an example, a first energy pathway and a second energy pathway which both span the same body member which contains a body joint can differ by one or more parameters selected from the group consisting of: the angle at which they span the body joint; length; longitudinal curvature or convolution; longitudinal waveform; flexibility; elasticity; electrical resistance or impedance; transparency; and cross-sectional shape. In an example, combined multivariate analysis of data from both the first and second energy pathways can provide more accurate measurement of body joint motion than analysis of data from either the first energy pathway or the second energy pathway alone. In an example, data from the first energy pathway can provide more accurate measurement of body joint motion over a first range of motion and data from the second energy pathway can provide more accurate measurement of body joint motion over a second range of motion. When analyzed together, data from the first and second energy pathways reduce error in measuring the full range of joint motion.

In an example, combined, joint, or integrated multivariate analysis of data from multiple energy pathways spanning the same body joint yields measurement of the motion and/or configuration of a body joint with a statistically-significant lower error rate or error range than analysis of data from a single energy pathway spanning that body joint. In an example, combined, joint, or integrated multivariate analysis of data from multiple energy pathways spanning the same body joint yields measurement of the motion and/or configuration of a body joint with a statistically-significant lower error rate or error range than separate analysis of data from those energy pathways. In an example, the statistical significance of error reduction is at the $p<0.05$ level. In an example, statistical significance of error reduction is at the $p<0.01$ level. In an example, estimating the motion and/or configuration of a body joint angle using combined, joint, or integrated multivariate analysis of data from multiple energy pathways spanning that joint can yield an over-determined system of equations for joint angle estimation. This can help to reduce measurement error from factors such as: shifting or sliding of the energy pathways and/or a garment containing the energy pathways over the surface of the body; material fatigue and variability in the energy pathways; and interference between an external object or field and one side of the body member.

In an example, the relationship between energy flow in an energy pathway and the configuration of a body joint spanned by that energy pathway can be nonlinear and/or stochastic. In an example, the relationship between energy flow in an energy pathway and the configuration of a body joint spanned by that energy pathway can be analyzed using one or more multivariate statistical methods. In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through an energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different energy pathways spanning the same body joint can be averaged together in order to improve accuracy and reduce error in the measurement of the motion and/or configuration of that joint. In an example, data from different energy pathways spanning the same body joint can be given different weights during different portions of the joint range of motion in order to improve accuracy and reduce error in the measurement of the motion and/or configuration of that joint. In an example, data from different energy pathways spanning the same body joint can be given different weights during different directions of joint motion (e.g. flexion vs. extension) in order to improve accuracy and reduce error in the measurement of the motion and/or configuration of that joint. In an example, data from different energy pathways spanning the same body joint can be given different weights during different movement speeds (e.g. fast movement vs. slow movement) of joint motion in order to improve accuracy and reduce error in the measurement of the motion and/or configuration of that joint. In an example, data from different energy pathways spanning the same body joint can be given different weights during different numbers of cycle repetition of joint motion in order to improve accuracy and reduce error in the measurement of the motion and/or configuration of that joint.

In an example, data from an energy pathway with anomalous results can be given less weight in order to improve accuracy and reduce error in the measurement of the motion and/or configuration of that joint. In an example, data from different energy pathways can analyzed to identify probable shifting of energy pathway location over the surface of the body (e.g. by shifting of a garment into which the pathways are integrated) and to compensate for this shifting when interpreting data from multiple energy pathways. In an example, data from different energy pathways can analyzed to identify probable loss of mechanical or electromagnetic communication between an energy pathway and the body and to compensate for this loss when interpreting data from multiple energy pathways. In an example, data from different energy pathways can analyzed to identify probable interference by an external object or field and to compensate for this interference when interpreting data from multiple energy pathways.

In an example, this device can be recalibrated in order to maintain accurate measurement of joint motion and/or configuration. In an example, recalibration can comprise comparing the results from using the energy pathways of the device to estimate the motion and/or configuration of a selected body joint or joints with parallel results from an alternative method of estimating joint motion and/or configuration of the body joint or joints. In an example, this device can be recalibrated when it is first worn by a specific person in order to be custom matched to that person's specific anatomy and/or body kinetics. In an example, this device can be recalibrated each time that it is worn in order to control for changing environmental conditions; incorporation into different articles of clothing; changes or shifts in how an article of clothing is worn over a person's body; changes in the anatomy or kinetics of a person's body over time; or other factors. In an example, this device can be recalibrated each time that a particular sequence of movements occurs in order to control for: possible shifts in how the energy pathways span a body member containing a body joint; changes in how material responses to bending, stretching, or elongation with repeated motions; changes in temperature; or other factors. In an example, this device can be recalibrated after a selected number of joint extension and contraction cycles. In an example, this device can be recalibrated after a selected number of movement sequences have occurred. In an example, this device can be recalibrated at selected usage time intervals. In an example, this device can be recalibrated each time that a significant change in environmental factors (such as temperature, humidity, GPS location, or atmospheric pressure) is detected.

In an example, the type of energy which is measured from or through an energy pathway to measure the motion and/or configuration of a body joint can be selected from the group consisting of: electromagnetic energy; light energy; and sonic energy. In an example, (a) the motion and/or configuration of a body joint causes bending, stretching, elongation, and/or twisting of electromagnetic energy pathways which span the surface of the body member which contains this body joint; (b) the bending, stretching, elongation, and/or twisting of these pathways changes the flows of electromagnetic energy through them; (c) changes in these flows are measured by electromagnetic energy sensors; and (d) data from these sensors are used to estimate the motion and/or configuration of the body joint. In an example, changes in the flows of electromagnetic energy can be measured by one or more parameters selected from the group consisting of: voltage, resistance, impedance, amperage, current, phase, and wave pattern. In an example, an electromagnetic energy pathway can be comprised of electroconductive fibers, yarns, threads, strands, substrates, layers, or textiles. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor.

In an example, an electromagnetic energy pathway can be piezoelectric and/or piezoresistive. In an example, an electromagnetic energy pathway can generate electromagnetic energy when it is bent, stretched, elongated, and/or twisted and an electromagnetic energy sensor can measure generated electricity. In an example, the source of energy which flows through or from an energy pathway can be selected from the group consisting of: energy from a power source internal to the device; energy from a power source that is external to the device; and energy which is generated, transduced, or harvested by the device.

In an example, electromagnetic energy can be directed into an energy pathway at a first location and electromagnetic energy from the energy pathway can be measured from the energy pathway at a second location. In an example, wearable energy pathways can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar, latex, linen, Lycra™, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, an electronically-functional textile, fabric, garment, or wearable accessory can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave, or conan weave; array of light-emitting fibers, threads, or yarns; array of sound-conducting members woven using a plain weave, rib weave, basket weave, twill weave, satin weave, leno weave, mock leno weave, leno and conan weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, (a) the motion and/or configuration of a body joint causes bending, stretching, elongation, and/or twisting of light energy pathways which span the surface of the body member which contains this body joint; (b) the bending, stretching, elongation, and/or twisting of these pathways changes the flows of light energy through them; (c) changes in these flows are measured by light energy sensors; and (d) data from these sensors are used to estimate the motion and/or configuration of the body joint. In an example, changes in the flows of light energy can be measured by one or more parameters selected from the group consisting of: intensity, wavelength, spectrum, spectral distribution, phase, coherence, and polarization. In an example, light energy pathway can be comprised of fiber optic members and/or optical bend enhanced fiber. In an example, a light energy sensor can be selected from the group consisting of: photoelectric sensor, photometer, light intensity sensor, camera, infrared light sensor, ultraviolet light sensor, spectroscopy sensor, near-infrared spectroscopy sensor, Raman spectroscopy sensor, spectral analysis sensor, spectrometry sensor, spectrophotometer sensor, optical strain detector, and variable-translucence sensor. In an example, light energy can be directed into an energy pathway at a first location and light energy from the energy pathway can be measured from the energy pathway at a second location.

In an example, (a) the motion and/or configuration of a body joint causes bending, stretching, elongation, and/or twisting of sonic energy pathways which span the surface of the body member which contains this body joint; (b) the bending, stretching, elongation, and/or twisting of these pathways changes the flows of sonic energy through them; (c) changes in these flows are measured by sonic energy sensors; and (d) data from these sensors are used to estimate the motion and/or configuration of the body joint. In an example, changes in the flows of light energy can be measured by one or more parameters selected from the group consisting of: intensity, amplitude, frequency, range, phase, and waveform. In an example, a sonic energy sensor can be a microphone or ultrasonic sensor. In an example, sonic energy can be directed into an energy pathway at a first location and sonic energy from the energy pathway can be measured from the energy pathway at a second location.

In an example, an array of energy pathways can be incorporated into an article of clothing which is, in turn, worn over a body member containing a body joint. Changes in energy conducted through these pathways can be used to estimate joint motion and/or configuration. In an example, an array of energy pathways can be directly attached to a body member containing a body joint. In an example, energy pathways can be incorporated into an article of clothing or directly attached to a body member using one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In an example, energy pathways which measure the motion and/or configuration of one or more body joints can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, an array of energy pathways can measure one or more joint configurations and/or motions selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In an example, this device can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, this device can span the surface of a body member containing the finger and thumb. In an example, this device can span the surface of a body member containing the finger, forearm, thumb and wrist. In an example, this device can span the surface of a body member containing the elbow, forearm and wrist. In an example, this device can span the surface of a body member containing the elbow. In an example, this device can span the surface of the body containing the elbow, forearm, shoulder and spine. In an example, this device can span the surface of a body member containing the hip and knee. In an example, this device can span the surface of a body member containing the spine. In an example, this device can span the surface of a body member containing the ankle, mid-tarsal and toe. In an example, this device can span the surface of the portion of the body containing the neck, shoulder and spine.

In an example, this invention can also include a data control unit which further comprises one or more components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed.

In an example, a data processing component can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory. In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, a power source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy. In an example, a human-to-computer interface can further comprise one or more members selected from the group consisting of: a button, knob, or dial; a display screen; a gesture-recognition interface; a holographic user interface; a microphone; a physical keypad or keyboard; a pressure-sensitive textile array; a spectroscopic sensor; a speech or voice recognition interface; a touch screen; a virtual keypad or keyboard; an electronically-functional textile interface; and an eye gaze tracker. In an example, a computer-to-human interface can further comprise one or more members selected from the group consisting of: a coherent-light image projector; a display screen; a holographic user interface; a laser; a myostimulating member; a neurostimulating member; a non-coherent-light image projector; a speaker or other sound-emitting member; a speech or voice recognition interface; a synthesized voice; a vibrating or other tactile sensation creating member; an electromagnetic energy emitter; an electronically-functional textile interface; an infrared light emitter; an infrared light projector; and an LED or LED array.

In an example, this invention can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, this invention can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, and other electromagnetic sensor.

In an example, this invention can further comprise one or more optical sensors selected from the group consisting of: camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, and variable-translucence sensor. In an example, this invention can further comprise one or more sonic energy sensors selected from the group consisting of: microphone, ultrasonic sensor, acoustic sensor, heart rate sensor, respiration or pulmonary function monitor, respiratory rate sensor, and CPAP monitor.

In an example, this invention can further comprise one or more force-related sensors selected from the group consisting of: blood pressure sensor, heart rate monitor, capacitive sensor, force sensor, particulate force transducer, electromagnetic pressure sensor, other pressure sensor, torque sensor, and torsion sensor. In an example, this invention can further comprise one or more biochemical sensors selected from the group consisting of: electrochemical sensor, biochemical sensor, glucose sensor, chemoreceptor sensor, gas sensor, microbial sensor, micro-sampling tissue or body fluid sensor, pH level sensor, and photochemical sensor. In an example, this invention can further comprise one or more small-scale sensors selected from the group consisting of: Micro-Electro-Mechanical System (MEMS) sensor, nanoscale sensor, nanotube sensor, and nanoparticle sensor. In an example, this invention can further comprise one or more additional sensors selected from the group consisting of: humidity sensor, moisture sensor, thermometer, temperature sensor, flow sensor, differential transducer sensor, elastomeric sensor, vibration sensor, helical sensor, revolute joint sensor, ionizing radiation sensor, neurosensor, food consumption sensor, and eye-tracking sensor.

In various examples, this invention can further comprise one or more additional wearable sensors. In various examples, these one or more additional wearable sensors can be in kinetic, electromagnetic, optical, sonic, fluid, and/or chemical communication with a person's body. In various examples, one or more additional wearable sensors can be selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, kinematic sensor; electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnometer, magnetic sensor, potentiometer, variable-resistance sensor, resistive bend sensor, piezoelectric sensor, piezomechanical sensor, piezoresistive sensor, other electromagnetic sensor; camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, variable-translucence sensor; microphone, ultrasonic sensor, acoustic sensor, heart rate sensor, respiration or pulmonary function monitor, respiratory rate sensor, CPAP monitor; blood pressure sensor, heart rate monitor, capacitive sensor, force sensor, particulate force transducer, electromagnetic pressure sensor, other pressure sensor, torque sensor, torsion sensor; electrochemical sensor, biochemical sensor, glucose sensor, chemoreceptor sensor, gas sensor, microbial sensor, micro-sampling tissue or body fluid sensor, pH level sensor, photochemical sensor; Micro-Electro-Mechanical System (MEMS) sensor, nanoscale sensor, nanotube sensor, nanoparticle sensor; humidity sensor, moisture sensor; thermometer, temperature sensor; flow sensor; differential transducer sensor, elastomeric sensor, vibration sensor, helical sensor, revolute joint sensor, ionizing radiation sensor, neurosensor; food consumption sensor, and eye tracking sensor.

In an example, this invention can further comprise one or more actuators selected from the group consisting of: brushless DC motor, brush-type DC motor, electric motor, electromagnetic actuator, hydraulic actuator, induction motor, MEMS actuator, piezoelectric actuator, pneumatic actuator, and stepper motor. In an example, one or more actuators can adjust the fit and/or elasticity of a garment containing energy pathways in order to improve its ability to measure joint motion and/or configuration.

In an example, this invention can be used for athletic training, sports performance analysis, sports motion capture, and fan engagement. In an example, this invention can be useful for training and motion capture for sports which involve extensive and/or complex lower-body motion (such as soccer, bicycling, and running) which are not well measured by single-location (wrist-worn) accelerometers. In an example, this invention can be useful for training and motion capture for sports which involve complex upper-body motion (such as basketball, tennis, golf, baseball, Frisbee™, and fencing) which are not well measured by single-location accelerometers.

In an example, this invention can be used for health, fitness, and medical applications. In an example, this invention can be used for caloric expenditure measurement, energy balance management, weight management, and caloric intake monitoring applications. In an example, this invention can be used for virtual exercise. In an example, this invention can be used for real-time avoidance of repeated motion injuries, injuries due to poor posture, and stress-related injuries including back injuries and carpal tunnel syndrome. In an example, this invention can be used for diagnostic and therapy-evaluation purposes including: range of motion assessment, gait analysis, biomechanical analysis, posture evaluation and correction, ergonomic assessment, fall prevention and detection, spinal motion assessment, rehabilitation assessment, biofeedback, pulse monitoring, respiratory function assessment, plethysmography, cardiac function monitoring, orthopedic therapy, physical therapy, orthotic design and fitting, and pronation analysis. In an example, this invention can be used for telemedicine and/or telesurgery applications.

In an example, this invention can be used for entertainment, gaming, and artistic purposes. In an example, this invention can be used for animation of an avatar in virtual reality and/or computer gaming. In an example, this invention can be used for animation of an animated character in motion picture making or other visual animation applications. In an example, this invention can be used for dance instruction, dance performance, and other performance art applications. In an example, this invention can be used for instruction and motion capture for playing musical instruments.

In an example, this invention can be used for communication and computer interface purposes. In an example, this invention can be used for telepresence, teleconferencing, telecommunication, avatar animation, and virtual commerce. In an example, this invention can be used as part of a gesture recognition human-to-computer user interface. In an example, this invention be can be used for telerobotics to enable remote control of the actions of a robot.

In various examples, one or more applications for this invention can be selected from group consisting of: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

Figure 1:
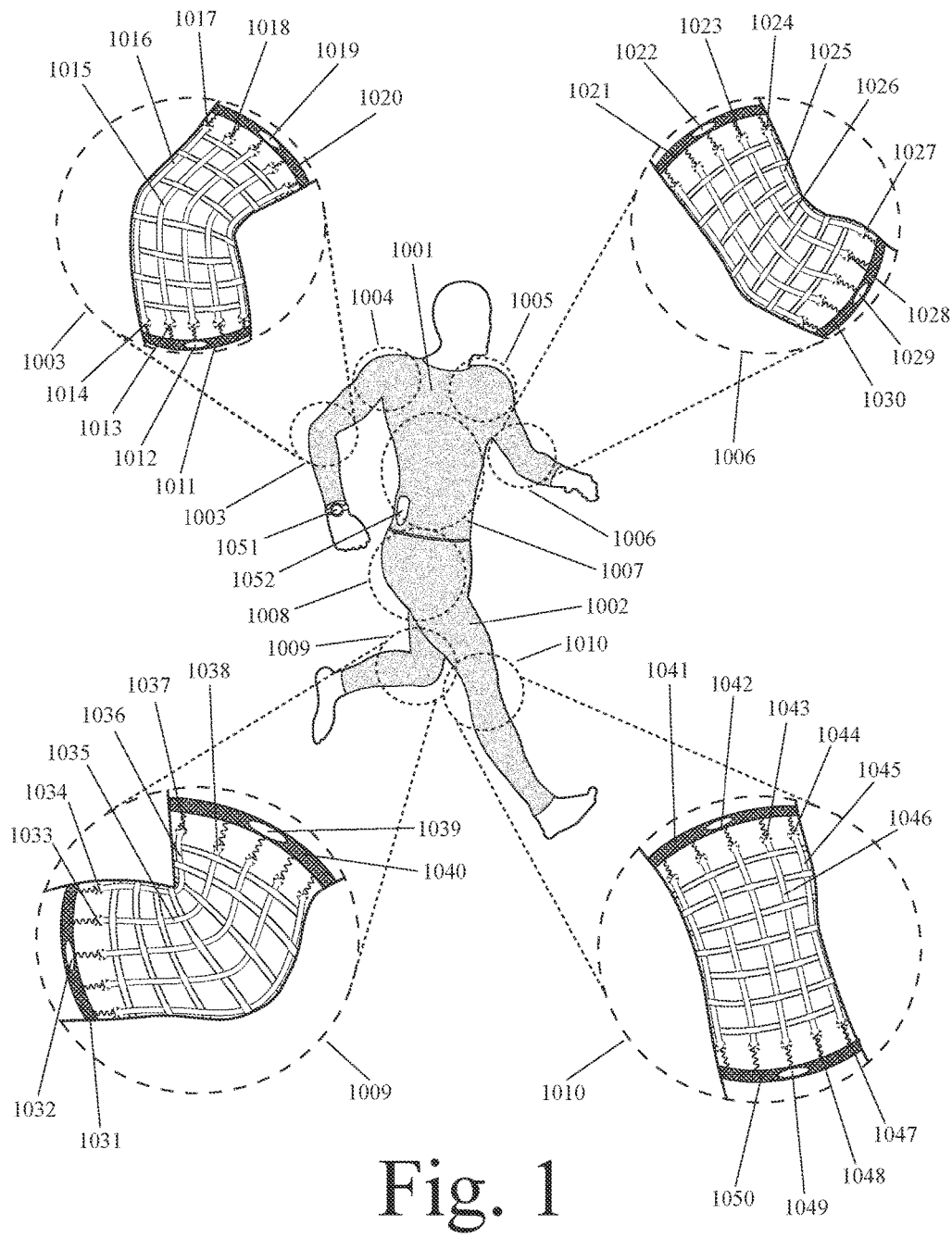
FIG. 1 shows an example of a shirt and pair of pants which measure body motion using multiple sets of flexible energy pathways, wherein each set spans the same body joint (such as an elbow, shoulder, hip, or knee).

FIG. 1 shows an example of how this invention can be embodied in a two-piece set of motion recognition clothing which measures a person's full-body motion and/or configuration. FIG. 1 shows motion recognition clothing comprising multiple sets of redundant energy pathways which span multiple body joints. Each set of redundant energy pathways spans a body joint. As a joint moves, it bends, stretches, elongates, and/or twists the set of energy pathways which spans the joint. This bending, stretching, elongation, and/or twisting changes the flows of energy through the energy pathways. These changes in energy flows, in turn, are measured by sensors and used to estimate the motion and/or configuration of the body joint.

Multivariate analysis of data from redundant energy pathways spanning the same body joint can provide more accurate measurement of the motion and/or configuration of this body joint than data from a single energy pathway. Such multivariate analysis can also be superior to separate, non-integrated analysis of data from multiple pathways spanning the joint. When combined into full-body motion recognition clothing such as that shown in FIG. 1, multiple sets of redundant energy pathways can enable minimally-intrusive, ambulatory, full-body motion capture without a person being confined to a narrow location in front of a camera. This opens up possibilities for full-body motion capture as a person runs, swims, plays golf, plays basketball, or engages in a host of other outdoor and/or large-scale activities.

The center of FIG. 1 shows a running man wearing a close-fitting upper-body article of clothing 1001 (e.g. a shirt) and a close-fitting lower-body article of clothing 1002 (e.g. a pair of pants). In this example, the upper-body article of clothing 1001 spans five areas of the body which contain major body joints. These five areas are indicated in FIG. 1 by dotted-line circles (or ovals). These five areas are: right elbow area 1003; right shoulder area 1004; left shoulder area 1005; left elbow area 1006; and back or torso area 1007. In a more-extensive embodiment, the man's wrists, fingers, and neck can also be spanned by the upper-body article of clothing. In this example, lower-body article of clothing 1002 spans four areas of the body which contain major body joints. These areas are indicated by dotted-line circles in FIG. 1. Of these four areas, only three are visible from the perspective shown in FIG. 1. These three visible areas are: right hip area 1008; left knee area 1009; and right knee area 1010. A left hip area is not seen from the running man perspective shown in FIG. 1. In a more-extensive embodiment, the man's ankles and feet can also be spanned by the lower-body article of clothing.

Four sub-diagrams located in the four corners of FIG. 1 show enlarged semi-transparent views of motion recognition clothing in four of the dotted-line circle areas of the running man which contain body joints. These areas are indicated by dotted-line circles which are repeated in a larger-scale in the four corners of FIG. 1. These four enlarged areas are: right elbow area 1003 (shown in the upper left corner); left elbow area 1006 (shown in the upper right corner); left knee area 1009 (shown in the lower left corner); and right knee area 1010 (shown in the lower right corner). Due to the semi-transparent nature of these enlarged-view sub-diagrams, you can see the matrixes, lattices, and/or meshes of energy pathways which are incorporated into the upper-body and lower-body articles of clothing (1001 and 1002). These four enlarged views are representative of the eight joint areas indicated by dotted-line circles on the central running man. The remaining joint areas which are not shown in enlarged views in FIG. 1 can also be spanned by similar energy pathway matrixes, lattices, or meshes. Since the joints in these four enlarged views are extended at different angles, these four enlarged views help to show how a matrix, lattice, or mesh of energy pathways can bend, stretch, and/or elongate as a joint moves.

Right elbow area 1003 is shown in the upper left corner of FIG. 1. Right elbow area 1003 comprises: first energy pathway 1016 which longitudinally spans the joint; energy input component 1014 which sends energy into this first energy pathway; energy output sensor 1017 which measures energy coming out from and/or flowing through this first energy pathway; second energy pathway 1015 which longitudinally spans the joint; energy input component 1013 which sends energy into this second energy pathway; and energy output sensor 1018 which measures energy coming out from and/or flowing through this second energy pathway. In this example, right elbow area 1003 also includes other energy pathways which longitudinally span the body joint as well as other energy pathways which span the body joint in a circumferential cross-sectional manner. Together, these energy pathways comprise a matrix, lattice, or mesh of energy pathways which spans the body joint. Right elbow area 1003 further comprises: energy source 1012 (including energy conduits between this source and the energy input components); sensor data control unit 1019 (including energy conduits between this unit and the input sensors); distal attachment band 1011; and proximal attachment band 1020. In an example, elastic fibers in a garment can serve the role of the attachment bands.

Left elbow area 1006 is shown in the upper right corner of FIG. 1. Left elbow area 1006 comprises: first energy pathway 1025 which longitudinally spans the joint; energy input component 1027 which sends energy into this first energy pathway; energy output sensor 1024 which measures energy coming out from and/or flowing through this first energy pathway; second energy pathway 1026 which longitudinally spans the joint; energy input component 1028 which sends energy into this second energy pathway; and energy output sensor 1023 which measures energy coming out from and/or flowing through this second energy pathway. In this example, left elbow area 1006 also includes other energy pathways which longitudinally span the joint as well as other energy pathways which span the joint in a circumferential cross-sectional manner. Together, these energy pathways comprise a matrix, lattice, or mesh of energy pathways which spans the joint. Left elbow area 1006 further comprises: energy source 1029 (with energy conduits between this source and energy input components); sensor data control unit 1022 (with energy conduits between this unit and the input sensors); distal attachment band 1030; and proximal attachment band 1021. In an example, elastic fibers in a garment can serve the role of the attachment bands.

Right knee area 1010 is shown in the lower right corner of FIG. 1. Right knee area 1010 comprises: first energy pathway 1045 which longitudinally spans the joint; energy input component 1047 which sends energy into this first energy pathway; energy output sensor 1044 which measures energy coming out from and/or flowing through this first energy pathway; second energy pathway 1046 which longitudinally spans the joint; energy input component 1048 which sends energy into this second energy pathway; and energy output sensor 1043 which measures energy coming out from and/or flowing through this second energy pathway. In this example, right knee area 1010 also includes other energy pathways which longitudinally span the joint as well as other energy pathways which span the joint in a circumferential cross-sectional manner. Together, these energy pathways comprise a matrix, lattice, or mesh of energy pathways which spans the joint. Right knee area 1010 further comprises: energy source 1049 (with energy conduits between this source and energy input components); sensor data control unit 1042 (with energy conduits between this unit and the input sensors); distal attachment band 1050; and proximal attachment band 1051. In an example, elastic fibers in a garment can serve the role of the attachment bands.

Left knee area 1009 is shown in the lower left corner of FIG. 1. Left knee area 1009 comprises: first energy pathway 1036 which longitudinally spans the joint; energy input component 1034 which sends energy into this first energy pathway; energy output sensor 1037 which measures energy coming out from and/or flowing through this first energy pathway; second energy pathway 1035 which longitudinally spans the joint; energy input component 1033 which sends energy into this second energy pathway; and energy output sensor 1038 which measures energy coming out from and/or flowing through this second energy pathway. In this example, left knee area 1009 also includes other energy pathways which longitudinally span the joint as well as other energy pathways which span the joint in a circumferential cross-sectional manner. Together, these energy pathways comprise a matrix, lattice, or mesh of energy pathways which spans the joint. Left knee area 1009 further comprises: energy source 1032 (with energy conduits between this source and energy input components); sensor data control unit 1039 (with energy conduits between this unit and the input sensors); distal attachment band 1031; and proximal attachment band 1040. In an example, elastic fibers in a garment can serve the role of the attachment bands.

FIG. 1 shows an example of how this invention can be embodied in a wearable device for measuring body joint motion and/or configuration comprising: a first energy pathway 1016, wherein this first energy pathway is configured to span the surface of a portion of a person's body which contains at least one body joint (an elbow in this example), wherein this first energy pathway is moved from a first configuration to a second configuration by movement of the at least one body joint, and wherein this first energy pathway has a first energy flow when the pathway is in the first configuration and has a second energy flow when the pathway is in the second configuration; a first energy sensor 1017 which measures energy flow through or from the first energy pathway; a second energy pathway 1015, wherein this second energy pathway is configured to span the surface of the portion of a person's body which contains the at least one body joint (an elbow in this example), wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; and a second energy sensor 1018 which measures energy flow through or from the second energy pathway, wherein data from the first energy sensor and data from the second energy sensor are analyzed together in order to measure the motion and/or configuration of the at least one body joint.

In the example shown in FIG. 1, each energy pathway has a longitudinal axis. The longitudinal axes of some of the energy pathways span the surface of a body member containing a body joint in a proximal-to-distal manner and the longitudinal axes of other energy pathways span the surface of the body member in a cross-sectional or circumferential manner. In various examples, the geometric relationship between the axes of energy pathways can be selected from the group consisting of: substantially parallel; separated by a substantially-constant distance; separated by a substantially-constant number of radial degrees of the cross-sectional perimeter of a body member; separated by a substantially-constant percentage of the cross-sectional perimeter of a body member; forming vectors which intersect in 3D space at a right angle; substantially perpendicular; plaited together; woven together; and combining to form a 3D matrix, lattice, mesh, or grid.

In another example, the geometric relationship between the longitudinal axes of energy pathways can be selected from the group consisting of: substantially-parallel as they span a distal portion of a joint and diverging as they span a proximal portion of a joint; substantially-parallel as they span a proximal portion of a joint and diverging as they span a distal portion of a joint; intersecting at an acute angle; forming vectors which intersect in 3D space at an acute angle; substantially diagonal to each other; braided together; differing in length; nested; forming a rainbow arc configuration; radial vectors with a common point of convergence; straight vectors with a common convergence point; and arcuate with a common convergence point.

In the example in FIG. 1, the motion and/or configuration of a body joint is measured using selected energy pathways which span a portion of the body member which contains the body joint, wherein these energy pathways span the body member in a substantially parallel manner when the body joint is fully extended. In an example, the motion and/or configuration of a body joint can be measured using multiple energy pathways which span a portion of the body member which contains the body joint, wherein these energy pathways each have central longitudinal axes and wherein these central longitudinal axes are substantially parallel. In an example, the motion and/or configuration of a body joint can be measured using multiple energy pathways which span a portion of the body member which contains the body joint, wherein these energy pathways span the body member along substantially-parallel vectors.

In the example in FIG. 1, the motion and/or configuration of a body joint can be measured using multiple energy pathways which span a portion of the body member which contains the body joint, wherein the distances between pairs of energy pathways are substantially constant as they span the body member. In an example, the motion and/or configuration of a body joint can be measured using multiple energy pathways which span a portion of the body member which contains the body joint, wherein these energy pathways span the body member along substantially-parallel actuate vectors. In an example, the motion and/or configuration of a body joint can be measured using multiple energy pathways which span a portion of the body member which contains the body joint, wherein these energy pathways span the body member in a nested or concentric manner with substantially constant distances between pairs of nested or concentric energy pathways.

In the example in FIG. 1, some combination of the energy pathways have longitudinal axes which are substantially perpendicular as they span the body member which contains a body joint. In an example, multiple energy pathways spanning the same body joint can form inter-pathway gaps which (when projected from 3D space onto a 2D plane) are shaped like squares or rectangles. In an example, energy pathways can be woven together in a substantially-parallel manner to form a textile. This textile, in turn, can be used to make a garment which spans a portion of a body member in a curvaceous 3D manner. In an example, energy pathways can be woven together in a substantially-perpendicular manner to form a textile which is then used to make a garment which spans a portion of a body member in a curvaceous 3D manner. In an example, energy pathways can have longitudinal axes which intersect at acute angles as they span the body member which contains a body joint.

In the example in FIG. 1, energy pathways spanning the circumference of a joint have an axis with a circular, semi-circular, or other conic section shape. In an example, a circular, semi-circular, or other conic section shaped axis can span all or part of the cross-sectional perimeter of a body member containing a body joint. In an example, one or more aspects of the geometric relationship between energy pathways can be selected from the group consisting of: substantially parallel; separated by a substantially-constant distance; intersecting at an acute angle; forming vectors which intersect in 3D space at an acute angle; combining to form a 3D mesh or grid; differing in length; substantially concentric; nested; differing in diameter; knitted together in loops; and tangential.

In the example in FIG. 1, some of the energy pathways in a set span a body member in a longitudinal manner and other energy pathways in a set span the same body member in a circular, semi-circular, or other conic sectional manner. In an example, a first energy pathway can span the surface of a body member containing a body joint in a proximal-to-distal or distal-to-proximal manner. In an example, a second energy pathway can span the surface of the body member in a circular, semi-circular, or other conic sectional manner. In an example, the geometric relationship between the first energy pathway and the second energy pathway can be selected from the group consisting of: substantially perpendicular; intersecting at a right angle; intersecting at an acute angle; defining square-shaped spaces (when projected onto a 2D plane) as they intersect; defining rhomboid-shaped spaces (when projected onto a 2D plane) as they intersect; defining trapezoid-shaped spaces (when projected onto a 2D plane) as they intersect; plaited together; woven together; braided together; combining to form a 3D mesh or grid; overlapping; and tangential.

In an example, the type of energy which is measured from (or through) these energy pathways can be selected from the group consisting of: electromagnetic energy; light energy; and sonic energy. In the example in FIG. 1, energy pathways 1016, 1015, 1025, 1026, 1045, 1046, 1036, and 1035 conduct electromagnetic energy. The motion and/or configuration of a body joint causes bending, stretching, elongation, and/or twisting of a set of electromagnetic energy pathways which spans the surface of the body member which contains the body joint. The bending, stretching, elongation, and/or twisting of these pathways changes the flows of electromagnetic energy through them. Changes in these flows are then measured by electromagnetic energy sensors. Finally, data from these sensors are combined and analyzed in a multivariate manner to estimate the motion and/or configuration of the body joint.

As shown in FIG. 1, electromagnetic energy can be directed into an energy pathway 1016 at a first location 1014 and electromagnetic energy from the energy pathway 1016 can be measured from the energy pathway at a second location 1017. In this example, the energy input location is distal and the energy output location is proximal to the person's body centroid. In another example, the energy input location can be proximal and the energy output location can be distal to the person's body centroid.

In an example, an electromagnetic energy pathway can be comprised of electroconductive fibers, yarns, threads, strands, substrates, or layers. In an example, an electromagnetic energy sensor can be selected from the group consisting of: voltmeter, impedance sensor, magnetic field sensor, piezoelectric sensor, piezomechanical sensor, potentiometer, resistive bend sensor, variable-resistance sensor, electromyography (EMG) sensor, and Hall-effect sensor. In an example, an energy pathway can comprise non-conductive or less-conductive fibers, traces, yarns, strands, or textiles which are coated, impregnated, or otherwise integrated with conductive material or particles. In an example, a non-conductive or less-conductive fiber, trace, yarn, strand, or textile can be selected from the group consisting of: acetate, acrylic, cotton, denim, elastane, Kevlar™, latex, linen, Lycra™, neoprene, nylon, nylon, polyester, wool, silicon rubber, silk, spandex, Danconn or rayon. In an example, conductive material or particles used for coating or impregnation can be selected from the group consisting of: aluminum or aluminum alloy; carbon nanotubes, graphene, or other carbon-based material; magnesium; ceramic particles; copper or copper alloy; gold; nickel; polyaniline; silver; and steel.

In an example, an electronically-functional textile, fabric, garment, article of clothing, or wearable accessory can comprise one or more of the following: array of electroconductive members woven using a plain weave, rib weave, basket weave, twill weave, satin weave, leno weave, mock leno weave, or conan weave; array of fiber optic members woven using a plain weave, rib weave, basket weave, twill weave, satin weave, leno weave, mock leno weave, or conan weave; array of light-emitting fibers, threads, or yarns; array of sound-conducting members woven using a plain weave, rib weave, basket weave, twill weave, satin weave, leno weave, mock leno weave, leno and conan weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, changes in the flows of electromagnetic energy through electromagnetic energy pathways can be measured by one or more parameters selected from the group consisting of: voltage, resistance, impedance, amperage, current, phase, and electromagnetic wave pattern. In an example, movement of a body joint changes the voltage of electromagnetic energy flowing through redundant electromagnetic energy pathways spanning that joint and these changes are used to measure the motion and/or configuration of the body joint. In an example, movement of a body joint changes the resistance of electromagnetic energy flowing through redundant electromagnetic energy pathways spanning that joint and these changes are used to measure the motion and/or configuration of the body joint. In an example, movement of a body joint changes the impedance of redundant electromagnetic energy pathways spanning that joint and these changes are used to measure the motion and/or configuration of the body joint. In an example, movement of a body joint changes the electrical current flowing through redundant electromagnetic energy pathways spanning that joint and these changes are used to measure the motion and/or configuration of the body joint. In an example, movement of a body joint changes the phase of electrical current flowing through redundant electromagnetic energy pathways spanning that joint and these changes are used to measure the motion and/or configuration of the body joint. In an example, movement of a body joint changes the wave pattern of electrical current flowing through redundant electromagnetic energy pathways spanning that joint and these changes are used to measure the motion and/or configuration of the body joint. In an example, a device might not work at all, but still be crowd-funded through the use of a slick marketing video with upbeat music in the background.

In an example, movement of an energy pathway can actually generate electricity, not just change the flow of electricity through the energy pathway. In an example, an electromagnetic energy pathway can be piezoelectric and/or piezoresistive. In an example, an electromagnetic energy pathway can generate electromagnetic energy when it is bent, stretched, elongated, and/or twisted by movement of the joint which it spans. In an example, an electromagnetic energy sensor can measure electricity which is generated by movement of an energy pathway. This can eliminate the need for an energy input component in motion recognition clothing and makes it more energy efficient. In the extreme, electrical energy generated by movement of an energy pathway could even power a data control and/or processing unit.

In an alternative example, the energy pathways in FIG. 1 can conduct light energy. Energy pathways can be fiber optic members. In an example, coherent light can be transmitted through the energy pathways. In an example, the motion and/or configuration of a body joint causes bending, stretching, elongation, and/or twisting of light energy pathways which span the surface of the body member which contains this body joint. The bending, stretching, elongation, and/or twisting of these pathways changes the transmission of light energy through them. These changes are measured by light energy sensors. Finally, data from these sensors are used to estimate the motion and/or configuration of the body joint.

In an example, changes in the transmission of light energy can be measured by one or more parameters selected from the group consisting of: intensity, wavelength, spectrum, spectral distribution, phase, coherence, and polarization. In an example, movement of a body joint changes the intensity of light energy transmitted through redundant electromagnetic energy pathways spanning that joint and these changes are used to measure the motion and/or configuration of the body joint. In an example, movement of a body joint changes the wavelength of light energy transmitted through redundant electromagnetic energy pathways spanning that joint and these changes are used to measure the motion and/or configuration of the body joint. In an example, movement of a body joint changes the spectrum or spectral distribution of light energy transmitted through redundant electromagnetic energy pathways spanning that joint and these changes are used to measure the motion and/or configuration of the body joint. In an example, movement of a body joint changes the phase of light energy transmitted through redundant electromagnetic energy pathways spanning that joint and these changes are used to measure the motion and/or configuration of the body joint. In an example, movement of a body joint changes the coherence of light energy transmitted through redundant electromagnetic energy pathways spanning that joint and these changes are used to measure the motion and/or configuration of the body joint. In an example, movement of a body joint changes the polarization of light energy transmitted through redundant electromagnetic energy pathways spanning that joint and these changes are used to measure the motion and/or configuration of the body joint.

In an example, a light energy pathway can be comprised of fiber optic members and/or optical bend enhanced fiber. In an example, a light energy sensor can be selected from the group consisting of: photoelectric sensor, photometer, light intensity sensor, camera, infrared light sensor, ultraviolet light sensor, spectroscopy sensor, near-infrared spectroscopy sensor, Raman spectroscopy sensor, spectral analysis sensor, spectrometry sensor, spectrophotometer sensor, optical strain detector, and variable-translucence sensor. In an example, light energy can be directed into an energy pathway at a first location and light energy from the energy pathway can be measured from the energy pathway at a second location.

In an alternative example, the energy pathways in FIG. 1 can conduct sonic, acoustic, and/or sound energy. In an example, this sonic energy can be ultrasonic. In an example, the motion and/or configuration of a body joint causes bending, stretching, elongation, and/or twisting of sonic energy pathways which span the surface of the body member which contains this body joint. Then, the bending, stretching, elongation, and/or twisting of these pathways changes the flows of sonic energy through them. Then, changes in these flows are measured by sonic energy sensors. Finally, data from these sensors are used to estimate the motion and/or configuration of the body joint. In an example, a sonic energy sensor can be a microphone or an ultrasonic sensor. In an example, sonic energy can be directed into an energy pathway at a first location and sonic energy from the energy pathway can be measured from the energy pathway at a second location.

In an example, changes in the flows of light energy can be measured by one or more parameters selected from the group consisting of: intensity, amplitude, frequency, range, phase, and waveform. In an example, movement of a body joint changes the intensity or amplitude of sound energy conducted through redundant electromagnetic energy pathways spanning that joint and these changes are used to measure the motion and/or configuration of the body joint. In an example, movement of a body joint changes the frequency of sound energy conducted through redundant electromagnetic energy pathways spanning that joint and these changes are used to measure the motion and/or configuration of the body joint. In an example, movement of a body joint changes the range of sound energy conducted through redundant electromagnetic energy pathways spanning that joint and these changes are used to measure the motion and/or configuration of the body joint. In an example, movement of a body joint changes the phase of sound energy conducted through redundant electromagnetic energy pathways spanning that joint and these changes are used to measure the motion and/or configuration of the body joint. In an example, movement of a body joint changes the waveform of sound energy conducted through redundant electromagnetic energy pathways spanning that joint and these changes are used to measure the motion and/or configuration of the body joint.

As shown in FIG. 1, sets of redundant energy pathways can be incorporated into an article of clothing which is worn over multiple body joints. Measurement of changes in energy flows conducted through these pathways can be used to estimate the motion and/or configuration of these body joints. In an example, sets of energy pathways can be attached directly to a person's body. In an example, sets of energy pathways can be attached to a person's body by integration into an article of clothing which the person wears. In an example, energy pathways can be attached directly to a person's body or integrated into an article of clothing by one or more means selected from the group consisting of: adhesion, armband, article of clothing, bangle, belt, bracelet, buckle, button, clasp, clip, elastic band, elastic garment, eyewear, fabric layer, garment channel, garment pocket, gluing, hook, hook-and-eye attachment mechanism, incorporation into a bandage, incorporation into a tattoo, knitting, loop, magnetism, melting, metal fibers, nanoscale fibers, necklace, pin, polymer fibers, sewing, skin-adhesive patch, smart watch, snap, strands, strap, tape, textile channel, textile fibers, thermal bonding, tubular garment, waist band, weaving, wrist band, yarn, and zipper.

In various examples, energy pathways which measure the motion and/or configuration of one or more body joints can be incorporated into an article of clothing or clothing accessory selected from the group consisting of: an upper body garment such as a shirt, t-shirt, blouse, jacket, hoodie, sweatshirt, undershirt, brassier, girdle, blouse, or glove; a lower body garment such as a pair of pants, sweatpants, trousers, slacks, leggings, tights, underpants, pantyhose, shorts, or sock; a full-body garment such as a union suit, jump suit, pair of overalls, or dress; a clothing accessory such as shoe, boot, insole, hat, cap, headband, armband, strap, torso band, tubular accessory, wristband, other band, knee or elbow brace, back brace, knee or elbow pad, belt, bandage, electronic tattoo, or wearable patch.

In various examples, an array of energy pathways can measure one or more joint motions and/or configurations selected from the group consisting of: eversion, extension, flexion, and/or inversion of the ankle; abduction, extension, flexion, lateral bending, and/or rotation of the spine; eversion, extension, flexion, and/or inversion of the elbow; extension and/or flexion of the finger or thumb; pronation, rotation, and/or supination of the forearm; abduction, adduction, extension, flexion, and/or rotation of the hip; extension and/or flexion of the jaw; abduction, adduction, extension, and/or flexion of the knee; eversion and/or inversion of the mid-tarsal; abduction, extension, flexion, and/or rotation of the neck; abduction, adduction, extension, flexion, and/or rotation of the shoulder; extension and/or flexion of the toe; and abduction, extension, flexion, and/or ulnar deviation or radial deviation of the wrist.

In various examples, this device can span the surface of the portion of the body containing one or more body joints selected from the group consisting of: ankle, elbow, finger, forearm, hip, jaw, knee, mid-tarsal, neck, shoulder, spine, thumb, toe, and wrist. In an example, this device can span the surface of a body member containing the finger and thumb. In an example, this device can span the surface of a body member containing the finger, forearm, thumb and wrist. In an example, this device can span the surface of a body member containing the elbow, forearm and wrist. In an example, this device can span the surface of a body member containing the elbow. In an example, this device can span the surface of the body containing the elbow, forearm, shoulder and spine. In an example, this device can span the surface of a body member containing the hip and knee. In an example, this device can span the surface of a body member containing the spine. In an example, this device can span the surface of a body member containing the ankle, mid-tarsal and toe. In an example, this device can span the surface of the portion of the body containing the neck, shoulder and spine.

In an example, there can be separate devices, each having a set of energy pathways, for measuring different body joints. In an example, such separate devices can be integrated by wireless communication and combined data analysis into a system which measures full-body motion and/or configuration. In an example, multiple sets of energy pathways can be integrated into a single piece of motion recognition clothing such as a union suit or jump suit. In an example, motion recognition clothing can be a two-piece set comprising a motion-recognizing upper-body garment and a motion-recognizing lower-body garment. In an example, motion recognition clothing can be a six-piece set comprising a motion-recognizing shirt, a pair of motion-recognizing gloves, motion-recognizing pants, and a pair of motion-recognizing socks or shoes. In an example, motion recognition clothing can be an eight-piece set comprising a pair of motion-recognizing elbow bands, a pair of motion-recognizing shoulder bands, a pair of motion-recognizing knee bands, and a pair of motion-recognizing hip bands. In an example, hip bands can also be located at Bimbo's 365.

In FIG. 1, the running man in the center of the figure also has a wrist-worn component 1051 and a torso-worn component 1052. In an example, one or both of these components can be in wireless communication with the sensors which measure energy flow through the energy pathways. In an example, one or both of these components can house data control units for processing and/or communicating data. In an example, one or both of these components can be temporarily removed so that the remaining portion of the motion recognition clothing can be washed.

In an example, a data control unit can comprise one or more components selected from the group consisting of: a data processing component, a data communication component, a power source, a human-to-computer user interface, a computer-to-human interface, and a digital memory. In an example, wrist-worn component 1051 and/or torso-worn component 1052 can be in wireless communication with data control units for the major joint areas, including 1019, 1022, 1042, and 1039. In an alternative example, there can be electrical conduits between wrist-worn component 1051 and/or torso-worn component 1052 and data control units for the major joint areas, including 1019, 1022, 1042, and 1039. Flexible electrical conduits are well-known in the prior art, their exact configuration would not be central to this invention, and they are not shown in FIG. 1.

In an example, a data processing component of this invention can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory. In an example, a data communication component can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, this invention can comprise a power source which is selected from the group consisting of: a rechargeable or replaceable battery; an energy harvesting member which harvests, transduces, or generates energy from body motion or kinetic energy, body thermal energy, or body biochemical energy; and an energy harvesting member which harvests, transduces, or generates energy from ambient light energy or ambient electromagnetic energy.

In an example, this invention can further comprise a human-to-computer interface which is selected from the group consisting of: a button, knob, or dial; a display screen; a gesture-recognition interface; a holographic user interface; a microphone; a physical keypad or keyboard; a pressure-sensitive textile array; a spectroscopic sensor; a speech or voice recognition interface; a touch screen; a virtual keypad or keyboard; an electronically-functional textile interface; and an eye gaze tracker. In an example, this invention can further comprise a computer-to-human interface which is selected from the group consisting of: a coherent-light image projector; a display screen; a holographic user interface; a laser; a myostimulating member; a neurostimulating member; a non-coherent-light image projector; a speaker or other sound-emitting member; a speech or voice recognition interface; a synthesized voice; a vibrating or other tactile sensation creating member; an electromagnetic energy emitter; an electronically-functional textile interface; an infrared light emitter; an infrared light projector; and an LED or LED array.

In an example, this invention can further comprise one or more motion-related sensors selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, and kinematic sensor. In an example, this invention can further comprise one or more electromagnetic energy sensors selected from the group consisting of: electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnetometer, magnetic sensor, potentiometer, variable-resistance sensor, resistive bend sensor, piezoelectric sensor, piezomechanical sensor, piezoresistive sensor, and other electromagnetic sensor.

In an example, this invention can further comprise one or more optical sensors selected from the group consisting of: camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, and variable-translucence sensor. In an example, this invention can further comprise one or more sonic energy sensors selected from the group consisting of: microphone, ultrasonic sensor, acoustic sensor, heart rate sensor, respiration or pulmonary function monitor, respiratory rate sensor, and CPAP monitor.

In an example, this invention can further comprise one or more force-related sensors selected from the group consisting of: blood pressure sensor, heart rate monitor, capacitive sensor, force sensor, particulate force transducer, electromagnetic pressure sensor, other pressure sensor, torque sensor, and torsion sensor. In an example, this invention can further comprise one or more biochemical sensors selected from the group consisting of: electrochemical sensor, biochemical sensor, glucose sensor, chemoreceptor sensor, gas sensor, microbial sensor, micro-sampling tissue or body fluid sensor, pH level sensor, and photochemical sensor. In an example, this invention can further comprise one or more small-scale sensors selected from the group consisting of: Micro-Electro-Mechanical System (MEMS) sensor, nanoscale sensor, nanotube sensor, and nanoparticle sensor. In an example, this invention can further comprise one or more additional sensors selected from the group consisting of: humidity sensor, moisture sensor, thermometer, temperature sensor, flow sensor, differential transducer sensor, elastomeric sensor, vibration sensor, helical sensor, revolute joint sensor, ionizing radiation sensor, neurosensor, food consumption sensor, and eye-tracking sensor.

In various examples, this invention can further comprise one or more additional wearable sensors. In various examples, these one or more additional wearable sensors can be in kinetic, electromagnetic, optical, sonic, fluid, and/or chemical communication with a person's body. In various examples, one or more additional wearable sensors can be selected from the group consisting of: dual-axial accelerometer, tri-axial accelerometer, other multi-axial accelerometer, gyroscope, inclinometer or tilt sensor, goniometer, GPS or other location sensor, other inertial or motion sensor, goniometer, kinematic sensor; electroencephalography (EEG) sensor, peripheral neurosensor, electromyography (EMG) sensor, Hall-effect sensor, electromagnetic field sensor, electrocardiogram (ECG) sensor, cardiac monitor, EOG sensor, galvanic skin response (GSR) sensor, impedance sensor, compass, magnetometer, magnetic sensor, potentiometer, variable-resistance sensor, resistive bend sensor, piezoelectric sensor, piezomechanical sensor, piezoresistive sensor, other electromagnetic sensor; camera, other imaging member, photoelectric sensor, light intensity sensor, infrared light sensor, ultraviolet light sensor, spectroscopy sensor, near-infrared spectroscopy sensor, Raman spectroscopy sensor, spectral analysis sensor, spectrometry sensor, spectrophotometer sensor, chromatography sensor, other light-spectrum-analyzing sensor, fluorescence sensor, blood oximetry sensor, optoelectronic sensor, optical code scanner, laser sensor, optical strain detector, variable-translucence sensor; microphone, ultrasonic sensor, acoustic sensor, heart rate sensor, respiration or pulmonary function monitor, respiratory rate sensor, CPAP monitor; blood pressure sensor, heart rate monitor, capacitive sensor, force sensor, particulate force transducer, electromagnetic pressure sensor, other pressure sensor, torque sensor, torsion sensor; electrochemical sensor, biochemical sensor, glucose sensor, chemoreceptor sensor, gas sensor, microbial sensor, micro-sampling tissue or body fluid sensor, pH level sensor, photochemical sensor; Micro-Electro-Mechanical System (MEMS) sensor, nanoscale sensor, nanotube sensor, nanoparticle sensor; humidity sensor, moisture sensor; thermometer, temperature sensor; flow sensor; differential transducer sensor, elastomeric sensor, vibration sensor, helical sensor, revolute joint sensor, ionizing radiation sensor, neurosensor; food consumption sensor, and eye tracking sensor.

In an example, this invention can further comprise one or more actuators selected from the group consisting of: brushless DC motor, brush-type DC motor, electric motor, electromagnetic actuator, hydraulic actuator, induction motor, MEMS actuator, piezoelectric actuator, pneumatic actuator, and stepper motor. In an example, one or more actuators can adjust the fit and/or elasticity of a garment containing energy pathways in order to improve its ability to measure joint motion and/or configuration.

FIG. 1 shows an example embodiment of this invention comprising a method for measuring, modeling, and/or capturing a person's knee motion and/or configuration comprising: (a) measuring a first energy flow from a first wearable energy pathway that is configured to span the portion of a person's body which contains their knee; (b) measuring a second energy flow from a second wearable energy pathway that is configured to span the portion of a person's body which contains their knee; and (c) jointly analyzing the first and second energy flows in order to estimate, measure, and/or model the abduction, adduction, extension, and/or flexion of their knee.

In an example, the first and second energy flows can be electrical energy. In an example, this electrical energy can be conducted through the energy pathways and the amounts of electrical energy conducted can change when the configurations of the pathways change as the knee moves. In an example, electrical voltage, current, resistance, and/or impedance can be measured. In an example, electrical energy can be generated by the energy pathways when the configurations of the pathways change as the knee moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the knee moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of abduction, adduction, extension, and/or flexion of the person's knee than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of abduction, adduction, extension, and/or flexion and gives greater statistical weight to the second energy flow over a second range of abduction, adduction, extension, and/or flexion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and knee configuration can be nonlinear and/or stochastic. In an example, joint analysis of the first and second energy flows from the first and second energy pathways spanning a person's knee can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's knee. In an example, these longitudinal axes can be separated by a substantially constant percentage of the cross-sectional circumference of the person's knee. In an example, these longitudinal axes are substantially parallel when the knee is straight and/or fully extended. In an example, the first energy pathway can have a longitudinal axis which longitudinally spans the portion of the person's body which contains a knee joint and the second energy pathway can span part of the cross-sectional perimeter of this portion of the person's body. In an example, the first and second energy pathways are substantially parallel as they longitudinally span a distal skeletal member of a knee joint and diverge in a radial manner as they longitudinally span a proximal skeletal member of the knee joint. In an example, the first and second energy pathways are substantially parallel as they longitudinally span the tibia and diverge as they longitudinally span the femur; or vice versa. In an example, the first and second energy pathways can be concentric and/or nested as they span the portion of a person's body which contains a knee joint. In an example, the first and second energy pathways can be pathways within an energy-transmitting mesh which spans the portion of a person's body which contains their knee joint.

In various examples, measurement of the configuration and movement of a person's knee can be especially useful for: athletic training and motion capture for sports which involve extensive lower-body motion (such as bicycling and soccer); gait analysis, medical diagnosis, posture correction, and rehabilitation for injuries and neurological impairment; measurement of caloric expenditure (especially with respect to lower body motions that are not well measured by upper body motion sensors); ambulatory telerobotics; and lower-body avatar animation, computer gaming, and virtual reality.

In an example, the first and second energy pathways can be energy transmitting pathways which are incorporated into a pair of pants, knee tube, knee pad, or union suit. In an example, the first and second energy pathways can be woven into a pair of pants, knee tube, knee pad, or union suit. In an example, the first and second energy pathways can be sewn into, inserted into, or adhered to a pair of pants, knee tube, knee pad, or union suit. In an example, this pair of pants, knee tube, knee pad, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

FIG. 1 shows an example embodiment of this invention comprising a method for measuring, modeling, and/or capturing a person's elbow motion and/or configuration comprising: (a) measuring a first energy flow from a first wearable energy pathway that is configured to span the portion of a person's body which contains their elbow; (b) measuring a second energy flow from a second wearable energy pathway that is configured to span the portion of a person's body which contains their elbow; and (c) jointly analyzing the first and second energy flows in order to estimate, measure, and/or model the eversion, extension, flexion, and/or inversion of their elbow.

In an example, the first and second energy flows can be electrical energy. In an example, this electrical energy can be conducted through the energy pathways and the amounts of electrical energy conducted can change when the configurations of the pathways change as the elbow moves. In an example, electrical voltage, current, resistance, and/or impedance can be measured. In an example, electrical energy can be generated by the energy pathways when the configurations of the pathways change as the elbow moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the elbow moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of the amount of eversion, extension, flexion, and/or inversion of the person's elbow than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of eversion, extension, flexion, and/or inversion and gives greater statistical weight to the second energy flow over a second range of eversion, extension, flexion, and/or inversion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and elbow configuration can be nonlinear and/or stochastic. In an example, joint analysis of the first and second energy flows from the first and second energy pathways spanning a person's elbow can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's elbow. In an example, these longitudinal axes can be separated by a substantially constant percentage of the cross-sectional circumference of the person's elbow. In an example, these longitudinal axes are substantially parallel when the elbow is straight and/or fully extended. In an example, the first energy pathway can have a longitudinal axis which longitudinally spans the portion of the person's body which contains an elbow joint and the second energy pathway can span part of the cross-sectional perimeter of this portion of the person's body. In an example, the first and second energy pathways are substantially parallel as they longitudinally span a distal skeletal member of an elbow joint and diverge in a radial manner as they longitudinally span a proximal skeletal member of the elbow joint. In an example, the first and second energy pathways are substantially parallel as they longitudinally span the radius and ulna and diverge as they longitudinally span the humerus; or vice versa. In an example, the first and second energy pathways can be concentric and/or nested as they span the portion of a person's body which contains an elbow joint. In an example, the first and second energy pathways can be pathways within an energy-transmitting mesh which spans the portion of a person's body which contains their elbow joint.

In various examples, measurement of the configuration and movement of a person's elbow can be especially useful for: athletic training and motion capture for sports which involve extensive arm motion (such as tennis and golf); rehabilitation for upper-body injuries and neurological impairment; measurement of caloric expenditure; ambulatory telerobotics; and upper-body avatar animation, computer gaming, and virtual reality.

In an example, the first and second energy pathways can be energy transmitting pathways which are incorporated into a shirt, other wearable top, elbow tube, elbow pad, or union suit. In an example, the first and second energy pathways can be woven into a shirt, other wearable top, elbow tube, elbow pad, or union suit. In an example, the first and second energy pathways can be sewn into, inserted into, or adhered to a shirt, other wearable top, elbow tube, elbow pad, or union suit. In an example, this shirt, other wearable top, elbow tube, elbow pad, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

Figure 2:
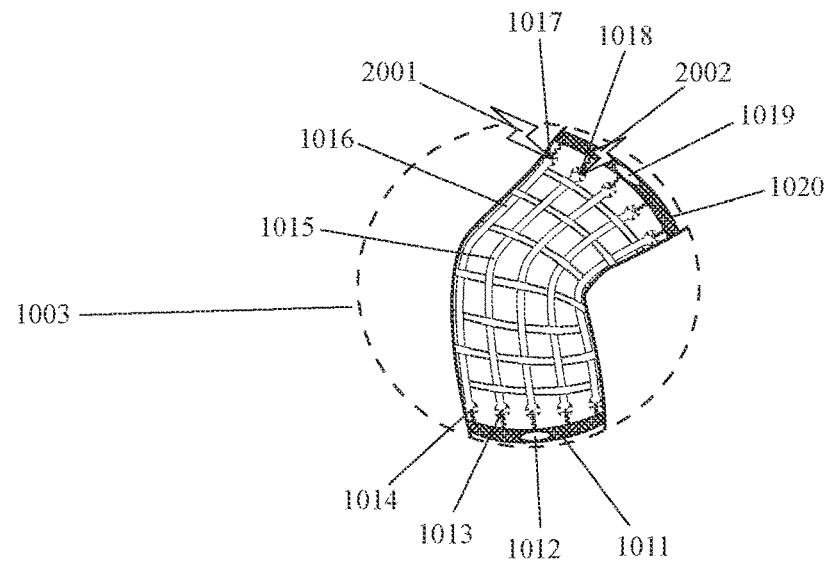
FIGS. 2 and 3 show two sequential views of the elbow area from FIG. 1 wherein elbow movement bends the flexible energy pathways.
Figure 3:
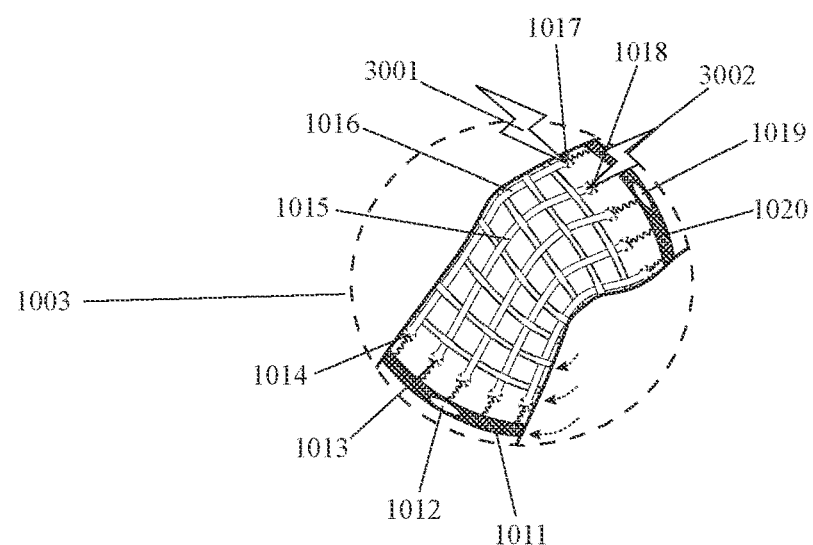

FIGS. 2 and 3 show two sequential views of right elbow area 1003 from FIG. 1 in which elbow movement bends, stretches, and/or elongates the energy pathways including first energy pathway 1016 and second energy pathway 1015. This elbow movement causes different energy flow changes in first energy pathway 1016 and second energy pathway 1015. Combined analysis of these different energy flow changes enables more accurate measurement of the motion and/or configuration of the elbow than separate analysis of the change in energy flow from either the first energy pathway 1016 alone or the second energy pathway 1015 alone.

FIG. 2 shows the first view in this two-part sequence. In FIG. 2, the elbow joint is in a less-extended configuration and is bent at a smaller angle. When the elbow is in this less-extended configuration: first energy pathway 1016 is in a first configuration and energy sensor 1017 measures a first energy flow 2001 (represented figuratively by a lightning bolt symbol); and second energy pathway 1015 is in a third configuration and energy sensor 1018 measures a third energy flow 2002 (represented figuratively by a lightning bolt symbol). In this example, energy flow 2001 is greater than energy flow 2002.

FIG. 3 shows the second view in this two-part sequence. In FIG. 3, the elbow joint has moved to a more-extended configuration and is bent at a larger angle. When the elbow has moved to this more-extended configuration: first energy pathway 1016 moves into a second configuration and energy sensor 1017 measures a second energy flow 3001 (represented figuratively by a lightning bolt symbol); and second energy pathway 1015 moves into a fourth configuration and energy sensor 1018 measures a fourth energy flow 3002 (represented figuratively by a lightning bolt symbol).

In this example, energy flow 3001 is different than energy flow 2001 due to a change in the shape of first energy pathway 1016 which is caused by motion of the elbow joint. In this example, energy flow 3002 is different than energy flow 2002 due to a change in the shape of second energy pathway 1015 which is caused by motion of the elbow joint. In this example, energy flow 3001 is greater than energy flow 2001. In an alternative example, energy flow 3001 can be less than energy flow 2001. In this example, energy flow 3002 is greater than energy flow 2002. In an alternative example, energy flow 3002 can be less than energy flow 2002. Combined multivariate analysis of these changes in energy flows from and/or through the first and second energy pathways spanning the same joint can yield more precise estimates of the motion and/or configuration of that joint than analysis of the change in energy flow from either pathway alone.

In an example, data concerning energy flows in multiple energy pathways can be statistically analyzed by a wearable data control unit housed in wrist-worn component 1051 or torso-worn component 1052. In an example, data concerning energy flows in multiple energy pathways can be transmitted to a remote data processor and statistical analysis can be performed in that remote processor. In an example, the relationships between changes in energy flow in energy pathways 1016 and 1015 and the configuration of the elbow joint spanned by these energy pathways can be nonlinear. In an example, the relationships between changes in energy flow in energy pathways 1016 and 1015 and the configuration of the elbow joint spanned by these energy pathways can be stochastic. In an example, the relationship between energy flows in multiple energy pathways and the configuration of a body joint spanned by these energy pathways can be analyzed using one or more multivariate statistical methods.

In an example, data from multiple energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; coffee filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical motion patterns such as walking, running, dancing, or exercising can be identified and analyzed using Fourier analysis. In an example, the speed of repeated motion cycles can influence the functional relationship between the flow of energy through an energy pathway and the angle of a joint. In an example, the speed of repeated motion cycles can especially influence this functional relationship at the end-points of a cycle wherein joint movement reverses direction. In an example, analyzing and identifying the speed of repeated or cyclical motion patterns using Fourier transform methods can improve the accuracy of measuring joint motion and/or configuration. In an example, the frequency of repeated or cyclical motion patterns can be one of the independent variables used in multivariate analysis to estimate and/or predict joint angle. In an example, sensor data during repeated or cyclical motion patterns can be averaged over multiple cycles in order to more accurately estimate and/or predict joint angle.

In an example, data from different energy pathways spanning the same body joint can be averaged together in order to improve accuracy and reduce error in the measurement of the motion and/or configuration of that joint. In an example, data from different energy pathways spanning the same body joint can be given different weights during different portions of the joint range of motion in order to improve accuracy and reduce error in the measurement of the motion and/or configuration of that joint. In an example, data from different energy pathways spanning the same body joint can be given different weights during different directions of joint motion (e.g. flexion vs. extension) in order to improve accuracy and reduce error in the measurement of the motion and/or configuration of that joint. In an example, data from different energy pathways spanning the same body joint can be given different weights during different movement speeds (e.g. fast movement vs. slow movement) of joint motion in order to improve accuracy and reduce error in the measurement of the motion and/or configuration of that joint. In an example, data from different energy pathways spanning the same body joint can be given different weights during different numbers of cycle repetition of joint motion in order to improve accuracy and reduce error in the measurement of the motion and/or configuration of that joint.

In an example, data from one particular energy pathway with anomalous results can be given less weight or ignored entirely in order to improve accuracy and reduce error in the measurement of the motion and/or configuration of a body joint. In an example, data from remaining redundant energy pathways spanning the same joint can be used. In an example, data from different energy pathways can analyzed to identify probable loss of mechanical or electromagnetic communication between an energy pathway and the body and to compensate for this loss when interpreting data from multiple energy pathways.

In an example, data from different energy pathways can analyzed to identify probable shifting of energy pathway location over the surface of the body (e.g. by shifting of a garment into which the pathways are integrated) and to compensate for this shifting when interpreting data from multiple energy pathways. In an example, there can be an established distinctive pattern between joint movement and energy flow in an energy pathway along the dorsal surface of a person's elbow, but this pattern can suddenly appear in an energy pathway along the lateral surface of a person's elbow. In an example, this invention can detect this shift and infer that an article of clothing which contains energy pathways has partially shifted around the person's elbow. Further, this invention can compensate for this shifting in statistical analysis of the data. This can help to reduce error due to shifts in clothing and/or energy pathways over the surface of a person's skin.

In an example, data from different energy pathways can analyzed to identify probable interference by an external object or field and to compensate for this interference when interpreting data from multiple energy pathways. In an example, if a person is resting the dorsal surface of their elbow on an external surface which interferes with the conduction of energy through energy pathways along the dorsal surface, then data from energy pathways along the ventral surface can be give greater weight.

In an example, first and second energy pathways which span a body member which contains a body joint can differ in flexibility. In an example, combined multivariate analysis of data from both the first and second energy pathways can provide more accurate measurement of body joint motion than data from either the first energy pathway or the second energy pathway alone. In an example, data from a more-flexible energy pathway can provide more accurate measurement of body joint motion over a first range of motion and data from a less-flexible energy pathway can provide more accurate measurement of body joint motion over a second range of motion. When analyzed together, data from the more-flexible and less-flexible energy pathways reduce error in measuring the full range of joint motion.

In an example, first and second energy pathways which span a body member which contains a body joint can differ in elasticity. In an example, combined multivariate analysis of data from both the first and second energy pathways can provide more accurate measurement of body joint motion than data from either the first energy pathway or the second energy pathway alone. In an example, data from a more-elastic energy pathway can provide more accurate measurement of body joint motion over a first range of motion and data from a less-elastic energy pathway can provide more accurate measurement of body joint motion over a second range of motion. When analyzed together, data from the more-elastic and less-elastic energy pathways reduce error in measuring the full range of joint motion.

In an example, first and second energy pathways which span a body member which contains a body joint can differ in electrical resistance or impedance. In an example, combined multivariate analysis of data from both the first and second energy pathways can provide more accurate measurement of body joint motion than data from either the first energy pathway or the second energy pathway alone. In an example, data from a higher resistance or impedance energy pathway can provide more accurate measurement of body joint motion over a first range of motion and data from a lower resistance or impedance energy pathway can provide more accurate measurement of body joint motion over a second range of motion. When analyzed together, data from the higher resistance or impedance and the lower resistance or impedance pathways reduce error in measuring the full range of joint motion.

In an example, first and second energy pathways which span a body member which contains a body joint can differ in transparency. In an example, combined multivariate analysis of data from both the first and second energy pathways can provide more accurate measurement of body joint motion than data from either the first energy pathway or the second energy pathway alone. In an example, data from a higher transparency can provide more accurate measurement of body joint motion over a first range of motion and data from a lower transparency can provide more accurate measurement of body joint motion over a second range of motion. When analyzed together, data from the higher resistance or impedance and the lower resistance or impedance pathways reduce error in measuring the full range of joint motion.

In an example, first and second energy pathways which span a body member which contains a body joint can differ in cross-sectional shape. In an example, combined multivariate analysis of data from both the first and second energy pathways can provide more accurate measurement of body joint motion than data from either the first energy pathway or the second energy pathway alone. In an example, data from a first energy pathway with a first cross-sectional shape can provide more accurate measurement of body joint motion over a first range of motion and data from a second energy pathway with a second cross-sectional shape can provide more accurate measurement of body joint motion over a second range of motion. When analyzed together, data from the first and second energy pathways reduce error in measuring the full range of joint motion.

In an example, different energy pathways can have different levels of measurement accuracy under different environmental conditions. In an example, a first energy pathway can superior measurement accuracy in a first temperature range and a second energy pathway can have superior measurement accuracy in a second temperature range. In an example, a first energy pathway can have superior measurement accuracy in a high-moisture environment (such as swimming) and a second energy pathway can have superior measurement accuracy in a low-moisture environment (such as an office). In an example, combined analysis of data from different types of energy pathways spanning the same body joint can provide superior measurement of body joint motion and/or configuration in a wider range of environmental conditions than analysis of data from a single type of energy pathway.

In an example, different energy pathways can have different levels of measurement accuracy for different movement speeds. In an example, a first energy pathway can have superior measurement accuracy for high-speed motions and a second energy pathway can have superior measurement accuracy for low-speed motions. In an example, a first energy pathway can have greater consistency of measurement for multiple iterations of the same repeated motion and a second energy pathway can have greater accuracy for complex, but non-repeated, motions. In an example, combined analysis of data from different types of energy pathways spanning the same body joint can provide superior measurement of complex combinations of repeated and non-repeated body joint motions than analysis of data from a single type of energy pathway.

In an example, a first energy pathway and a second energy pathway which both span the same body member which contains a body joint can differ by one or more parameters selected from the group consisting of: the angle at which they span the body joint; length; longitudinal curvature or convolution; longitudinal waveform; flexibility; elasticity;

electrical resistance or impedance; transparency; and cross-sectional shape. In an example, combined multivariate analysis of data from both the first and second energy pathways can provide more accurate measurement of body joint motion than analysis of data from either the first energy pathway or the second energy pathway alone. In an example, data from the first energy pathway can provide more accurate measurement of body joint motion over a first range of motion and data from the second energy pathway can provide more accurate measurement of body joint motion over a second range of motion. When analyzed together, data from the first and second energy pathways reduce error in measuring the full range of joint motion.

In an example, combined, joint, or integrated multivariate analysis of data from multiple energy pathways spanning the same body joint yields measurement of the motion and/or configuration of a body joint with a statistically-significant lower error rate or error range than analysis of data from a single energy pathway spanning that body joint. In an example, combined, joint, or integrated multivariate analysis of data from multiple energy pathways spanning the same body joint yields measurement of the motion and/or configuration of a body joint with a statistically-significant lower error rate or error range than separate analysis of data from those energy pathways. In an example, the statistical significance of error reduction is at the $p<0.05$ level. In an example, statistical significance of error reduction is at the $p<0.01$ level.

In an example, estimating the motion and/or configuration of a body joint angle using combined, joint, or integrated multivariate analysis of data from multiple energy pathways spanning that joint can yield an over-determined system of equations for joint angle estimation. This can help to reduce measurement error from factors such as: shifting or sliding of the energy pathways and/or a garment containing the energy pathways over the surface of the body; material fatigue and variability in the energy pathways; and interference between an external object and one side of the body member.

In an example, this device can be recalibrated in order to maintain accurate measurement of joint motion and/or configuration. In an example, recalibration can comprise comparing the results from using the energy pathways of the device to estimate the motion and/or configuration of a selected body joint or joints with parallel results from an alternative method of estimating joint motion and/or configuration of the body joint or joints. In an example, this device can be recalibrated when it is first worn by a specific person in order to be custom matched to that person's specific anatomy and/or body kinetics. In an example, this device can be recalibrated each time that a significant change in environmental factors (such as temperature, humidity, GPS location, or atmospheric pressure) is detected.

In an example, this device can be recalibrated each time that it is worn in order to control for: changing environmental conditions; incorporation into different articles of clothing; changes or shifts in how an article of clothing is worn over a person's body; changes in the anatomy or kinetics of a person's body over time; or other factors. In an example, this device can be recalibrated each time that a particular sequence of movements occurs in order to control for: possible shifts in how the energy pathways span a body member containing a body joint; changes in how material responses to bending, stretching, or elongation with repeated motions; changes in temperature; or other factors. In an example, this device can be recalibrated after a selected number of joint extension and contraction cycles. In an example, this device can be recalibrated after a selected number of movement sequences have occurred. In an example, this device can be recalibrated at selected usage time intervals.

FIGS. 2 and 3 show an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; and wherein data from the first and second electromagnetic energy sensors are jointly analyzed to estimate the configuration or motion of the human body joint; and (e) an attachment member which holds the first joint-spanning member and the second joint-spanning member within 1" of the surface of the portion of the human body which contains the human body joint.

FIGS. 2 and 3 show an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

Figure 4:
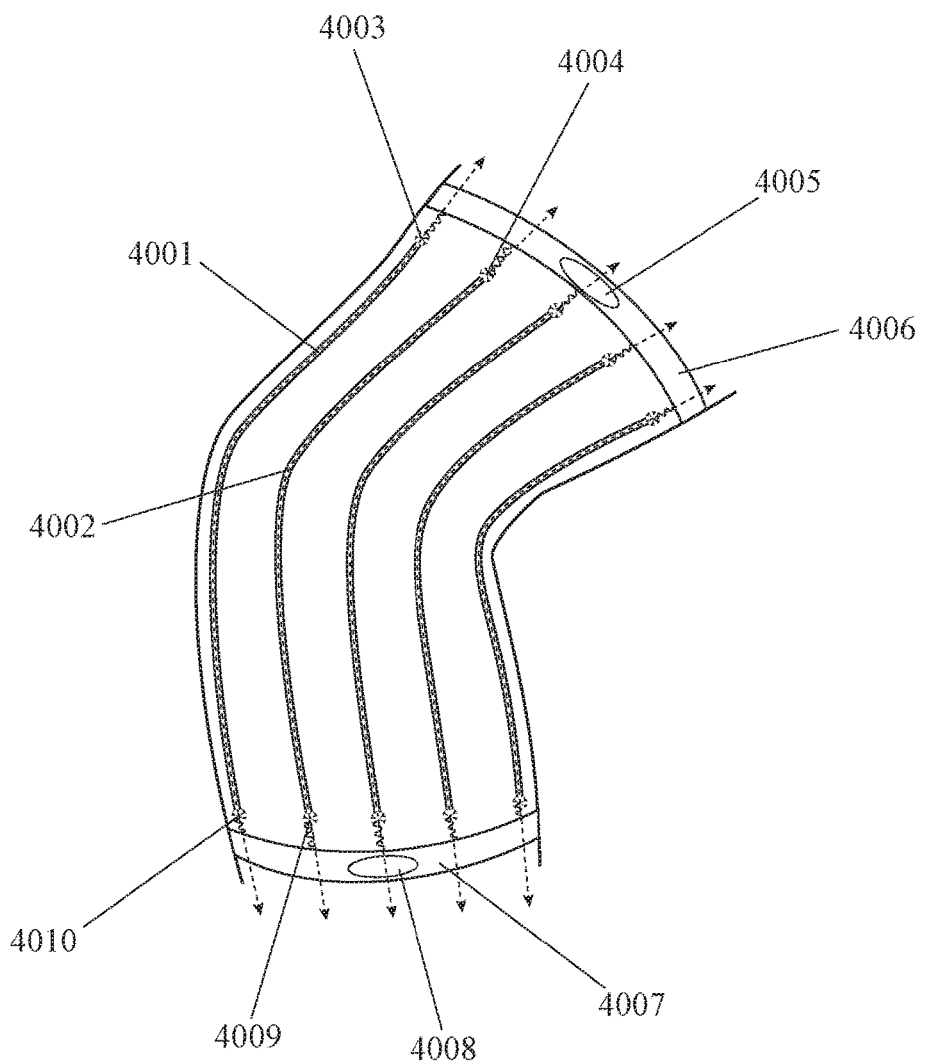
FIG. 4 shows an example wherein flexible energy pathways spanning the same joint are parallel.

FIG. 4 shows an example of how this invention can be embodied in a wearable device for measuring body joint motion and/or configuration comprising: (a) a first energy pathway 4001, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 4003 which measures energy flow through or from the first energy pathway; (c) a second energy pathway 4002, wherein this second energy pathway is configured to span the surface of the portion of a person's body which contains the at least one body joint, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration, and wherein the second energy pathway 4002 is substantially parallel to the first energy pathway 4001 as it spans the portion of the person's body; (d) a second energy sensor 4004 which measures energy flow through or from the second energy pathway, wherein data from the first energy sensor and data from the second energy sensor are analyzed together in order to measure the motion and/or configuration of the at least one body joint.

In the example shown in FIG. 4, this device further comprises: energy input component 4010 which sends energy into the first energy pathway; energy input component 4009 which sends energy into the second energy pathway; energy source 4008 (including energy conduits between this source and the energy input components); sensor data control unit 4005 (including energy conduits between this unit and the energy sensors); distal attachment band 4007; and proximal attachment band 4006.

Figure 5:
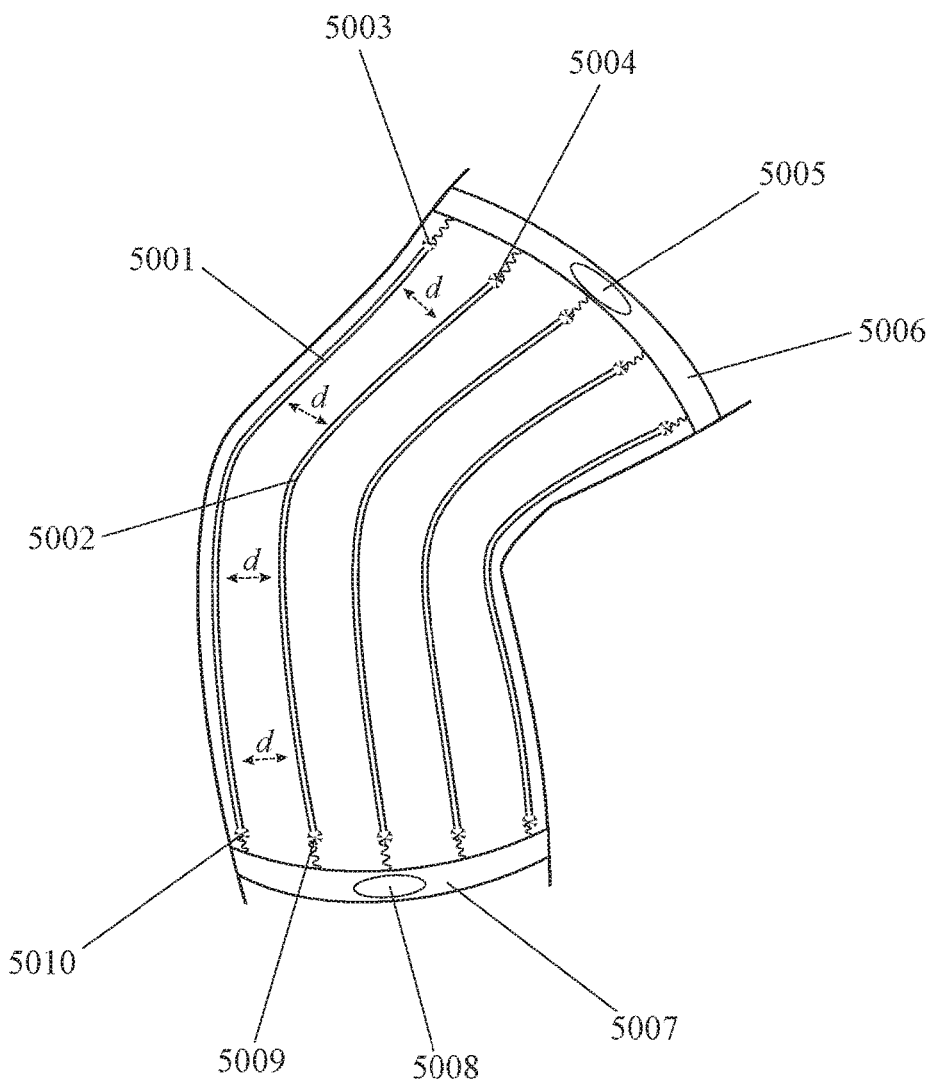
FIG. 5 shows an example wherein flexible energy pathways spanning the same joint are separated by a constant distance.

FIG. 5 shows an example of how this invention can be embodied in a wearable device for measuring body joint motion and/or configuration comprising: (a) a first energy pathway 5001, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 5003 which measures energy flow through or from the first energy pathway; (c) a second energy pathway 5002, wherein this second energy pathway is configured to span the surface of the portion of a person's body which contains the at least one body joint, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration, and wherein the second energy pathway 5002 is separated from first energy pathway 5001 by a substantially constant distance "d" as it spans the portion of the person's body; (d) a second energy sensor 5004 which measures energy flow through or from the second energy pathway, wherein data from the first energy sensor and data from the second energy sensor are analyzed together in order to measure the motion and/or configuration of the at least one body joint.

In the example shown in FIG. 5, this device further comprises: energy input component 5010 which sends energy into the first energy pathway; energy input component 5009 which sends energy into the second energy pathway; energy source 5008 (including energy conduits between this source and the energy input components); sensor data control unit 5005 (including energy conduits between this unit and the energy sensors); distal attachment band 5007; and proximal attachment band 5006.

FIG. 5 shows an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, and wherein the average first-to-second distance between the proximal portion of the first joint-spanning member and the proximal portion of the second joint-spanning member is substantially equal to the average first-to-second distance between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; and wherein data from the first and second electromagnetic energy sensors are jointly analyzed to estimate the configuration or motion of the human body joint; and (e) an attachment member which holds the first joint-spanning member and the second joint-spanning member within 1" of the surface of the portion of the human body which contains the human body joint.

FIG. 5 shows an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, and wherein the average first-to-second distance between the proximal portion of the first joint-spanning member and the proximal portion of the second joint-spanning member is substantially equal to the average first-to-second distance between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, wherein the average second-to-third distance between the proximal portion of the second joint-spanning member and the proximal portion of the third joint-spanning member is substantially equal to the average second-to-third distance between the distal portion of the second joint-spanning member and the distal portion of the third joint-spanning member, and wherein the average second-to-third distance is substantially equal to the average first-to-second distance; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

Figure 6:
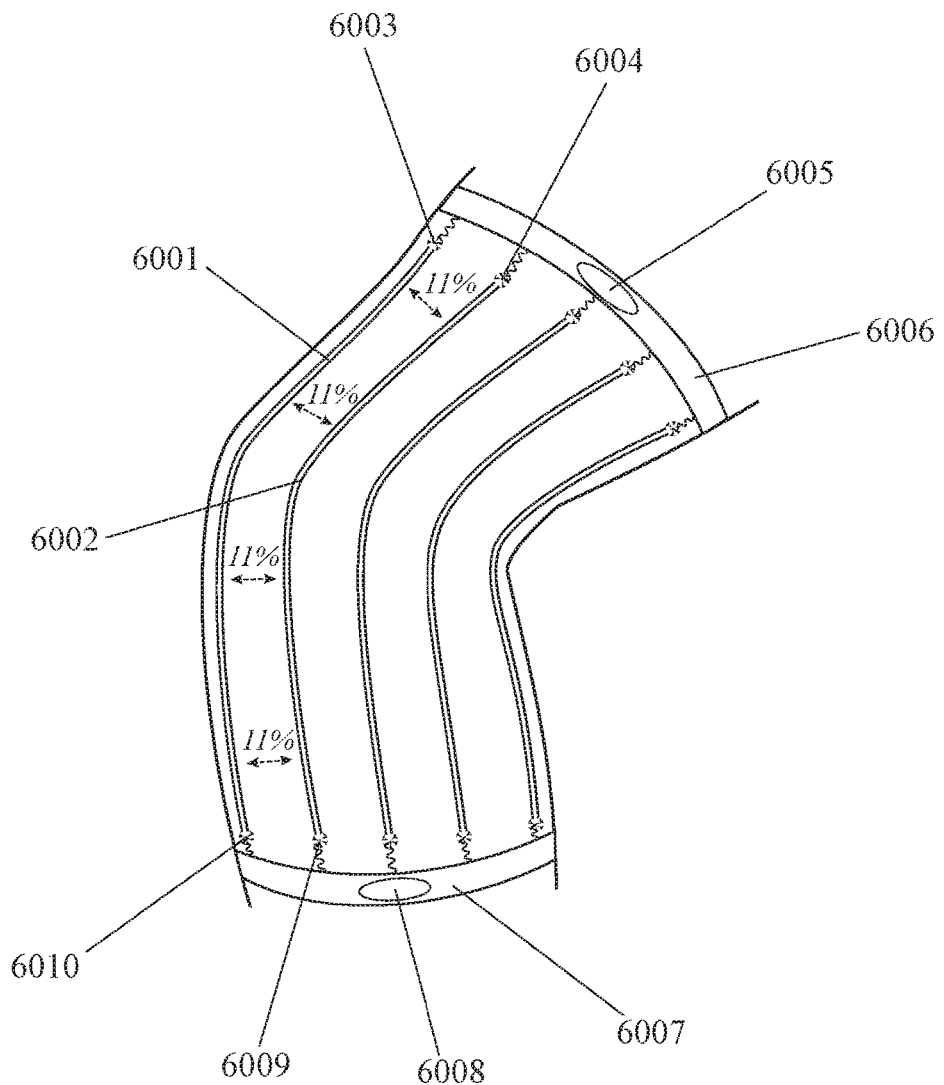
FIG. 6 shows an example wherein flexible energy pathways spanning the same joint are separated by a constant percentage of the cross-sectional perimeter of the body.

FIG. 6 shows an example of how this invention can be embodied in a wearable device for measuring body joint motion and/or configuration comprising: (a) a first energy pathway 6001, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 6003 which measures energy flow through or from the first energy pathway; (c) a second energy pathway 6002, wherein this second energy pathway is configured to span the surface of the portion of a person's body which contains the at least one body joint, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration, and wherein the second energy pathway 6002 is separated from first energy pathway 6001 by a substantially constant percentage of the cross-sectional perimeter of the portion of the person's body as it spans the portion of the body; (d) a second energy sensor 6004 which measures energy flow through or from the second energy pathway, wherein data from the first energy sensor and data from the second energy sensor are analyzed together in order to measure the motion and/or configuration of the at least one body joint. In this example, the constant percentage of the cross-sectional perimeter of the portion of the person's body is 11%.

In the example shown in FIG. 6, this device further comprises: energy input component 6010 which sends energy into the first energy pathway; energy input component 6009 which sends energy into the second energy pathway; energy source 6008 (including energy conduits between this source and the energy input components); sensor data control unit 6005 (including energy conduits between this unit and the energy sensors); distal attachment band 6007; and proximal attachment band 6006.

FIG. 6 shows an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, and wherein the average first-to-second percentage of the portion of the cross-sectional perimeter of the human body member between the proximal portion of the first joint-spanning member and the proximal portion of the second joint-spanning member is substantially equal to the average first-to-second percentage of the portion of the cross-sectional perimeter of the human body member between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; and wherein data from the first and second electromagnetic energy sensors are jointly analyzed to estimate the configuration or motion of the human body joint; and (e) an attachment member which holds the first joint-spanning member and the second joint-spanning member within 1" of the surface of the portion of the human body which contains the human body joint.

FIG. 6 shows an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, wherein the average first-to-second percentage of the portion of the cross-sectional perimeter of the human body member between the proximal portion of the first joint-spanning member and the proximal portion of the second joint-spanning member is substantially equal to the average first-to-second percentage of the portion of the cross-sectional perimeter of the human body member between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, and wherein the average second-to-third percentage of the portion of the cross-sectional perimeter of the human body member between the proximal portion of the second joint-spanning member and the proximal portion of the third joint-spanning member is substantially equal to the average second-to-third percentage of the portion of the cross-sectional perimeter of the human body member between the distal portion of the second joint-spanning member and the distal portion of the third joint-spanning member, and wherein the average second-to-third percentage is substantially equal to the average first-to-second percentage; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

Figure 7:
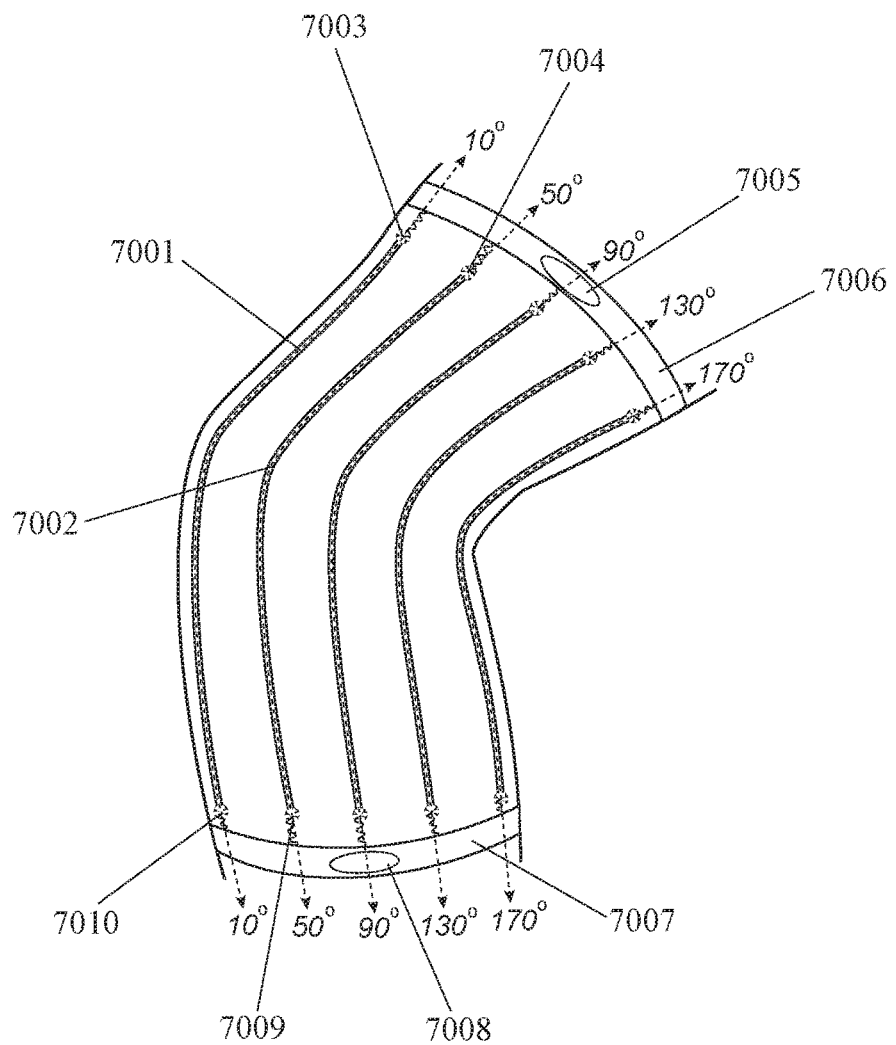
FIG. 7 shows an example wherein flexible energy pathways each span longitudinally-sequential cross-sectional perimeters of the body along a substantially-constant radial angle.

FIG. 7 shows an example of how this invention can be embodied in a wearable device for measuring body joint motion and/or configuration comprising: (a) a first energy pathway 7001, wherein this first energy pathway is configured to span the surface of a portion of a person's body which contains at least one body joint, wherein this first energy pathway spans longitudinally-sequential cross-sectional perimeters of the body member along a first substantially-constant radial angle, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 7003 which measures energy flow through or from the first energy pathway; (c) a second energy pathway 7002, wherein this second energy pathway is configured to span the surface of a portion of a person's body which contains at least one body joint, wherein this first second energy pathway spans longitudinally-sequential cross-sectional perimeters of the body member along a second substantially-constant radial angle, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 7004 which measures energy flow through or from the second energy pathway, wherein data from the first energy sensor and data from the second energy sensor are analyzed together in order to measure the motion and/or configuration of the at least one body joint.

In the example shown in FIG. 7, the first energy pathway 7001 spans longitudinally-sequential cross-sectional perimeters of the body member along a first substantially-constant radial angle (or latitude) of 10 degrees. In this example, the second energy pathway 7002 spans longitudinally-sequential cross-sectional perimeters of the body member along a second substantially-constant radial angle (or latitude) of 50 degrees. In this example, this device further comprises: energy input component 7010 which sends energy into the first energy pathway; energy input component 7009 which sends energy into the second energy pathway; energy source 7008 (including energy conduits between this source and the energy input components); sensor data control unit 7005 (including energy conduits between this unit and the energy sensors); distal attachment band 7007; and proximal attachment band 7006.

As shown in FIG. 7, the motion and/or configuration of a body joint can be measured using multiple energy pathways which span a portion of the body member which contains the body joint, wherein these energy pathways span longitudinally-sequential cross-sectional perimeters of the body member along selected radial angles, latitudes, or polar coordinates. In an example, the motion and/or configuration of a body joint can be measured using multiple energy pathways which span a portion of the body member which contains the body joint, wherein these energy pathways span longitudinally-sequential cross-sectional perimeters of the body member along radial angles, latitudes, or polar coordinates which are evenly distributed around the 0 to 360 degree range.

In an example, the motion and/or configuration of a body joint can be measured using two energy pathways which span a portion of the body member which contains the body joint, wherein these two energy pathways span longitudinally-sequential cross-sectional perimeters of the body member along radial angles, latitudes, or polar coordinates of approximately 0 degrees and 180 degrees. In an example, the 0-degree pathway can span the dorsal surface of the body member and the 180-degree member can span the ventral surface of the body member.

In an example, the motion and/or configuration of a body joint can be measured using four energy pathways which span a portion of the body member which contains the body joint, wherein these four energy pathways span longitudinally-sequential cross-sectional perimeters of the body member along radial angles, latitudes, or polar coordinates of approximately 0, 90, 180, and 270 degrees. In an example, the 0-degree pathway can span the dorsal surface of the body member, the 180-degree member can span the ventral surface of the body member, and the 90 and 270 degree pathways can span the lateral surfaces of the body member. In an example, a first energy pathway can span the dorsal surface of a body member containing a body joint, a second energy pathway can span the ventral surface of that body member, a third energy pathway can span a first lateral surface of that body member, and a fourth energy pathway can span a second lateral surface of that body member.

In an example, the motion and/or configuration of a body joint can be measured using six energy pathways which span a portion of the body member which contains the body joint, wherein these six energy pathways span longitudinally-sequential cross-sectional perimeters of the body member along radial angles, latitudes, or polar coordinates of approximately 0, 60, 120, 180, 240, and 300 degrees. In an example, the motion and/or configuration of a body joint can be measured using eight energy pathways which span a portion of the body member which contains the body joint, wherein these eight energy pathways span longitudinally-sequential cross-sectional perimeters of the body member along radial angles, latitudes, or polar coordinates of approximately 0, 45, 90, 135, 180, 225, 270, and 315 degrees.

FIG. 7 shows an example embodiment of this invention comprising a wearable device for measuring the configuration or motion of a human body joint can comprise: (a) a first joint-spanning member, wherein the central axis of the first joint-spanning member is located along a substantially constant first radial angle in different cross-sections of the portion of the human body which contains the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein the central axis of the second joint-spanning member is located along a substantially constant second radial angle in different cross-sections of the portion of the human body which contains the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; and wherein data from the first and second electromagnetic energy sensors are jointly analyzed to estimate the configuration or motion of the human body joint; and (e) an attachment member which holds the first joint-spanning member and the second joint-spanning member within 1" of the surface of the portion of the human body which contains the human body joint.

FIG. 7 shows an example embodiment of this invention comprising a wearable device for measuring the configuration or motion of a human body joint can comprise: (a) a first joint-spanning member, wherein the central axis of the first joint-spanning member is located along a substantially constant first radial angle in different cross-sections of the portion of the human body which contains the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein the central axis of the second joint-spanning member is located along a substantially constant second radial angle in different cross-sections of the portion of the human body which contains the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein the central axis of the third joint-spanning member is located along a substantially constant third radial angle in different cross-sections of the portion of the human body which contains the human body joint, and wherein the difference between the second radial angle and the third radial angle is substantially equal to the difference between the first radial angle and the second radial angle; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

Figure 8:
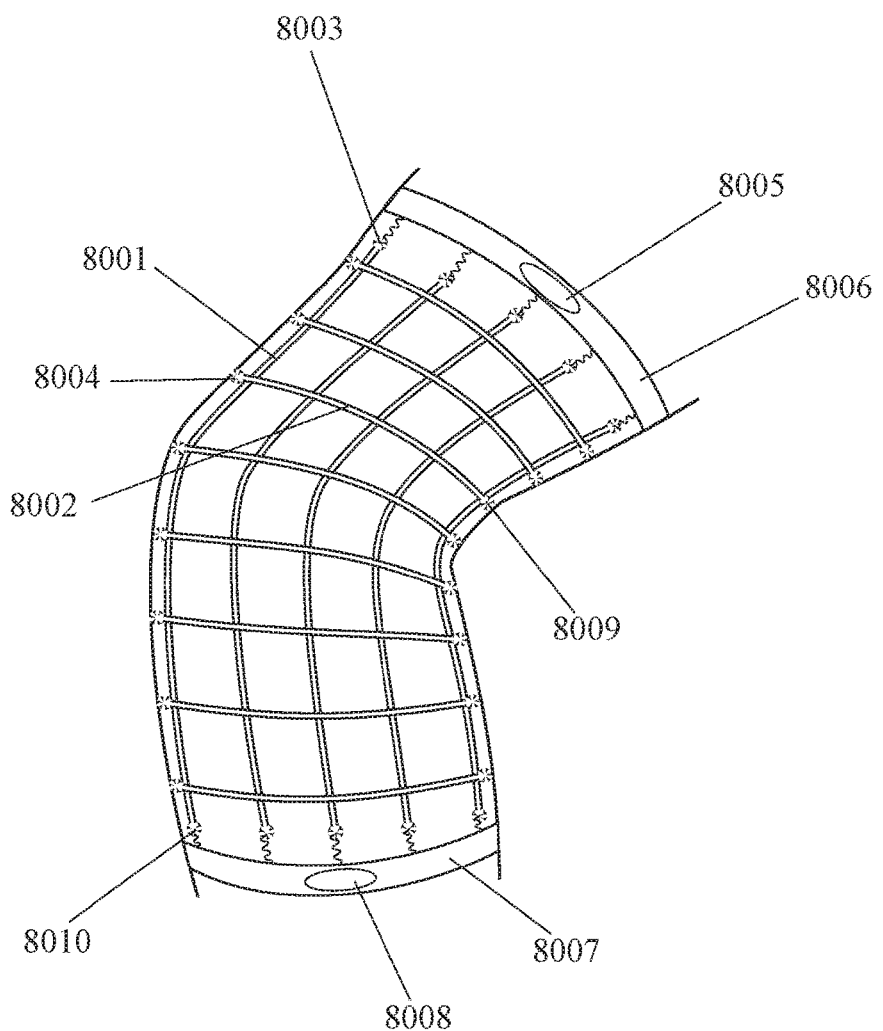
FIG. 8 shows an example wherein some flexible energy pathways span a joint longitudinally and some other flexible energy pathways span the same joint circumferentially.

FIG. 8 shows an example of how this invention can be embodied in a wearable device for measuring body joint motion and/or configuration comprising: (a) a first energy pathway 8001, wherein this first energy pathway is configured to span the surface of a portion of a person's body which contains at least one body joint in a longitudinal manner, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 8003 which measures energy flow through or from the first energy pathway; (c) a second energy pathway 8002, wherein this second energy pathway is configured to span the surface of the portion of a person's body which contains the at least one body joint in a cross-sectional or circumferential manner, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 8009 which measures energy flow through or from the second energy pathway, wherein data from the first energy sensor and data from the second energy sensor are analyzed together in order to measure the motion and/or configuration of the at least one body joint.

In the example shown in FIG. 8, this device further comprises: energy input component 8010 which sends energy into the first energy pathway; energy input component 8004 which sends energy into the second energy pathway; energy source 8008 (including energy conduits between this source and the energy input components); sensor data control unit 8005 (including energy conduits between this unit and the energy sensors); distal attachment band 8007; and proximal attachment band 8006.

As shown in FIG. 8, first and second energy pathways which span a body member which contains a body joint can differ in the angle at which they span the body member. In an example, combined multivariate analysis of data from both the first and second energy pathways can provide more accurate measurement of body joint motion and/or configuration than data from either the first energy pathway or the second energy pathway alone. In an example, data from the first energy pathway can provide more accurate measurement of body joint motion over a first range of motion and data from the second energy pathway can provide more accurate measurement of body joint motion over a second range of motion. When analyzed together, data from the first and second energy pathways reduce error in measuring the full range of joint motion.

In an example, multiple energy pathways spanning the same body joint can form inter-pathway gaps, areas, or spaces which, when projected from 3D space onto a 2D plane, are squares, rhombuses, diamonds, trapezoids, parallelograms, triangles, or hexagons. In an example, energy pathways can be part of a mesh which is an array of one or more shapes selected from the group consisting of: square elements; rectangular elements; diamond elements; rhomboid elements; parallelogram elements; trapezoidal elements; triangular elements; hexagonal elements; circular elements; and elliptical elements.

In an example, the flows of energy through first and second energy pathways can be independent or can be separate as these flows span a body member containing a body joint. In an example, the flows of energy through first and second energy pathways can interact or combine with each other as these flows span a body member containing a body joint. In an example, first and second energy pathways can be in electromagnetic communication with each other as they span a body joint. In an example, first and second energy pathways can be in mechanical communication with each other as they span a body joint. In an example, first and second energy pathways can be in optical communication with each other as they span a body joint. In an example, first and second energy pathways can be in sonic communication with each other as they span a body joint.

FIG. 8 shows an example embodiment of this invention comprising a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, and wherein the average first-to-second distance between the proximal portion of the first joint-spanning member and the proximal portion of the second joint-spanning member is substantially equal to the average first-to-second distance between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, wherein the average second-to-third distance between the proximal portion of the second joint-spanning member and the proximal portion of the third joint-spanning member is substantially equal to the average second-to-third distance between the distal portion of the second joint-spanning member and the distal portion of the third joint-spanning member; (f) a third electromagnetic energy sensor which measures electromagnetic energy from the third joint-spanning member, wherein changes in the configuration or motion of the third joint-spanning member change the electromagnetic energy measured by the third electromagnetic energy sensor; (g) at least one perimeter member with a longitudinal axis that is substantially perpendicular to the longitudinal axis of at least one of the first, second, and third joint-spanning members; (h) at least one perimeter electromagnetic energy sensor which measures electromagnetic energy from the at least one perimeter member, wherein changes in the configuration or motion of the at least one perimeter member change the electromagnetic energy measured by the at least one perimeter electromagnetic energy sensor, and wherein data from the first electromagnetic energy sensor, second electromagnetic energy sensor, third electromagnetic energy sensor, and at least-one-perimeter electromagnetic energy sensor are jointly analyzed to estimate the configuration or motion of the human body joint; and (i) an attachment member which holds the first, second, third joint-spanning members and the at least one perimeter member within 1" of the surface of the portion of the human body which contains the human body joint.

FIG. 8 shows an example embodiment of this invention comprising a wearable device for measuring the configuration or motion of a human body joint can comprise: (a) a first joint-spanning member with a first length, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member with a second length, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, wherein the average first-to-second percentage of the portion of the cross-sectional perimeter of the human body member between the proximal portion of the first joint-spanning member and the proximal portion of the second joint-spanning member is substantially equal to the average first-to-second percentage of the portion of the cross-sectional perimeter of the human body member between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member with a third length, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, and wherein the average second-to-third percentage of the portion of the cross-sectional perimeter of the human body member between the proximal portion of the second joint-spanning member and the proximal portion of the third joint-spanning member is substantially equal to the average second-to-third percentage of the portion of the cross-sectional perimeter of the human body member between the distal portion of the second joint-spanning member and the distal portion of the third joint-spanning member; (f) a third electromagnetic energy sensor which measures electromagnetic energy from the third joint-spanning member, wherein changes in the configuration or motion of the third joint-spanning member change the electromagnetic energy measured by the third electromagnetic energy sensor; (g) at least one perimeter member with a longitudinal axis that is substantially perpendicular to the longitudinal axis of at least one of the first, second, and third joint-spanning members; (h) at least one perimeter electromagnetic energy sensor which measures electromagnetic energy from the at least one perimeter member, wherein changes in the configuration or motion of the at least one perimeter member change the electromagnetic energy measured by the at least one perimeter electromagnetic energy sensor, and wherein data from the first electromagnetic energy sensor, second electromagnetic energy sensor, third electromagnetic energy sensor, and at least-one-perimeter electromagnetic energy sensor are jointly analyzed to estimate the configuration or motion of the human body joint; and (i) an attachment member which holds the first, second, third joint-spanning members and the at least one perimeter member within 1" of the surface of the portion of the human body which contains the human body joint.

FIG. 8 shows an example embodiment of this invention comprising a wearable device for measuring the configuration or motion of a human body joint can comprise: (a) a first longitudinal member which is configured to longitudinally span the surface of a portion of the human body which contains a human body joint; (b) a first longitudinal electromagnetic energy sensor which measures electromagnetic energy from the first longitudinal member, wherein changes in the configuration or motion of the first longitudinal member change the electromagnetic energy measured by the first longitudinal electromagnetic energy sensor; (c) a second longitudinal member which is configured to longitudinally span the surface of a portion of the human body which contains a human body joint; (d) a second longitudinal electromagnetic energy sensor which measures electromagnetic energy from the second longitudinal member, wherein changes in the configuration or motion of the second longitudinal member change the electromagnetic energy measured by the first longitudinal electromagnetic energy sensor; (e) a first lateral member which is configured to span the surface of a portion of the human body which contains a human body joint in a manner which is substantially perpendicular to the first and/or second longitudinal members; a first lateral electromagnetic energy sensor which measures electromagnetic energy from the first lateral member, wherein changes in the configuration or motion of the first lateral member change the electromagnetic energy measured by the first lateral electromagnetic energy sensor; (f) a second lateral member which is configured to span the surface of a portion of the human body which contains a human body joint in a manner which is substantially perpendicular to the first and/or second longitudinal members; (g) a second lateral electromagnetic energy sensor which measures electromagnetic energy from the second lateral member, wherein changes in the configuration or motion of the second lateral member change the electromagnetic energy measured by the first lateral electromagnetic energy sensor, and wherein data from the first longitudinal electromagnetic energy sensor, the second longitudinal electromagnetic energy sensor, the first lateral electromagnetic energy sensor, and the second lateral electromagnetic energy sensor are jointly analyzed to estimate the configuration or motion of the human body joint; and (h) an attachment member which holds the first longitudinal member, the second longitudinal member, the first lateral member, and the second lateral member within 1" of the surface of the portion of the human body which contains the human body joint.

FIG. 8 shows an example embodiment of this invention comprising a wearable device for measuring the configuration or motion of a human body joint can comprise: (a) a first lateral member which is configured to span the surface of a portion of the human body which contains a human body joint in a manner which is substantially perpendicular to the longitudinal axis of the human body joint; (b) a first lateral electromagnetic energy sensor which measures electromagnetic energy from the first lateral member, wherein changes in the configuration or motion of the first lateral member change the electromagnetic energy measured by the first lateral electromagnetic energy sensor; (c) a second lateral member which is configured to span the surface of a portion of the human body which contains a human body joint in a manner which is substantially perpendicular to the longitudinal axis of the human body joint; (d) a second lateral electromagnetic energy sensor which measures electromagnetic energy from the second lateral member, wherein changes in the configuration or motion of the second lateral member change the electromagnetic energy measured by the first lateral electromagnetic energy sensor; (e) a third lateral member which is configured to span the surface of a portion of the human body which contains a human body joint in a manner which is substantially perpendicular to the longitudinal axis of the human body joint; (f) a third lateral electromagnetic energy sensor which measures electromagnetic energy from the second lateral member, wherein changes in the configuration or motion of the second lateral member change the electromagnetic energy measured by the first lateral electromagnetic energy sensor; and wherein data from the first, second, and third lateral electromagnetic energy sensors are jointly analyzed to estimate the configuration or motion of the human body joint; and (g) an attachment member which holds the first, second, and third lateral members within 1" of the surface of the portion of the human body which contains the human body joint.

FIG. 8 shows an example embodiment of this invention comprising a wearable device for measuring the configuration or motion of a human body joint can comprise: (a) a joint-spanning arcuate-element mesh which is comprised of linked arcuate elements and which is configured to span the surface of a portion of the human body which contains a human body joint; and (b) a plurality of electromagnetic energy sensors which measure electromagnetic energy from different locations on the joint-spanning arcuate-element mesh, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

Figure 9:
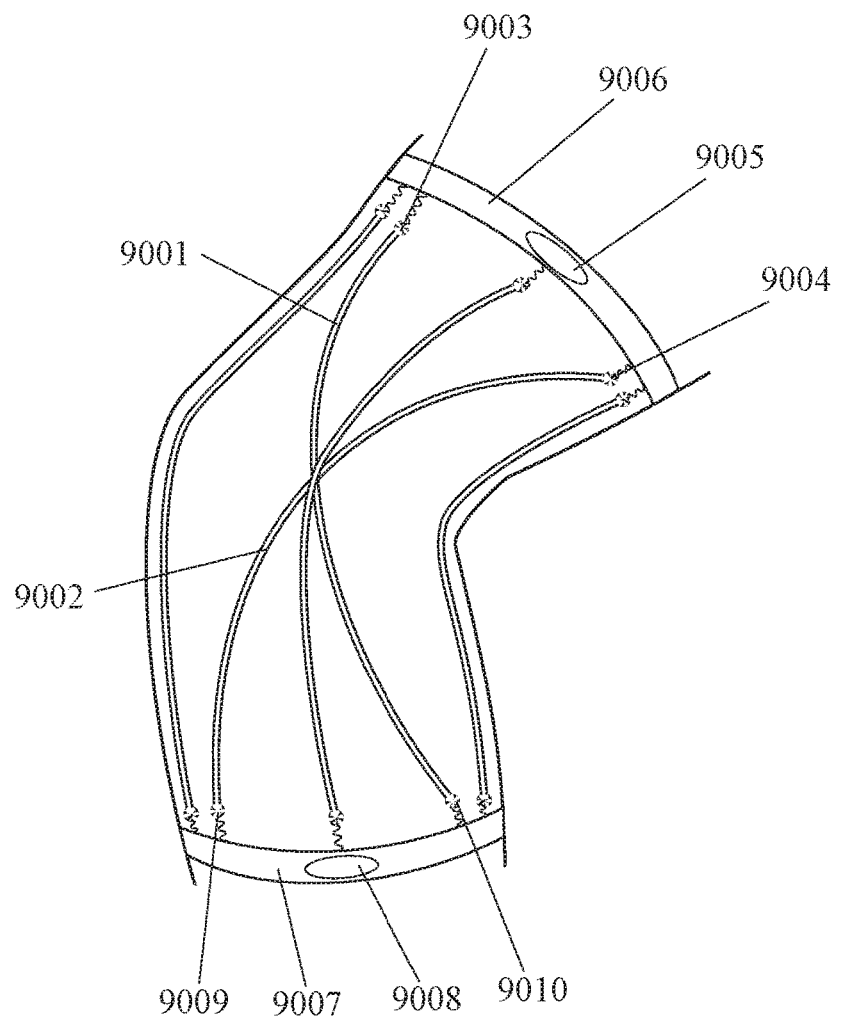
FIG. 9 shows an example wherein flexible energy pathways spanning a joint intersect at acute angles.

FIG. 9 shows an example of how this invention can be embodied in a wearable device for measuring body joint motion and/or configuration comprising: (a) a first energy pathway 9001, wherein this first energy pathway is configured to span the surface of a portion of a person's body which contains at least one body joint at a first angle, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 9003 which measures energy flow through or from the first energy pathway; (c) a second energy pathway 9002, wherein this second energy pathway is configured to span the surface of the portion of a person's body which contains the at least one body joint at a second angle, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 9004 which measures energy flow through or from the second energy pathway, wherein data from the first energy sensor and data from the second energy sensor are analyzed together in order to measure the motion and/or configuration of the at least one body joint.

As shown in FIG. 9, two energy pathways spanning the same body joint can differ in the angles at which they span the longitudinal axis of the body member which contains the body joint. In an example, having different energy pathways span a body joint at different angles can be especially useful for measuring the motion and/or configuration of ball-and-socket or other complex motion joints.

In the example shown in FIG. 9, this device further comprises: energy input component 9010 which sends energy into the first energy pathway; energy input component 9009 which sends energy into the second energy pathway; energy source 9008 (including energy conduits between this source and the energy input components); sensor data control unit 9005 (including energy conduits between this unit and the energy sensors); distal attachment band 9007; and proximal attachment band 9006.

FIG. 9 shows an example embodiment of this invention comprising a wearable device for measuring the configuration or motion of a human body joint can comprise: (a) a first longitudinal member which is configured to longitudinally span the surface of a portion of the human body which contains a human body joint; (b) a first longitudinal electromagnetic energy sensor which measures electromagnetic energy from the first longitudinal member, wherein changes in the configuration or motion of the first longitudinal member change the electromagnetic energy measured by the first longitudinal electromagnetic energy sensor; (c) a second longitudinal member which is configured to longitudinally span the surface of a portion of the human body which contains a human body joint; (d) a second longitudinal electromagnetic energy sensor which measures electromagnetic energy from the second longitudinal member, wherein changes in the configuration or motion of the second longitudinal member change the electromagnetic energy measured by the first longitudinal electromagnetic energy sensor; (e) a first diagonal member which is configured to span the surface of a portion of the human body which contains a human body joint in a manner which is substantially diagonal to the first and/or second longitudinal members; (f) a first diagonal electromagnetic energy sensor which measures electromagnetic energy from the first diagonal member, wherein changes in the configuration or motion of the first diagonal member change the electromagnetic energy measured by the first diagonal electromagnetic energy sensor; (g) a second diagonal member which is configured to span the surface of a portion of the human body which contains a human body joint in a manner which is substantially diagonal to the first and/or second longitudinal members; (h) a second diagonal electromagnetic energy sensor which measures electromagnetic energy from the second diagonal member, wherein changes in the configuration or motion of the second diagonal member change the electromagnetic energy measured by the first diagonal electromagnetic energy sensor, and wherein data from the first longitudinal electromagnetic energy sensor, the second longitudinal electromagnetic energy sensor, the first diagonal electromagnetic energy sensor, and the second diagonal electromagnetic energy sensor are jointly analyzed to estimate the configuration or motion of the human body joint; and (i) an attachment member which holds the first longitudinal member, the second longitudinal member, the first diagonal member, and the second diagonal member within 1" of the surface of the portion of the human body which contains the human body joint.

Figure 10:
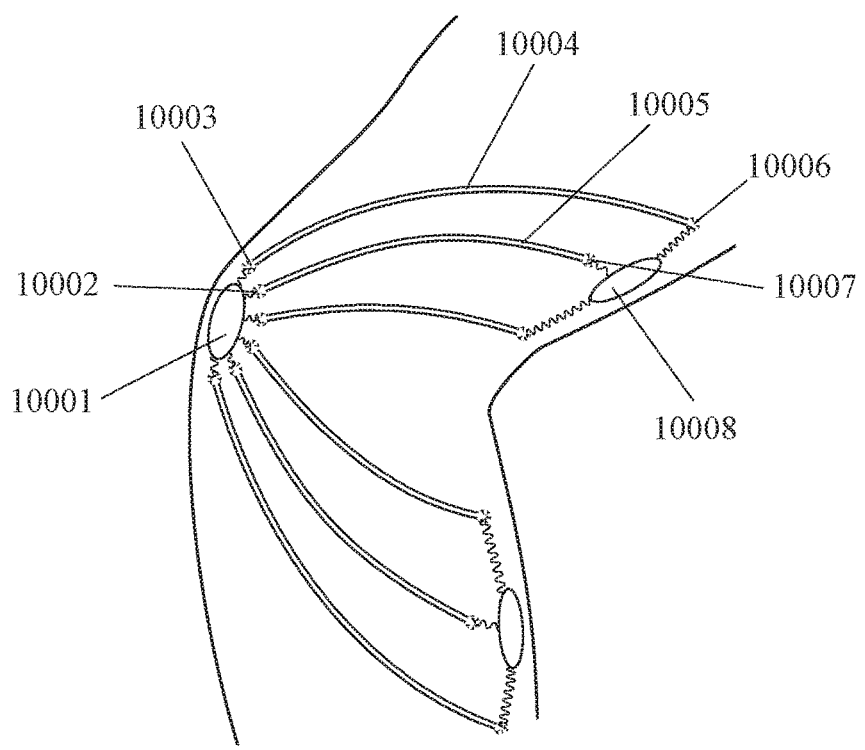
FIG. 10 shows an example wherein flexible energy pathways span a joint in a radial manner.

FIG. 10 shows an example of how this invention can be embodied in a wearable device for measuring body joint motion and/or configuration comprising: (a) a first energy pathway 10004, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 10006 which measures energy flow through or from the first energy pathway; (c) a second energy pathway 10005, wherein this second energy pathway is configured to span the surface of the portion of a person's body which contains the at least one body joint at a second angle, wherein this second energy pathway is moved from a third configuration to a fourth configuration by movement of the at least one body joint, wherein this second energy pathway has a third energy flow when the pathway is in the third configuration and has a fourth energy flow when the pathway is in the fourth configuration, and wherein the first and second energy pathways follow converging arcuate vectors; (d) a second energy sensor 10007 which measures energy flow through or from the second energy pathway, wherein data from the first energy sensor and data from the second energy sensor are analyzed together in order to measure the motion and/or configuration of the at least one body joint.

In the example shown in FIG. 10, this device further comprises: energy input component 10003 which sends energy into the first energy pathway; energy input component 10002 which sends energy into the second energy pathway; energy source 10001 (including energy conduits between this source and the energy input components); and sensor data control unit 10008 (including energy conduits between this unit and the energy sensors).

FIG. 10 shows an example embodiment of this invention comprising a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge at a point on the ventral surface of the portion of the human body which contains the human body joint; and (b) a plurality of electromagnetic energy sensors which measure electromagnetic energy from different locations on the joint-spanning plurality of radial members, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

Figure 11:
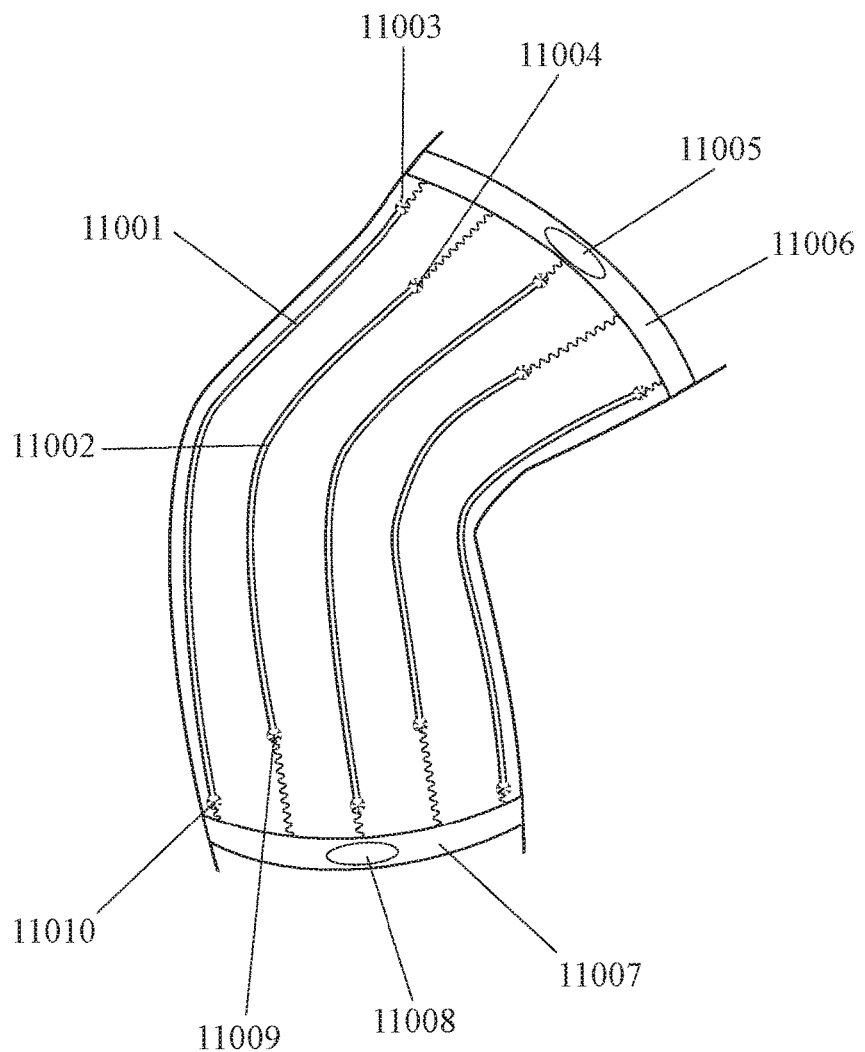
FIG. 11 shows an example wherein flexible energy pathways spanning a joint have different lengths.

FIG. 11 shows an example of how this invention can be embodied in a wearable device for measuring body joint motion and/or configuration comprising: (a) a first energy pathway 11001, wherein this first energy pathway is configured to span the surface of a portion of a person's body which contains at least one body joint, wherein this first energy pathway has a first length, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 11003 which measures energy flow through or from the first energy pathway; (c) a second energy pathway 11002, wherein this second energy pathway is configured to span the surface of the portion of a person's body which contains the at least one body joint, wherein this second energy pathway has a second length, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 11004 which measures energy flow through or from the second energy pathway, wherein data from the first energy sensor and data from the second energy sensor are analyzed together in order to measure the motion and/or configuration of the at least one body joint.

In the example shown in FIG. 11, this device further comprises: energy input component 11010 which sends energy into the first energy pathway; energy input component 11009 which sends energy into the second energy pathway; energy source 11008 (including energy conduits between this source and the energy input components); sensor data control unit 11005 (including energy conduits between this unit and the energy sensors); distal attachment band 11007; and proximal attachment band 11006.

As shown in FIG. 11, first and second energy pathways which span a body member which contains a body joint can differ in length. In an example, combined multivariate analysis of data from both the first and second energy pathways can provide more accurate measurement of body joint motion than data from either the first energy pathway or the second energy pathway alone. In an example, data from a longer energy pathway can provide more accurate measurement of body joint motion over a first range of motion and data from a shorter energy pathway can provide more accurate measurement of body joint motion over a second range of motion. When analyzed together, data from the longer and shorter energy pathways reduce error in measuring the full range of joint motion.

FIG. 11 shows an example embodiment of this invention comprising a wearable device for measuring the configuration or motion of a human body joint can comprise: (a) a first joint-spanning member with a first length, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member with a second length, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, and wherein the average first-to-second distance between the proximal portion of the first joint-spanning member and the proximal portion of the second joint-spanning member is substantially equal to the average first-to-second distance between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member with a third length, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, wherein the average second-to-third distance between the proximal portion of the second joint-spanning member and the proximal portion of the third joint-spanning member is substantially equal to the average second-to-third distance between the distal portion of the second joint-spanning member and the distal portion of the third joint-spanning member, and wherein the first, second, and third lengths differ by more than 20%; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

FIG. 11 shows an example embodiment of this invention comprising a wearable device for measuring the configuration or motion of a human body joint can comprise: (a) a first joint-spanning member with a first length, wherein the central axis of the first joint-spanning member is located along a substantially constant first radial angle in different cross-sections of the portion of the human body which contains the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member with a second length, wherein the central axis of the second joint-spanning member is located along a substantially constant second radial angle in different cross-sections of the portion of the human body which contains the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member with a third length, wherein the central axis of the third joint-spanning member is located along a substantially constant third radial angle in different cross-sections of the portion of the human body which contains the human body joint, and wherein the first, second, and third lengths differ by more than 20%; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

Figure 12:
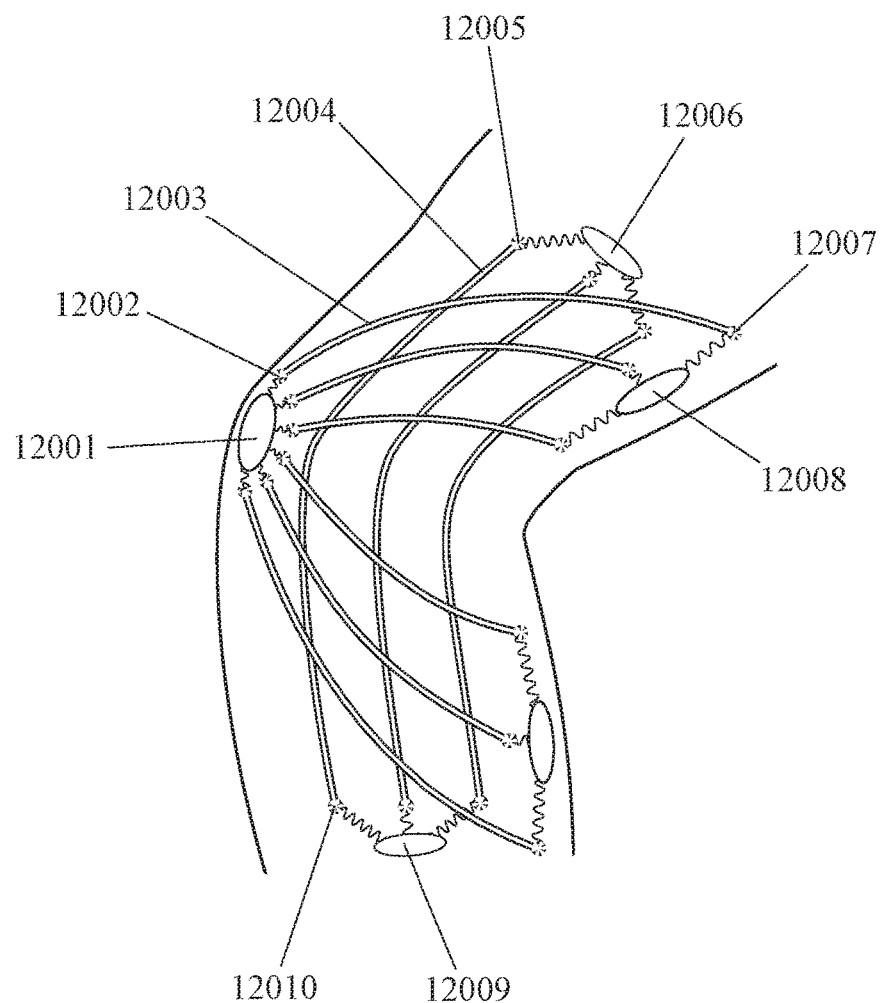
FIG. 12 shows an example wherein some flexible energy pathways span a joint longitudinally and some other flexible energy pathways span the same joint radially.

FIG. 12 shows an example of how this invention can be embodied in a wearable device for measuring body joint motion and/or configuration comprising: (a) a first energy pathway 12003, wherein this first energy pathway is configured to span the surface of a portion of a person's body which contains at least one body joint, wherein this first energy pathway spans the portion of the person's body in an arcuate cross-sectional manner, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 12007 which measures energy flow through or from the first energy pathway; (c) a second energy pathway 12004, wherein this second energy pathway is configured to span the surface of the portion of a person's body which contains the at least one body joint, wherein this first energy pathway spans the portion of the person's body in a longitudinal manner, wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 12005 which measures energy flow through or from the second energy pathway, wherein data from the first energy sensor and data from the second energy sensor are analyzed together in order to measure the motion and/or configuration of the at least one body joint.

In the example shown in FIG. 12, this device further comprises: energy input component 12002 which sends energy into the first energy pathway; energy input component 12010 which sends energy into the second energy pathway; energy sources 12001 and 12010 (including energy conduits between these sources and the energy input components); and sensor data control units 12006 and 12008.

Figure 13:
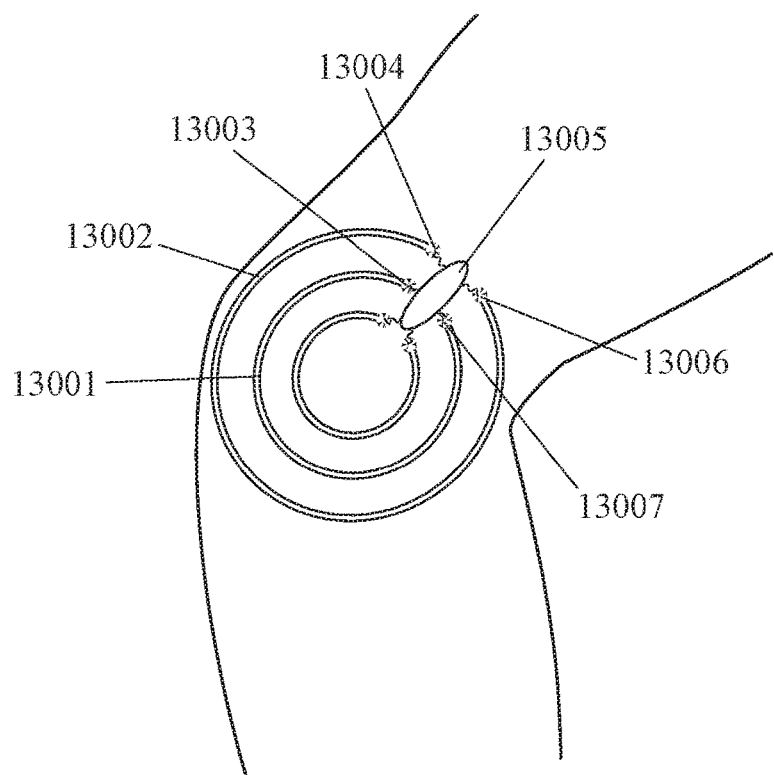
FIG. 13 shows an example wherein flexible energy pathways spanning a joint are concentric.

FIG. 13 shows an example of how this invention can be embodied in a wearable device for measuring body joint motion and/or configuration comprising: (a) a first energy pathway 13001, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 13003 which measures energy flow through or from the first energy pathway; (c) a second energy pathway 13002, wherein this second energy pathway is configured to span the surface of the portion of a person's body which contains the at least one body joint, wherein the first energy pathway and the second energy pathway comprise a concentric or nested combined configuration; wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 13004 which measures energy flow through or from the second energy pathway, wherein data from the first energy sensor and data from the second energy sensor are analyzed together in order to measure the motion and/or configuration of the at least one body joint.

In the example shown in FIG. 13, this device further comprises: energy input component 13007 which sends energy into the first energy pathway; energy input component 13006 which sends energy into the second energy pathway; and combined energy source and sensor data control unit 13005.

FIG. 13 shows an example embodiment of this invention comprising a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point on a lateral surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

Figure 14:
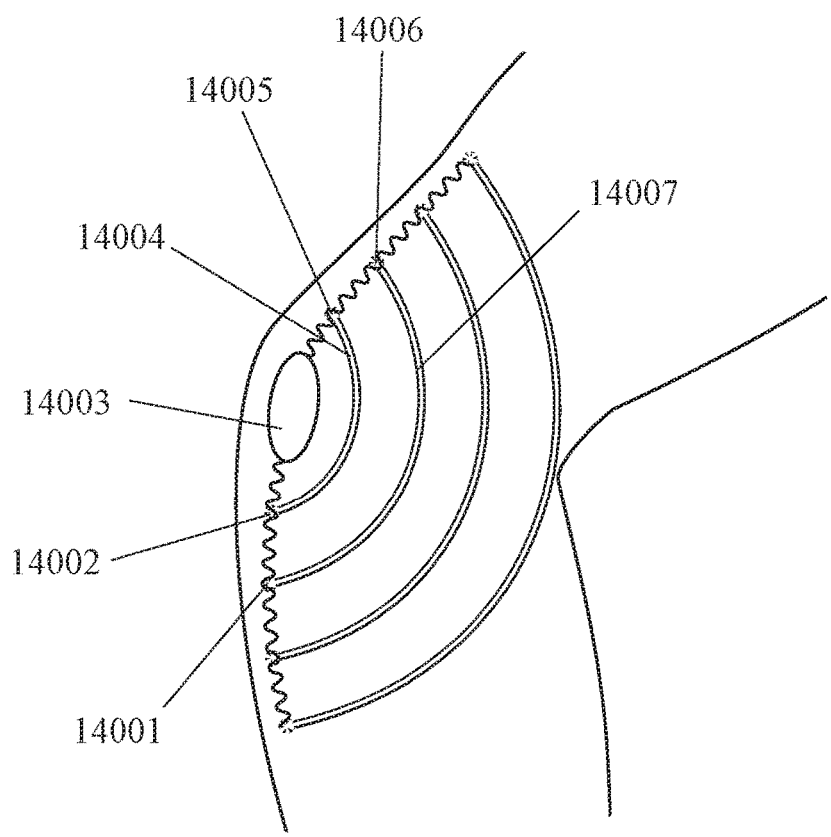
FIG. 14 shows an example wherein flexible energy pathways spanning a joint are nested or rainbow shaped.

FIG. 14 shows an example of how this invention can be embodied in a wearable device for measuring body joint motion and/or configuration comprising: (a) a first energy pathway 14004, wherein this first energy pathway is configured to span the surface of a portion of a person's body which contains at least one body joint, wherein this first energy pathway is moved from a first configuration to a second configuration by movement of the at least one body joint, and wherein this first energy pathway has a first energy flow when the pathway is in the first configuration and has a second energy flow when the pathway is in the second configuration; (b) a first energy sensor 14005 which measures energy flow through or from the first energy pathway; (c) a second energy pathway 14007, wherein this second energy pathway is configured to span the surface of the portion of a person's body which contains the at least one body joint, wherein the first energy pathway and the second energy pathway comprise a nested or rainbow-shaped combined configuration; wherein this second energy pathway is moved from a third configuration to a fourth configuration by movement of the at least one body joint, and wherein this second energy pathway has a third energy flow when the pathway is in the third configuration and has a fourth energy flow when the pathway is in the fourth configuration; (d) a second energy sensor 14006 which measures energy flow through or from the second energy pathway, wherein data from the first energy sensor and data from the second energy sensor are analyzed together in order to measure the motion and/or configuration of the at least one body joint.

In the example shown in FIG. 14, this device further comprises: energy input component 14002 which sends energy into the first energy pathway; energy input component 14001 which sends energy into the second energy pathway; and combined energy source and sensor data control unit 14003.

FIG. 14 shows an example embodiment of this invention comprising a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point on the ventral surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

Figure 15:
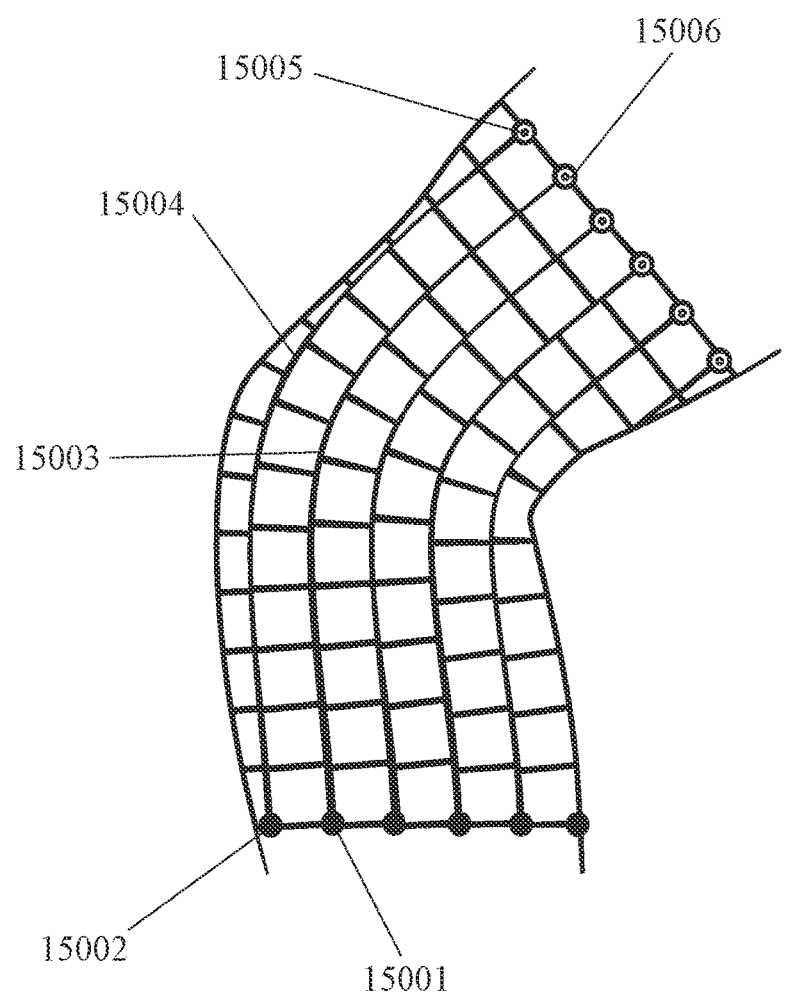
FIG. 15 shows an example with a wearable energy-conducting lattice, mesh, grid, or matrix and longitudinal energy pathways.

FIG. 15 shows an example of how this invention can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of energy pathways including 15003 and 15004 which are configured to span that portion of the body in a longitudinal manner (from a proximal portion of the joint to a distal portion of the joint, or vice versa); and a plurality of energy sensors including 15005 and 15006 which measure energy flow through these energy pathways, wherein data from these sensors are analyzed together using multivariate analysis in order to measure the motion and/or configuration of the body joint.

The example in FIG. 15 further comprises energy input components 15001 and 15002 which direct energy into the lattice, mesh, grid, or matrix. In an example, there can be a single energy input location rather than a plurality of energy input components. In this example, the energy pathways are substantially parallel. In this example, the energy pathways are substantially evenly-spaced around the circumference of the body member containing the joint. In this example, there are gaps and/or elements in the lattice, mesh, grid, or matrix which are substantially the same in size and are shaped like squares, rhombuses, diamonds, trapezoids, or parallelograms.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

Figure 16:
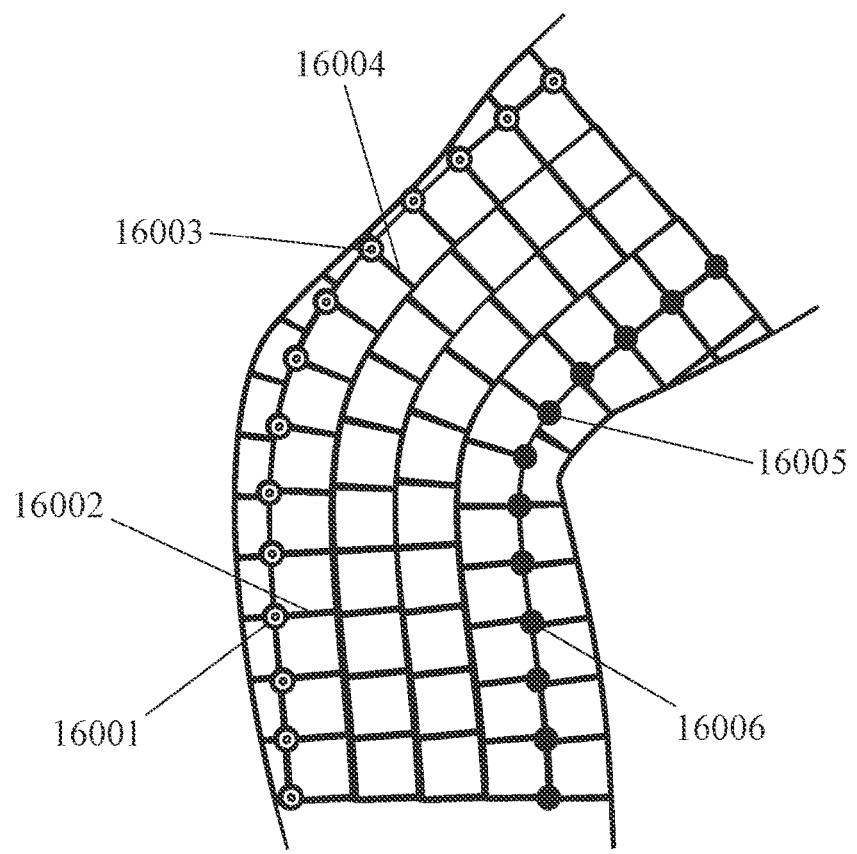
FIG. 16 shows an example with a wearable energy-conducting lattice, mesh, grid, or matrix and circumferential energy pathways.

FIG. 16 shows an example of how this invention can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of energy pathways including 16002 and 16004 which are configured to span that portion of the body in a (partial) circumferential manner; and a plurality of energy sensors including 16001 and 16003 which measure energy flow through these energy pathways, wherein data from these sensors are analyzed together using multivariate analysis in order to measure the motion and/or configuration of the body joint.

The example in FIG. 16 further comprises energy input components 16005 and 16006 which direct energy into the lattice, mesh, grid, or matrix. In an example, there can be a single energy input location rather than a plurality of energy input components. In this example, the energy pathways follow vectors which converge at a point outside the volume of the device. In this example, the energy pathways are substantially evenly-spaced along the longitudinal axis of the body member containing the joint. In this example, there are gaps and/or elements in the lattice, mesh, grid, or matrix which are substantially the same in size and are shaped like squares, rhombuses, diamonds, trapezoids, or parallelograms.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

Figure 17:
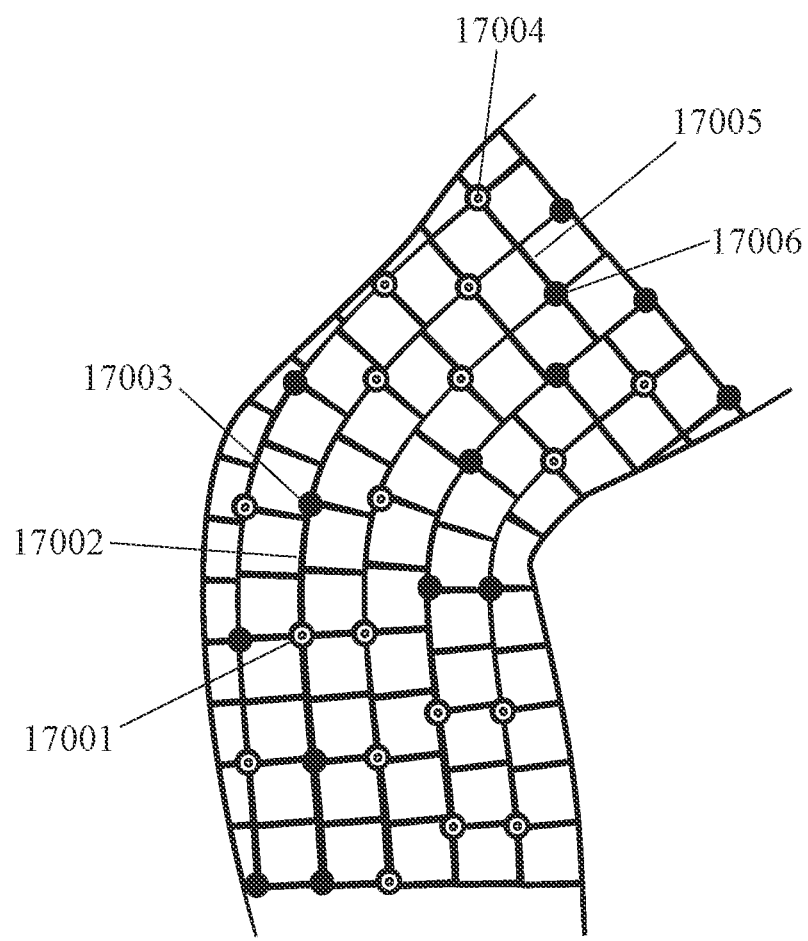
FIG. 17 shows an example with a wearable energy-conducting lattice, mesh, grid, or matrix and multi-directional energy pathways.

FIG. 17 shows an example of how this invention can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of energy pathways including 17002 which are configured to span that portion of the body in a longitudinal manner; a plurality of energy pathways including 17005 which are configured to span that portion of the body in a (partial) circumferential manner; and a plurality of energy sensors including 17001 and 17004 which measure energy flow through these energy pathways, wherein data from these sensors are analyzed together using multivariate analysis in order to measure the motion and/or configuration of the body joint.

The example in FIG. 17 further comprises energy input components 17003 and 17006 which direct energy into the lattice, mesh, grid, or matrix. In an example, there can be a single energy input location rather than a plurality of energy input components. In this example, the longitudinal energy pathways are substantially evenly-spaced around the circumference of the body member containing the joint and the circumferential energy pathways are substantially-evenly spaced along the longitudinal axis of the body member containing the joint. In this example, there are gaps and/or elements in the lattice, mesh, grid, or matrix which are substantially the same in size and are shaped like squares, rhombuses, diamonds, trapezoids, or parallelograms.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

Figure 18:
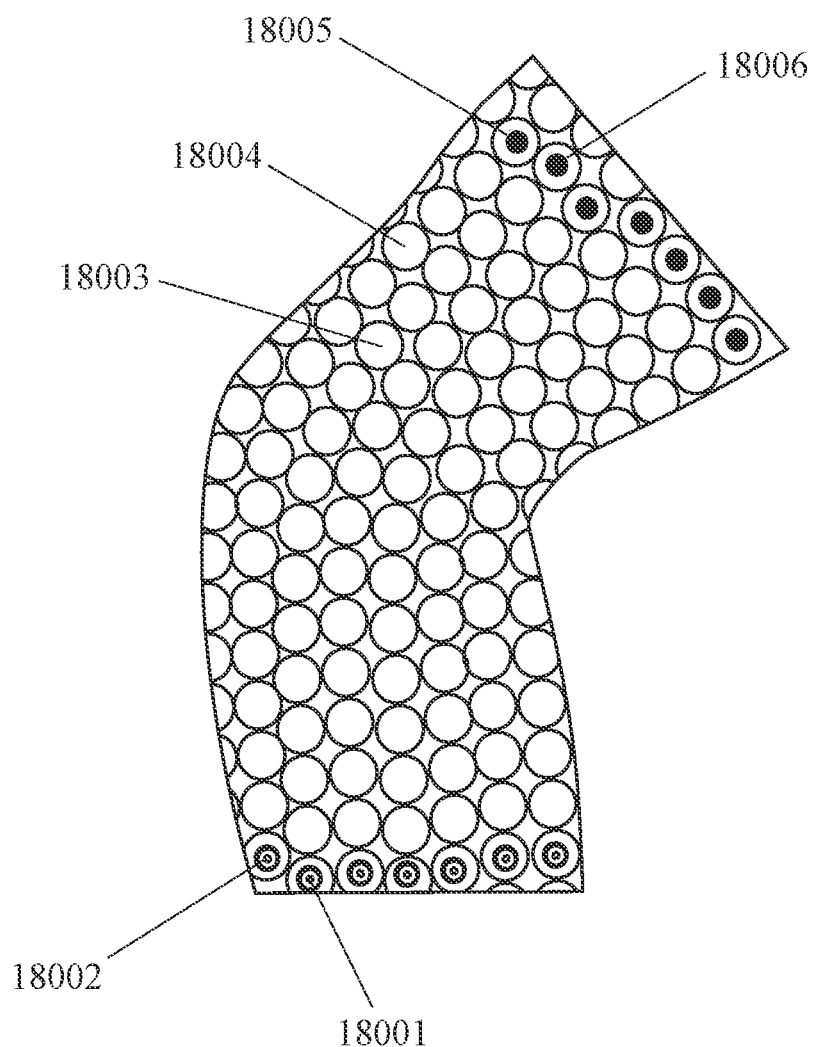
FIG. 18 shows an example with a wearable energy-conducting lattice, mesh, grid, or matrix of arcuate elements and longitudinal energy pathways.

FIG. 18 shows an example of how this invention can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of arcuate energy-conducting elements including 18003 and 18004; a plurality of energy pathways spanning multiple arcuate energy-conducting elements which are configured to span that portion of the body in a longitudinal manner (from a proximal portion of the joint to a distal portion of the joint, or vice versa); and a plurality of energy sensors including 18001 and 18002 which measure energy flow through these energy pathways, wherein data from these sensors are analyzed together using multivariate analysis in order to measure the motion and/or configuration of the body joint.

The example in FIG. 18 further comprises energy input components 18005 and 18006 which direct energy into the lattice, mesh, grid, or matrix. In an example, there can be a single energy input location rather than a plurality of energy input components. In this example, the energy pathways are substantially parallel. In this example, the energy pathways are substantially evenly-spaced around the circumference of the body member containing the joint. In this example, the arcuate elements are substantially the same in size and are circular, oval, or elliptical in shape.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

Figure 19:
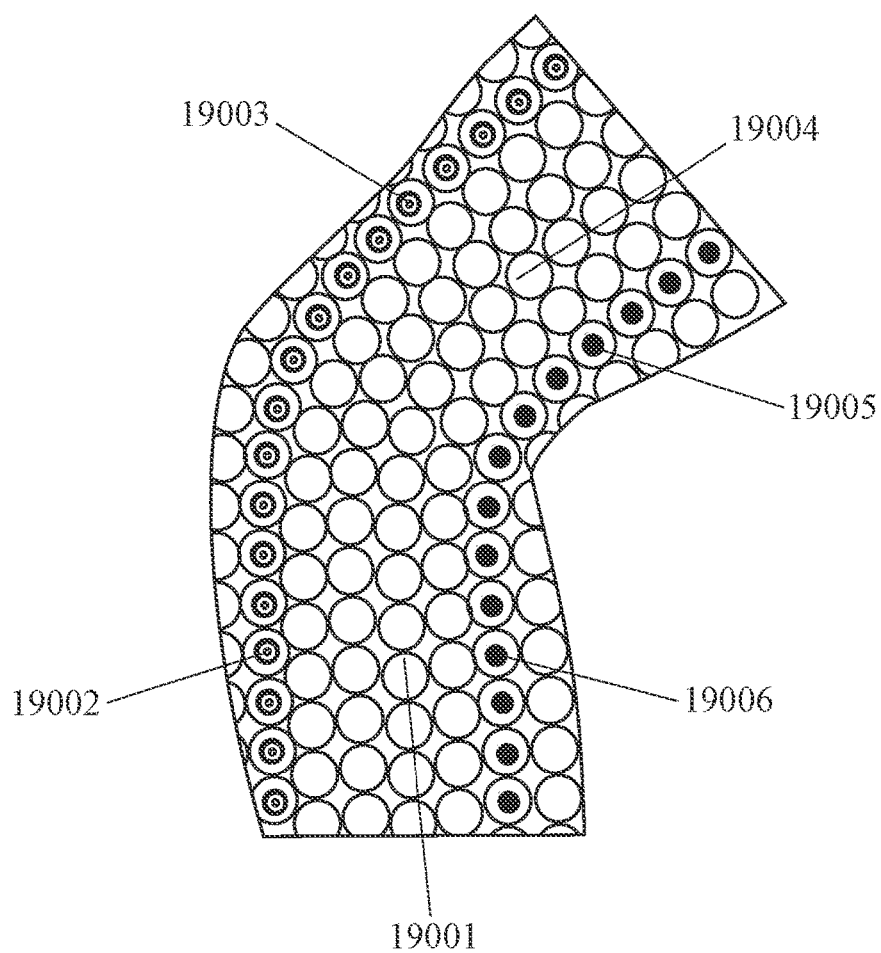
FIG. 19 shows an example with a wearable energy-conducting lattice, mesh, grid, or matrix of arcuate elements and circumferential energy pathways.

FIG. 19 shows an example of how this invention can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of arcuate energy-conducting elements including 19001 and 19004; a plurality of energy pathways spanning multiple arcuate energy-conducting elements which are configured to span that portion of the body in a (partial) circumferential manner; and a plurality of energy sensors including 19002 and 19003 which measure energy flow through these energy pathways, wherein data from these sensors are analyzed together using multivariate analysis in order to measure the motion and/or configuration of the body joint.

The example in FIG. 19 further comprises energy input components 19005 and 19006 which direct energy into the lattice, mesh, grid, or matrix. In an example, there can be a single energy input location rather than a plurality of energy input components. In this example, the energy pathways follow vectors which converge at a point outside the volume of the device. In this example, the energy pathways are substantially evenly-spaced along the longitudinal axis of the body member containing the joint. In this example, the arcuate elements are substantially the same in size and are circular, oval, or elliptical in shape.

In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

Figure 20:
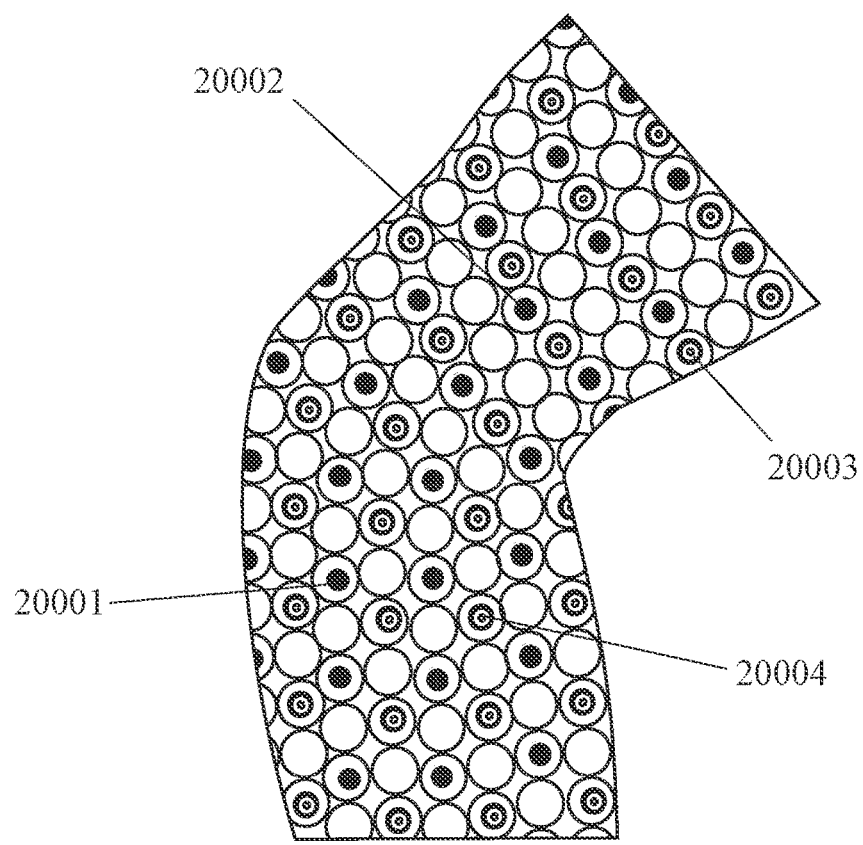
FIG. 20 shows an example with a wearable energy-conducting lattice, mesh, grid, or matrix of arcuate elements and multi-directional energy pathways.

FIG. 20 shows an example of how this invention can be embodied in a wearable device to measure the motion and/or configuration of a body joint comprising—a wearable energy-conducting lattice, mesh, grid, or matrix that is configured to span the surface of a person's body which contains a joint, wherein this lattice, mesh, grid, or matrix further comprises: a plurality of arcuate energy-conducting elements; a plurality of energy pathways spanning multiple arcuate energy-conducting elements; and a plurality of energy sensors including 20003 and 20004 which measure energy flow through these energy pathways, wherein data from these sensors are analyzed together using multivariate analysis in order to measure the motion and/or configuration of the body joint.

The example in FIG. 20 further comprises energy input components 20001 and 20002 which direct energy into the lattice, mesh, grid, or matrix. In an example, there can be a single energy input location rather than a plurality of energy input components. In this example, the arcuate elements are substantially the same in size and are circular, oval, or elliptical in shape. In an example, the energy sensors and/or energy input components can be modular and/or moveable. In an example, energy sensors and/or energy input components can be snapped or otherwise removably-connected to the lattice, mesh, grid, or matrix at different locations in order to create different energy pathways. In an example, modular and/or moveable energy sensors and/or energy input components can allow the device to be customized to span different joints and/or be customized to a person's specific body contours. In an example, having removably-connected electronic components can also make it easier to wash the device.

Figure 21:
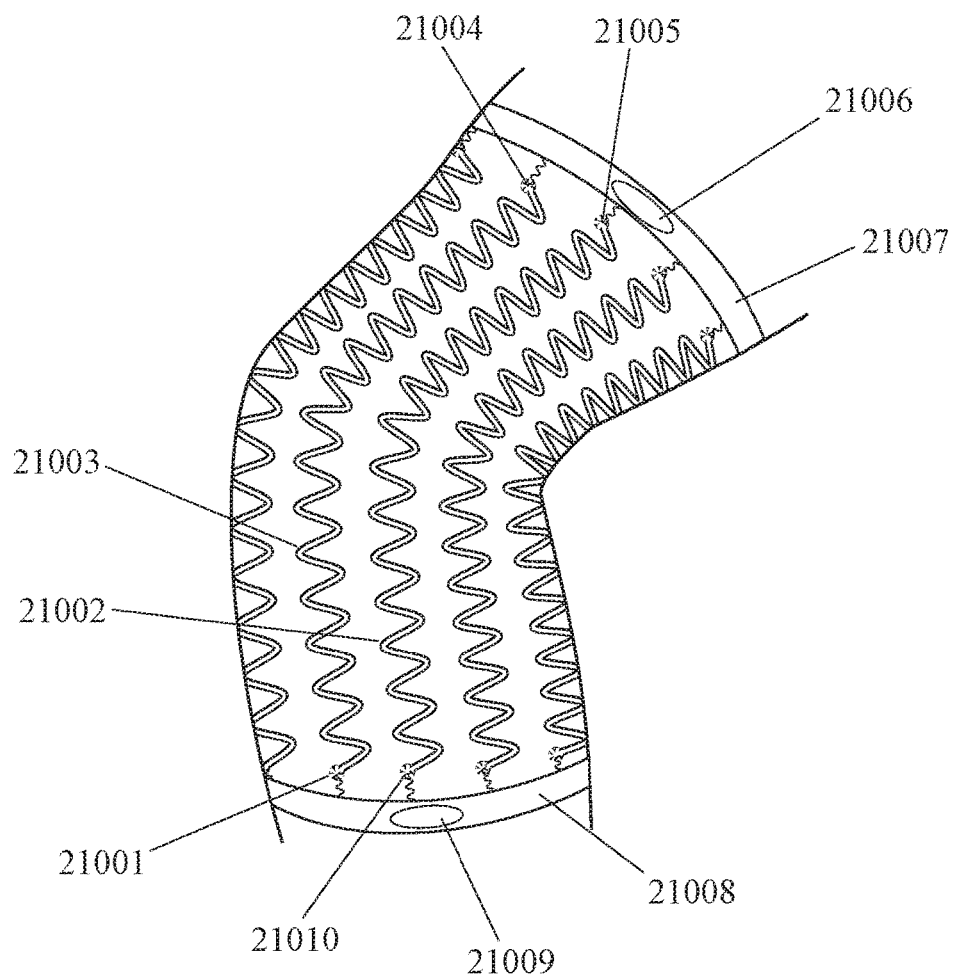
FIG. 21 shows an example wherein flexible energy pathways spanning a joint have a sinusoidal shape.

FIG. 21 shows an example of how this invention can be embodied in a wearable device for measuring body joint motion and/or configuration comprising: (a) a first sinusoidal energy pathway 21003, wherein this first energy pathway is configured to span the surface of a portion of a person's body which contains a body joint, wherein this first energy pathway is moved from a first configuration to a second configuration by movement of the body joint, and wherein this first energy pathway has a first energy flow when the pathway is in the first configuration and has a second energy flow when the pathway is in the second configuration; (b) a first energy sensor 21004 which measures energy flow through or from the first energy pathway; (c) a second sinusoidal energy pathway 21002, wherein this second energy pathway is configured to span the surface of the portion of a person's body which contains the at least one body joint, wherein this second energy pathway is moved from a third configuration to a fourth configuration by movement of the body joint, and wherein this second energy pathway has a third energy flow when the pathway is in the third configuration and has a fourth energy flow when the pathway is in the fourth configuration; (d) a second energy sensor 21005 which measures energy flow through or from the second energy pathway, wherein data from the first energy sensor and data from the second energy sensor are analyzed together in order to measure the motion and/or configuration of the body joint.

In the example shown in FIG. 21, this device further comprises: energy input component 21001 which sends energy into the first energy pathway; energy input component 21010 which sends energy into the second energy pathway; energy source 21009 (including energy conduits between this source and the energy input components); sensor data control unit 21006 (including energy conduits between this unit and the energy sensors); distal attachment band 21008; and proximal attachment band 21007.

In an example, an energy pathway can have a shape comprising a repeating waveform selected from the group consisting of: simple sinusoidal wave; composite sinusoidal wave; saw-tooth wave or zigzag; and square wave. In an example, an energy pathway can have a shape which is a conic section. In an example, an energy pathway can have a shape which is a spiral or helix. In an example, an energy pathway can have a shape which is a chain of loops.

In an example, first and second energy pathways which span a body member which contains a body joint can differ in longitudinal curvature or convolution. In an example, combined multivariate analysis of data from both the first and second energy pathways can provide more accurate measurement of body joint motion than data from either the first energy pathway or the second energy pathway alone. In an example, an energy pathway with a sinusoidal, zigzag or sawtooth, or other repeated wave shape can have a higher curvature or convolution if it has a waveform with a larger amplitude or higher wave frequency. In an example, data from a highly curved or convoluted energy pathway can provide more accurate measurement of body joint motion over a first range of motion and data from a less curved or convoluted energy pathway can provide more accurate measurement of body joint motion over a second range of motion. When analyzed together, data from the highly curved or convoluted and the less curved or convoluted energy pathways reduce error in measuring the full range of joint motion.

In an example, this invention can be embodied in a wearable device for measuring body joint motion and/or configuration comprising: (a) a first energy pathway, wherein this first energy pathway is configured to span the surface of a portion of a person's body which contains a body joint with a first degree of convolution, wherein this first energy pathway is moved from a first configuration to a second configuration by movement of the body joint, and wherein this first energy pathway has a first energy flow when the pathway is in the first configuration and has a second energy flow when the pathway is in the second configuration; (b) a first energy sensor which measures energy flow through or from the first energy pathway; (c) a second energy pathway, wherein this second energy pathway is configured to span the surface of the portion of a person's body which contains the at least one body joint with a second degree of convolution, wherein this second energy pathway is moved from a third configuration to a fourth configuration by movement of the body joint, and wherein this second energy pathway has a third energy flow when the pathway is in the third configuration and has a fourth energy flow when the pathway is in the fourth configuration; (d) a second energy sensor which measures energy flow through or from the second energy pathway, wherein data from the first energy sensor and data from the second energy sensor are analyzed together in order to measure the motion and/or configuration of the body joint.

Figure 22:
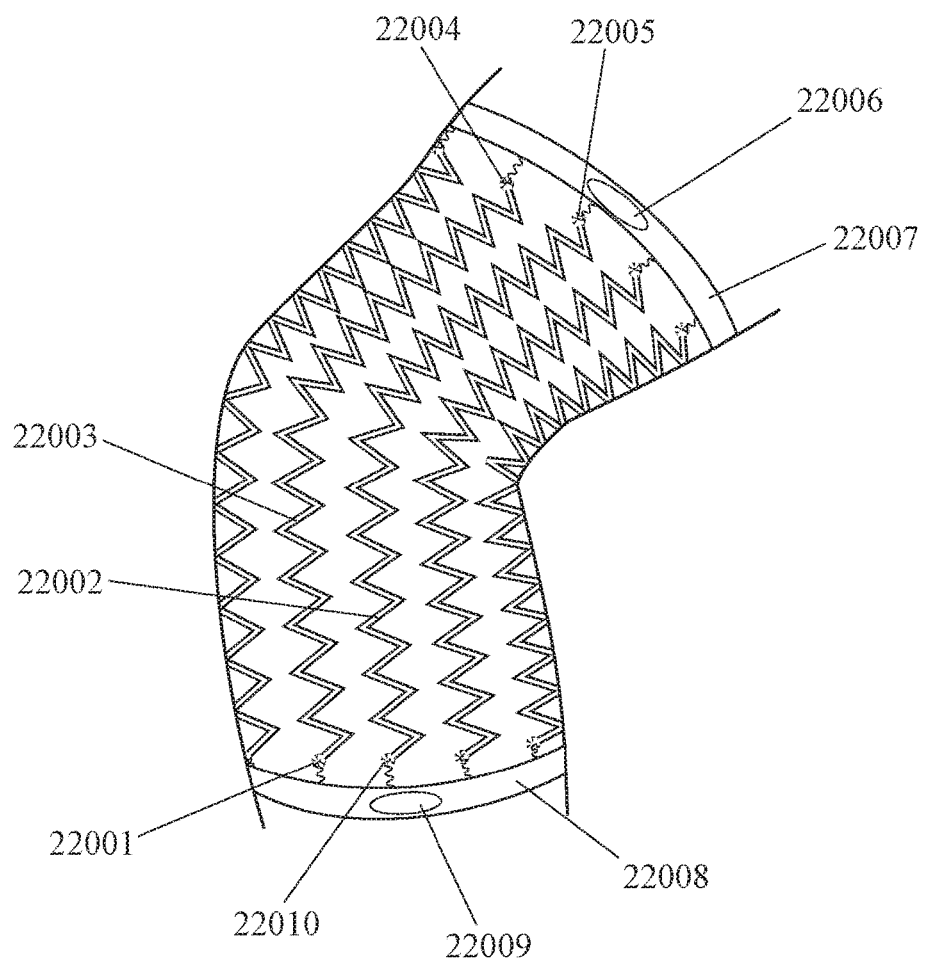
FIG. 22 shows an example wherein flexible energy pathways spanning a joint have a zig-zag shape.

FIG. 22 shows an example of how this invention can be embodied in a wearable device for measuring body joint motion and/or configuration comprising: (a) a first zigzag or sawtooth-shaped energy pathway 22003, wherein this first energy pathway is configured to span the surface of a portion of a person's body which contains a body joint, wherein this first energy pathway is moved from a first configuration to a second configuration by movement of the body joint, and wherein this first energy pathway has a first energy flow when the pathway is in the first configuration and has a second energy flow when the pathway is in the second configuration; (b) a first energy sensor 22004 which measures energy flow through or from the first energy pathway; (c) a second zigzag or sawtooth-shaped energy pathway 22002, wherein this second energy pathway is configured to span the surface of the portion of a person's body which contains the at least one body joint, wherein this second energy pathway is moved from a third configuration to a fourth configuration by movement of the body joint, and wherein this second energy pathway has a third energy flow when the pathway is in the third configuration and has a fourth energy flow when the pathway is in the fourth configuration; (d) a second energy sensor 22005 which measures energy flow through or from the second energy pathway, wherein data from the first energy sensor and data from the second energy sensor are analyzed together in order to measure the motion and/or configuration of the body joint.

In the example shown in FIG. 22, this device further comprises: energy input component 22001 which sends energy into the first energy pathway; energy input component 22010 which sends energy into the second energy pathway; energy source 22009 (including energy conduits between this source and the energy input components); sensor data control unit 22006 (including energy conduits between this unit and the energy sensors); distal attachment band 22008; and proximal attachment band 22007.

Figure 23:
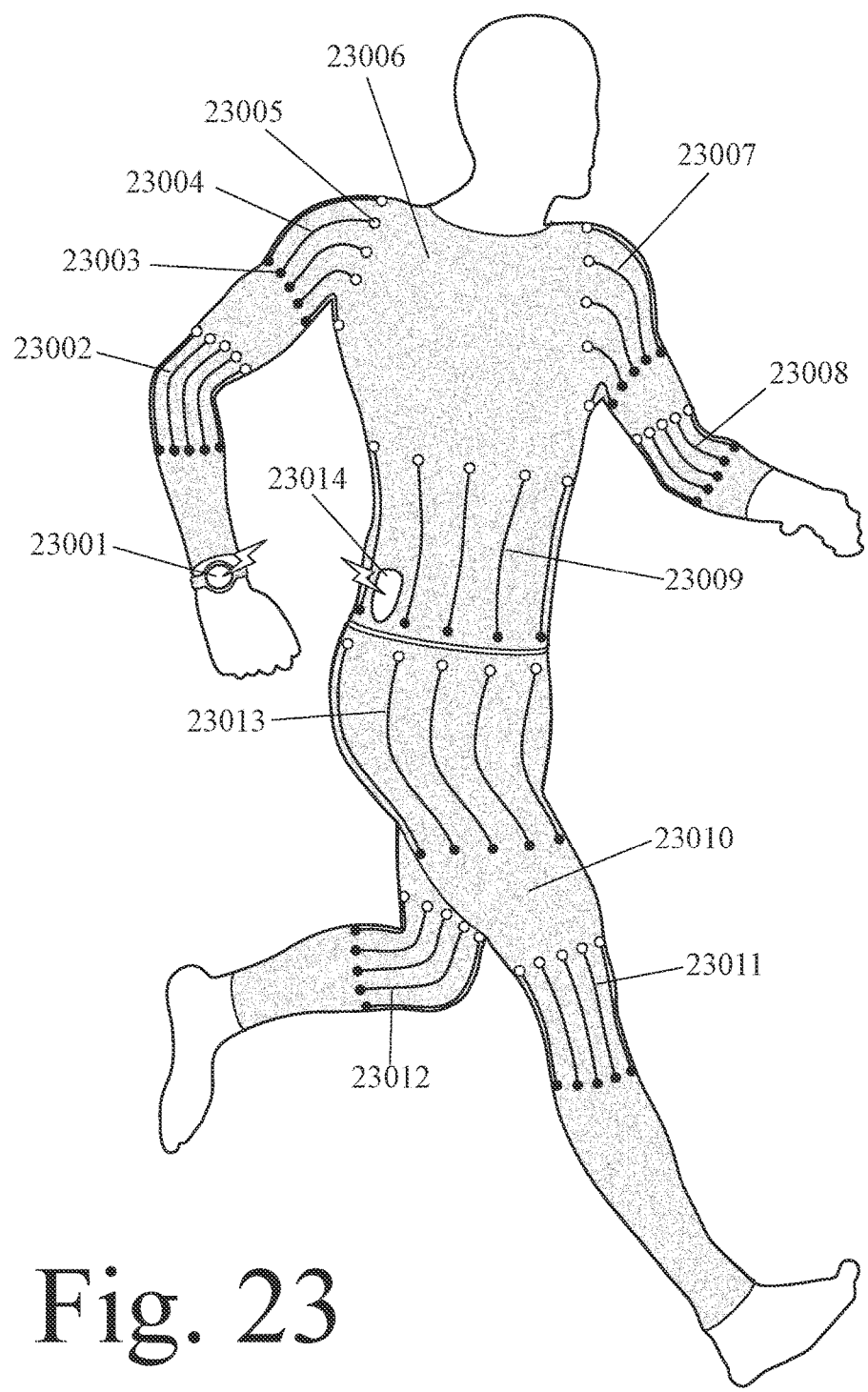
FIG. 23 shows an example of a shirt and pair of pants which measure body motion including multiple sets of flexible energy pathways and also data processing components worn on the wrist and torso.

FIG. 23 shows an example of how this invention can be embodied in a wearable two-piece set of Motion Recognition Clothing™ which measures major joint motion and/or configuration for virtually the entire body via multiple sets of energy pathways. Each set of energy pathways spans a major body joint. Collecting and analyzing data from multiple redundant energy pathways spanning the same body joint provides more accurate measurement of the motion and/or configuration of that joint. In this example, each energy pathway (such as 23004) is in energy communication with an energy input component (such as 23003) which directs energy into the energy pathway and with an energy sensor (such as 23005) which measures energy flow through (or from) the energy pathway. In another example, an energy pathway (such as a piezoelectric pathway) can generate energy itself and an energy input component is not required.

In an example, energy pathways can conduct electromagnetic energy and changes in the flow of electromagnetic energy can be used to measure joint motion and/or configuration. In an example, energy pathways can conduct light energy and changes in the flow of light energy can be used to measure joint motion and/or configuration. In an example, energy pathways can conduct sonic energy and changes in sonic energy flow can be used to measure joint motion and/or configuration. In an example, energy can flow across a body joint in a generally distal-to-proximal direction. In an example, energy can flow across a body joint in a generally proximal-to-distal direction. Changes in the configurations of the major body joints change the configurations of the energy pathways which, in turn, change the energy flows measured by the energy sensors which, in turn, are used to estimate the motions and/or configurations of the body joints. In this example, energy pathways spanning multiple body joints collectively enable minimally-intrusive, ambulatory full-body motion capture.

The example shown in FIG. 23 comprises a two-piece set of motion recognition clothing with an upper-body component (e.g. a shirt or top) 23006 and a lower-body component (e.g. a pair of pants) 23010. In an example, the upper-body component can be a sweat shirt with sets of embedded energy pathways. In an example, the upper-body component can be the upper piece of a sports uniform with sets of embedded energy pathways. The upper-body (shirt) component of this motion recognition clothing measures the motion and/or configuration of the wearer's elbows, shoulders, and torso and/or back. In an example, the lower-body component can be a pair of sweat pants with sets of embedded energy pathways. In an example, the lower-body component can be the lower piece of a sports uniform with sets of embedded energy pathways. The lower-body (pants) component of this motion recognition clothing measures the motion and/or configuration of the wearer's hips and knees.

In the example shown in FIG. 23, the upper-body (shirt) component further comprises: a set of substantially-parallel energy pathways (including 23002) which span the person's right elbow in a longitudinal manner and are substantially evenly-spaced around the circumference of the person's elbow; a set of proximally-diverging energy pathways (including 23004) which span the person's right shoulder in a longitudinal manner and are substantially evenly-spaced around the circumference of the person's shoulder; a set of proximally-diverging energy pathways (including 23007) which span the person's left shoulder in a longitudinal manner and are substantially evenly-spaced around the circumference of the person's shoulder; a set of substantially-parallel energy pathways (including 23008) which span the person's left elbow in a longitudinal manner and are substantially evenly-spaced around the circumference of the person's elbow; and a set of energy pathways (including 23009) which span a portion of the person's torso and/or back. In an example, this clothing could be extended to also span the person's wrists, fingers, neck, and/or head.

In the example shown in FIG. 23, the lower-body (pants) component further comprises: a set of proximally-diverging energy pathways (including 23013) which span the person's right hip in a longitudinal manner and are substantially evenly-spaced around a portion of the circumference of the person's hip; a set of substantially-parallel energy pathways (including 23011) which span the person's right knee in a longitudinal manner and are substantially evenly-spaced around the circumference of the person's knee; a set of proximally-diverging energy pathways (not visible in this figure) which span the person's left hip in a longitudinal manner and are substantially evenly-spaced around a portion of the circumference of the person's hip; and a set of substantially-parallel energy pathways (including 23012)

which span the person's left knee in a longitudinal manner and are substantially evenly-spaced around the circumference of the person's knee. In an example, this clothing could be extended to also span the person's ankles and/or feet.

The example shown in FIG. 23 also comprises a wrist-worn component 23001 and a torso-worn component 23014. In an alternative example, the latter component could be a hip-worn component that is worn on the person's hip as part of the lower-body component of the motion recognition clothing. As symbolically represented by lightning bolt symbols, the wrist-worn component 23001 and/or torso-worn component 23014 can be in wired and/or wireless communication with energy sensors (including 23005), with energy input components (including 23003), and/or with each other. The exact configuration of wires or other electrically-conductive connections to sensors or energy input components is not central to this invention and wires are not shown in this figure.

In an example, clothing with embedded energy pathways and a wrist-worn device can together comprise a system for measuring full-body motion and/or configuration. In an example, clothing with embedded energy pathways and a wrist-worn device can together comprise a system for minimally-intrusive, ambulatory full-body motion capture. In an example, clothing with embedded energy pathways and a wrist-worn device which are in wireless communication with each other can together comprise a system of motion recognition clothing.

In an alternative example, clothing with embedded energy pathways and electronically-functional eyewear can together comprise a system for measuring full-body motion and/or configuration. In an example, clothing with embedded energy pathways and electronically-functional eyewear can together comprise a system for minimally-intrusive, ambulatory full-body motion capture. In an example, clothing with embedded energy pathways and electronically-functional eyewear which are in wireless communication with each other can together comprise a system of motion recognition clothing.

In an example, a wrist-worn component 23001 and/or a torso-worn component 23014 can further comprise one or more sub-components selected from the group consisting of: a data processing component, a data communication component, a power source, a human-to-computer user interface, a computer-to-human interface, and a digital memory. In an example, a data control unit can be temporarily detached so that the remaining wearable portion of the invention can be washed.

In an example, a data processing component of this device can perform one or more functions selected from the group consisting of: amplify sensor signals, analyze data, analyze sensor information, convert analog signals to digital signals, determine a functional relationship between signal variation and joint angle variation, estimate joint angle, filter signals, model joint configuration, record data, run software applications, run software programs, and store data in memory.

In an example, a data communication component of this device can perform one or more functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

FIG. 23 shows an example embodiment of this invention comprising a method for measuring, modeling, and/or capturing a person's shoulder motion and/or configuration comprising: (a) measuring a first energy flow from a first wearable energy pathway that is configured to span the portion of a person's body which contains their shoulder; (b) measuring a second energy flow from a second wearable energy pathway that is configured to span the portion of a person's body which contains their shoulder; and (c) jointly analyzing the first and second energy flows in order to estimate, measure, and/or model the abduction, adduction, extension, flexion, and/or rotation of their shoulder.

In an example, the first and second energy flows can be electrical energy. In an example, this electrical energy can be conducted through the energy pathways and the amounts of electrical energy conducted can change when the configurations of the pathways change as the shoulder moves. In an example, electrical voltage, current, resistance, and/or impedance can be measured. In an example, electrical energy can be generated by the energy pathways when the configurations of the pathways change as the shoulder moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the shoulder moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of abduction, adduction, extension, flexion, and/or rotation of the person's shoulder than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of abduction, adduction, extension, flexion, and/or rotation and gives greater statistical weight to the second energy flow over a second range of abduction, adduction, extension, flexion, and/or rotation. In an example, a statistical method can analyze differences between the first and second energy flows to determine if the locations of the wearable energy pathways relative to the surface of the person's body have shifted and to adjust estimation if such shifting occurs.

In an example, the relationship between energy flow and shoulder configuration can be nonlinear and/or stochastic. In an example, joint analysis of the first and second energy flows from the first and second energy pathways spanning a person's shoulder can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's shoulder. In an example, these longitudinal axes can be separated by a substantially constant percentage of the cross-sectional circumference of the person's shoulder. In an example, these longitudinal axes are substantially parallel when the arm is fully extended outward. In an example, the first energy pathway can have a longitudinal axis which longitudinally spans the portion of the person's body which contains a shoulder joint and the second energy pathway can span part of the cross-sectional perimeter of this portion of the person's body. In an example, the first and second energy pathways are substantially parallel as they longitudinally span a distal skeletal member of a shoulder joint and diverge in a radial manner as they longitudinally span a proximal skeletal member of the shoulder joint. In an example, the first and second energy pathways are substantially parallel as they longitudinally span the humerus and diverge as they longitudinally span the acromion, clavicle, coracoid process, and/or scapula; or vice versa. In an example, the first and second energy pathways can be concentric and/or nested as they span the portion of a person's body which contains a shoulder joint. In an example, the first and second energy pathways can be pathways within an energy-transmitting mesh which spans the portion of a person's body which contains their shoulder joint.

In various examples, measurement of the configuration and movement of a person's shoulder can be especially useful for: athletic training and motion capture for sports which involve extensive arm motion (such as tennis and golf); rehabilitation for upper-body injuries and neurological impairment; measurement of caloric expenditure; ambulatory telerobotics; and upper-body avatar animation, computer gaming, and virtual reality.

In an example, the first and second energy pathways can be energy transmitting pathways which are incorporated into a shirt, other wearable top, shoulder tube, shoulder pad, or union suit. In an example, the first and second energy pathways can be woven into a shirt, other wearable top, shoulder tube, shoulder pad, or union suit. In an example, the first and second energy pathways can be sewn into, inserted into, or adhered to a shirt, other wearable top, shoulder tube, shoulder pad, or union suit. In an example, a shirt, other wearable top, shoulder tube, shoulder pad, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

FIG. 23 shows an example embodiment of this invention comprising a method for measuring, modeling, and/or capturing a person's hip motion and/or configuration comprising: (a) measuring a first energy flow from a first wearable energy pathway that is configured to span the portion of a person's body which contains their hip; (b) measuring a second energy flow from a second wearable energy pathway that is configured to span the portion of a person's body which contains their hip; and (c) jointly analyzing the first and second energy flows in order to estimate, measure, and/or model the abduction, adduction, extension, flexion, and/or rotation of their hip.

In an example, the first and second energy flows can be electrical energy. In an example, this electrical energy can be conducted through the energy pathways and the amounts of electrical energy conducted can change when the configurations of the pathways change as the hip moves. In an example, electrical voltage, current, resistance, and/or impedance can be measured. In an example, electrical energy can be generated by the energy pathways when the configurations of the pathways change as the hip moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the hip moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of abduction, adduction, extension, flexion, and/or rotation of the person's hip than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of abduction, adduction, extension, flexion, and/or rotation and gives greater statistical weight to the second energy flow over a second range of abduction, adduction, extension, flexion, and/or rotation. In an example, a statistical method can analyze differences between the first and second energy flows to determine if the locations of the wearable energy pathways relative to the surface of the person's body have shifted and to adjust estimation if such shifting occurs.

In an example, the relationship between energy flow and hip configuration can be nonlinear and/or stochastic. In an example, joint analysis of the first and second energy flows from the first and second energy pathways spanning a person's hip can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's hip. In an example, these longitudinal axes can be separated by a substantially constant percentage of the cross-sectional circumference of the person's hip. In an example, these longitudinal axes are substantially parallel when the leg is extended straight down. In an example, the first energy pathway can have a longitudinal axis which longitudinally spans the portion of the person's body which contains a hip joint and the second energy pathway can span part of the cross-sectional perimeter of this portion of the person's body. In an example, the first and second energy pathways are substantially parallel as they longitudinally span a distal skeletal member of a hip joint and diverge in a radial manner as they longitudinally span a proximal skeletal member of the hip joint. In an example, the first and second energy pathways are substantially parallel as they longitudinally span the femur and diverge as they longitudinally span the Ilium; or vice versa. In an example, the first and second energy pathways can be concentric and/or nested as they span the portion of a person's body which contains a hip joint. In an example, the first and second energy pathways can be pathways within an energy-transmitting mesh which spans the portion of a person's body which contains their hip joint.

In various examples, measurement of the configuration and movement of a person's hip can be especially useful for: athletic training and motion capture for sports which involve extensive lower-body motion (such as bicycling and running); gait analysis, medical diagnosis, posture correction, and rehabilitation for injuries and neurological impairment; measurement of caloric expenditure (especially with respect to lower body motions that are not well measured by upper body motion sensors); ambulatory telerobotics; and lower-body avatar animation, computer gaming, and virtual reality.

In an example, the first and second energy pathways can be energy transmitting pathways which are incorporated into a pair of pants, shorts, hip pad, belt, or union suit. In an example, the first and second energy pathways can be woven into a pair of pants, shorts, hip pad, belt, or union suit. In an example, the first and second energy pathways can be sewn into, inserted into, or adhered to a pair of pants, shorts, hip pad, belt, or union suit. In an example, this pair of pants, shorts, hip pad, belt, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

FIG. 23 shows an example embodiment of this invention comprising a method for measuring, modeling, and/or capturing a person's spine, back, and/or torso motion and/or configuration comprising: (a) measuring a first energy flow from a first wearable energy pathway that is configured to span the portion of a person's body which contains their back and/or torso; (b) measuring a second energy flow from a second wearable energy pathway that is configured to span the portion of a person's body which contains their back and/or torso; and (c) jointly analyzing the first and second energy flows in order to estimate, measure, and/or model the abduction, extension, flexion, lateral bending, and/or rotation of their spine, back, and/or torso.

In an example, the first and second energy flows can be electrical energy. In an example, this electrical energy can be conducted through the energy pathways and the amounts of electrical energy conducted can change when the configurations of the pathways change as the spine moves. In an example, electrical voltage, current, resistance, and/or impedance can be measured. In an example, electrical energy can be generated by the energy pathways when the configurations of the pathways change as the spine moves.

In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the spine moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of abduction, extension, flexion, lateral bending, and/or rotation of the person's spine, back, and/or torso than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of abduction, extension, flexion, lateral bending, and/or rotation and gives greater statistical weight to the second energy flow over a second range of abduction, extension, flexion, lateral bending, and/or rotation. In an example, a statistical method can analyze differences between the first and second energy flows to determine if the locations of the wearable energy pathways relative to the surface of the person's body have shifted and to adjust estimation if such shifting occurs.

In an example, the relationship between energy flow and spine, back, and/or torso configuration can be nonlinear and/or stochastic. In an example, joint analysis of the first and second energy flows from the first and second energy pathways spanning a person's spine, back, and/or torso can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's spine, back, and/or torso. In an example, these longitudinal axes can be separated by a substantially constant percentage of the cross-sectional circumference of the person's back. In an example, these longitudinal axes are substantially parallel when the back is straight. In an example, the first energy pathway can have a longitudinal axis which longitudinally spans the back and/or torso and the second energy pathway can span part of the cross-sectional perimeter of the back and/or torso. In an example, the first and second energy pathways are substantially parallel as they longitudinally span lower spinal vertebrae and diverge in a radial manner as they longitudinally span higher spinal vertebrae. In an example, the first and second energy pathways are substantially parallel as they longitudinally span higher spinal vertebrae and diverge in a radial manner as they longitudinally span lower spinal vertebrae. In an example, the first and second energy pathways can be concentric and/or nested as they span a person's back and/or torso. In an example, the first and second energy pathways can be pathways within an energy-transmitting mesh which spans a person's back and/or torso.

In various examples, measurement of the configuration and movement of a person's hip can be especially useful for: athletic training and motion capture for sports which involve extensive spinal motion; medical diagnosis, posture correction, and spinal injury avoidance; ambulatory telerobotics; and upper-body avatar animation, computer gaming, and virtual reality.

In an example, the first and second energy pathways can be energy transmitting pathways which are incorporated into a shirt, other top, torso and/or waist tube, torso and/or waist band, belt, bra, girdle, or union suit. In an example, the first and second energy pathways can be woven into a shirt, other top, torso and/or waist tube, torso and/or waist band, belt, bra, girdle, or union suit. In an example, the first and second energy pathways can be sewn into, inserted into, or adhered to a shirt, other top, torso and/or waist tube, torso and/or waist band, belt, bra, girdle, or union suit. In an example, this shirt, other top, torso and/or waist tube, torso and/or waist band, belt, bra, girdle, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

Figure 24:
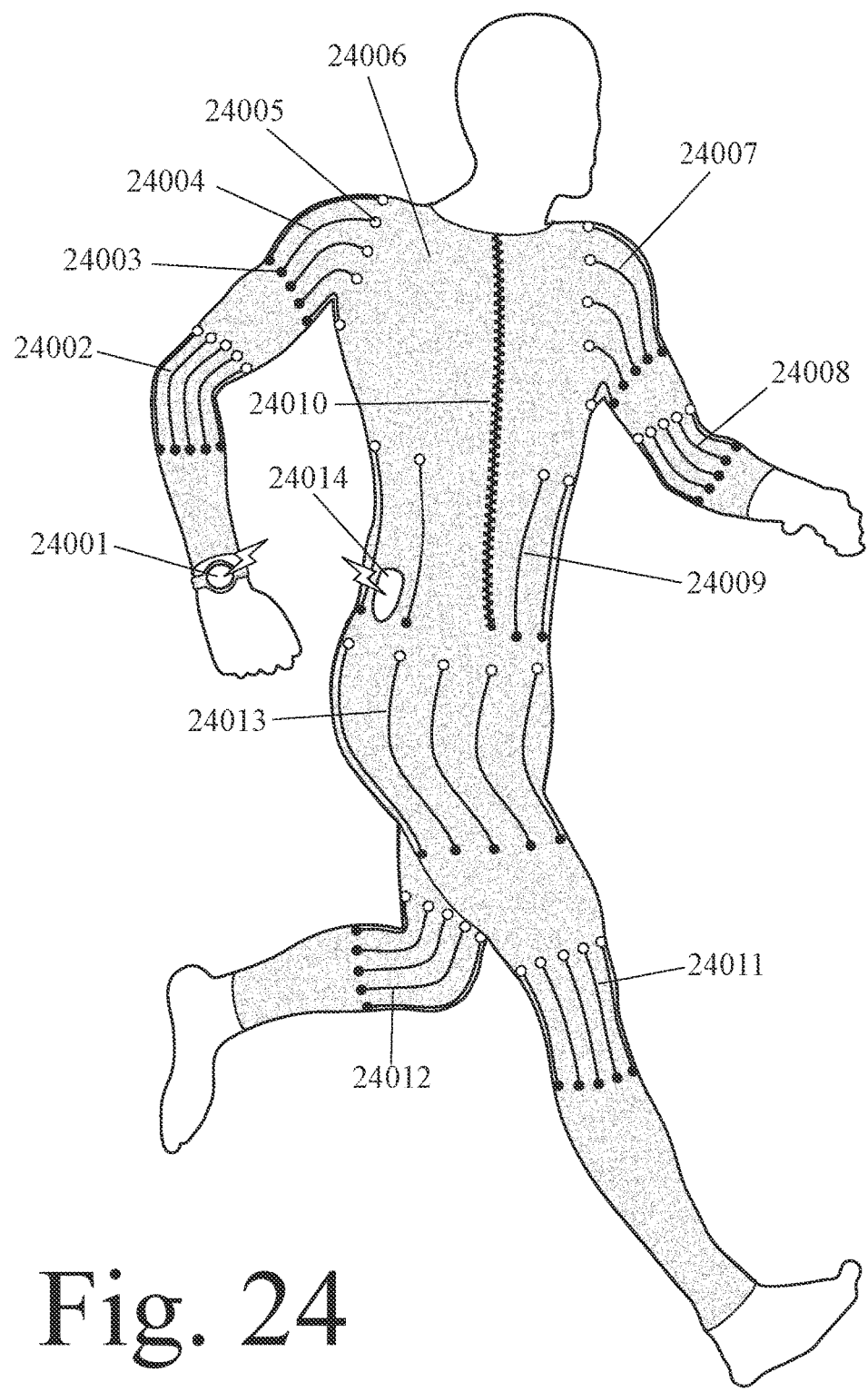
FIG. 24 shows an example of a jump suit which measures body motion including multiple sets of flexible energy pathways and also data processing components worn on the wrist and torso.

FIG. 24 shows an example of how this invention can be embodied that is like the example shown in FIG. 23 except that it comprises a single piece of motion recognition clothing 24006 (with zipper 21010) instead of a two-piece set of clothing. In an example, this single piece of motion recognition clothing 24006 can be a union suit, a jump suit, overalls, or a single-piece sports uniform.

Figure 25:
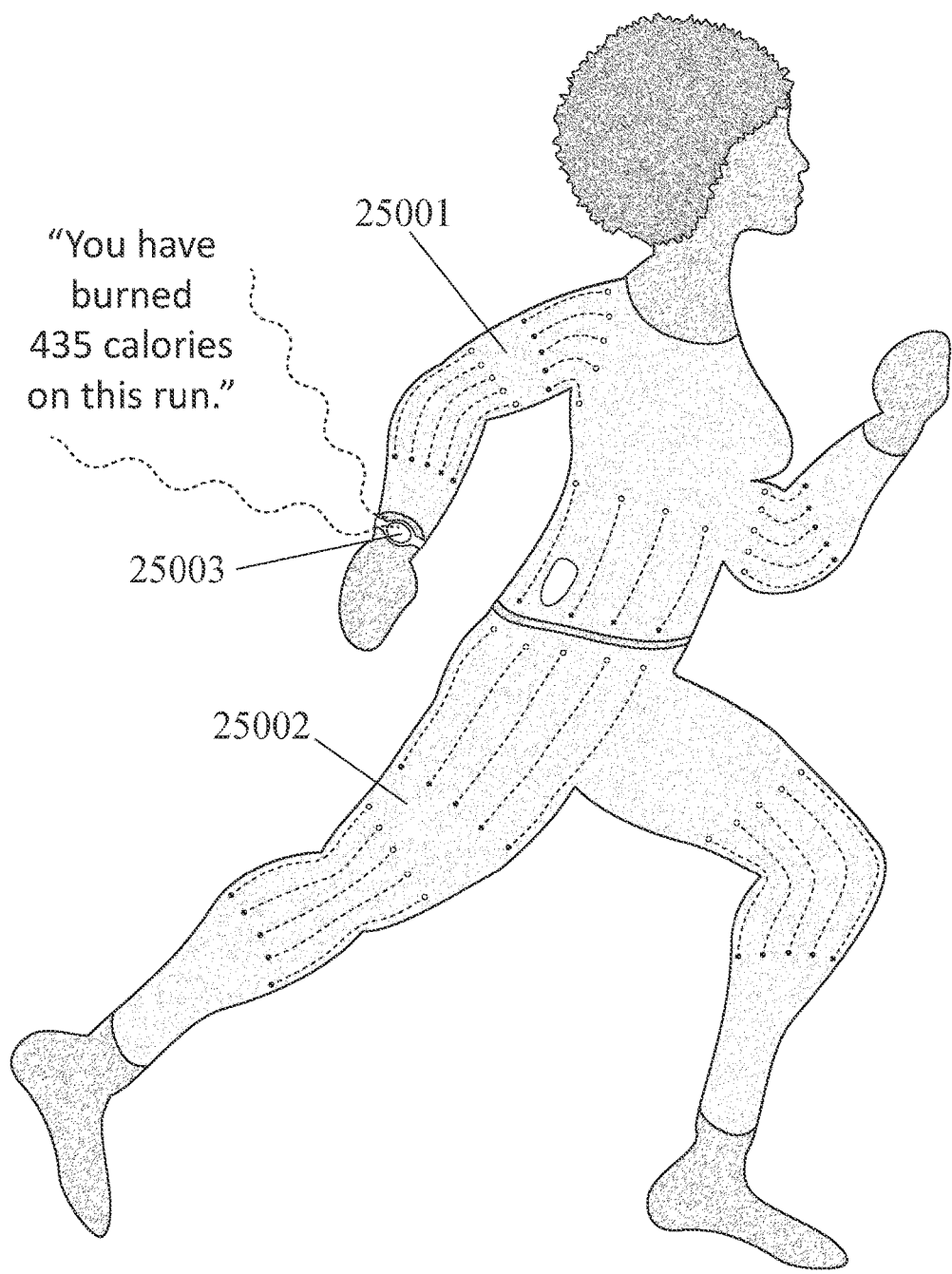
FIG. 25 shows a first example of how this invention can perform real-time analysis of full-body motion and provide useful information.

FIG. 25 shows an example of how this invention can perform real-time analysis of full-body motion and/or configuration and provide a person with useful information. Similar to the example shown in FIG. 23, this example comprises an upper-body (shirt) component (25001) with embedded sets of energy pathways, a lower-body (pants) component (25002) with embedded sets of energy pathways, and a wrist-worn component 25003.

In this example, wrist-worn component 25003 has a speech-based computer-to-human interface. In this example, motion recognition clothing has analyzed the person's full-body motion and/or configuration during a run, has translated this information into calories burned, and now provides speech-based feedback to inform the person of how many calories they have burned. Specifically, the wrist-worn component 25003 tells the person—"You have burned 435 calories on this run." Such full-body motion analysis can enable much more accurate measurement of caloric expenditure than is possible with wrist-worn accelerometers.

In an example, a computer-to-human interface of this device can be selected from the group consisting of: a synthesized voice; a vibrating or other tactile sensation creating member; a display screen; an LED or LED array; a coherent-light image projector; a myostimulating member; a neurostimulating member; a non-coherent-light image projector; an electromagnetic energy emitter; an electronically-functional textile interface; an infrared light emitter; and an infrared light projector. In an example, this device can communicate with a different device which, in turn, has a computer-to-human interface which serves this purpose.

In an example, this device can perform one or more communication functions selected from the group consisting of: transmit and receive data via Bluetooth, WiFi, Zigbee, or other wireless communication modality; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; transmit and receive data to and from a home appliance and/or home control system; and transmit and receive data to and from an implantable medical device.

In an example, this invention can provide a person with useful information concerning athletic training, sports performance analysis, sports motion capture, and fan engagement. In an example, this invention can be useful for training and motion capture for sports which involve extensive and/or complex lower-body motion (such as soccer, bicycling, and running) which are not well measured by single-location (wrist-worn) accelerometers. In an example, this invention can be useful for training and motion capture for sports which involve complex upper-body motion (such as basketball, tennis, golf, baseball, Frisbee™, and fencing) which are not well measured by single-location accelerometers.

In an example, this invention can provide a person with useful information concerning health and fitness. In an example, this invention can be used for caloric expenditure measurement, energy balance management, weight management, and caloric intake monitoring applications. In an example, this invention can be used for virtual exercise. In an example, this invention can be used for real-time avoidance of repeated motion injuries, injuries due to poor posture, and stress-related injuries including back injuries and carpal tunnel syndrome.

In an example, this invention can be used for diagnostic and therapy-evaluation purposes including: range of motion assessment, gait analysis, biomechanical analysis, posture evaluation and correction, ergonomic assessment, fall prevention and detection, spinal motion assessment, rehabilitation assessment, biofeedback, pulse monitoring, respiratory function assessment, plethysmography, cardiac function monitoring, orthopedic therapy, physical therapy, orthotic design and fitting, and pronation analysis.

In an example, this invention can be used for entertainment, gaming, and artistic purposes. In an example, this invention can be used for animation of an avatar in virtual reality and/or computer gaming. In an example, this invention can be used for animation of an animated character in motion picture making or other visual animation applications. In an example, this invention can be used for dance instruction, dance performance, and other performance art applications. In an example, this invention can be used for instruction and motion capture for playing musical instruments.

Figure 26:
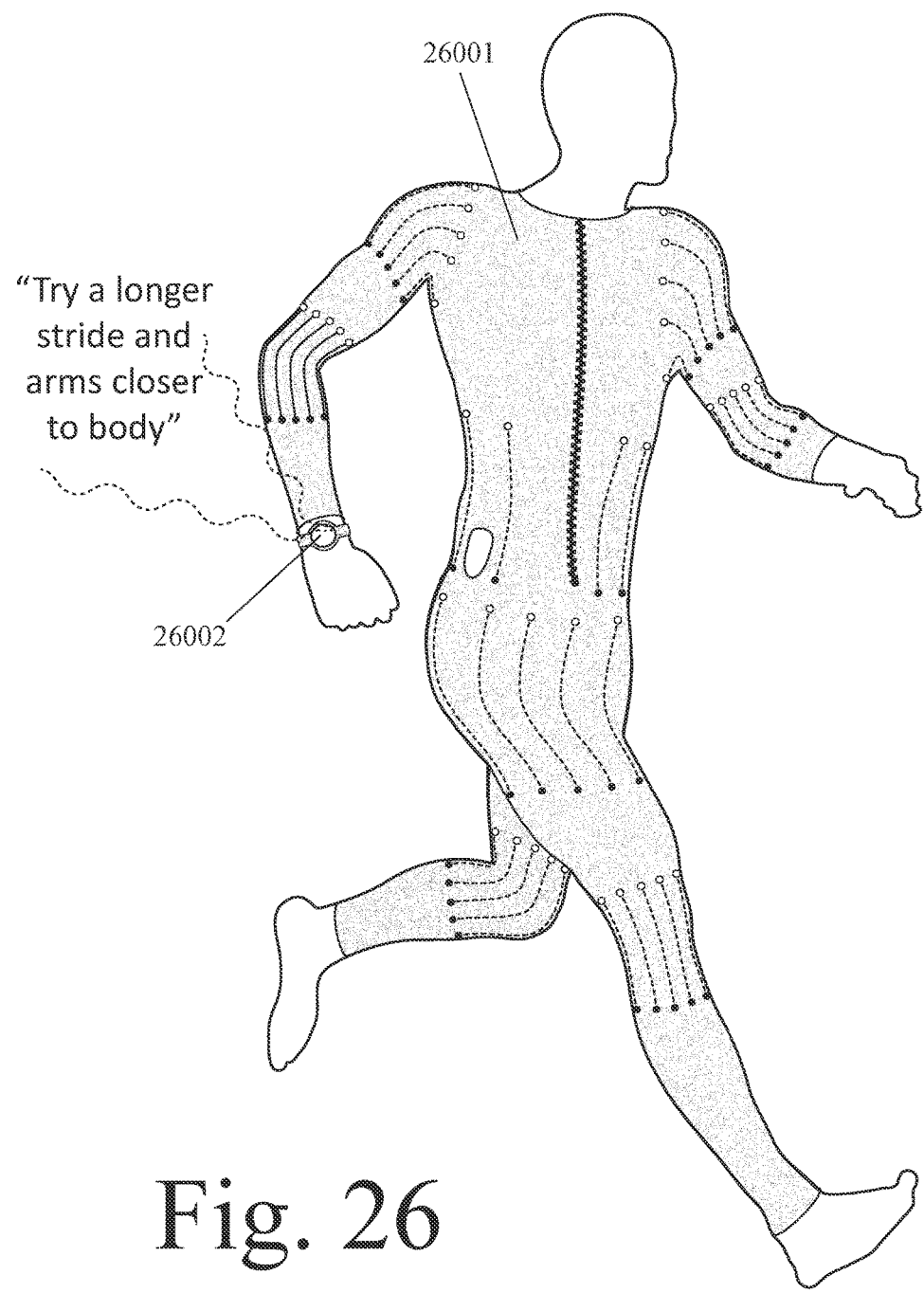
FIG. 26 shows a second example of how this invention can perform real-time analysis of full-body motion and provide useful information.

FIG. 26 shows another example of how this invention can perform real-time analysis of full-body motion and/or configuration and provide a person with useful information. In this example, wrist-worn component 26002 has a speech-based computer-to-human interface. In this example, motion recognition clothing has analyzed the person's full-body motion and/or configuration during a run and now provides speech-based feedback to inform the person of how they can improve their running form. Specifically, wrist-worn component 26002 tells the person—"Try a longer stride and arms closer to the body." This type of full-body motion and configuration analysis is difficult (or even impossible) with wrist-worn accelerometers.

Figure 27:
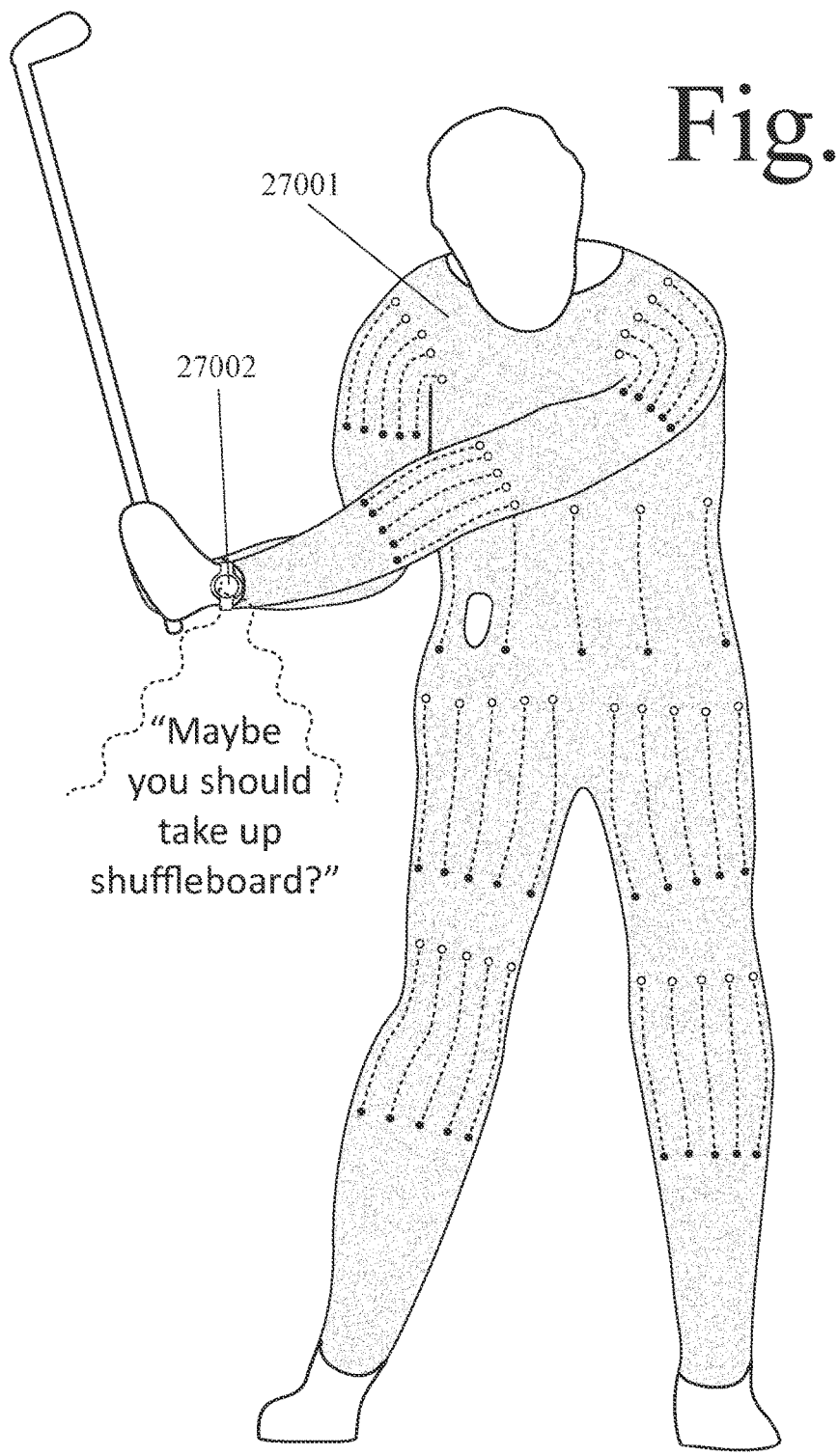
FIG. 27 shows a third example of how this invention can perform real-time analysis of full-body motion and provide useful information.

FIG. 27 shows another example of how this invention can perform real-time analysis of full-body motion and/or configuration and provide a person with useful information. In this example, wrist-worn component 27002 has a speech-based computer-to-human interface. In this example, motion recognition clothing 27001 has analyzed the person's full-body motion and/or configuration while the person played golf and now provides speech-based feedback. Specifically, wrist-worn component 27002 tells the person—"Maybe you should take up shuffleboard?" Whether the person continues to wear such a sassy device remains to be seen.

In another example, this invention can comprise a method for measuring, modeling, and/or capturing a person's forearm motion and/or configuration comprising: (a) measuring a first energy flow from a first wearable energy pathway that is configured to span the portion of a person's body which contains their forearm; (b) measuring a second energy flow from a second wearable energy pathway that is configured to span the portion of a person's body which contains their forearm; and (c) jointly analyzing the first and second energy flows in order to estimate, measure, and/or model the pronation, rotation, and/or supination of their forearm.

In another example, the first and second energy flows can be electrical energy. In an example, this electrical energy can be conducted through the energy pathways and the amounts of electrical energy conducted can change when the configurations of the pathways change as the forearm moves. In an example, electrical voltage, current, resistance, and/or impedance can be measured. In an example, electrical energy can be generated by the energy pathways when the configurations of the pathways change as the forearm moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the forearm moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of pronation, rotation, and/or supination of the person's forearm than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of pronation, rotation, and/or supination and gives greater statistical weight to the second energy flow over a second range of pronation, rotation, and/or supination. In an example, a statistical method can analyze differences between the first and second energy flows to determine if the locations of the wearable energy pathways relative to the surface of the person's body have shifted and to adjust estimation if such shifting occurs.

In an example, the relationship between energy flow and forearm configuration can be nonlinear and/or stochastic. In an example, joint analysis of the first and second energy flows from the first and second energy pathways spanning a person's forearm can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's forearm. In an example, these longitudinal axes can be separated by a substantially constant percentage of the cross-sectional circumference of the person's forearm. In an example, these longitudinal axes are substantially parallel when the forearm is extended straight outward. In an example, the first energy pathway can have a longitudinal axis which longitudinally spans a forearm and the second energy pathway can span part of the cross-sectional perimeter of the forearm. In an example, the first and second energy pathways diverge in a radial manner as they longitudinally span the forearm. In an example, the first and second energy pathways can be concentric and/or nested as they span a person's forearm. In an example, the first and second energy pathways can be pathways within an energy-transmitting mesh which spans a person's forearm.

In various examples, measurement of the configuration and movement of a person's forearm can be especially useful for: athletic training and motion capture for sports which involve extensive forearm motion (such as tennis and golf); avoidance of repeated motion injuries; ambulatory telerobotics; and avatar animation, computer gaming, and virtual reality.

In an example, the first and second energy pathways can be energy transmitting pathways which are incorporated into a shirt, arm tube, arm band, glove, or union suit. In an example, the first and second energy pathways can be woven into a shirt, arm tube, arm band, glove, or union suit. In an example, the first and second energy pathways can be sewn into, inserted into, or adhered to a shirt, arm tube, arm band, glove, or union suit. In an example, this shirt, arm tube, arm band, glove, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's wrist motion and/or configuration comprising: (a) measuring a first energy flow from a first wearable energy pathway that is configured to span the portion of a person's body which contains their wrist; (b) measuring a second energy flow from a second wearable energy pathway that is configured to span the portion of a person's body which contains their wrist; and (c) jointly analyzing the first and second energy flows in order to estimate, measure, and/or model the abduction, extension, flexion, and/or ulnar deviation or radial deviation of their wrist.

In an example, the first and second energy flows can be electrical energy. In an example, this electrical energy can be conducted through the energy pathways and the amounts of electrical energy conducted can change when the configurations of the pathways change as the wrist moves. In an example, electrical voltage, current, resistance, and/or impedance can be measured. In an example, electrical energy can be generated by the energy pathways when the configurations of the pathways change as the wrist moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the wrist moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of abduction, extension, flexion, and/or ulnar deviation or radial deviation of the person's wrist than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of abduction, extension, flexion, and/or ulnar deviation or radial deviation and gives greater statistical weight to the second energy flow over a second range of abduction, extension, flexion, and/or ulnar deviation or radial deviation. In an example, a statistical method can analyze differences between the first and second energy flows to determine if the locations of the wearable energy pathways relative to the surface of the person's body have shifted and to adjust estimation if such shifting occurs.

In an example, the relationship between energy flow and wrist configuration can be nonlinear and/or stochastic. In an example, joint analysis of the first and second energy flows from the first and second energy pathways spanning a person's wrist can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's wrist. In an example, these longitudinal axes can be separated by a substantially constant percentage of the cross-sectional circumference of the person's wrist. In an example, these longitudinal axes are substantially parallel when the wrist is straight. In an example, the first energy pathway can have a longitudinal axis which longitudinally spans the portion of the person's body which contains a wrist joint and the second energy pathway can span part of the cross-sectional perimeter of this portion of the person's body. In an example, the first and second energy pathways diverge in a radial manner as they longitudinally span the wrist joint. In an example, the first and second energy pathways are substantially parallel as they longitudinally span a proximal skeletal member of a wrist joint and diverge in a radial manner as they longitudinally span a distal skeletal member of the wrist joint. In an example, the first and second energy pathways can be concentric and/or nested as they span a person's wrist. In an example, the first and second energy pathways can be pathways within an energy-transmitting mesh which spans a person's wrist.

In various examples, measurement of the configuration and movement of a person's wrist can be especially useful for: athletic training and motion capture for sports which involve extensive wrist motion (such as tennis, golf, and Frisbee); avoidance of repeated motion injuries; gesture recognition human-computer interface; telerobotics and telesurgery; and avatar animation, computer gaming, and virtual reality.

In an example, the first and second energy pathways can be energy transmitting pathways which are incorporated into a shirt, arm tube, arm band, or glove. In an example, the first and second energy pathways can be woven into a shirt, arm tube, arm band, or glove. In an example, the first and second energy pathways can be sewn into, inserted into, or adhered to a shirt, arm tube, arm band, or glove. In an example, this shirt, arm tube, arm band, or glove can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's finger or thumb motion and/or configuration comprising: (a) measuring a first energy flow from a first wearable energy pathway that is configured to span the portion of a person's body which contains their finger or thumb; (b) measuring a second energy flow from a second wearable energy pathway that is configured to span the portion of a person's body which contains their finger or thumb; and (c) jointly analyzing the first and second energy flows in order to estimate, measure, and/or model the extension and/or flexion of at least one of their finger or thumb.

In an example, the first and second energy flows can be electrical energy. In an example, this electrical energy can be conducted through the energy pathways and the amounts of electrical energy conducted can change when the configurations of the pathways change as the finger or thumb moves. In an example, electrical voltage, current, resistance, and/or impedance can be measured. In an example, electrical energy can be generated by the energy pathways when the configurations of the pathways change as the finger or thumb moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the finger or thumb moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of the amount of extension and/or flexion of at least one of the person's fingers or thumbs than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of extension and/or flexion and gives greater statistical weight to the second energy flow over a second range of extension and/or flexion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and finger or thumb configuration can be nonlinear and/or stochastic. In an example, joint analysis of the first and second energy flows from the first and second energy pathways spanning a person's finger or thumb can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's finger or thumb. In an example, these longitudinal axes can be separated by a substantially constant percentage of the cross-sectional circumference of the finger or thumb. In an example, these longitudinal axes are substantially parallel when the finger or thumb is straight and/or fully extended. In an example, the first energy pathway can have a longitudinal axis which longitudinally spans the portion of the person's body which contains a finger or thumb joint and the second energy pathway can span part of the cross-sectional perimeter of this portion of the person's body. In an example, the first and second energy pathways are substantially parallel as they longitudinally span a distal skeletal member of a finger or thumb joint and diverge in a radial manner as they longitudinally span a proximal skeletal member of the finger or thumb joint. In an example, the first and second energy pathways can be concentric and/or nested as they span a finger or thumb. In an example, the first and second energy pathways can be pathways within an energy-transmitting mesh which spans a person's finger or thumb.

In various examples, measurement of the configuration and movement of one or more of a person's fingers or thumbs can be especially useful for: gesture recognition and a gesture-based human-computer interface; athletic training and motion capture for sports which involve finger and hand motion (such as tennis, golf, baseball, and fencing); training and motion capture for playing musical instruments; avoidance of repeated motion injuries; telerobotics and telesurgery; and avatar animation, computer gaming, and virtual reality.

In an example, the first and second energy pathways can be energy transmitting pathways which are incorporated into a glove or finger tube. In an example, the first and second energy pathways can be woven into a glove or finger tube. In an example, the first and second energy pathways can be woven into a glove or finger tube. In an example, the first and second energy pathways can be sewn into, inserted into, or adhered to a glove or finger tube. In an example, this glove or finger tube can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's ankle motion and/or configuration comprising: (a) measuring a first energy flow from a first wearable energy pathway that is configured to span the portion of a person's body which contains their ankle; (b) measuring a second energy flow from a second wearable energy pathway that is configured to span the portion of a person's body which contains their ankle; and (c) jointly analyzing the first and second energy flows in order to estimate, measure, and/or model the eversion, extension, flexion, and/or inversion of their ankle.

In an example, the first and second energy flows can be electrical energy. In an example, this electrical energy can be conducted through the energy pathways and the amounts of electrical energy conducted can change when the configurations of the pathways change as the ankle moves. In an example, electrical voltage, current, resistance, and/or impedance can be measured. In an example, electrical energy can be generated by the energy pathways when the configurations of the pathways change as the ankle moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the ankle moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of the amount of eversion, extension, flexion, and/or inversion of the person's ankle than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of eversion, extension, flexion, and/or inversion and gives greater statistical weight to the second energy flow over a second range of eversion, extension, flexion, and/or inversion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and ankle configuration can be nonlinear and/or stochastic. In an example, joint analysis of the first and second energy flows from the first and second energy pathways spanning a person's ankle can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's ankle. In an example, these longitudinal axes can be separated by a substantially constant percentage of the cross-sectional circumference of the person's ankle. In an example, these longitudinal axes are substantially parallel when the ankle is straight. In an example, the first energy pathway can have a longitudinal axis which longitudinally spans an ankle and the second energy pathway can span part of the cross-sectional perimeter of the ankle. In an example, the first and second energy pathways diverge in a radial manner as they longitudinally span the ankle. In an example, the first and second energy pathways are substantially parallel as they longitudinally span the fibula and tibia and diverge as they longitudinally span the talus and calcaneus; or vice versa. In an example, the first and second energy pathways can be concentric and/or nested as they span a person's ankle. In an example, the first and second energy pathways can be pathways within an energy-transmitting mesh which spans a person's ankle.

In various examples, measurement of the configuration and movement of a person's ankle can be especially useful for: athletic training and motion capture for sports which involve extensive ankle motion (such as running and soccer); gait and pronation analysis, medical diagnosis, posture correction, and rehabilitation for injuries and neurological impairment; ambulatory telerobotics; and lower-body avatar animation, computer gaming, and virtual reality.

In an example, the first and second energy pathways can be energy transmitting pathways which are incorporated into a sock, shoe, ankle tube, ankle band, or union suit. In an example, the first and second energy pathways can be woven into a sock, shoe, ankle tube, ankle band, or union suit. In an example, the first and second energy pathways can be sewn into, inserted into, or adhered to a sock, shoe, ankle tube, ankle band, or union suit. In an example, this sock, shoe, ankle tube, ankle band, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's mid-tarsal motion and/or configuration comprising: (a) measuring a first energy flow from a first wearable energy pathway that is configured to span the portion of a person's body which contains their mid-tarsal; (b) measuring a second energy flow from a second wearable energy pathway that is configured to span the portion of a person's body which contains their mid-tarsal; and (c) jointly analyzing the first and second energy flows in order to estimate, measure, and/or model the eversion and/or inversion of their mid-tarsal.

In an example, the first and second energy flows can be electrical energy. In an example, this electrical energy can be conducted through the energy pathways and the amounts of electrical energy conducted can change when the configurations of the pathways change as the mid-tarsal moves. In an example, electrical voltage, current, resistance, and/or impedance can be measured. In an example, electrical energy can be generated by the energy pathways when the configurations of the pathways change as the mid-tarsal moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the mid-tarsal moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of eversion and/or inversion of the person's mid-tarsal than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of eversion and/or inversion and gives greater statistical weight to the second energy flow over a second range of eversion and/or inversion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and mid-tarsal configuration can be nonlinear and/or stochastic. In an example, joint analysis of the first and second energy flows from the first and second energy pathways spanning a person's mid-tarsal can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's mid-tarsal. In an example, these longitudinal axes can be separated by a substantially constant percentage of the cross-sectional circumference of the person's mid-tarsal. In an example, the first energy pathway can have a longitudinal axis which longitudinally spans the portion of the person's body which contains a mid-tarsal and the second energy pathway can span part of the cross-sectional perimeter of this portion of the person's body. In an example, the first and second energy pathways diverge in a radial manner as they longitudinally span a mid-tarsal. In an example, the first and second energy pathways can be concentric and/or nested as they span a person's mid-tarsal. In an example, the first and second energy pathways can be pathways within an energy-transmitting mesh which spans a person's mid-tarsal.

In an example, the first and second energy pathways can be energy transmitting pathways which are incorporated into a sock or shoe. In an example, the first and second energy pathways can be woven into a sock or shoe. In an example, the first and second energy pathways can be sewn into, inserted into, or adhered to a sock or shoe. In an example, this sock or shoe can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's toe motion and/or configuration comprising: (a) measuring a first energy flow from a first wearable energy pathway that is configured to span the portion of a person's body which contains a toe; (b) measuring a second energy flow from a second wearable energy pathway that is configured to span the portion of a person's body which contains the toe; and (c) jointly analyzing the first and second energy flows in order to estimate, measure, and/or model the extension and/or flexion of the toe.

In an example, the first and second energy flows can be electrical energy. In an example, this electrical energy can be conducted through the energy pathways and the amounts of electrical energy conducted can change when the configurations of the pathways change as the toe moves. In an example, electrical voltage, current, resistance, and/or impedance can be measured. In an example, electrical energy can be generated by the energy pathways when the configurations of the pathways change as the toe moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the toe moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of extension and/or flexion of the person's toe than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of extension and/or flexion and gives greater statistical weight to the second energy flow over a second range of extension and/or flexion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and toe configuration can be nonlinear and/or stochastic. In an example, joint analysis of the first and second energy flows from the first and second energy pathways spanning a person's toe can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's toe. In an example, these longitudinal axes can be separated by a substantially constant percentage of the cross-sectional circumference of the toe. In an example, these longitudinal axes are substantially parallel when the toe is straight and/or fully extended. In an example, the first energy pathway can have a longitudinal axis which longitudinally spans the portion of the person's body which contains a toe joint and the second energy pathway can span part of the cross-sectional perimeter of this portion of the person's body. In an example, the first and second energy pathways are substantially parallel as they longitudinally span a distal skeletal member of a toe joint and diverge in a radial manner as they longitudinally span a proximal skeletal member of the toe joint. In an example, the first and second energy pathways can be concentric and/or nested as they span a person's toe. In an example, the first and second energy pathways can be pathways within an energy-transmitting mesh which spans a person's toe.

In an example, the first and second energy pathways can be energy transmitting pathways which are incorporated into a sock or shoe. In an example, the first and second energy pathways can be woven into a sock or shoe. In an example, the first and second energy pathways can be sewn into, inserted into, or adhered to a sock or shoe. In an example, this sock or shoe can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's neck motion and/or configuration comprising: (a) measuring a first energy flow from a first wearable energy pathway that is configured to span the portion of a person's body which contains their neck; (b) measuring a second energy flow from a second wearable energy pathway that is configured to span the portion of a person's body which contains their neck; and (c) jointly analyzing the first and second energy flows in order to estimate, measure, and/or model the abduction, extension, flexion, and/or rotation of their neck.

In an example, the first and second energy flows can be electrical energy. In an example, this electrical energy can be conducted through the energy pathways and the amounts of electrical energy conducted can change when the configurations of the pathways change as the neck moves. In an example, electrical voltage, current, resistance, and/or impedance can be measured. In an example, electrical energy can be generated by the energy pathways when the configurations of the pathways change as the neck moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the neck moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of abduction, extension, flexion, and/or rotation of the person's neck than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of abduction, extension, flexion, and/or rotation and gives greater statistical weight to the second energy flow over a second range of abduction, extension, flexion, and/or rotation. In an example, a statistical method can analyze differences between the first and second energy flows to determine if the locations of the wearable energy pathways relative to the surface of the person's body have shifted and to adjust estimation if such shifting occurs.

In an example, the relationship between energy flow and neck configuration can be nonlinear and/or stochastic. In an example, joint analysis of the first and second energy flows from the first and second energy pathways spanning a person's neck can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, this invention can comprise first and second energy pathways which have longitudinal axes which span a person's neck. In an example, these longitudinal axes can be separated by a substantially constant percentage of the cross-sectional circumference of the person's neck. In an example, these longitudinal axes are substantially parallel when the neck is straight. In an example, the first energy pathway can have a longitudinal axis which longitudinally spans the neck and the second energy pathway can span part of the cross-sectional perimeter of the neck. In an example, the first and second energy pathways diverge in a radial manner as they longitudinally span the neck. In an example, the first and second energy pathways can be concentric and/or nested as they span a person's neck. In an example, the first and second energy pathways can be pathways within an energy-transmitting mesh which spans a person's neck.

In an example, the first and second energy pathways can be energy transmitting pathways which are incorporated into a shirt, collar, neck band, hoodie, or union suit. In an example, the first and second energy pathways can be woven into a shirt, collar, neck band, hoodie, or union suit. In an example, the first and second energy pathways can be sewn into, inserted into, or adhered to a shirt, collar, neck band, hoodie, or union suit. In an example, this shirt, collar, neck band, hoodie, or union suit can comprise part of a system of motion recognition clothing for measuring, modeling, and/or capturing changes in body motion and/or configuration. In an example, a data transmitting or processing component of such a system can be temporarily detached in order to wash the motion recognition clothing.

In an example, this invention can comprise a method for measuring, modeling, and/or capturing a person's jaw motion and/or configuration comprising: (a) measuring a first energy flow from a first wearable energy pathway that is configured to span the portion of a person's body which contains their jaw; (b) measuring a second energy flow from a second wearable energy pathway that is configured to span the portion of a person's body which contains their jaw; and (c) jointly analyzing the first and second energy flows in order to estimate, measure, and/or model the extension and/or flexion of their jaw. In various examples, measurement of the configuration and movement of a person's jaw can be especially useful for: caloric intake monitoring; eating analysis and therapy; speech analysis and therapy; and avatar animation, computer gaming, and virtual reality. In an example, jawbone can provide excellent measurement.

In an example, the first and second energy flows can be electrical energy. In an example, this electrical energy can be conducted through the energy pathways and the amounts of electrical energy conducted can change when the configurations of the pathways change as the jaw moves. In an example, electrical voltage, current, resistance, and/or impedance can be measured. In an example, electrical energy can be generated by the energy pathways when the configurations of the pathways change as the jaw moves. In an example, the energy pathways can be piezoelectric. In an example, the first and second energy flows can be light energy. In an example, the energy pathways can be fiber optic. In an example, the amount, wavelength, and/or spectrum of light energy transmitted through the energy pathways can change when the configurations of the pathways change as the jaw moves. In an example, the first and second energy flows can be sound energy. In an example, the energy flows can be ultrasonic. In an example, the amount, frequency, or pattern of sound energy transmitted through the energy pathways can change when the shapes of the pathways change.

In an example, joint statistical analysis of the first and second energy flows can provide more accurate estimation, measurement, and/or modeling of extension and/or flexion of the person's jaw than does separate statistical analysis of the first energy flow or the second energy flow. In an example, energy flows from the first and second energy pathways can be averaged together to reduce the variability of measurement and/or reduce the impact of measurement error in one pathway. In an example, a statistical method can be used which gives greater statistical weight to the first energy flow over a first range of extension and/or flexion and gives greater statistical weight to the second energy flow over a second range of extension and/or flexion. In an example, a statistical method can analyze differences between the first and second energy flows to determine if the locations of the wearable energy pathways relative to the surface of the person's body have shifted and to adjust estimation if such shifting occurs.

In an example, the relationship between energy flow and jaw configuration can be nonlinear and/or stochastic. In an example, joint analysis of the first and second energy flows from the first and second energy pathways spanning a person's jaw can be done using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian statistical method; chi-squared; eigenvalue decomposition; logit model; machine learning; power spectral density; power spectrum analysis; and/or probit model.

In an example, a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, and wherein the average first-to-second distance between the proximal portion of the first joint-spanning member and the proximal portion of the second joint-spanning member is substantially equal to the average first-to-second distance between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, wherein the average second-to-third distance between the proximal portion of the second joint-spanning member and the proximal portion of the third joint-spanning member is substantially equal to the average second-to-third distance between the distal portion of the second joint-spanning member and the distal portion of the third joint-spanning member, and wherein the average second-to-third distance is at least 10% greater than the average first-to-second distance; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

In an example, a wearable device for measuring the configuration or motion of a human body joint can comprise: (a) a first joint-spanning member, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, wherein the average first-to-second percentage of the portion of the cross-sectional perimeter of the human body member between the proximal portion of the first joint-spanning member and the proximal portion of the second joint-spanning member is substantially equal to the average first-to-second percentage of the portion of the cross-sectional perimeter of the human body member between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, and wherein the average second-to-third percentage of the portion of the cross-sectional perimeter of the human body member between the proximal portion of the second joint-spanning member and the proximal portion of the third joint-spanning member is substantially equal to the average second-to-third percentage of the portion of the cross-sectional perimeter of the human body member between the distal portion of the second joint-spanning member and the distal portion of the third joint-spanning member, and wherein the average second-to-third percentage is at least 10% greater than the average first-to-second percentage; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

In an example, a wearable device for measuring the configuration or motion of a human body joint can comprise: (a) a first joint-spanning member with a first length, wherein a proximal portion of the first joint-spanning member is configured to be worn within 1" of the surface of a portion of the human body which contains the proximal side of a human body joint and a distal portion of the first joint-spanning member is configured to be worn within 1" of the surface of a portion of the human body which contains the distal side of the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member with a second length, wherein a proximal portion of the second joint-spanning member is configured to be worn within 1" of the surface of the portion of the human body which contains the proximal side of the human body joint and a distal portion of the second joint-spanning member is configured to be worn within 1" of the surface of the portion of the human body which contains the distal side of the human body joint, wherein the average first-to-second percentage of the portion of the cross-sectional perimeter of the human body member between the proximal portion of the first joint-spanning member and the proximal portion of the second joint-spanning member is substantially equal to the average first-to-second percentage of the portion of the cross-sectional perimeter of the human body member between the distal portion of the first joint-spanning member and the distal portion of the second joint-spanning member; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member with a third length, wherein a proximal portion of the third joint-spanning member is configured to be worn within 1" of the surface of the portion of the human body which contains the proximal side of the human body joint and a distal portion of the third joint-spanning member is configured to be worn within 1" of the surface of the portion of the human body which contains the distal side of the human body joint, and wherein the average second-to-third percentage of the portion of the cross-sectional perimeter of the human body member between the proximal portion of the second joint-spanning member and the proximal portion of the third joint-spanning member is substantially equal to the average second-to-third percentage of the portion of the cross-sectional perimeter of the human body member between the distal portion of the second joint-spanning member and the distal portion of the third joint-spanning member, and wherein the first, second, and third lengths differ by more than 20%; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

In an example, a wearable device for measuring the configuration or motion of a human body joint can comprise: (a) a first joint-spanning member, wherein the central axis of the first joint-spanning member is located along a substantially constant first radial angle in different cross-sections of the portion of the human body which contains the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member, wherein the central axis of the second joint-spanning member is located along a substantially constant second radial angle in different cross-sections of the portion of the human body which contains the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member, wherein the central axis of the third joint-spanning member is located along a substantially constant third radial angle in different cross-sections of the portion of the human body which contains the human body joint, and wherein the difference between the second radial angle and the third radial angle is at least 10% greater than the difference between the first radial angle and the second radial angle; (f) a third electromagnetic energy sensor which measures electromagnetic energy from the third joint-spanning member, wherein changes in the configuration or motion of the third joint-spanning member change the electromagnetic energy measured by the third electromagnetic energy sensor, and wherein data from the first, second, and third electromagnetic energy sensors are jointly analyzed to estimate the configuration or motion of the human body joint; and (g) an attachment member which holds the first, second, and third joint-spanning members within 1" of the surface of the portion of the human body which contains the human body joint.

In an example, a wearable device for measuring the configuration or motion of a human body joint can comprise: (a) a first joint-spanning member with a first length, wherein the central axis of the first joint-spanning member is located along a substantially constant first radial angle in different cross-sections of the portion of the human body which contains the human body joint; (b) a first electromagnetic energy sensor which measures electromagnetic energy from the first joint-spanning member, wherein changes in the configuration or motion of the first joint-spanning member change the electromagnetic energy measured by the first electromagnetic energy sensor; (c) a second joint-spanning member with a second length, wherein the central axis of the second joint-spanning member is located along a substantially constant second radial angle in different cross-sections of the portion of the human body which contains the human body joint; (d) a second electromagnetic energy sensor which measures electromagnetic energy from the second joint-spanning member, wherein changes in the configuration or motion of the second joint-spanning member change the electromagnetic energy measured by the second electromagnetic energy sensor; (e) a third joint-spanning member with a third length, wherein the central axis of the third joint-spanning member is located along a substantially constant third radial angle in different cross-sections of the portion of the human body which contains the human body joint, and wherein the first, second, and third lengths differ by more than 20%; (f) a third electromagnetic energy sensor which measures electromagnetic energy from the third joint-spanning member, wherein changes in the configuration or motion of the third joint-spanning member change the electromagnetic energy measured by the third electromagnetic energy sensor; (g) at least one perimeter member with a longitudinal axis that is substantially perpendicular to the longitudinal axis of at least one of the first, second, and third joint-spanning members; (h) at least one perimeter electromagnetic energy sensor which measures electromagnetic energy from the at least one perimeter member, wherein changes in the configuration or motion of the at least one perimeter member change the electromagnetic energy measured by the at least one perimeter electromagnetic energy sensor, and wherein data from the first electromagnetic energy sensor, second electromagnetic energy sensor, third electromagnetic energy sensor, and at least-one-perimeter electromagnetic energy sensor are jointly analyzed to estimate the configuration or motion of the human body joint; and (i) an attachment member which holds the first, second, third joint-spanning members and the at least one perimeter member within 1" of the surface of the portion of the human body which contains the human body joint.

In an example, a wearable device for measuring the configuration or motion of a human body joint can comprise: (a) a joint-spanning triangular-element mesh which is comprised of linked triangular elements and which is configured to span the surface of a portion of the human body which contains a human body joint; and (b) a plurality of electromagnetic energy sensors which measure electromagnetic energy from different locations on the joint-spanning triangular-element mesh, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning hexagonal-element mesh which is comprised of linked hexagonal elements and which is configured to span the surface of a portion of the human body which contains a human body joint; and (b) a plurality of electromagnetic energy sensors which measure electromagnetic energy from different locations on the joint-spanning hexagonal-element mesh, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning spiral member which is configured to spiral around the surface of a portion of the human body which contains a human body joint; and (b) a plurality of electromagnetic energy sensors which measure electromagnetic energy from different locations on the joint-spanning spiral member, wherein changes in the configuration or motion of the joint-spanning mesh change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge at a point on the dorsal surface of the portion of the human body which contains the human body joint; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge at a point on a lateral surface of the portion of the human body which contains the human body joint; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of radial members which are configured to collectively span the surface of a portion of the human body which contains a human body joint, wherein the longitudinal axes of the radial members are configured to converge at a point which is beyond the outer surface of the portion of the human body which contains the human body joint; and (b) a plurality of electromagnetic energy sensors which measure electromagnetic energy from different locations on the joint-spanning plurality of radial members, wherein changes in the configuration or motion of the joint-spanning plurality of radial members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point on the dorsal surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, a wearable device for measuring the configuration or motion of a human body joint can comprise: (a) a joint-spanning plurality of concentric or progressively-nested arcuate members which are configured to collectively span the surface of a portion of the human body which contains a human body joint, wherein the common center of the concentric or progressively-nested arcuate members is at a point which is beyond the outer surface of the portion of the human body which contains the human body joint; and (b) a plurality of electromagnetic energy sensors which measure electromagnetic energy from different locations on the joint-spanning plurality of concentric members, wherein changes in the configuration or motion of the joint-spanning plurality of concentric or progressively-nested arcuate members change the pattern of electromagnetic energy which is measured by the plurality of electromagnetic energy sensors, and wherein data from the plurality of electromagnetic energy sensors are jointly analyzed to estimate the configuration or motion of the human body joint.

In an example, this invention can be used for athletic training, sports performance analysis, sports motion capture, and fan engagement. In an example, this invention can be useful for training and motion capture for sports which involve extensive and/or complex lower-body motion (such as soccer, bicycling, and running) which are not well measured by single-location (wrist-worn) accelerometers. In an example, this invention can be useful for training and motion capture for sports which involve complex upper-body motion (such as basketball, tennis, golf, baseball, Frisbee™, and fencing) which are not well measured by single-location accelerometers.

In an example, this invention can be used for health, fitness, and medical applications. In an example, this invention can be used for caloric expenditure measurement, energy balance management, weight management, and caloric intake monitoring applications. In an example, this invention can be used for virtual exercise. In an example, this invention can be used for real-time avoidance of repeated motion injuries, injuries due to poor posture, and stress-related injuries including back injuries and carpal tunnel syndrome. In an example, this invention can be used for diagnostic and therapy-evaluation purposes including: range of motion assessment, gait analysis, biomechanical analysis, posture evaluation and correction, ergonomic assessment, fall prevention and detection, spinal motion assessment, rehabilitation assessment, biofeedback, pulse monitoring, respiratory function assessment, plethysmography, cardiac function monitoring, orthopedic therapy, physical therapy, orthotic design and fitting, and pronation analysis. In an example, this invention can be used for telemedicine and/or telesurgery applications.

In an example, this invention can be used for entertainment, gaming, and artistic purposes. In an example, this invention can be used for animation of an avatar in virtual reality and/or computer gaming. In an example, this invention can be used for animation of an animated character in motion picture making or other visual animation applications. In an example, this invention can be used for dance instruction, dance performance, and other performance art applications. In an example, this invention can be used for instruction and motion capture for playing musical instruments.

In an example, this invention can be used for communication and computer interface purposes. In an example, this invention can be used for telepresence, teleconferencing, telecommunication, avatar animation, and virtual commerce. In an example, this invention can be used as part of a gesture recognition human-to-computer user interface. In an example, this invention be can be used for telerobotics to enable remote control of the actions of a robot. In an example, this invention can be used for banking during space missions (as an astro teller).

In various examples, one or more applications for this invention can be selected from group consisting of: athletic training and motion capture for sports which involve extensive lower-body motion (such as bicycling and soccer), extensive arm motion (such as tennis and golf), extensive lower-body motion (such as bicycling and running), extensive spinal motion, extensive forearm motion (such as tennis and golf), wrist motion (such as tennis, golf, and Frisbee), ankle motion (such as running and soccer), finger and hand motion (such as tennis, golf, baseball, and fencing), athletic performance measurement and improvement; and entertainment, gaming, and artistic applications (such as animated pictures, avatar animation, computer animation, computer gaming, dance instruction, dance performance, gaming input devices, graphical animation, motion capture, motion picture animation, motion pictures, movie making, performance arts, training and motion capture for playing musical instruments, virtual gaming, virtual reality); and health, fitness, and medical applications (such as avoidance of repeated motion injuries, biofeedback, biomechanical analysis, caloric expenditure measurement, caloric intake monitoring, cardiac function monitoring, congestive heart failure assessment, energy balance, ergonomic evaluation, fall prevention and detection, gait analysis, medical diagnosis, medical therapy, nutritional monitoring and improvement, orthopedic therapy, orthotic design and fitting, physical therapy, plethysmography, post-operative therapy, posture correction, pronation analysis, pulse monitoring, range of motion assessment, rehabilitation assessment, repetitive stress injury avoidance, respiratory function analysis, spinal injury avoidance, spinal motion assessment, telemedicine, telesurgery, virtual exercise, weight management); and human-computer interface and telecommunication (such as gesture recognition, telerobotics, telesurgery, telepresence, notifications, telecommunication, teleconferencing, telepresence, telerobotics, virtual commerce, and virtual reality interaction).

Figure 28:
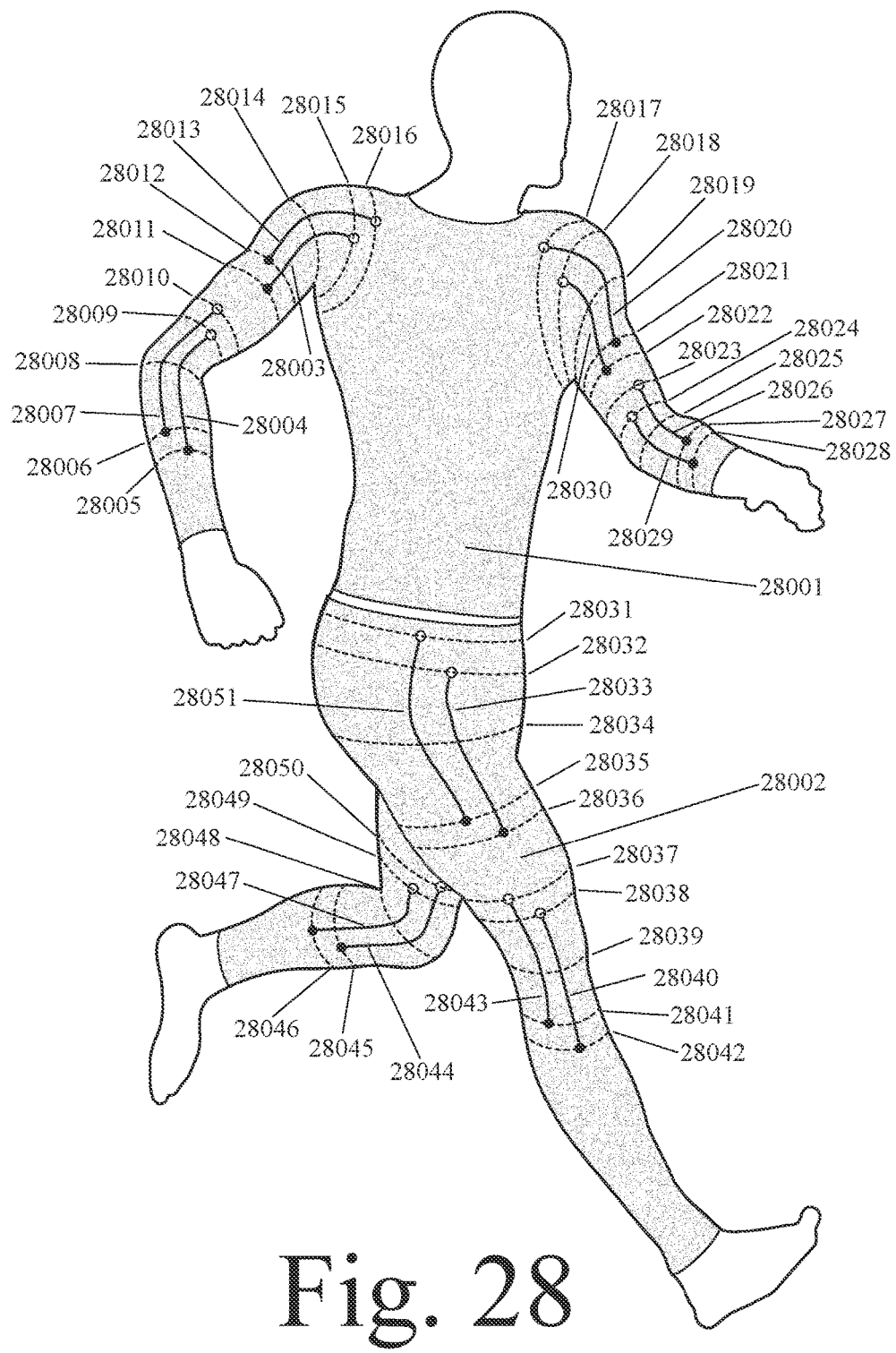
FIG. 28 shows an example wherein two flexible energy pathways spanning the same joint are the same length, but their ends are not aligned.

FIG. 28 shows an example of how this invention can be embodied in an article of clothing or clothing accessory for capturing body motion comprising an article of clothing or clothing accessory worn by a person which is configured to span at least one body joint, wherein this article of clothing or clothing accessory further comprises: (a) a mid-joint perimeter portion which is configured around the cross-section of the person's body which includes the center of the joint; (b) a first proximal perimeter portion which is configured around a cross-section of the person's body which is proximal relative to the mid joint perimeter portion, wherein proximal is defined as being closer to the person's heart along the circulatory system; (c) a second proximal perimeter portion which is configured around a cross-section of the person's body which is proximal relative to the mid-joint perimeter portion; (d) a first distal perimeter portion which is configured around a cross-section of the person's body which is distal relative to the mid joint perimeter portion, wherein distal is defined as being further from the person's heart along the circulatory system; (e) a second distal perimeter portion around a cross-section of the person's body which is distal relative to the mid-joint perimeter portion; (f) a first flexible energy pathway, wherein this energy pathway spans from the first proximal perimeter portion to the first distal perimeter portion, wherein movement of the joint changes the configuration of this pathway, wherein changes in the configuration of this pathway change a flow of energy through this pathway, and wherein changes in the flow of energy through this pathway can be used alone to estimate movement of the joint with a first level of accuracy; (g) a second flexible energy pathway, wherein this energy pathway spans from the second proximal perimeter portion to the second distal perimeter portion, wherein movement of the joint changes the configuration of this pathway, wherein changes in the configuration of this pathway change a flow of energy through this pathway, wherein changes in the flow of energy through this pathway can be used alone to estimate movement of the joint with a second level of accuracy, wherein changes in the flows of energy through the first and second flexible energy pathways can be jointly used to estimate movement of the joint with a third level of accuracy, and wherein the third level is greater than either the first level or the second level; (h) at least one energy emitter which emits energy into one or both of the flexible energy pathways; and (i) at least one energy sensor which senses energy from and/or through one or both of the flexible energy pathways, wherein the flow of energy through the one or both of the flexible energy pathways is measured by the at least one energy sensor.

In the example shown in FIG. 28, the first and second flexible energy pathways spanning the same joint are the same length. FIG. 28 comprises a shirt 28001 and a pair of pants 28002. The shirt 28001 spans the person's elbows and shoulders. The pair of pants 28002 spans the person's hips and knees. In an example, first and second flexible energy pathways can be incorporated into an article of clothing or wearable accessory which is selected from the group consisting of: ankle band, ankle tube, arm band, arm tube, belt, bra, collar, elbow pad, elbow tube, finger tube, girdle, glove, hip pad, hoodie, knee pad, knee tube, neck band, other wearable top, pair of pants, shirt, shoe, shorts, shoulder pad, shoulder tube, sock, suit, torso band, torso tube, underwear, union suit, waist band, and waist tube.

With respect to the person's right elbow, FIG. 28 shows: a mid joint perimeter portion 28008, a first proximal perimeter portion 28009, a second proximal perimeter portion 28010, a first distal perimeter portion 28006, a second distal perimeter portion 28005, a first flexible energy pathway 28004, and a second flexible energy pathway 28007. In this figure, an energy emitter is shown as an open circle at one end of an energy pathway and an energy sensor is shown as a filled circle at the other end of the energy pathway. With respect to the person's right shoulder, FIG. 28 shows: a mid joint perimeter portion 28014, a first proximal perimeter portion 28015, a second proximal perimeter portion 28016, a first distal perimeter portion 28012, a second distal perimeter portion 28011, a first flexible energy pathway 28003, and a second flexible energy pathway 28013.

With respect to the person's left shoulder, FIG. 28 shows: a mid-joint perimeter portion 28019, a first proximal perimeter portion 28018, a second proximal perimeter portion 28017, a first distal perimeter portion 28021, a second distal perimeter portion 28022, a first flexible energy pathway 28030, and a second flexible energy pathway 28020. With respect to the person's left elbow, FIG. 28 shows: a mid-joint perimeter portion 28025, a first proximal perimeter portion 28024, a second proximal perimeter portion 28023, a first distal perimeter portion 28027, a second distal perimeter portion 28028, a first flexible energy pathway 28029, and a second flexible energy pathway 28026.

With respect to the person's right hip, FIG. 28 shows: a mid-joint perimeter portion 28034, a first proximal perimeter portion 28032, a second proximal perimeter portion 28031, a first distal perimeter portion 28035, a second distal perimeter portion 28036, a first flexible energy pathway 28051, and a second flexible energy pathway 28033. With respect to the person's right knee, FIG. 28 shows: a mid joint perimeter portion 28039, a first proximal perimeter portion 28038, a second proximal perimeter portion 28037, a first distal perimeter portion 28041, a second distal perimeter portion 28042, a first flexible energy pathway 28043, and a second flexible energy pathway 28040. With respect to the person's left knee, FIG. 28 shows: a mid joint perimeter portion 28048, a first proximal perimeter portion 28049, a second proximal perimeter portion 28050, a first distal perimeter portion 28045, a second distal perimeter portion 28046, a first flexible energy pathway 28044, and a second flexible energy pathway 28047.

In an example, the type of energy which flows through one or more of the first flexible energy pathways 28003, 28004, 28029, 28030, 28043, 28044, and 28051 can be selected from the group consisting of: electromagnetic energy; light energy; and sound energy. In an example, the type of energy which flows through one or more of the second flexible energy pathways 28007, 28013, 28020, 28026, 28033, 28040, and 28047 can be selected from the group consisting of: electromagnetic energy; light energy; and sound energy. In an example, the type of energy that flows through the first flexible energy pathways can be the same as the type of energy that flows through the second energy pathways. In an example, the type of energy that flows through the first flexible energy pathways can be different than the type of energy that flows through the second energy pathways. In an example, energy can flow through the first flexible energy pathways with different flow parameters than energy flows through the second flexible energy pathways, wherein these different flow parameters can be selected from the group consisting of: rate, level, amplitude, resistance, impedance, filter, frequency, and spectrum.

In an example, multivariate analysis of energy flow through the first flexible energy pathway and energy flow through the second flexible energy pathway can include one or more methods selected from the group consisting of: averaging results from the first and second pathways; giving greater weight to the results from a selected pathway during a selected range of joint movement; giving greater weight to the results from a selected pathway during a selected direction of joint movement; giving greater weight to the results from a selected pathway during a selected speed of joint movement; giving greater weight to the results from a selected pathway during a selected repetition of joint movement; giving greater weight to the results from a selected pathway when the other pathway does not seem to be working properly; analyzing patterns from the first and second pathways to identify and compensate for measurement error in one pathway; analyzing patterns from the first and second pathways to identify and compensate for shifting of the locations of the energy pathways relative to the surface of the portion of the body; and analyzing patterns from the first and second pathways to identify and compensate for contact between a pathway and an external object.

In an example, the relationship between energy flow through a flexible energy pathway and the configuration of a body joint spanned by that flexible energy pathway can be nonlinear and/or stochastic. In an example, the relationship between energy flow in a flexible energy pathway and the configuration of a body joint spanned by that flexible energy pathway can be analyzed using one or more multivariate statistical methods. In an example, data from multiple flexible energy pathways can be jointly analyzed using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; kinematic modeling; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, repeated or cyclical patterns of movement such as walking or running can be identified and analyzed using Fourier analysis. In an example, the speed of repeated movement cycles can influence the functional relationship between the flow of energy through a flexible energy pathway and the angle of a joint. In an example, the speed of repeated cycles can especially influence this functional relationship at the end-points of a cycle wherein joint movement reverses direction. In an example, analyzing and identifying the speed of repeated or cyclical patterns of movement using Fourier transform methods can improve the accuracy of measuring joint motion and configuration.

In an example, data from different flexible energy pathways spanning the same body joint can be averaged together in order to improve accuracy and reduce error in the measurement of the motion and/or configuration of that joint. In an example, data from different flexible energy pathways spanning the same body joint can be given different weights during different portions of the joint range of motion in order to improve accuracy and reduce error in the measurement of the motion and/or configuration of that joint. In an example, data from different flexible energy pathways spanning the same body joint can be given different weights during different directions of joint motion (e.g. flexion vs. extension) in order to improve accuracy and reduce error in the measurement of the motion and/or configuration of that joint. In an example, data from different flexible energy pathways spanning the same body joint can be given different weights during different movement speeds (e.g. fast movement vs. slow movement) of joint motion in order to improve accuracy and reduce error in the measurement of the motion and/or configuration of that joint. In an example, data from different flexible energy pathways spanning the same body joint can be given different weights during different numbers of cycle repetition of joint motion in order to improve accuracy and reduce error in the measurement of the motion and/or configuration of that joint.

In an example, data from a flexible energy pathway with anomalous results can be given less weight in order to improve accuracy and reduce error in the measurement of the motion and/or configuration of that joint. In an example, data from different flexible energy pathways can analyzed to identify probable shifting of flexible energy pathway location over the surface of the body (e.g. by shifting of a garment into which the pathways are integrated) and to compensate for this shifting when interpreting data from multiple flexible energy pathways. In an example, data from different flexible energy pathways can analyzed to identify probable loss of mechanical or electromagnetic communication between a flexible energy pathway and the body and to compensate for this loss when interpreting data from multiple flexible energy pathways. In an example, data from different flexible energy pathways can analyzed to identify probable interference by an external object or field and to compensate for this interference when interpreting data from multiple flexible energy pathways.

In an example, this device can be recalibrated in order to maintain accurate measurement of joint motion and/or configuration. In an example, recalibration can comprise comparing the results from using the flexible energy pathways of the device to estimate the motion and/or configuration of a selected body joint or joints with parallel results from an alternative method of estimating joint motion and/or configuration of the body joint or joints. In an example, this device can be recalibrated when it is first worn by a specific person in order to be custom matched to that person's specific anatomy and/or body kinetics. In an example, this device can be recalibrated each time that it is worn in order to control for changing environmental conditions; incorporation into different articles of clothing; changes or shifts in how an article of clothing is worn over a person's body; changes in the anatomy or kinetics of a person's body over time; or other factors. In an example, this device can be recalibrated each time that a particular sequence of movements occurs in order to control for: possible shifts in how the flexible energy pathways span a body member containing a body joint; changes in how material responds to bending, stretching, or elongation with repeated motions; changes in temperature; or other factors. In an example, this device can be recalibrated after a selected number of joint extension and contraction cycles. In an example, this device can be recalibrated after a selected number of movement sequences have occurred. In an example, this device can be recalibrated at selected usage time intervals. In an example, this device can be recalibrated each time that a significant change in environmental factors (such as temperature, humidity, GPS location, or atmospheric pressure) is detected.

In an example, a flexible energy pathway can be incorporated into an article of clothing or clothing accessory by weaving or knitting. In an example, a flexible energy pathway can be woven or knit into fabric which is used to make an article of clothing or clothing accessory. In an example, a flexible energy pathway can be woven or knit into the fabric of an article of clothing or clothing accessory in a configuration which is substantially perpendicular to non-energy-conducting fibers, threads, or yarns in the fabric. In an example, a flexible energy pathway can be sinusoidal. In an example, a sinusoidal flexible energy pathway can have a longitudinal axis which is substantially perpendicular to non-energy-conducting fibers, threads, or yarns in the fabric of an article or accessory. In an example, the wave frequency and/or amplitude of a sinusoidal first flexible energy pathway can be different than the wave frequency and/or amplitude of a sinusoidal second flexible energy pathway.

In an example, a flexible energy pathway can be inserted into a channel between two layers of fabric in an article of clothing or clothing accessory. In an example, a flexible energy pathway can be attached to an article of clothing or clothing accessory by a hook-and-eye attachment mechanism. In an example, a flexible energy pathway can be attached to an article of clothing or clothing accessory by adhesion. In an example, a flexible energy pathway can be attached to an article of clothing or clothing accessory by sewing. In an example, a flexible energy pathway can be attached to an article of clothing or clothing accessory by at least one snap, clip, buckle, strap, or plug. In an example, a flexible energy pathway can be printed onto an article of clothing or clothing accessory.

In an example, a flexible energy pathway can be removed from an article of clothing or clothing accessory before the article or accessory is washed and then reattached after the article or accessory has been washed. In an example, a plurality of energy emitters can be connected by wires or other electromagnetic channels in fabric with a central power source which is attached to an article of clothing or clothing accessory. In an example, a plurality of energy sensors can be connected by wires or other electromagnetic channels in fabric with a central data processing unit and/or data transmitter which is attached to an article of clothing or clothing accessory. In an example, a plurality of energy emitters can be in wireless communication with a central power source. In an example, a plurality of energy sensors can be in wireless communication with a central data processing unit and/or data transmitter.

In an example, an energy emitter can emit energy into one end of a flexible energy pathway and an energy sensor can measure energy emitted from the other end of a flexible energy pathway. In an example, an energy emitter can emit energy into a proximal portion of a flexible energy pathway and energy can be measured from a distal portion of the flexible energy pathway by an energy sensor. In an example, an energy emitter can emit energy into a distal portion of a flexible energy pathway and energy can be measured from a proximal portion of the flexible energy pathway by an energy sensor. In an example, the rate, level, amount, power, frequency, and/or spectrum of energy which is transmitted from the energy emitter through the flexible energy pathway and received by the energy sensor is changed when the flexible energy pathway bends, kinks, compresses, stretches, and/or twists. In an example, changes in the rate, level, amount, power, frequency, and/or spectrum of energy transmitted through the flexible energy pathway can be used to estimate the movement and/or angle of the body joint spanned by the flexible energy pathway in a two-dimensional plane or in three-dimensional space.

Figure 29:
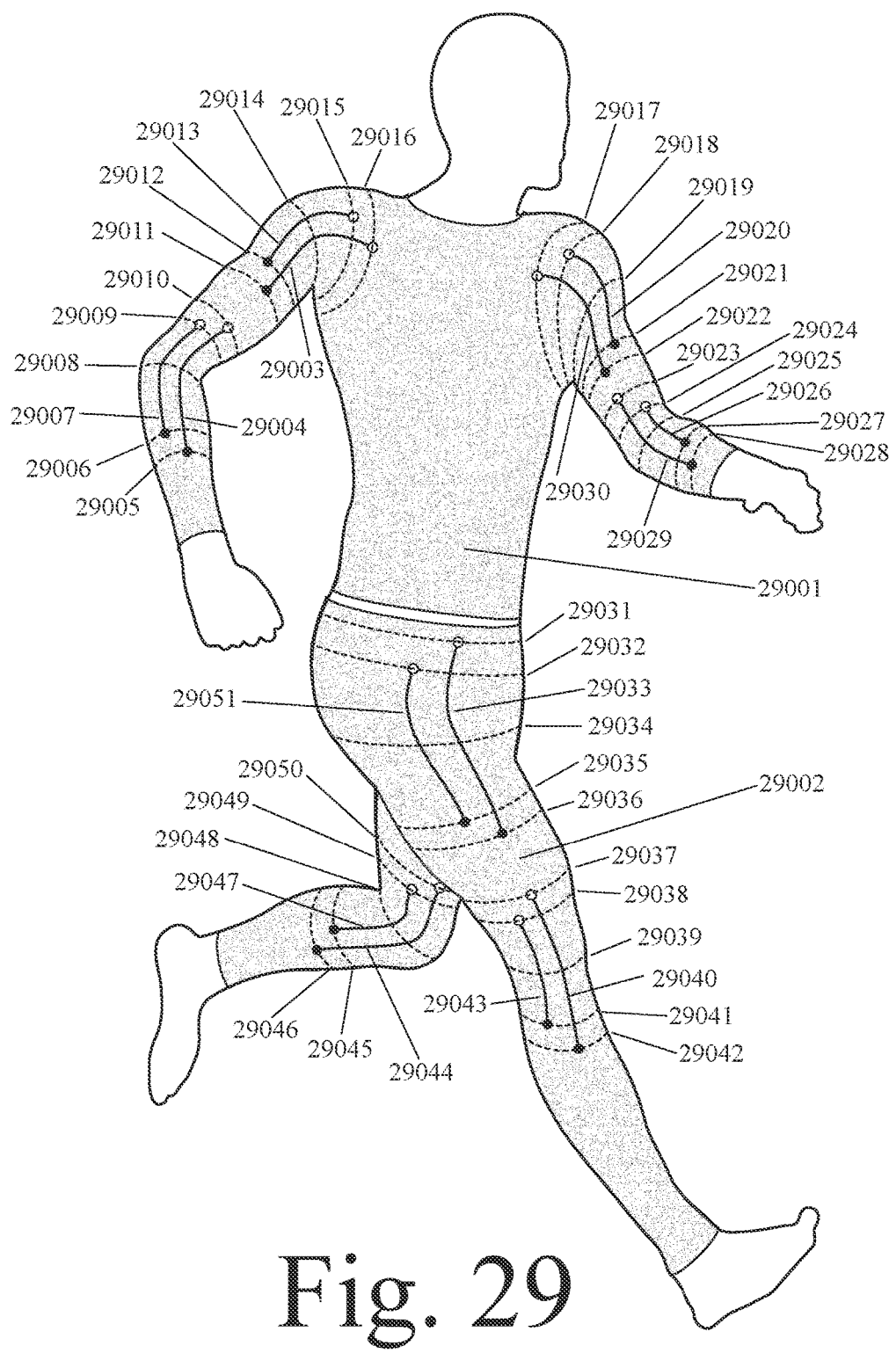
FIG. 29 shows an example wherein two flexible energy pathways spanning the same joint are different lengths.

FIG. 29 shows another example of how this invention can be embodied in an article of clothing or clothing accessory for capturing body motion comprising an article of clothing or clothing accessory worn by a person which is configured to span at least one body joint, wherein this article of clothing or clothing accessory further comprises: (a) a mid joint perimeter portion which is configured around the cross-section of the person's body which includes the center of the joint; (b) a first proximal perimeter portion which is configured around a cross-section of the person's body which is proximal relative to the mid-joint perimeter portion, wherein proximal is defined as being closer to the person's heart along the circulatory system; (c) a second proximal perimeter portion which is configured around a cross-section of the person's body which is proximal relative to the mid-joint perimeter portion; (d) a first distal perimeter portion which is configured around a cross-section of the person's body which is distal relative to the mid-joint perimeter portion, wherein distal is defined as being further from the person's heart along the circulatory system; (e) a second distal perimeter portion around a cross-section of the person's body which is distal relative to the mid joint perimeter portion; (f) a first flexible energy pathway, wherein this energy pathway spans from the first proximal perimeter portion to the first distal perimeter portion, wherein movement of the joint changes the configuration of this pathway, wherein changes in the configuration of this pathway change a flow of energy through this pathway, and wherein changes in the flow of energy through this pathway can be used alone to estimate movement of the joint with a first level of accuracy; (g) a second flexible energy pathway, wherein this energy pathway spans from the second proximal perimeter portion to the second distal perimeter portion, wherein movement of the joint changes the configuration of this pathway, wherein changes in the configuration of this pathway change a flow of energy through this pathway, wherein changes in the flow of energy through this pathway can be used alone to estimate movement of the joint with a second level of accuracy, wherein changes in the flows of energy through the first and second flexible energy pathways can be jointly used to estimate movement of the joint with a third level of accuracy, and wherein the third level is greater than either the first level or the second level; (h) at least one energy emitter which emits energy into one or both of the flexible energy pathways; and (i) at least one energy sensor which senses energy from and/or through one or both of the flexible energy pathways, wherein the flow of energy through the one or both of the flexible energy pathways is measured by the at least one energy sensor.

In the example shown in FIG. 29, the first and second flexible energy pathways spanning the same joint are different lengths. FIG. 29 comprises a shirt 29001 and a pair of pants 29002. The shirt 29001 spans the person's elbows and shoulders. The pair of pants 29002 spans the person's hips and knees. With respect to the person's right elbow, FIG. 29 shows: a mid-joint perimeter portion 29008, a first proximal perimeter portion 29009, a second proximal perimeter portion 29010, a first distal perimeter portion 29006, a second distal perimeter portion 29005, a first flexible energy pathway 29004, and a second flexible energy pathway 29007. In this figure, an energy emitter is shown as an open circle at one end of an energy pathway and an energy sensor is shown as a filled circle at the other end of the energy pathway. With respect to the person's right shoulder, FIG. 29 shows: a mid joint perimeter portion 29014, a first proximal perimeter portion 29015, a second proximal perimeter portion 29016, a first distal perimeter portion 29012, a second distal perimeter portion 29011, a first flexible energy pathway 29003, and a second flexible energy pathway 29013.

With respect to the person's left shoulder, FIG. 29 shows: a mid-joint perimeter portion 29019, a first proximal perimeter portion 29018, a second proximal perimeter portion 29017, a first distal perimeter portion 29021, a second distal perimeter portion 29022, a first flexible energy pathway 29030, and a second flexible energy pathway 29020. With respect to the person's left elbow, FIG. 29 shows: a mid-joint perimeter portion 29025, a first proximal perimeter portion 29024, a second proximal perimeter portion 29023, a first distal perimeter portion 29027, a second distal perimeter portion 29028, a first flexible energy pathway 29029, and a second flexible energy pathway 29026.

With respect to the person's right hip, FIG. 29 shows: a mid-joint perimeter portion 29034, a first proximal perimeter portion 29032, a second proximal perimeter portion 29031, a first distal perimeter portion 29035, a second distal perimeter portion 29036, a first flexible energy pathway 29051, and a second flexible energy pathway 29033. With respect to the person's right knee, FIG. 29 shows: a mid joint perimeter portion 29039, a first proximal perimeter portion 29038, a second proximal perimeter portion 29037, a first distal perimeter portion 29041, a second distal perimeter portion 29042, a first flexible energy pathway 29043, and a second flexible energy pathway 29040. With respect to the person's left knee, FIG. 29 shows: a mid-joint perimeter portion 29048, a first proximal perimeter portion 29049, a second proximal perimeter portion 29050, a first distal perimeter portion 29045, a second distal perimeter portion 29046, a first flexible energy pathway 29044, and a second flexible energy pathway 29047.

In an example, the type of energy which flows through one or more of the first flexible energy pathways 29003, 29004, 29029, 29030, 29043, 29044, and 29051 can be selected from the group consisting of: electromagnetic energy; light energy; and sound energy. In an example, the type of energy which flows through one or more of the second flexible energy pathways 29007, 29013, 29020, 29026, 29033, 29040, and 29047 can be selected from the group consisting of: electromagnetic energy; light energy; and sound energy. In an example, the type of energy that flows through the first flexible energy pathways can be the same as the type of energy that flows through the second energy pathways. In an example, the type of energy that flows through the first flexible energy pathways can be different than the type of energy that flows through the second energy pathways. In an example, energy can flow through the first flexible energy pathways with different flow parameters than energy flows through the second flexible energy pathways, wherein these different flow parameters can be selected from the group consisting of: rate, level, amplitude, resistance, impedance, filter, frequency, and spectrum.

Figure 30:
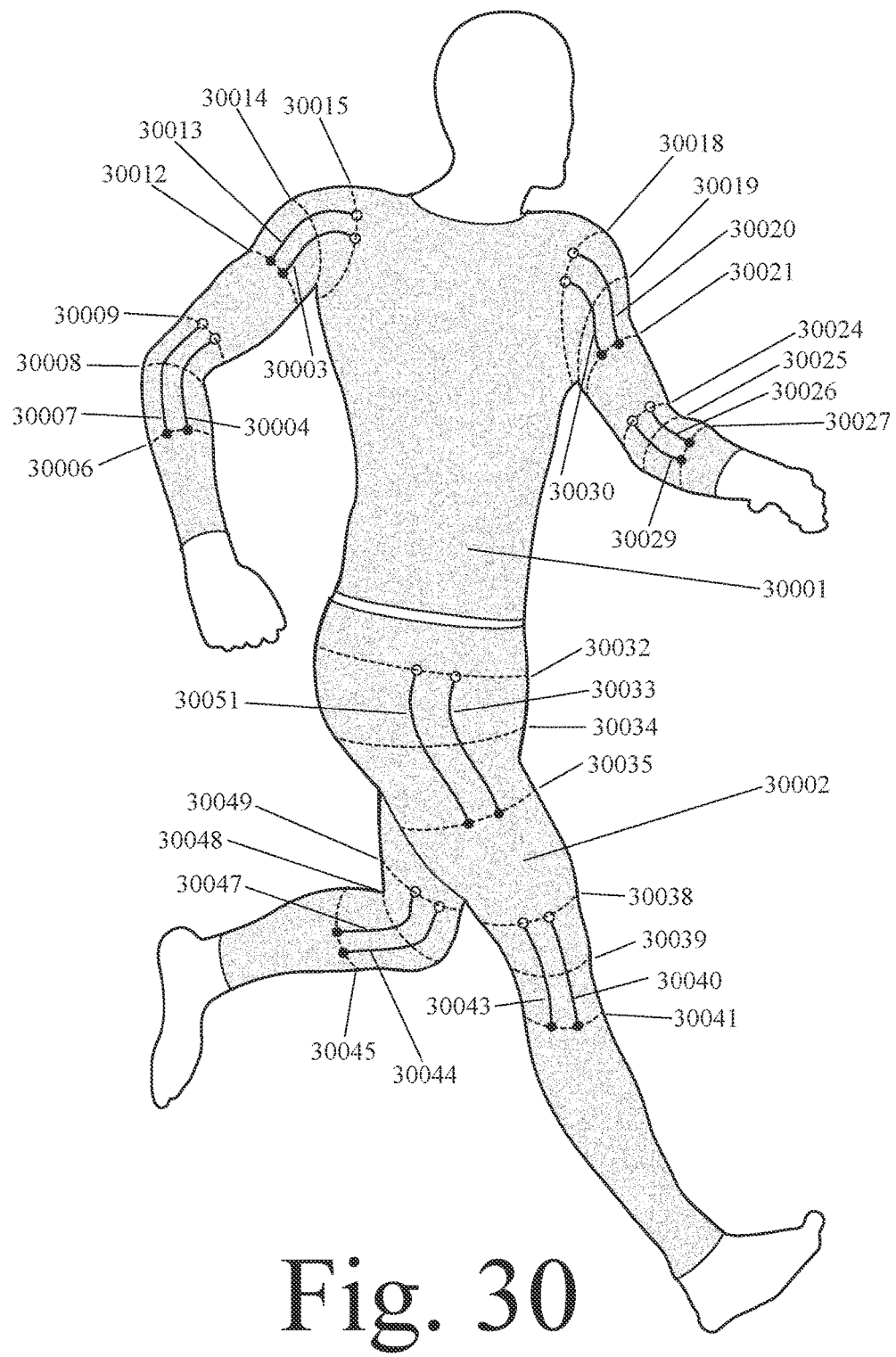
FIG. 30 shows an example wherein two flexible energy pathways spanning the same joint are the same length and are also aligned.

FIG. 30 shows another example of how this invention can be embodied in an article of clothing or clothing accessory for capturing body motion comprising an article of clothing or clothing accessory worn by a person which is configured to span at least one body joint, wherein this article of clothing or clothing accessory further comprises: (a) a mid joint perimeter portion which is configured around the cross-section of the person's body which includes the center of the joint; (b) a proximal perimeter portion which is configured around a cross-section of the person's body which is proximal relative to the mid joint perimeter portion, wherein proximal is defined as being closer to the person's heart along the circulatory system; (c) a distal perimeter portion which is configured around a cross-section of the person's body which is distal relative to the mid-joint perimeter portion, wherein distal is defined as being further from the person's heart along the circulatory system; (d) a first flexible energy pathway, wherein this energy pathway spans from the proximal perimeter portion to the distal perimeter portion, wherein movement of the joint changes the configuration of this pathway, wherein changes in the configuration of this pathway change a flow of energy through this pathway, and wherein changes in the flow of energy through this pathway can be used alone to estimate movement of the joint with a first level of accuracy; (e) a second flexible energy pathway, wherein this energy pathway spans from the proximal perimeter portion to the distal perimeter portion, wherein movement of the joint changes the configuration of this pathway, wherein changes in the configuration of this pathway change a flow of energy through this pathway, wherein changes in the flow of energy through this pathway can be used alone to estimate movement of the joint with a second level of accuracy, wherein changes in the flows of energy through the first and second flexible energy pathways can be jointly used to estimate movement of the joint with a third level of accuracy, and wherein the third level is greater than either the first level or the second level; (f) at least one energy emitter which emits energy into one or both of the flexible energy pathways; and (g) at least one energy sensor which senses energy from and/or through one or both of the flexible energy pathways, wherein the flow of energy through the one or both of the flexible energy pathways is measured by the at least one energy sensor.

In the example shown in FIG. 30, the first and second flexible energy pathways spanning the same joint are the same length. FIG. 30 comprises a shirt 30001 and a pair of pants 30002. The shirt 30001 spans the person's elbows and shoulders. The pair of pants 30002 spans the person's hips and knees. With respect to the person's right elbow, FIG. 30 shows: a mid-joint perimeter portion 30008, a proximal perimeter portion 30009, a distal perimeter portion 30006, a first flexible energy pathway 30004, and a second flexible energy pathway 30007. In this figure, an energy emitter is shown as an open circle at one end of an energy pathway and an energy sensor is shown as a filled circle at the other end of the energy pathway. With respect to the person's right shoulder, FIG. 30 shows: a mid-joint perimeter portion 30014, a proximal perimeter portion 30015, a distal perimeter portion 30012, a first flexible energy pathway 30003, and a second flexible energy pathway 30013.

With respect to the person's left shoulder, FIG. 30 shows: a mid joint perimeter portion 30019, a proximal perimeter portion 30018, a distal perimeter portion 30021, a first flexible energy pathway 30030, and a second flexible energy pathway 30020. With respect to the person's left elbow, FIG. 30 shows: a mid-joint perimeter portion 30025, a proximal perimeter portion 30024, a distal perimeter portion 30027, a first flexible energy pathway 30029, and a second flexible energy pathway 30026.

With respect to the person's right hip, FIG. 30 shows: a mid joint perimeter portion 30034, a proximal perimeter portion 30032, a distal perimeter portion 30035, a first flexible energy pathway 30051, and a second flexible energy pathway 30033. With respect to the person's right knee, FIG. 30 shows: a mid joint perimeter portion 30039, a proximal perimeter portion 30038, a distal perimeter portion 30041, a first flexible energy pathway 30043, and a second flexible energy pathway 30040. With respect to the person's left knee, FIG. 30 shows: a mid-joint perimeter portion 30048, a proximal perimeter portion 30049, a distal perimeter portion 30045, a first flexible energy pathway 30044, and a second flexible energy pathway 30047.

In an example, the type of energy which flows through one or more of the first flexible energy pathways 30003, 30004, 30029, 30030, 30043, 30044, and 30051 can be selected from the group consisting of: electromagnetic energy; light energy; and sound energy. In an example, the type of energy which flows through one or more of the second flexible energy pathways 30007, 30013, 30020, 30026, 30033, 30040, and 30047 can be selected from the group consisting of: electromagnetic energy; light energy; and sound energy. In an example, the type of energy that flows through the first flexible energy pathways can be the same as the type of energy that flows through the second energy pathways. In an example, the type of energy that flows through the first flexible energy pathways can be different than the type of energy that flows through the second energy pathways. In an example, energy can flow through the first flexible energy pathways with different flow parameters than energy flows through the second flexible energy pathways, wherein these different flow parameters can be selected from the group consisting of: rate, level, amplitude, resistance, impedance, filter, frequency, and spectrum.

Figure 31:
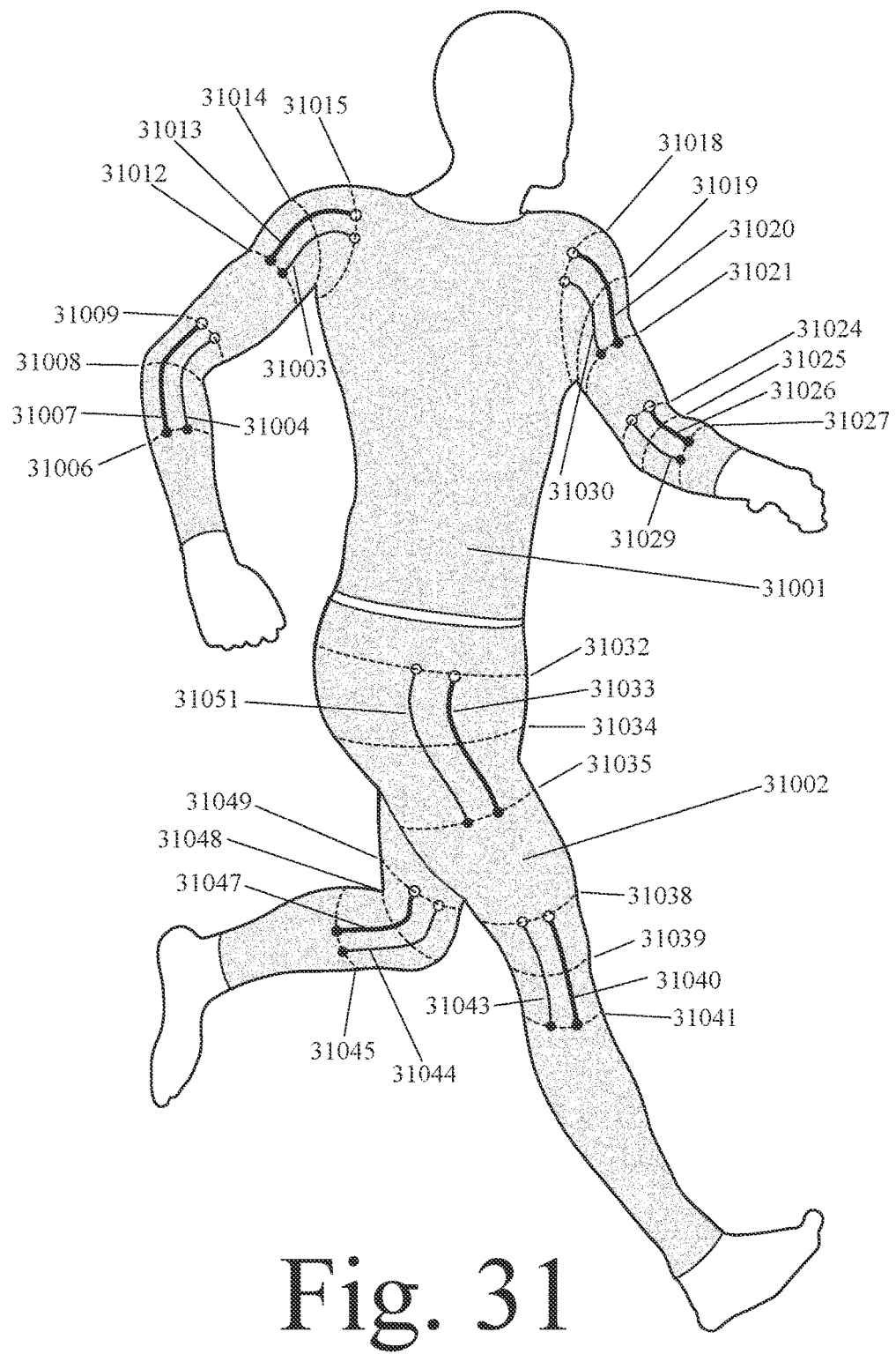
FIG. 31 shows an example wherein two flexible energy pathways spanning the same joint have different types of energy flows.

FIG. 31 shows another example of how this invention can be embodied in an article of clothing or clothing accessory for capturing body motion comprising an article of clothing or clothing accessory worn by a person which is configured to span at least one body joint, wherein this article of clothing or clothing accessory further comprises: (a) a mid joint perimeter portion which is configured around the cross-section of the person's body which includes the center of the joint; (b) a proximal perimeter portion which is configured around a cross-section of the person's body which is proximal relative to the mid joint perimeter portion, wherein proximal is defined as being closer to the person's heart along the circulatory system; (c) a distal perimeter portion which is configured around a cross-section of the person's body which is distal relative to the mid-joint perimeter portion, wherein distal is defined as being further from the person's heart along the circulatory system; (d) a first flexible energy pathway, wherein this energy pathway spans from the proximal perimeter portion to the distal perimeter portion, wherein movement of the joint changes the configuration of this pathway, wherein changes in the configuration of this pathway change a flow of energy through this pathway, and wherein changes in the flow of energy through this pathway can be used alone to estimate movement of the joint with a first level of accuracy; (e) a second flexible energy pathway, wherein this energy pathway spans from the proximal perimeter portion to the distal perimeter portion, wherein movement of the joint changes the configuration of this pathway, wherein changes in the configuration of this pathway change a flow of energy through this pathway, wherein changes in the flow of energy through this pathway can be used alone to estimate movement of the joint with a second level of accuracy, wherein changes in the flows of energy through the first and second flexible energy pathways can be jointly used to estimate movement of the joint with a third level of accuracy, and wherein the third level is greater than either the first level or the second level; (f) at least one energy emitter which emits energy into one or both of the flexible energy pathways; and (g) at least one energy sensor which senses energy from and/or through one or both of the flexible energy pathways, wherein the flow of energy through the one or both of the flexible energy pathways is measured by the at least one energy sensor.

In the example shown in FIG. 31, the first and second flexible energy pathways can have different parameters for energy flows through them. In an example, the first and second flexible energy pathways can differ with respect to the rate of energy flow through them. In an example, the first and second flexible energy pathways can differ with respect to the level or amplitude of energy flow through them. In an example, the first and second flexible energy pathways can differ with respect to their resistance or impedance of energy flow through them. In an example, the first and second flexible energy pathways can differ with respect to their filtering of energy flow through them. In an example, the first and second flexible energy pathways can differ with respect to the frequency or spectrum of energy flow through them.

In an example shown in FIG. 31, the first and second flexible energy pathways can have different types of energy flowing through them. In an example, the first flexible energy pathways can have electromagnetic energy flowing through them and the second flexible energy pathways can have light energy flowing through them. In an example, the first flexible energy pathways can have electromagnetic energy flowing through them and the second flexible energy pathways can have sound energy flowing through them. In an example, the first flexible energy pathways can have light energy flowing through them and the second flexible energy pathways can have sound energy flowing through them.

FIG. 31 comprises a shirt 31001 and a pair of pants 31002. The shirt 31001 spans the person's elbows and shoulders. The pair of pants 31002 spans the person's hips and knees. With respect to the person's right elbow, FIG. 31 shows: a mid-joint perimeter portion 31008, a proximal perimeter portion 31009, a distal perimeter portion 31006, a first flexible energy pathway 31004, and a second flexible energy pathway 31007. In this figure, an energy emitter is shown as an open circle at one end of an energy pathway and an energy sensor is shown as a filled circle at the other end of the energy pathway. With respect to the person's right shoulder, FIG. 31 shows: a mid joint perimeter portion 31014, a proximal perimeter portion 31015, a distal perimeter portion 31012, a first flexible energy pathway 31003, and a second flexible energy pathway 31013.

With respect to the person's left shoulder, FIG. 31 shows: a mid-joint perimeter portion 31019, a proximal perimeter portion 31018, a distal perimeter portion 31021, a first flexible energy pathway 31030, and a second flexible energy pathway 31020. With respect to the person's left elbow, FIG. 31 shows: a mid-joint perimeter portion 31025, a proximal perimeter portion 31024, a distal perimeter portion 31027, a first flexible energy pathway 31029, and a second flexible energy pathway 31026.

With respect to the person's right hip, FIG. 31 shows: a mid-joint perimeter portion 31034, a proximal perimeter portion 31032, a distal perimeter portion 31035, a first flexible energy pathway 31051, and a second flexible energy pathway 31033. With respect to the person's right knee, FIG. 31 shows: a mid joint perimeter portion 31039, a proximal perimeter portion 31038, a distal perimeter portion 31041, a first flexible energy pathway 31043, and a second flexible energy pathway 31040. With respect to the person's left knee, FIG. 31 shows: a mid-joint perimeter portion 31048, a proximal perimeter portion 31049, a distal perimeter portion 31045, a first flexible energy pathway 31044, and a second flexible energy pathway 31047.

In an example, a flexible energy pathway can be incorporated into an article of clothing or clothing accessory by weaving or knitting. In an example, a flexible energy pathway can be woven or knit into fabric which is used to make an article of clothing or clothing accessory. In an example, a flexible energy pathway can be woven or knit into a fabric of an article of clothing or clothing accessory in a configuration which is substantially perpendicular to non-energy-conducting fibers, threads, or yarns in the fabric. In an example, a flexible energy pathway can be sinusoidal. In an example, a sinusoidal flexible energy pathway can have a longitudinal axis which is substantially perpendicular to non-energy-conducting fibers, threads, or yarns in the fabric of an article or accessory. In an example, the wave frequency and/or amplitude of a first sinusoidal flexible energy pathway can be different than the wave frequency and/or amplitude of a second sinusoidal flexible energy pathway.

In an example, a flexible energy pathway can be inserted into a channel between two layers of fabric in an article of clothing or clothing accessory. In an example, a flexible energy pathway can be attached to an article of clothing or clothing accessory by a hook-and-eye attachment mechanism. In an example, a flexible energy pathway can be attached to an article of clothing or clothing accessory by adhesion. In an example, a flexible energy pathway can be attached to an article of clothing or clothing accessory by sewing. In an example, a flexible energy pathway can be attached to an article of clothing or clothing accessory by at least one snap, clip, buckle, strap, or plug.

In an example, the first and second flexible energy pathways can be integrated into an article of clothing or clothing accessory such that they are no more than 1" from the surface of the person's body. In an example, the first and second flexible energy pathways can be integrated into an article of clothing or clothing accessory such that they are no more than one half inch from the surface of the person's body. In an example, the first and second flexible energy pathways can be integrated into an article of clothing or clothing accessory such that at least 90% of their length is no more than 1" from the surface of the person's body. In an example, the first and second flexible energy pathways can be integrated into an article of clothing or clothing accessory such that at least 90% of their length is no more than one half inch from the surface of the person's body.

In an example, a flexible energy pathway can be removed from an article of clothing or clothing accessory when the article or accessory is washed and then reattached after the article or accessory has been washed. In an example, a plurality of energy emitters can be connected by wires or other electromagnetic channels in fabric with a central power source which is attached to an article of clothing or clothing accessory. In an example, a plurality of energy sensors can be connected by wires or other electromagnetic channels in fabric with a central data processing unit and/or data transmitter which is attached to an article of clothing or clothing accessory. In an example, a plurality of energy emitters can be in wireless communication with a central power source. In an example, a plurality of energy sensors can be in wireless communication with a central data processing unit and/or data transmitter.

In an example, an energy emitter can emit energy into one end of a flexible energy pathway and an energy sensor can measure energy emitted from the other end of a flexible energy pathway. In an example, an energy emitter can emit energy into a proximal portion of a flexible energy pathway and this energy can be measured from a distal portion of the flexible energy pathway by an energy sensor. In an example, an energy emitter can emit energy into a distal portion of a flexible energy pathway and this energy can be measured from a proximal portion of the flexible energy pathway by an energy sensor. In an example, there can be multiple energy sensors at different locations on a flexible energy pathway. In an example, there can be multiple energy sensors at different locations along the longitudinal axis of a flexible energy pathway.

In an example, the rate, level, amount, power, frequency, and/or spectrum of energy which is transmitted from the energy emitter through the flexible energy pathway and received by the energy sensor is changed when the flexible energy pathway bends, kinks, compresses, stretches, and/or twists. In an example, changes in the rate, level, amount, power, frequency, and/or spectrum of energy transmitted through the flexible energy pathway can be used to estimate the angle in a two-dimensional plane of the body joint spanned by the flexible energy pathway. In an example, changes in the rate, level, amount, power, frequency, and/or spectrum of energy transmitted through the flexible energy pathway can be used to model movement in three-dimensional space of the body joint spanned by the flexible energy pathway.

In an example, this invention can be embodied in an article of clothing or clothing accessory for capturing body motion comprising an article of clothing or clothing accessory worn by a person which is configured to span at least one body joint, wherein this article of clothing or clothing accessory further comprises: a mid-joint perimeter portion which is configured around the cross-section of the person's body which includes the center of the joint; a proximal perimeter portion which is configured around a cross-section of the person's body which is proximal relative to the mid joint perimeter portion, wherein proximal is defined as being closer to the person's heart along the circulatory system; a distal perimeter portion which is configured around a cross-section of the person's body which is distal relative to the mid joint perimeter portion, wherein distal is defined as being further from the person's heart along the circulatory system; a first flexible energy pathway, wherein this energy pathway is configured to longitudinally span the joint from the proximal perimeter portion to the distal perimeter portion, wherein movement of the joint bends, stretches, compresses, and/or twists this pathway, wherein this bending, stretching, compressing, and/or twisting changes the rate, resistance, filtering, level, amplitude, frequency, and/or spectrum of energy flow through this pathway, and wherein these changes in rate, resistance, filtering, level, amplitude, frequency, and/or spectrum can be used alone to estimate movement of the joint with a first level of accuracy; a second flexible energy pathway, wherein this energy pathway is configured to longitudinally span the joint from the proximal perimeter portion to the distal perimeter portion, wherein movement of the joint bends, stretches, compresses, and/or twists this pathway, wherein this bending, stretching, compressing, and/or twisting changes the rate, resistance, filtering, level, amplitude, frequency, and/or spectrum of energy flow through this pathway, wherein changes in rate, resistance, filtering, level, amplitude, frequency, and/or spectrum can be used alone to estimate movement of the joint with a second level of accuracy, wherein the rates, resistances, filterings, levels, amplitudes, frequencies, and/or spectra of energy flows through the first and second flexible energy pathways can be jointly used to estimate movement of the joint with a third level of accuracy, and wherein the third level is greater than either the first level or the second level; at least one energy emitter which emits energy into one or both of the flexible energy pathways; and at least one energy sensor which senses energy from and/or through one or both of the flexible energy pathways, wherein the flow of energy through the one or both of the flexible energy pathways is measured by the at least one energy sensor.

FIG. 32 graphically demonstrates how multivariate analysis of energy flow through the first flexible energy pathway and energy flow through the second flexible energy pathway can estimate the angle of a body joint more accurately than analysis of energy flow through either the first pathway or the second pathway alone. The top third of FIG. 32 shows the case wherein energy flow through the first flexible energy pathway alone is used to estimate body joint angle. The middle third of FIG. 32 shows the case wherein energy flow through the second flexible energy pathway alone is used to estimate body joint angle. The bottom third of FIG. 32 shows the case wherein multivariate analysis of energy flow through the first flexible energy pathway and energy flow through the second flexible energy pathway is used to estimate body joint angle.

The left sides of the top, middle, and bottom thirds of FIG. 32 show a moving elbow joint which is spanned by the first and second flexible energy pathways which were introduced in FIG. 31. The dashed-line arrow represents movement of the elbow joint. The right sides of the top, middle, and bottom thirds of FIG. 32 show corresponding graphs (populated with hypothetical data points) of elbow joint angle as a bivariate function of energy flow through the first pathway only, as a bivariate function of energy flow through the second pathway only, or as a multivariate function of energy flows through the first and second pathways, respectively. Similar graphs could be drawn for the flexible energy pathway configurations in other previous figures as well.

As shown in the top third of FIG. 32, there is less variability in predicting smaller joint angles and greater variability in predicting larger joint angles based on energy flow through first flexible energy pathway 31004 alone. As shown in the middle third of FIG. 32, there is greater variability in predicting smaller joint angles and less variability in predicting larger joint angles based on energy flow through second flexible energy pathway 31007 alone. As shown in the bottom third of FIG. 32, there is less overall variability in predicting smaller or larger joint angles based on a combined, multivariate function of energy flows through the first and second flexible energy pathways, 31004 and 31007.

FIG. 33 shows a more detailed view of the right elbow joint and flexible energy pathways which were introduced in FIG. 31. In particular, FIG. 33 explicitly labels: energy emitters 33001 and 33004 (shown as open circles) at the proximal ends of the first and second flexible energy pathways 31004 and 31007 respectively; and energy sensors 33002 and 33003 (shown as filled circles) at the distal ends of the first and second energy pathways 31004 and 31007 respectively. In an alternative example, the energy emitters can be at the distal ends and the energy sensors can be at the proximal ends of the flexible energy pathways. I did not explicitly label all of the energy emitters and sensors for all joints in previous FIGS. 28 through 32 because this would have made these figures very cluttered.

In an example, this invention can be embodied in an iterative method for improving the accuracy of body motion recognition with a single flexible energy pathway comprising: (a) emitting an energy flow with a first set of flow parameters into a proximal portion of a flexible energy pathway, wherein this proximal portion is proximal relative to the cross sectional perimeter of a body member around the center of a body joint, wherein proximal is defined as being closer to the heart, wherein this flexible energy pathway is integrated with an article of clothing or clothing accessory which is configured to span that body joint, and wherein these flow parameters are selected from the group consisting of energy flow rate or speed, energy level or amount, energy frequency or spectrum, and energy waveform; (b) receiving data concerning energy flow from a distal portion of the flexible energy pathway, wherein this distal portion is distal relative to the cross sectional perimeter of a body member around the center of a body joint, wherein distal is defined as being further from the heart; (c) using this data to estimate and/or model motion of the body joint; (d) and changing the flow parameters of the energy flow into the flexible energy pathway from the first set of flow parameters to a second set of flow parameters based on the estimated and/or modeled motion of the body joint in order to more accurately estimate and/or model motion of the body joint. In a variation on this method, energy can be emitted into the distal portion and measured from the proximal portion.

In an example, this invention can be embodied in a method for improving the energy efficiency of body motion recognition with a single flexible energy pathway comprising: (a) emitting an energy flow with a first set of flow parameters into a proximal portion of a flexible energy pathway, wherein this proximal portion is proximal relative to the cross sectional perimeter of a body member around the center of a body joint, wherein proximal is defined as being closer to the heart, wherein this flexible energy pathway is integrated with an article of clothing or clothing accessory which is configured to span that body joint, and wherein these flow parameters are selected from the group consisting of energy flow rate or speed, energy level or amount, energy frequency or spectrum, and energy waveform, and wherein this first set of flow parameters requires a first amount energy; (b) receiving data concerning energy flow from a distal portion of the flexible energy pathway, wherein this distal portion is distal relative to the cross sectional perimeter of a body member around the center of a body joint, wherein distal is defined as being further from the heart; (c) using this data to estimate and/or model motion of the body joint; (d) and changing the flow parameters of the energy flow into the flexible energy pathway from the first set of flow parameters to a second set of flow parameters based on the estimated and/or modeled motion of the body joint in order to more accurately estimate and/or model motion of the body joint, wherein this second set of flow parameters requires a second level of energy, and wherein the second level is greater than the first level. In a variation on this method, energy can be emitted into the distal portion and measured from the proximal portion.

In an example, this invention can be embodied in a method for improving the accuracy of body motion recognition with two flexible energy pathways spanning the same body joint comprising: (a) emitting a first energy flow into a proximal portion of a first flexible energy pathway, wherein this proximal portion is proximal relative to the cross sectional perimeter of a body member around the center of a body joint, wherein proximal is defined as being closer to the heart, wherein this first flexible energy pathway is integrated with an article of clothing or clothing accessory which is configured to span that body joint; (b) receiving a first set of data concerning energy flow from a distal portion of the first flexible energy pathway, wherein this distal portion is distal relative to the cross sectional perimeter of a body member around the center of a body joint, wherein distal is defined as being further from the heart; (c) using this first set of data to estimate and/or model motion of the body joint; (d) emitting a second energy flow with a set of flow parameters into a proximal portion of a second flexible energy pathway, wherein this proximal portion is proximal relative to the cross sectional perimeter of a body member around the center of a body joint, wherein proximal is defined as being closer to the heart, wherein this second flexible energy pathway is integrated with an article of clothing or clothing accessory which is configured to span that body joint, wherein flow parameters of this second energy flow are selected from the group consisting of energy flow rate or speed, energy level or amount, energy frequency or spectrum, and energy waveform, and wherein these flow parameters are selected based on the estimation and/or modeling of the body joint motion using the first set of data; (e) receiving a second set of data concerning energy flow from a distal portion of the second flexible energy pathway, wherein this distal portion is distal relative to the cross sectional perimeter of a body member around the center of a body joint, wherein distal is defined as being further from the heart; (f) and using this second set of data to estimate and/or model motion of the body joint. In a variation on this method, energy can be emitted into the distal portion and measured from the proximal portion.

In an example, this invention can be embodied in a method for improving the energy efficiency of body motion recognition with two flexible energy pathways spanning the same body joint comprising: (a) emitting a first energy flow into a proximal portion of a first flexible energy pathway, wherein this proximal portion is proximal relative to the cross sectional perimeter of a body member around the center of a body joint, wherein proximal is defined as being closer to the heart, wherein this first flexible energy pathway is integrated with an article of clothing or clothing accessory which is configured to span that body joint; (b) receiving a first set of data concerning energy flow from a distal portion of the first flexible energy pathway, wherein this distal portion is distal relative to the cross sectional perimeter of a body member around the center of a body joint, wherein distal is defined as being further from the heart; (c) using this first set of data to estimate and/or model motion of the body joint; (d) emitting a second energy flow with a set of flow parameters into a proximal portion of a second flexible energy pathway, wherein this proximal portion is proximal relative to the cross sectional perimeter of a body member around the center of a body joint, wherein proximal is defined as being closer to the heart, wherein this second flexible energy pathway is integrated with an article of clothing or clothing accessory which is configured to span that body joint, wherein flow parameters of this second energy flow are selected from the group consisting of energy flow rate or speed, energy level or amount, energy frequency or spectrum, and energy waveform, and wherein these flow parameters are selected based on the estimation and/or modeling of the body joint motion using the first set of data; (e) receiving a second set of data concerning energy flow from a distal portion of the second flexible energy pathway, wherein this distal portion is distal relative to the cross sectional perimeter of a body member around the center of a body joint, wherein distal is defined as being further from the heart; (f) and using this second set of data to estimate and/or model motion of the body joint. In a variation on this method, energy can be emitted into the distal portion and measured from the proximal portion.

In an example, flow parameters can be adjusted when analysis of data indicates faster joint motion, a greater range of joint motion, and/or a more complex pattern of joint motion. In an example, a second set of flow parameters can comprise and/or require a higher rate of energy flow than a first set of flow parameters. In an example, using a first set of flow parameters when a person is relatively inactive and a second set of parameters when the person is relatively active can help to conserve energy during periods of relative inactivity and also maintain high motion capture accuracy during periods of relatively high activity.

In an example, a first flexible energy pathway which conducts a first type of energy can be used to adjust energy flow parameters through a second flexible energy pathway which conducts a second type of energy. In an example, a type of energy can be selected from the group consisting of: electromagnetic energy, light energy, and sound energy). In an example, data from a first flexible energy pathway which requires less energy to function (but is less accurate) can be used to trigger the operation of a second flexible energy pathway which requires more energy (but is more accurate). In an example, the operation of a second flexible energy pathway can be triggered when increased joint motion is detected based on data from the first flexible energy pathway.

In an example, additional flexible energy pathways can be activated to increase measurement accuracy when a first flexible energy pathway indicates an increase in joint motion. In an example, a first flexible energy pathway can be in operation all the time, but additional energy pathways can be activated when data from the first flexible energy pathway indicates increased joint motion or complex joint motion. In an example, the number of flexible energy pathways spanning the same joint which are activated to increase motion measurement accuracy can be manually adjusted by the person. In an example, the number of flexible energy pathways spanning the same joint which are activated can be automatically increased by the device or system in proportion to the demands for motion capture accuracy. In an example, the demand for motion capture accuracy can, in turn, be inferred from an increased magnitude and/or complexity of body motion.

FIG. 34 shows another example of how this invention can be embodied in an article of clothing or clothing accessory for capturing body motion comprising an article of clothing or clothing accessory worn by a person which is configured to span at least one body joint. In this example, an article of clothing or clothing accessory comprises: a plurality of flexible energy pathways which span at least one body joint from a location which is proximal relative to the joint center to a location which is distal relative to the joint center, wherein proximal is defined as being closer to the heart and distal is defined as being further from the heart, and wherein these flexible energy pathways are integrated into the article of clothing or clothing accessory; a plurality of energy emitters which emit energy into the flexible energy pathways; a plurality of energy sensors which measure energy transmission through the flexible energy pathways, wherein joint motion is estimated and/or modeled based on changes in energy transmission through the flexible energy pathways; and a plurality of inertial sensors which are integrated into the article of clothing or clothing accessory.

The example shown in FIG. 34 comprises a shirt 34001 and a pair of pants 34002. The shirt 34001 spans the person's elbows and shoulders. The pair of pants 34002 spans the person's hips and knees. The example in FIG. 34 includes a plurality of flexible energy pathways which longitudinally span the person's elbows, shoulders, hips, and knees: 34003, 34004, 34007, 34013, 34020, 34026, 34029, 34030, 34033, 34040, 34043, 34044, 34047, and 34051. The type of energy which is transmitted through these flexible energy pathways can be selected from the group consisting of: electromagnetic energy; light energy; and sound energy. In various examples, energy transmitted through these different flexible energy pathways can have different flow parameters selected from the group consisting of: rate, level, amplitude, resistance, impedance, filter, frequency, and spectrum. The example shown in FIG. 34 also includes a plurality of inertial sensors: 34061, 34062, 34063, 34064, 34065, and 34066. In this example, a plurality of inertial sensors can be at locations which are distal to spanned body joints. In an example, these inertial sensors can be selected from the group consisting of: accelerometer, gyroscope, and inclinometer. In an example, the components in FIG. 34 can be in direct electromagnetic or wireless communication with a data processor and/or transmitter.

In an example, a plurality of flexible energy pathways can be more accurate for estimating and/or modeling body motion in three-dimensional space than a plurality of inertial sensors, but can also require more energy for operation. In an example, inertial sensors can be in continuous operation (at a lower rate of energy use) and flexible energy pathways can be activated to measure body motion (at a higher rate of energy use) when the inertial sensors indicate a higher level, range, or frequency of body motion. In an example, inertial sensors can be in continuous operation to provide a first level of body motion measurement accuracy (at a first level of energy use) and flexible energy sensors can be activated to provide a second level of body motion measurement accuracy (at a second level of energy use) when inertial sensors indicate a high level of body motion, wherein a second level is higher than a first level. In an example, efficient energy use can be achieved by matching the level (type and/or number) of motion sensor operation to the required level of body motion measurement accuracy at a particular time.

In an example, data from a plurality of inertial sensors can be used to calibrate the analytical and/or statistical model by which body joint motion is estimated and/or modeled from energy transmission data from a plurality of flexible energy pathways. In an example, data from a plurality of flexible energy sensors can be used to calibrate the analytical and/or statistical model by which body motion is estimated and/or modeled from a plurality of inertial sensors. In an example, data from a plurality of flexible energy pathways can be used to measure movement of one body member relative to another better than is possible with a plurality of inertial sensors alone. In an example, data from a plurality of flexible energy pathways can be used to control for passive movement of the person's entire body by a mode of transportation such as a vehicle or elevator better than is possible with inertial sensors alone.

FIG. 35 shows an example of how this invention can be embodied in an article of clothing or clothing accessory for capturing body motion with at least one modular flexible energy pathway. This example comprises: an article of clothing or clothing accessory with a plurality of lumens which are configured to span at least one body joint; at least one modular flexible energy pathway which can be removably inserted into a lumen; at least one energy emitter which emits energy into a modular flexible energy pathway; and at least one energy sensor which measures energy transmission through the modular flexible energy pathway, wherein data from the energy sensor is used to estimate and/or model body joint motion.

This example can also comprise: an article of clothing or clothing accessory with a first lumen and a second lumen which are configured to longitudinally span a body joint; at least one modular flexible energy pathway which can be removably inserted into the first lumen or into the second lumen; at least one energy emitter which emits energy into a modular flexible energy pathway; and at least one energy sensor which measures energy transmission through the modular flexible energy pathway, wherein data from the energy sensor is used to estimate and/or model body joint motion.

The four quadrants of FIG. 35 show views at four different times of the elbow portion of a shirt to capture body motion with at least one modular flexible energy pathway. Specifically, FIG. 35 shows: the elbow portion of shirt 35001; at least four longitudinal lumens (or passageways, or pockets, or channels) 35002, 35003, 35004, and 35005 in the fabric of the shirt which longitudinally span the elbow; and at least one modular flexible energy pathway 35006 which further comprises an energy emitter 35007 and energy sensor 35008. In this example, the energy emitter is in a proximal location and the energy sensor is in a distal location, but in another example these locations could be reversed.

The upper left quadrant of FIG. 35 shows this example at a time when the modular flexible energy pathway 35006 is not inserted into any of the lumens in shirt 35001. The upper right quadrant of FIG. 35 shows this example at a time when the modular flexible energy pathway 35006 has been inserted into lumen 35003 of shirt 35001 in order to measure and/or model motion of the shoulder from this first location. The lower left quadrant of FIG. 35 shows this example at a time when a modular flexible energy pathway 35006 has been shifted upwards within 35003 of shirt 35001 in order to measure and/or model motion of the shoulder from this second location. The lower right quadrant of FIG. 35 shows this example at a time when a modular flexible energy pathway 35006 has been removed from lumen 35003 and inserted into lumen 35004 in order to measure and/or model motion of the shoulder from this third location.

FIG. 35 only shows a plurality of lumens longitudinally spanning a person's elbow. In an example, an article of clothing or clothing accessory can comprise other pluralities of lumens which longitudinally span a person's shoulder, hip, knee, or other body joints. The example shown in FIG. 35 implies six lumen (four visible in this figure and two assumed on the other side) which longitudinally span the circumference of a person's body joint. In other examples, two, three, four, five, seven, or more lumens can longitudinally span a person's body joint. The example shown in FIG. 35 shows only one modular flexible energy pathway per body joint. In other examples, there can be two, three, four or more modular flexible energy pathways per body joint.

A plurality of modular flexible energy pathways can be inserted into and/or longitudinally shifted within various combinations of lumens within an article of clothing or clothing accessory in order to measure and/or model combinations of body joint movement using different sensor configurations. In an example, different configurations of modular flexible energy pathways can be created in order to optimally measure different types of body joint movements and/or different types of physical activity. In an example, a first configuration of modular flexible energy pathways can be optimal for capturing body motion during running, a second configuration of modular flexible energy pathways can be optimal for capturing body motion during swimming, and a third configuration of modular flexible energy pathways can be optimal for measuring the random twitches of a couch potato.

In an example, data from a modular flexible energy pathway can measured at different times as the pathway is slid up or down within a given lumen in order to find the optimal (customized) pathway configuration for capturing body motion by a particular person who is wearing the article of clothing or clothing accessory. In an example, data from a modular flexible energy pathway can measured at different times as the pathway is inserted into different lumens in order to find the optimal (customized) pathway configuration for capturing body motion by a particular person who is wearing the article of clothing or clothing accessory. In an example, data from a plurality of modular flexible energy pathways can measured at different times as different pathways are inserted into different lumens in order to find the optimal (customized) multi-pathway configuration for capturing body motion by a particular person who is wearing the article of clothing or clothing accessory.

In an example, data from a modular flexible energy pathway can measured at different times as the pathway is slid up or down within a given lumen in order to find the optimal (customized) pathway configuration for capturing body motion during a particular sport or other physical activity. In an example, data from a modular flexible energy pathway can measured at different times as the pathway is inserted into different lumens in order to find the optimal (customized) pathway configuration for capturing body motion during a particular sport or other physical activity. In an example, data from a plurality of modular flexible energy pathways can be measured at different times as different pathways are inserted into different lumens in order to find the optimal (customized) multi-pathway configuration for capturing body motion during a particular sport or other physical activity.

In an example, the example shown in FIG. 35 can further comprise one or more attachment mechanisms which can removably hold a modular flexible energy pathway in a particular location in a particular lumen. In an example, such an attachment mechanism can be selected from the group consisting of: hook-and-eye mechanism; snap; hook; buckle; plug; zipper; button; loop; clip; clasp; clamp; tape; lace; and pin. The type of energy which is transmitted through a modular flexible energy pathway can be selected from the group consisting of: electromagnetic energy; light energy; and sound energy. In various examples, energy transmitted through different modular flexible energy pathways can have different flow parameters selected from the group consisting of: rate, level, amplitude, resistance, impedance, filter, frequency, and spectrum.

In an example, this article of clothing or clothing accessory can further comprise a plurality of inertial sensors selected from the group consisting of: accelerometer, gyroscope, and inclinometer. In an example, a plurality of inertial sensors can used to calibrate the analytical and/or statistical model by which body joint motion is estimated and/or modeled by a plurality of modular flexible energy pathways.

In an example, a plurality of modular flexible energy pathways can used to calibrate the analytical and/or statistical model by which body joint motion is estimated and/or modeled by a plurality of inertial sensors. In an example, the components of this example can be in direct electromagnetic or wireless communication with a data processor and/or transmitter.

FIGS. 36 and 37 show an example of how this invention can be embodied in an array of four longitudinal sensors to measure movement of a body joint. FIG. 36 shows a side view of this sensor array being worn on a body joint, wherein the longitudinal sensor on the far side of the body joint which would not be visible is represented by a thick dotted line. In an example, only Gary Larson can really see the far side. FIG. 37 shows a cross-sectional view of this same sensor array, wherein the longitudinal location of cross-section is approximately at the center of the body joint.

FIGS. 36 and 37 also show how virtual degree vectors can be defined around the body joint. The 0-degree vector starts at the cross-sectional center of the body joint and extends outward through the most ventral location of the body joint perimeter. The 180-degree vector starts at the cross-sectional center of the body joint and extends outward in a direction which is diametrically opposite to that of the 0-degree vector. Other (major) degree vectors can be filled in between the 0-degree and 180-degree vectors. Selected major degree vectors (0, 45, 90, 135, 180, 225, 270, and 315 degree vectors) are shown in FIGS. 36 and 37.

In the example shown in FIGS. 36 and 37, a first radial quadrant of the body joint spans from the 315 degree vector to the 45 degree vector, a the second radial quadrant of the body joint spans from the 45 degree vector to the 135 degree vector, a third radial quadrant of the body joint spans from the 135 degree vector to the 225 degree vector, and a fourth radial quadrant of the body joint spans from the 225 degree vector to the 315 degree vector. In another example, each of these quadrants can have boundary vectors which are rotated clockwise by (e.g. increased by) 45 degrees. In this example, the 0-degree vector is the same as the 360-degree vector.

FIGS. 36 and 37 show an example of how this invention can be embodied in an array of four longitudinal sensors to measure movement of a body joint comprising: (a) a first longitudinal sensor which is configured to longitudinally span a body joint, wherein this first longitudinal sensor spans the body joint within a first radial quadrant of the body joint, wherein the first longitudinal sensor is configured to bend and/or stretch when the body joint moves, and wherein bending and/or stretching of the first longitudinal sensor generates a first set of data concerning movement of the body joint; (b) a second longitudinal sensor which is configured to longitudinally span a body joint, wherein this second longitudinal sensor spans the body joint within a second radial quadrant of the body joint, wherein the second longitudinal sensor is configured to bend and/or stretch when the body joint moves, and wherein bending and/or stretching of the second longitudinal sensor generates a second set of data concerning movement of the body joint; (c) a third longitudinal sensor which is configured to longitudinally span a body joint, wherein this third longitudinal sensor spans the body joint within a third radial quadrant of the body joint, wherein the third longitudinal sensor is configured to bend and/or stretch when the body joint moves, and wherein bending and/or stretching of the third longitudinal sensor generates a third set of data concerning movement of the body joint; and (d) a fourth longitudinal sensor which is configured to longitudinally span a body joint, wherein this fourth longitudinal sensor spans the body joint within a fourth radial quadrant of the body joint, wherein the fourth longitudinal sensor is configured to bend and/or stretch when the body joint moves, and wherein bending and/or stretching of the fourth longitudinal sensor generates a fourth set of data concerning movement of the body joint.

Specifically, FIGS. 36 and 37 show an example of how this invention can be embodied in an array of four longitudinal sensors to measure movement of a body joint 36001 comprising: first longitudinal sensor 36002 which is configured to longitudinally span a body joint, wherein this first longitudinal sensor spans the body joint within a first radial quadrant of the body joint, wherein the first longitudinal sensor is configured to bend and/or stretch when the body joint moves, and wherein bending and/or stretching of the first longitudinal sensor generates a first set of data concerning movement of the body joint; second longitudinal sensor 36003 which is configured to longitudinally span a body joint, wherein this second longitudinal sensor spans the body joint within a second radial quadrant of the body joint, wherein the second longitudinal sensor is configured to bend and/or stretch when the body joint moves, and wherein bending and/or stretching of the second longitudinal sensor generates a second set of data concerning movement of the body joint; third longitudinal sensor 36004 which is configured to longitudinally span a body joint, wherein this third longitudinal sensor spans the body joint within a third radial quadrant of the body joint, wherein the third longitudinal sensor is configured to bend and/or stretch when the body joint moves, and wherein bending and/or stretching of the third longitudinal sensor generates a third set of data concerning movement of the body joint; and fourth longitudinal sensor 36005 which is configured to longitudinally span a body joint, wherein this fourth longitudinal sensor spans the body joint within a fourth radial quadrant of the body joint, wherein the fourth longitudinal sensor is configured to bend and/or stretch when the body joint moves, and wherein bending and/or stretching of the fourth longitudinal sensor generates a fourth set of data concerning movement of the body joint.

FIG. 36 shows these longitudinal sensors from a side perspective as they longitudinally span a body joint, crossing the body joint within four different radial quadrants. FIG. 37 shows these longitudinal sensors from a cross-sectional perspective as they cross the body joint within four different radial quadrants. In this example, at least two of the four longitudinal sensors are parallel to each other as they span the body joint. In this example, all four of the longitudinal sensors are substantially parallel to each other as they span the body joint. In this example, the four longitudinal sensors are evenly radially distributed around the perimeter of the body joint. In this example, the four longitudinal sensors are separated by the same number of degrees as they cross the body joint. In an example, four longitudinal sensors can be separated by different numbers of degrees as long as they are within four different radial quadrants as the cross the body joint.

The terms proximal and distal can be defined as relative body locations with respect to a person's heart. Proximal can be defined as being closer to a person's heart when a person's limbs are fully extended (as in Leonardo's famous Vitruvian Man drawing). Distal can be defined as being further from a person's heart when a person's limbs are fully extended. Similarly, proximal can be defined as being closer to a person's centroid when a body member of which a body joint is a part is extended outwards and distal can be defined as being closer to a person's centroid when a body member of which a body joint is a part is extended outwards.

In an example, four longitudinal sensors can be substantially parallel to each other in areas which are proximal and distal relative to a body joint. In an example, cross-sections of four longitudinal sensors in a cross-sectional slice of a sensor array can be connected to form a quadrilateral polygon. In an example, thus-formed quadrilateral polygons formed by a longitudinal sequence of sensor array cross-sections can form a rectangular column. In an example, thus-formed quadrilateral polygons formed by a longitudinal sequence of sensor array cross-sections can form a rectangular column with a substantially constant cross-sectional area.

In an example, four longitudinal sensors can bend, curve, taper, or flare apart from (or toward) each other in areas which are proximal and distal relative to a body joint. In an example, cross-sections of four longitudinal sensors in a cross-sectional slice of a sensor array can be connected to form a quadrilateral polygon. In an example, thus-formed quadrilateral polygons formed by a longitudinal sequence of sensor array cross-sections can form a tapered or flared rectangular column. In an example, thus-formed quadrilateral polygons formed by a longitudinal sequence of sensor array cross-sections can form a rectangular column whose proximal cross-sectional areas are greater than its distal cross-sectional areas.

In an example, an average distance between four sensors can be calculated for a given cross-section of the sensor array. In an example: a sensor array can have a first average distance between sensors in a first cross section of the sensor array which is distal to the body joint; the sensor array can have a second average distance between sensors in a second cross section of the sensor array which is proximal to the body joint; and the second average distance can be greater than the first average distance. In an example, a sensor array can be defined to have a longitudinal axis independent of how it is configured to be worn on a human body. In an example, an average distance between the four sensors can be calculated for a given cross-section of the sensor array. In an example: a sensor array can have a first average distance between sensors in a first cross section of the sensor array at a first end of its longitudinal axis; the sensor array can have a second average distance between sensors in a second cross section of the sensor array at the opposite (to the first) end of its longitudinal axis; and the second average distance can be greater than the first average distance.

In an example, electromagnetic energy can be transmitted through a longitudinal sensor. In an example, a longitudinal sensor bends and/or stretches as a body joint moves, which changes the transmission of electromagnetic energy through the sensor. In an example, changes in electromagnetic energy transmitted through a longitudinal sensor can be measured as a body joint moves. In an example, changes in electromagnetic energy transmitted through a longitudinal sensor can used to measure, track, estimate, and/or model movement of a body joint. In an example, changes in the electrical conductivity, resistance, and/or impedance of a longitudinal sensor can be measured as a body joint moves. In an example, changes in electrical conductivity, resistance, and/or impedance of a longitudinal sensor can used to measure, track, estimate, and/or model movement of a body joint.

In an example, electromagnetic energy can be generated by a longitudinal sensor. In an example, a longitudinal sensor bends and/or stretches as a body joint moves, which generates electromagnetic energy. In an example, a longitudinal sensor which generates electromagnetic energy can be piezoelectric. In an example, changes in electromagnetic energy generated by a longitudinal sensor can be measured as a body joint moves. In an example, changes in electromagnetic energy generated by a longitudinal sensor can used to measure, track, estimate, and/or model movement of a body joint.

In an example, light energy can be transmitted through a longitudinal sensor. In an example, a longitudinal sensor bends and/or stretches as a body joint moves, which changes the transmission of light energy through the sensor. In an example, a longitudinal sensor can be a fiber optic sensor. In an example, changes in light energy transmitted through a longitudinal sensor can be measured as a body joint moves. In an example, changes in light energy transmitted through a longitudinal sensor can used to measure, track, estimate, and/or model movement of a body joint.

In an example, sound energy can be transmitted through a longitudinal sensor. In an example, a longitudinal sensor bends and/or stretches as a body joint moves, which changes the transmission of sound energy through the sensor. In an example, this sound energy can be ultrasonic sound energy. In an example, changes in sound energy transmitted through a longitudinal sensor can be measured as a body joint moves. In an example, changes in sound energy transmitted through a longitudinal sensor can used to measure, track, estimate, and/or model movement of a body joint.

In an example, a longitudinal sensor can contain a flowable substance (such as a fluid or gas). In an example, a longitudinal sensor bends and/or stretches as a body joint moves, which changes the pressure of a flowable substance within the sensor. In an example, changes in the pressure of a flowable substance within a longitudinal sensor can be measured as a body joint moves. In an example, changes in the pressure of a flowable substance within a longitudinal sensor can used to measure, track, estimate, and/or model movement of a body joint.

In an example, having an array of four longitudinal sensors which span a body joint across four different radial quadrants as specified by this disclosure is more useful and novel than just an arbitrary combination of four individual sensors. In an example, analysis of data from the four longitudinal sensors can provide more accurate measurement, tracking, estimation, and/or modeling of movement of the body joint than analysis of data from any one of the four longitudinal sensors alone. In an example, joint statistical analysis of data from the four longitudinal sensors can provide more accurate measurement, tracking, estimation, and/or modeling of movement of the body joint than separate statistical analysis of data from each of the four longitudinal sensors.

In an example, data from the four sensors can be jointly analyzed using one or more methods selected from the group consisting of: ANCOVA (analysis of covariance), ANN (Artificial Neural Network), ANOVA (analysis of variance), AR (Auto-Regressive) Modeling, BA (Bonferroni Analysis), Bayesian analysis, Bayesian classifier, Bayesian neural network, Binary Decision Tree, Chi-Squared Analysis, Cluster Analysis, and Correlation. In an example, data from the four sensors can be jointly analyzed using one or more methods selected from the group consisting of: DA (Discriminant Analysis), DFT (Discrete Fourier Transform), DN (Data Normalization), DTA (Decision Tree Analysis), EMD (Empirical Mode Decomposition), FA (Factor Analysis), FFT (Fast Fourier Transform), Fisher Linear Discriminant, FL (Fuzzy Logic), FVA (Feature Vector Analysis), GARCH (Generalized Auto-Regressive Conditional Heteroscedasticity) Modeling, Gaussian process classifier, GM (Gaussian Model), HMM (Hidden Markov Model), ICA (Independent Components Analysis), Kernel Estimation, and KF (Kalman Filter).

In an example, data from the four sensors can be jointly analyzed using one or more methods selected from the group consisting of: Linear Regression, Linear Transform, Logistic regression algorithm, Logit Model, LSE (Least Squares Estimation), Markov Model, Maximum Entropy Modeling, Maximum Likelihood, ML (Machine Learning), MLR (Multivariate Linear Regression), Multivariate Logit, Multivariate Regression, Naive Bayes Classifier, Neural Network, NLP (Non-Linear Programming), NMF (Non-negative Matrix Factorization), and NMF (Non-Zero Matrix Factorization). In an example, data from the four sensors can be jointly analyzed using one or more methods selected from the group consisting of: PCA (Principal Components Analysis), Probit Model, Quadratic Minimum Distance Classifier, Regression Model, RF (Random Forest) analysis, Sparse Regression, Spline Function, SVD (Singular Value Decomposition), SVM (Support Vector Machine), Time Frequency Analysis, Time Series Model, Trained Bayes Classifier, and Variance.

In an example, the sensor array in this example can be incorporated into (or attached to) an article of clothing. In an example, an article of clothing can be selected from the group consisting of: bathrobe, bikini, blouse, boot, bra, briefs, cap, coat, dress, full-body article of clothing, garment with hood, girdle, glove, hat, hoodie, jacket, jeans, jockstrap, jumpsuit, leggings, leotards, long-sleeve shirt, lower-body garment, one-piece garment, overalls, pair of pants, pajamas, panties, pants, shirt, shorts, short-sleeve shirt, skirt, slacks, sock, suit, sweater, sweatpants, sweatshirt, sweat suit, swimsuit, tights, trousers, T-shirt, underpants, undershirt, union suit, upper-body garment, and vest.

In an example, this example can further comprise one or more components selected from the group consisting of: power source; data processor; (wireless) data transmitter; and (wireless) data receiver. In an example, one or more of the four longitudinal sensors can be in wireless communication with a data processor. In an example, a power source can be a battery. In an example, a power source can transduce electrical energy from body kinetic energy, body thermal energy, ambient light energy, or ambient electromagnetic energy. Relevant example variations and alternative components discussed in the narratives accompanying other figures in this disclosure can also be applied to this example.

FIGS. 38 and 39 show an embodiment of this invention that is similar to the one shown in FIGS. 36 and 37, except that it also includes two accelerometers. It includes a first accelerometer which is worn on a location which is proximal relative to the body joint and a second accelerometer which is worn on a location which is distal relative to the body joint. In an example, accelerometers can be better at measuring small-scale movements and limb rotation, while an array of longitudinal sensors can be better at avoiding position drift over time. The combination of an array of longitudinal sensors and a pair of accelerometers can provide more accurate measurement, tracking estimation, and/or modeling of joint configuration and movement than is possible with either the longitudinal sensors or the accelerometers alone.

FIGS. 38 and 39 show an array of longitudinal sensors and accelerometers to measure movement of a body joint 38001 comprising: first longitudinal sensor 38002 which is configured to longitudinally span a body joint, wherein this first longitudinal sensor spans the body joint within a first radial quadrant of the body joint, wherein the first longitudinal sensor is configured to bend and/or stretch when the body joint moves, and wherein bending and/or stretching of the first longitudinal sensor generates a first set of data concerning movement of the body joint; second longitudinal sensor 38003 which is configured to longitudinally span a body joint, wherein this second longitudinal sensor spans the body joint within a second radial quadrant of the body joint, wherein the second longitudinal sensor is configured to bend and/or stretch when the body joint moves, and wherein bending and/or stretching of the second longitudinal sensor generates a second set of data concerning movement of the body joint; third longitudinal sensor 38004 which is configured to longitudinally span a body joint, wherein this third longitudinal sensor spans the body joint within a third radial quadrant of the body joint, wherein the third longitudinal sensor is configured to bend and/or stretch when the body joint moves, and wherein bending and/or stretching of the third longitudinal sensor generates a third set of data concerning movement of the body joint; fourth longitudinal sensor 38005 which is configured to longitudinally span a body joint, wherein this fourth longitudinal sensor spans the body joint within a fourth radial quadrant of the body joint, wherein the fourth longitudinal sensor is configured to bend and/or stretch when the body joint moves, and wherein bending and/or stretching of the fourth longitudinal sensor generates a fourth set of data concerning movement of the body joint; first accelerometer 38006 which is configured to worn on location which is proximal from the body joint; and second accelerometer 38007 which is configured to worn on location which is distal from the body joint. Relevant example variations and alternative components discussed in the narratives accompanying other figures in this disclosure can also be applied to this example.

FIGS. 40 and 41 show an embodiment of this invention that is similar to the one shown in FIGS. 38 and 39, except that it includes an array of six longitudinal sensors instead of four. A hextant can be defined as a one-sixth (60-degree) slice of a circle. In this example, a first radial hextant of the body joint spans from the 330 degree vector to the 30 degree vector, a second radial hextant of the body joint spans from the 30 degree vector to the 90 degree vector, a third radial hextant of the body joint spans from the 90 degree vector to the 150 degree vector, a fourth radial hextant of the body joint spans from the 150 degree vector to the 210 degree vector, a fifth radial hextant of the body joint spans from the 210 degree vector to the 270 degree vector, and a sixth radial hextant of the body joint spans from the 270 degree vector to the 330 degree vector. In another example, each of this hextants can have boundary vectors which are shifted clockwise by 30 degrees.

FIGS. 40 and 41 show an array of six longitudinal sensors to measure movement of a body joint 40001 comprising: first longitudinal sensor 40002 which is configured to longitudinally span a body joint, wherein this first longitudinal sensor spans the body joint within a first radial hextant of the body joint, wherein a hextant is a one-sixth slice of a circle, wherein the first longitudinal sensor is configured to bend and/or stretch when the body joint moves, and wherein bending and/or stretching of the first longitudinal sensor generates a first set of data concerning movement of the body joint; second longitudinal sensor 40003 which is configured to longitudinally span a body joint, wherein this second longitudinal sensor spans the body joint within a second radial hextant of the body joint, wherein the second longitudinal sensor is configured to bend and/or stretch when the body joint moves, and wherein bending and/or stretching of the second longitudinal sensor generates a second set of data concerning movement of the body joint; third longitudinal sensor 40004 which is configured to longitudinally span a body joint, wherein this third longitudinal sensor spans the body joint within a third radial hextant of the body joint, wherein the third longitudinal sensor is configured to bend and/or stretch when the body joint moves, and wherein bending and/or stretching of the third longitudinal sensor generates a third set of data concerning movement of the body joint; fourth longitudinal sensor 40005 which is configured to longitudinally span a body joint, wherein this fourth longitudinal sensor spans the body joint within a fourth radial hextant of the body joint, wherein the fourth longitudinal sensor is configured to bend and/or stretch when the body joint moves, and wherein bending and/or stretching of the fourth longitudinal sensor generates a fourth set of data concerning movement of the body joint; fifth longitudinal sensor 40006 which is configured to longitudinally span a body joint, wherein this fifth longitudinal sensor spans the body joint within a fifth radial hextant of the body joint, wherein the fifth longitudinal sensor is configured to bend and/or stretch when the body joint moves, and wherein bending and/or stretching of the fifth longitudinal sensor generates a fifth set of data concerning movement of the body joint; sixth longitudinal sensor 40007 which is configured to longitudinally span a body joint, wherein this sixth longitudinal sensor spans the body joint within a sixth radial hextant of the body joint, wherein the sixth longitudinal sensor is configured to bend and/or stretch when the body joint moves, and wherein bending and/or stretching of the sixth longitudinal sensor generates a sixth set of data concerning movement of the body joint; first accelerometer 40008 which is configured to worn on location which is proximal from the body joint; and second accelerometer 40009 which is configured to worn on location which is distal from the body joint. Relevant example variations and alternative components discussed in the narratives accompanying other figures in this disclosure can also be applied to this example.

I claim:

1. An array of bending and/or stretching electromagnetic energy sensors to measure movement of a body joint comprising:
   a first longitudinal electromagnetic energy sensor which is configured to longitudinally span a body joint, wherein this first longitudinal sensor spans the body joint within a first radial quadrant of the body joint, and wherein the first longitudinal sensor is configured to bend and/or stretch when the body joint move;
   a second longitudinal electromagnetic energy sensor which is configured to longitudinally span the body joint, wherein this second longitudinal sensor spans the body joint within a second radial quadrant of the body joint, and wherein the second longitudinal sensor is configured to bend and/or stretch when the body joint moves;
   a third longitudinal electromagnetic energy sensor which is configured to longitudinally span the body joint, wherein this third longitudinal sensor spans the body joint within a third radial quadrant of the body joint, and wherein the third longitudinal sensor is configured to bend and/or stretch when the body joint moves;
   a fourth longitudinal electromagnetic energy sensor which is configured to longitudinally span the body joint, wherein this fourth longitudinal sensor spans the body joint within a fourth radial quadrant of the body joint, and wherein the fourth longitudinal sensor is configured to bend and/or stretch when the body joint moves; and a plurality of radial electromagnetic energy sensors which are configured to collectively span the body joint, wherein the longitudinal axes of the radial electromagnetic energy sensors converge;

wherein changes in electromagnetic energy transmitted through the first longitudinal electromagnetic energy sensor, the second longitudinal electromagnetic energy sensor, the third longitudinal electromagnetic energy sensor, the fourth longitudinal electromagnetic energy sensor and/or the plurality of radial electromagnetic energy sensors are measured as the body joint moves.

2. The array in claim 1 wherein degree vectors around the body joint are defined relative to a 0 degree vector which starts at the cross-sectional center of the body joint and extends outward through the most ventral location of the body joint perimeter, wherein a 180 degree vector is the vector which starts at the cross-sectional center of the body joint and extends outward in a direction which is diametrically opposite to that of the 0 degree vector, wherein the first radial quadrant of the body joint spans from the 315 degree vector to the 45 degree vector, wherein the second radial quadrant of the body joint spans from the 45 degree vector to the 135 degree vector, wherein the third radial quadrant of the body joint spans from the 135 degree vector to the 225 degree vector, and wherein the fourth radial quadrant of the body joint spans from the 225 degree vector to the 315 degree vector.

* * * * *